US009579430B2

(12) United States Patent
Hu et al.

(10) Patent No.: US 9,579,430 B2
(45) Date of Patent: Feb. 28, 2017

(54) CONTROLLED NEGATIVE PRESSURE APPARATUS AND ALARM MECHANISM

(71) Applicant: KCI Licensing, Inc., San Antonio, TX (US)

(72) Inventors: Dean Hu, San Leandro, CA (US); Thomas Yorkey, San Ramon, CA (US); Evan Anderson, San Francisco, CA (US); Kenneth Wu, San Francisco, CA (US); Tony Coxum, San Jose, CA (US)

(73) Assignee: KCI Licensing, Inc., San Antonio, TX (US)

( * ) Notice: Subject to any disclaimer, the term of this patent is extended or adjusted under 35 U.S.C. 154(b) by 475 days.

(21) Appl. No.: 14/267,786

(22) Filed: May 1, 2014

(65) Prior Publication Data

US 2014/0243767 A1 Aug. 28, 2014

Related U.S. Application Data

(63) Continuation of application No. 13/207,360, filed on Aug. 10, 2011, now Pat. No. 8,753,322, and a continuation-in-part of application No. 13/175,744, filed on Jul. 1, 2011, now Pat. No. 8,795,246.

(60) Provisional application No. 61/372,837, filed on Aug. 11, 2010, provisional application No. 61/372,419, filed on Aug. 10, 2010, provisional application No.
(Continued)

(51) Int. Cl.
*A61M 1/00* (2006.01)
(52) U.S. Cl.
CPC ........ *A61M 1/0068* (2014.02); *A61M 1/0066* (2013.01); *A61M 1/0088* (2013.01); *A61M 1/0096* (2014.02); *A61M 2202/0014* (2013.01);

*A61M 2205/18* (2013.01); *A61M 2205/702* (2013.01); *A61M 2205/8206* (2013.01)

(58) Field of Classification Search
CPC combination set(s) only.
See application file for complete search history.

(56) References Cited

U.S. PATENT DOCUMENTS

| | | |
|---|---|---|
| 2,198,666 A | 4/1940 | Gruskin |
| 2,472,116 A | 6/1949 | Maynes |
| 2,660,342 A | 11/1953 | Ruf |

(Continued)

FOREIGN PATENT DOCUMENTS

| | | |
|---|---|---|
| CN | 2851641 Y | 12/2006 |
| CN | 101547712 A | 9/2009 |

(Continued)

OTHER PUBLICATIONS

US 7,186,244, 03/2007, Hunt et al. (withdrawn)
(Continued)

*Primary Examiner* — Adam Marcetich
*Assistant Examiner* — Guy K Townsend

(57) ABSTRACT

Methods and devices for treatment of damaged tissue are disclosed, including treatment of wounds by employing non-electrically powered, reduced pressure therapy devices. The devices are capable of generating a substantially constant reduced pressure with low tolerance for pressure fluctuations. Also disclosed herein are reduced pressure therapy systems that comprise an alarm system to detect the depleted state of the suction device and provide an alert to the patient and/or practitioner.

20 Claims, 65 Drawing Sheets

Related U.S. Application Data

61/372,843, filed on Aug. 11, 2010, provisional application No. 61/470,423, filed on Mar. 31, 2011.

(56) References Cited

U.S. PATENT DOCUMENTS

| | | | |
|---|---|---|---|
| 2,863,452 A | 12/1958 | Ogle, Sr. | |
| 3,114,468 A | 12/1963 | Quase | |
| 3,334,628 A | 8/1967 | Saemann et al. | |
| 3,583,399 A | 6/1971 | Ritsky | |
| 3,628,325 A | 12/1971 | Morita | |
| 3,680,560 A | 8/1972 | Pannier, Jr. et al. | |
| 3,779,243 A | 12/1973 | Tussey et al. | |
| 3,809,086 A | 5/1974 | Schachet et al. | |
| 3,809,087 A | 5/1974 | Lewis, Jr. | |
| 3,833,030 A | 9/1974 | Waldbauer, Jr. et al. | |
| 3,841,331 A * | 10/1974 | Wilder | A61M 1/0066 604/152 |
| 3,982,546 A | 9/1976 | Friend | |
| 4,041,934 A | 8/1977 | Genese | |
| 4,080,970 A | 3/1978 | Miller | |
| 4,278,089 A * | 7/1981 | Huck | A61M 1/0011 141/26 |
| 4,287,819 A * | 9/1981 | Emerit | A61B 5/150389 116/DIG. 9 |
| 4,324,246 A | 4/1982 | Mullane et al. | |
| 4,333,456 A * | 6/1982 | Webb | A61M 5/24 604/121 |
| 4,333,458 A * | 6/1982 | Margulies | A61M 5/24 604/201 |
| 4,342,314 A | 8/1982 | Radel et al. | |
| 4,382,441 A | 5/1983 | Svedman | |
| 4,404,924 A * | 9/1983 | Goldberg | A61M 1/00 116/266 |
| 4,525,167 A | 6/1985 | Goldberg et al. | |
| 4,549,554 A | 10/1985 | Markham | |
| 4,569,674 A | 2/1986 | Phillips et al. | |
| 4,578,060 A * | 3/1986 | Huck | A61M 1/0011 604/133 |
| 4,648,870 A | 3/1987 | Goldberg et al. | |
| 4,664,128 A * | 5/1987 | Lee | A61B 10/025 401/176 |
| 4,743,232 A * | 5/1988 | Kruger | A61F 13/023 128/DIG. 26 |
| 4,758,232 A * | 7/1988 | Chak | A61B 5/15003 600/578 |
| 4,867,748 A | 9/1989 | Samuelsen | |
| 4,882,377 A | 11/1989 | Sweet et al. | |
| 4,889,250 A * | 12/1989 | Beyer | B67D 1/10 215/228 |
| 4,969,880 A | 11/1990 | Zamierowski | |
| 5,071,409 A * | 12/1991 | Rosenberg | A61M 1/0009 600/579 |
| 5,100,396 A | 3/1992 | Zamierowski | |
| 5,116,310 A | 5/1992 | Seder et al. | |
| 5,157,808 A | 10/1992 | Sterner, Jr. | |
| 5,261,893 A | 11/1993 | Zamierowski | |
| 5,263,922 A | 11/1993 | Sova et al. | |
| 5,266,476 A | 11/1993 | Sussman et al. | |
| 5,284,621 A | 2/1994 | Kaufman | |
| 5,358,494 A | 10/1994 | Svedman | |
| 5,395,345 A * | 3/1995 | Gross | A61B 10/0233 604/187 |
| 5,527,293 A | 6/1996 | Zamierowski | |
| 5,584,801 A | 12/1996 | Kuroyanagi et al. | |
| 5,636,643 A * | 6/1997 | Argenta | A61F 13/0216 128/897 |
| 5,645,081 A | 7/1997 | Argenta et al. | |
| 5,701,917 A | 12/1997 | Khouri | |
| 5,704,905 A | 1/1998 | Jensen et al. | |
| 5,711,969 A | 1/1998 | Patel et al. | |
| 5,990,377 A | 11/1999 | Chen et al. | |
| 6,071,267 A | 6/2000 | Zamierowski | |
| 6,142,982 A * | 11/2000 | Hunt | A61M 1/0023 604/313 |
| 6,228,056 B1 | 5/2001 | Boehringer et al. | |
| 6,235,964 B1 * | 5/2001 | Kadash | A61F 13/023 602/41 |
| 6,258,995 B1 | 7/2001 | Gilding et al. | |
| 6,261,276 B1 * | 7/2001 | Reitsma | A61M 1/0023 604/319 |
| 6,345,623 B1 * | 2/2002 | Heaton | A61F 13/023 128/897 |
| 6,387,082 B1 | 5/2002 | Freeman | |
| 6,458,109 B1 * | 10/2002 | Henley | A61M 1/0088 604/289 |
| 6,461,467 B2 | 10/2002 | Blatchford et al. | |
| 6,553,998 B2 | 4/2003 | Heaton et al. | |
| 6,685,681 B2 * | 2/2004 | Lockwood | A61M 1/0058 502/43 |
| 6,695,823 B1 | 2/2004 | Lina et al. | |
| 6,695,824 B2 * | 2/2004 | Howard | A61M 1/0058 604/304 |
| 6,752,794 B2 | 6/2004 | Lockwood et al. | |
| 6,755,807 B2 | 6/2004 | Risk, Jr. et al. | |
| 6,800,074 B2 | 10/2004 | Henley et al. | |
| 6,814,079 B2 | 11/2004 | Heaton et al. | |
| 6,825,246 B1 * | 11/2004 | Fattman | A61L 15/585 523/111 |
| 6,840,111 B2 | 1/2005 | Benzel et al. | |
| 6,855,135 B2 | 2/2005 | Lockwood et al. | |
| 6,979,324 B2 | 12/2005 | Bybordi et al. | |
| 6,986,234 B2 | 1/2006 | Liedtke | |
| 7,070,584 B2 * | 7/2006 | Johnson | A61M 1/0088 424/444 |
| 7,117,869 B2 | 10/2006 | Heaton et al. | |
| 7,198,046 B1 * | 4/2007 | Argenta | A61F 13/0246 128/897 |
| 7,216,651 B2 | 5/2007 | Argenta et al. | |
| 7,273,054 B2 | 9/2007 | Heaton et al. | |
| 7,316,672 B1 | 1/2008 | Hunt et al. | |
| 7,341,574 B2 | 3/2008 | Schreijag | |
| 7,438,705 B2 | 10/2008 | Karpowicz et al. | |
| 7,461,158 B2 | 12/2008 | Rider et al. | |
| 7,485,112 B2 | 2/2009 | Karpowicz et al. | |
| 7,520,872 B2 * | 4/2009 | Biggie | A61M 1/0088 601/6 |
| 7,569,742 B2 | 8/2009 | Haggstrom et al. | |
| 7,608,066 B2 | 10/2009 | Vogel | |
| 7,615,036 B2 | 11/2009 | Joshi et al. | |
| 7,699,823 B2 | 4/2010 | Haggstrom et al. | |
| 7,763,000 B2 | 7/2010 | Risk, Jr. et al. | |
| 7,779,625 B2 | 8/2010 | Joshi et al. | |
| 7,837,673 B2 | 11/2010 | Vogel | |
| 7,857,806 B2 | 12/2010 | Karpowicz et al. | |
| 7,959,624 B2 | 6/2011 | Riesinger | |
| 7,964,766 B2 * | 6/2011 | Blott | A61M 1/0084 602/41 |
| 7,967,810 B2 * | 6/2011 | Freedman | A61M 1/0031 604/305 |
| 8,007,491 B2 | 8/2011 | Pinto et al. | |
| 8,048,046 B2 * | 11/2011 | Hudspeth | A61M 1/0088 604/119 |
| 8,128,607 B2 | 3/2012 | Hu et al. | |
| 8,162,908 B2 | 4/2012 | Hu et al. | |
| 8,177,764 B2 | 5/2012 | Hu et al. | |
| 8,409,156 B2 | 4/2013 | Kazala, Jr. et al. | |
| 8,409,157 B2 | 4/2013 | Haggstrom et al. | |
| 8,409,160 B2 | 4/2013 | Locke et al. | |
| 2001/0031943 A1 * | 10/2001 | Urie | A61M 1/0088 604/43 |
| 2001/0043943 A1 * | 11/2001 | Coffey | A61F 13/02 424/447 |
| 2001/0056258 A1 | 12/2001 | Evans | |
| 2002/0150720 A1 | 10/2002 | Howard et al. | |
| 2002/0173808 A1 | 11/2002 | Houser et al. | |
| 2002/0183702 A1 | 12/2002 | Henley et al. | |
| 2002/0198503 A1 | 12/2002 | Risk, Jr. et al. | |
| 2003/0050594 A1 | 3/2003 | Zamierowski | |
| 2003/0190339 A1 | 10/2003 | Skover et al. | |
| 2004/0006319 A1 * | 1/2004 | Lina | A61F 13/0203 604/304 |
| 2004/0186424 A1 | 9/2004 | Hjertman | |

(56) References Cited

U.S. PATENT DOCUMENTS

| | | | |
|---|---|---|---|
| 2004/0249353 A1 | 12/2004 | Risks, Jr. et al. | |
| 2004/0261642 A1 | 12/2004 | Hess | |
| 2005/0101940 A1* | 5/2005 | Radl | A61M 1/0011 604/543 |
| 2005/0124946 A1* | 6/2005 | Landau | A61M 3/0262 604/317 |
| 2005/0192544 A1 | 9/2005 | Wolbring et al. | |
| 2005/0222528 A1 | 10/2005 | Weston | |
| 2005/0222544 A1* | 10/2005 | Weston | A61M 1/0001 604/313 |
| 2005/0261642 A1* | 11/2005 | Weston | A61M 1/0031 604/313 |
| 2006/0253090 A1* | 11/2006 | Bradley | A61F 5/4405 604/334 |
| 2006/0282028 A1 | 12/2006 | Howard et al. | |
| 2007/0027414 A1* | 2/2007 | Hoffman | A61M 1/0088 602/2 |
| 2007/0032763 A1 | 2/2007 | Vogel | |
| 2007/0066946 A1 | 3/2007 | Haggstrom et al. | |
| 2007/0219512 A1 | 9/2007 | Heaton et al. | |
| 2007/0219532 A1* | 9/2007 | Karpowicz | A61M 1/0031 604/540 |
| 2007/0265585 A1* | 11/2007 | Joshi | A61M 1/0088 604/313 |
| 2008/0004559 A1* | 1/2008 | Riesinger | A61F 13/00012 602/46 |
| 2008/0009812 A1* | 1/2008 | Riesinger | A61F 13/00012 604/305 |
| 2008/0033330 A1 | 2/2008 | Moore | |
| 2008/0063615 A1 | 3/2008 | MacDonald et al. | |
| 2008/0082059 A1* | 4/2008 | Fink | A61M 1/0001 604/305 |
| 2008/0086214 A1 | 4/2008 | Hardin et al. | |
| 2008/0108977 A1* | 5/2008 | Heaton | A61M 1/0011 604/543 |
| 2008/0109877 A1 | 5/2008 | Park et al. | |
| 2008/0200906 A1 | 8/2008 | Sanders et al. | |
| 2008/0234641 A1 | 9/2008 | Locke et al. | |
| 2008/0306448 A1 | 12/2008 | Lee | |
| 2008/0306456 A1* | 12/2008 | Riesinger | A61F 13/0203 604/316 |
| 2009/0012482 A1* | 1/2009 | Pinto | A61F 13/00029 604/313 |
| 2009/0069761 A1 | 3/2009 | Vogel | |
| 2009/0076467 A1 | 3/2009 | Pinto et al. | |
| 2009/0137973 A1 | 5/2009 | Karpowicz et al. | |
| 2009/0221977 A1 | 9/2009 | Blott et al. | |
| 2009/0240218 A1 | 9/2009 | Braga et al. | |
| 2009/0254066 A1 | 10/2009 | Heaton et al. | |
| 2009/0259203 A1* | 10/2009 | Hu | A61F 13/02 604/290 |
| 2010/0030166 A1 | 2/2010 | Tout et al. | |
| 2010/0036333 A1 | 2/2010 | Schenk, III et al. | |
| 2010/0042021 A1* | 2/2010 | Hu | A61M 1/0009 601/6 |
| 2010/0042059 A1 | 2/2010 | Pratt et al. | |
| 2010/0100063 A1 | 4/2010 | Joshi et al. | |
| 2010/0106118 A1 | 4/2010 | Heaton et al. | |
| 2010/0137775 A1 | 6/2010 | Hu et al. | |
| 2010/0145289 A1 | 6/2010 | Lina et al. | |
| 2010/0160879 A1 | 6/2010 | Weston | |
| 2010/0160901 A1 | 6/2010 | Hu et al. | |
| 2010/0168719 A1 | 7/2010 | Chen | |
| 2010/0174250 A1 | 7/2010 | Hu et al. | |
| 2010/0179493 A1 | 7/2010 | Heagle et al. | |
| 2010/0198173 A1* | 8/2010 | Hu | A61M 1/0009 604/319 |
| 2010/0198174 A1 | 8/2010 | Hu et al. | |
| 2010/0228205 A1* | 9/2010 | Hu | A61M 1/0037 604/319 |
| 2010/0262090 A1 | 10/2010 | Riesinger | |
| 2010/0262094 A1 | 10/2010 | Walton et al. | |
| 2011/0106026 A1* | 5/2011 | Wu | A61M 1/0088 604/319 |
| 2011/0130691 A1 | 6/2011 | Hu et al. | |
| 2011/0137270 A1 | 6/2011 | Hu et al. | |
| 2011/0313377 A1 | 12/2011 | Pinto et al. | |
| 2012/0016321 A1 | 1/2012 | Wu et al. | |
| 2012/0016325 A1 | 1/2012 | Pinto et al. | |
| 2012/0022475 A1 | 1/2012 | Hu et al. | |
| 2012/0071845 A1* | 3/2012 | Hu | A61M 1/0066 604/319 |
| 2012/0078207 A1 | 3/2012 | Hu et al. | |
| 2012/0083754 A1 | 4/2012 | Hu et al. | |
| 2013/0090615 A1 | 4/2013 | Jaeb et al. | |
| 2013/0096536 A1 | 4/2013 | Kazala, Jr. et al. | |

FOREIGN PATENT DOCUMENTS

| | | |
|---|---|---|
| DE | 202005019670 U1 | 6/2006 |
| GB | 2195255 A | 4/1988 |
| GB | 2306107 A | 4/1997 |
| GB | 2431351 A | 4/2007 |
| JP | 2001-509426 A | 7/2001 |
| JP | 2007-511252 A | 5/2007 |
| JP | 2009-66182 A | 4/2009 |
| JP | 2010-504816 A | 2/2010 |
| JP | 2010-506615 A | 3/2010 |
| WO | 80/02182 A1 | 10/1980 |
| WO | 99/02210 A1 | 1/1999 |
| WO | 2005/000378 A2 | 1/2005 |
| WO | 2006/005939 A1 | 1/2006 |
| WO | 2007/019038 A2 | 2/2007 |
| WO | 2007/030601 A2 | 3/2007 |
| WO | 2007/030601 A3 | 5/2007 |
| WO | 2007/067685 A2 | 6/2007 |
| WO | 2007/019038 A3 | 7/2007 |
| WO | 2008/039223 A1 | 4/2008 |
| WO | 2008/048527 A2 | 4/2008 |
| WO | 2008/100446 A2 | 8/2008 |
| WO | 2008/112304 A1 | 9/2008 |
| WO | 2008/100446 A3 | 10/2008 |
| WO | 2007/067685 A3 | 11/2008 |
| WO | 2009/039214 A2 | 3/2009 |
| WO | 2009/089016 A1 | 7/2009 |
| WO | 2009/103031 A1 | 8/2009 |
| WO | 2010/068502 A1 | 6/2010 |
| WO | 2010/102146 A1 | 9/2010 |

OTHER PUBLICATIONS

Final Office Action received for U.S. Appl. No. 12/047,739, mailed on Apr. 21, 2010, 16 pages.

Non Final Office Action received for U.S. Appl. No. 12/047,739, mailed on Feb. 13, 2012, 12 pages.

Non Final Office Action received for U.S. Appl. No. 12/047,739, mailed on Nov. 27, 2009, 21 pages.

Final Office Action received for U.S. Appl. No. 12/234,530 mailed on Apr. 22, 2010, 16 pages.

Non Final Office Action received for U.S. Appl. No. 12/234,530, mailed on Oct. 29, 2009, 17 pages.

Notice of Allowance received for U.S. Appl. No. 12/234,530, mailed on Jun. 24, 2011, 9 pages.

Preinterview First Office Action received for U.S. Appl. No. 12/372,661, mailed on Dec. 15, 2011, 4 pages.

Non Final Office Action received for U.S. Appl. No. 12/626,426 mailed on Oct. 12, 2011, 15 pages.

Non Final Office Action received for U.S. Appl. No. 12/646,856 mailed on Nov. 2, 2011, 16 pages.

Notice of Allowance received for U.S. Appl. No. 12/760,406, mailed on Dec. 22, 2011, 9 pages.

Non Final Office Action received for U.S. Appl. No. 13/030,042, mailed on Oct. 31, 2011, 17 pages.

Final Office Action received for U.S. Appl. No. 13/175,744 mailed on Jun. 18, 2013, 33 pages.

Non-Final Office Action received for U.S. Appl. No. 13/175,744, mailed on Oct. 25, 2012, 23 pages.

(56) References Cited

OTHER PUBLICATIONS

Notice of Allowance received for U.S. Appl. No. 13/175,744, mailed on Jun. 25, 2014, 2 pages.
Notice of Allowance received for U.S. Appl. No. 13/175,744, mailed on Mar. 3, 2014, 11 pages.
Final Office Action received for U.S. Appl. No. 13/207,360 mailed on Jun. 4, 2013, 17 pages.
Non-Final Office Action received for U.S. Appl. No. 13/207,360, mailed on Oct. 29, 2012, 16 pages.
Notice of Allowance received for U.S. Appl. No. 13/207,360, mailed on Jan. 14, 2014, 9 pages.
Non-Final Office Action received for U.S. Appl. No. 13/245,735, mailed on Nov. 18, 2011, 14 pages.
Final Office Action received for U.S. Appl. No. 13/245,742, mailed on Oct. 29, 2012, 22 pages.
Non Final Office Action received for U.S. Appl. No. 13/245,742, mailed on Jun. 5, 2013, 18 pages.
Non-Final Office Action received for U.S. Appl. No. 13/245,742, mailed on May 23, 2012, 15 pages.
Final Office Action received for U.S. Appl. No. 13/245,744, mailed on Nov. 5, 2013, 16 pages.
Final Office Action received for U.S. Appl. No. 13/245,744, mailed on Oct. 23, 2012, 15 pages.
Non Final Office Action received for U.S. Appl. No. 13/245,744, mailed on May 23, 2013, 18 pages.
Non-Final Office Action received for U.S. Appl. No. 13/245,744, mailed on Apr. 27, 2012, 19 pages.
Anonymous, "Drain and Suture Line Care for Wounds", The Cleveland Clinic Foundation, Feb. 10, 2000, 4 pages.
Bagautdinov, N. A., "Variant of External Vacuum Aspiration in the Treatment of Purulent Diseases of Soft Tissues", Current Problems in Modern Clinical Surgery, Cheboksary: Chuvashia State University, 1986, 14 pages.
Chariker et al., "Effective Management of Incisional and Cutaneous Fistulae with Closed Suction Wound Drainage", Contemporary Surgery, vol. 34, Jun. 1989, pp. 59-63.
Davydov et al., "Concepts for Clinical Biological Management of the Wound Process in the Treatment of Purulent Wounds Using Vacuum Therapy", The Kremlin Papers: Perspectives in Wound Care, Feb. 1991, pp. 15-17.
Davydov et al., "The Bacteriological and Cytological Assessment of Vacuum Therapy of Purulent Wounds", The Kremlin Papers: Perspectives in Wound Care, Oct. 1988, pp. 11-14.
Davydov et al., "Vacuum Therapy in the Treatment of Purulent Lactation Mastitis", The Kremlin Papers: Perspectives in Wound Care, Sep. 1986, pp. 5-7.
Herrmann et al., "The Conservative Treatment of Arteriosclerotic Peripheral Vascular Diseases: Passive Vascular Exercises (Pavaex Therapy)", Ann. Surgery, 1934, pp. 750-760.
Kostiuchenok et al., "The Vacuum Effect in the Surgical Treatment of Purulent Wounds", The Kremlin Papers: Perspectives in Wound Care, Sep. 1986, pp. 3-4.
Meyer et al., "Weight-Loaded Syringes as a Simple and Cheap Alternative to Pumps for Vacuum-Enhanced Wound Healing", Plastic and Reconstructive Surgery, vol. 115, No. 7, Jun. 2005, pp. 2174-2176.

International Search Report received for PCT Patent Application No. PCT/US2008/03412 mailed on Jul. 28, 2008, 3 pages.
International Preliminary Report on Patentability received for PCT Patent Application No. PCT/US2008/003412, issued on Sep. 15, 2009, 6 pages.
International Search Report received for PCT Patent Application No. PCT/US2009/034158, mailed on May 29, 2009, 6 pages.
International Preliminary Report on Patentability received for PCT Patent Application No. PCT/US2009/065959, mailed on Jun. 9, 2011, 9 pages.
International Search Report and Written Opinion received for PCT Patent Application No. PCT/US2009/065959, mailed on Jan. 21, 2010, 12 pages.
International Search Report and Written Opinion received for PCT Patent Application No. PCT/US2010/026269, mailed on May 4, 2010, 9 pages.
International Preliminary Report on Patentability received for PCT Patent Application No. PCT/US2011/047302, mailed on Feb. 21, 2013, 8 pages.
International Search Report and Written Opinion received for PCT Patent Application No. PCT/US2011/047302, mailed on Mar. 8, 2012, 11 pages.
Svedman, P. "A Dressing System Providing Fluid Supply and Suction Drainage Used for Continuous or Intermittent Irrigation", Annals of Plastic Surgery, vol. 17, No. 2, Aug. 1986, pp. 125-133.
Svedman, Paul, "Irrigation Treatment of Leg Ulcers", The Lancet, Sep. 3, 1983, pp. 532-534.
Ubbink et al., "Topical Negative Pressure for Treating Chronic Wounds", The Cochrane Collaboration, vol. 3, 2009, pp. 1-32.
Urschel et al., "The Effect of Mechanical Stress on Soft and Hard Tissue Repair; a Review", British Journal of Plastic Surgery, vol. 41, 1988, pp. 182-186.
Usupov et al., "Active Wound Drainage,", The Kremlin Papers: Perspectives in Wound Care, Apr. 1987, pp. 8-10.
Invitation to Pay Additional Fees received for PCT Patent Application No. PCT/US2011/047302, mailed on Dec. 16, 2011, 2 pages.
Notice of Allowance received for U.S. Appl. No. 13/245,742, mailed on Jan. 10, 2014, 14 pages.
Notice of Allowance received for U.S. Appl. No. 13/245,744, mailed on Jun. 9, 2014, 14 pages.
Office Action received for Australian Patent Application No. 2011289435, mailed on Jun. 2, 2015, 3 pages.
Office Action received for Chinese Patent Application No. 201180048840.X, mailed on Aug. 19, 2015, 9 pages (3 pages of English translation and 6 pages of official copy).
Office Action received for Chinese Patent Application No. 201180048840.X, mailed on Jan. 26, 2015, 17 pages (7 pages of English translation and 10 pages of Official Copy).
Office Action received for Japanese Patent Application No. 2013-524218, mailed on Jul. 30, 2015, 29 pages (18 pages of English Translation and 11 pages of Official copy).
Non Final Office Action received for U.S. Appl. No. 14/451,305, mailed on Jul. 9, 2015, 13 pages.

* cited by examiner

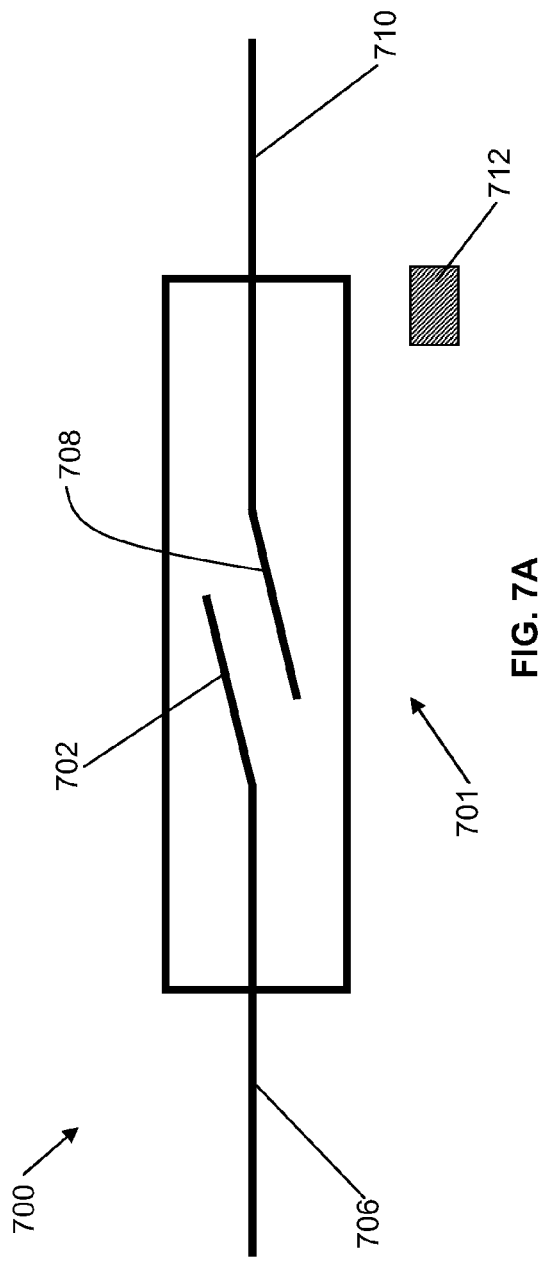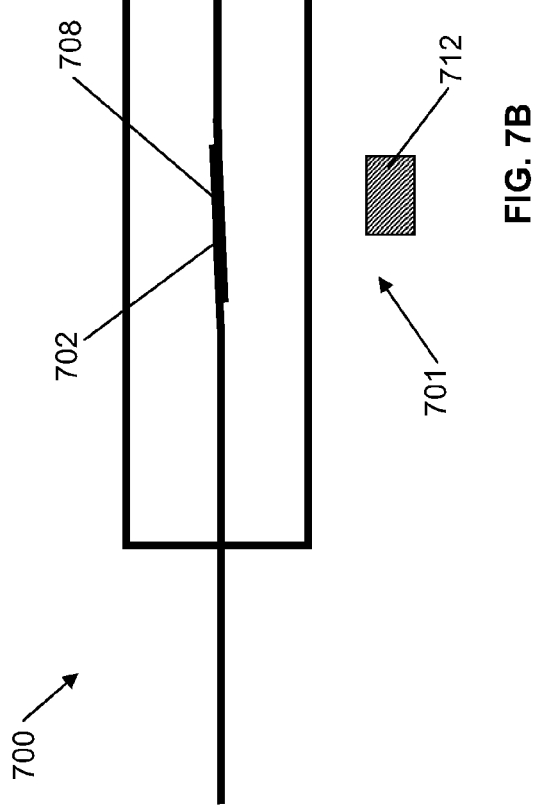

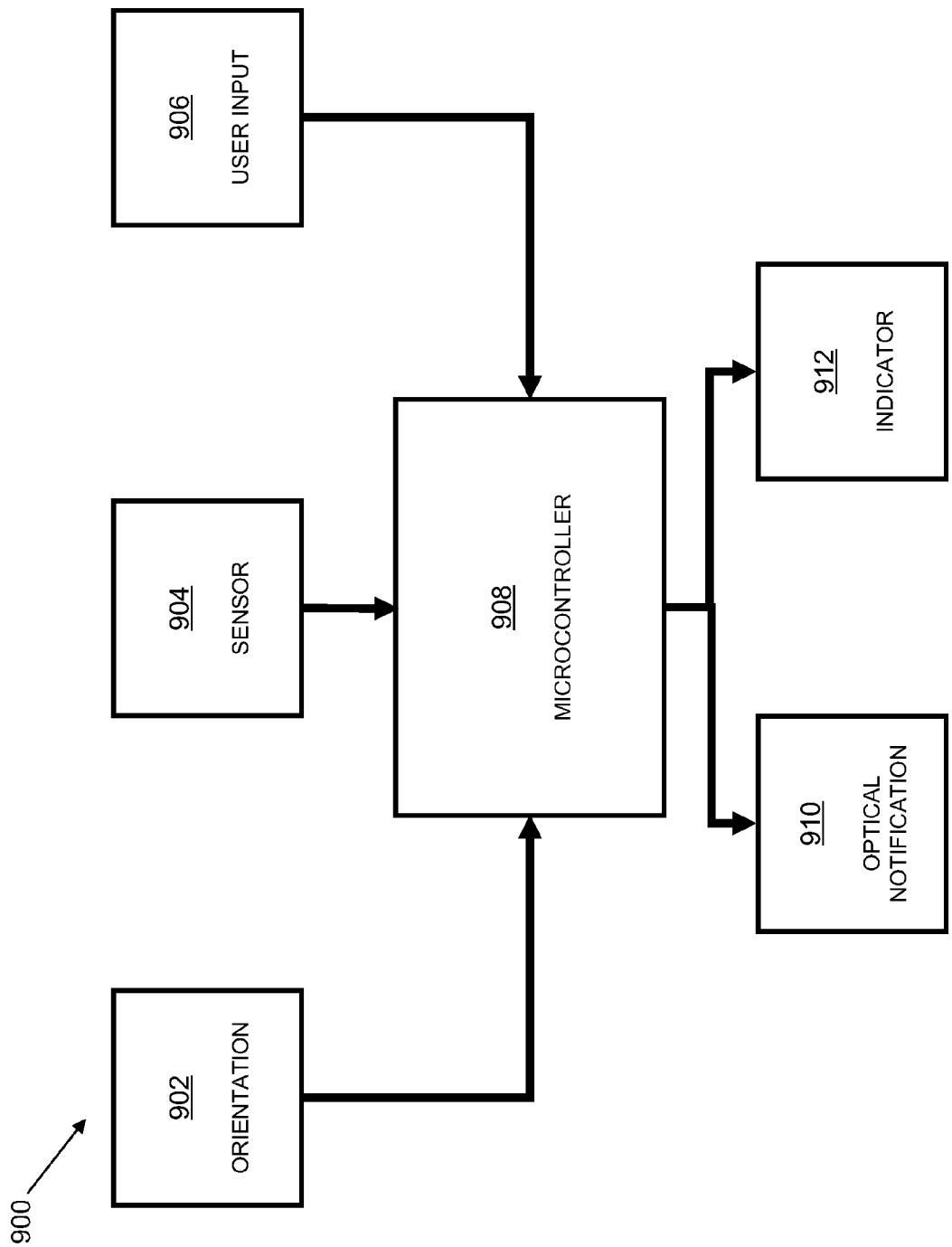

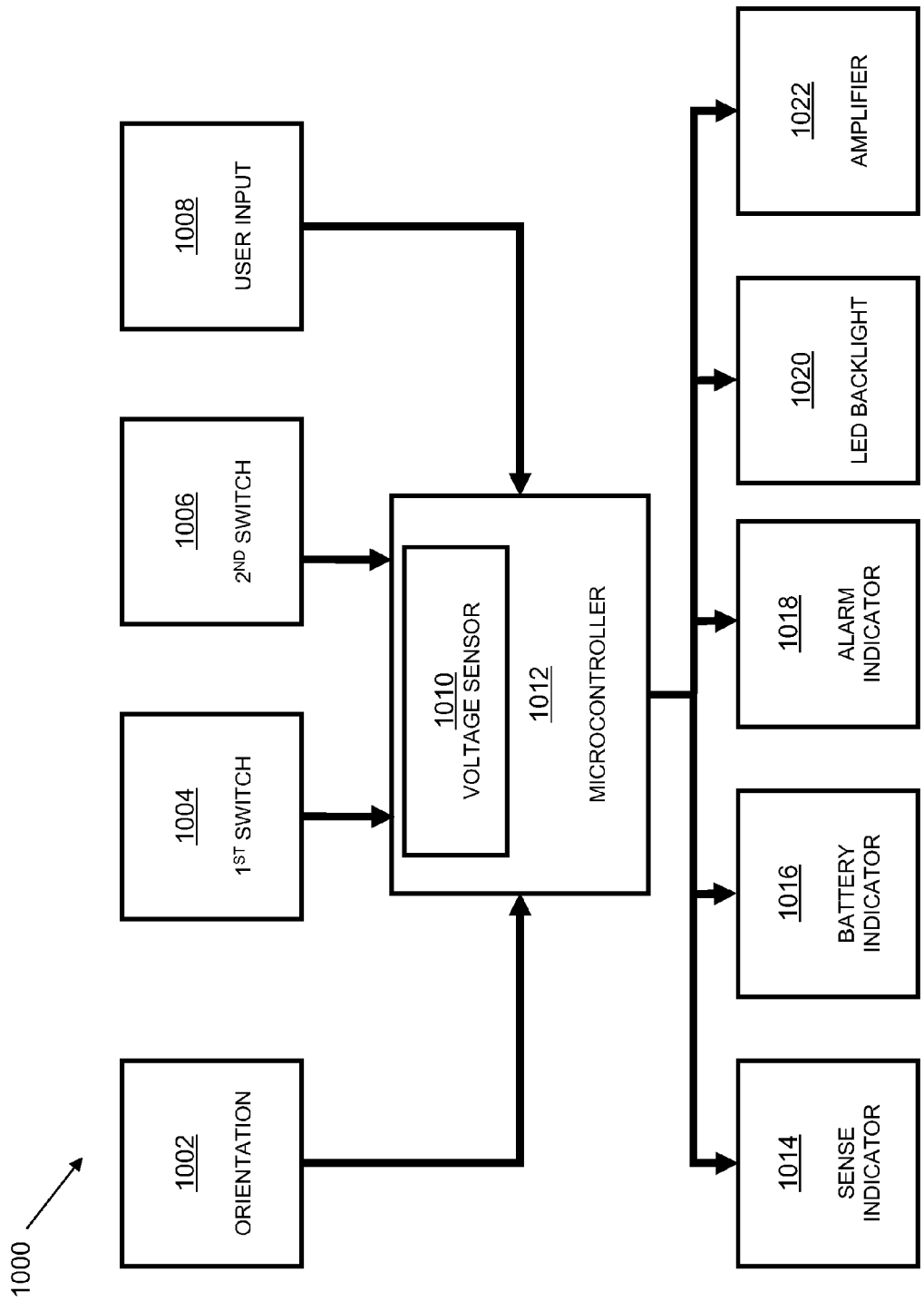

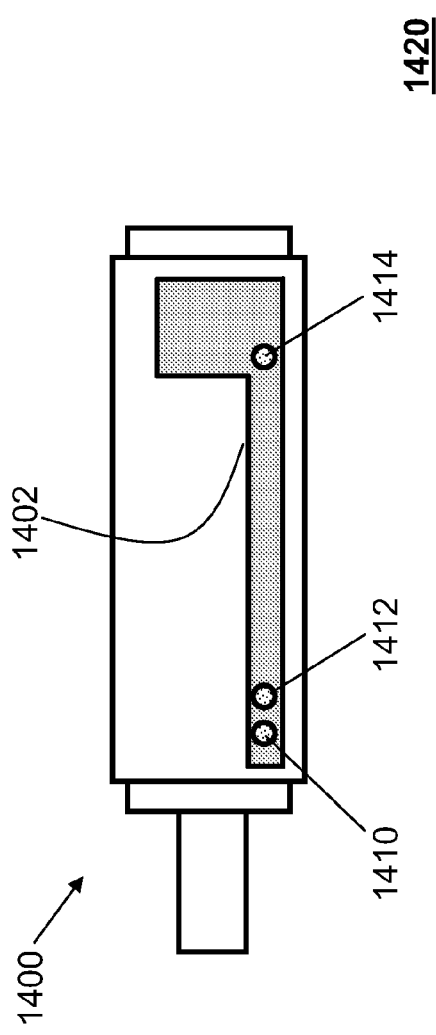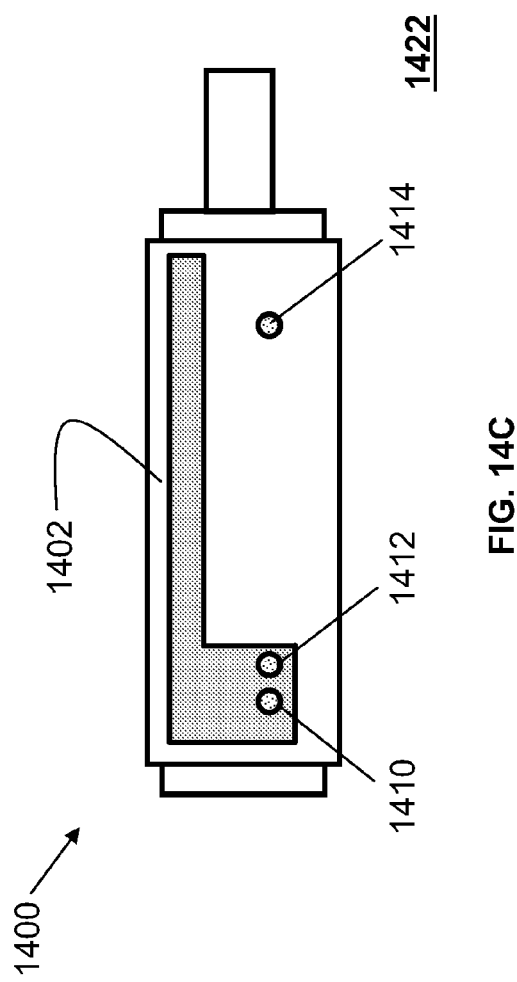

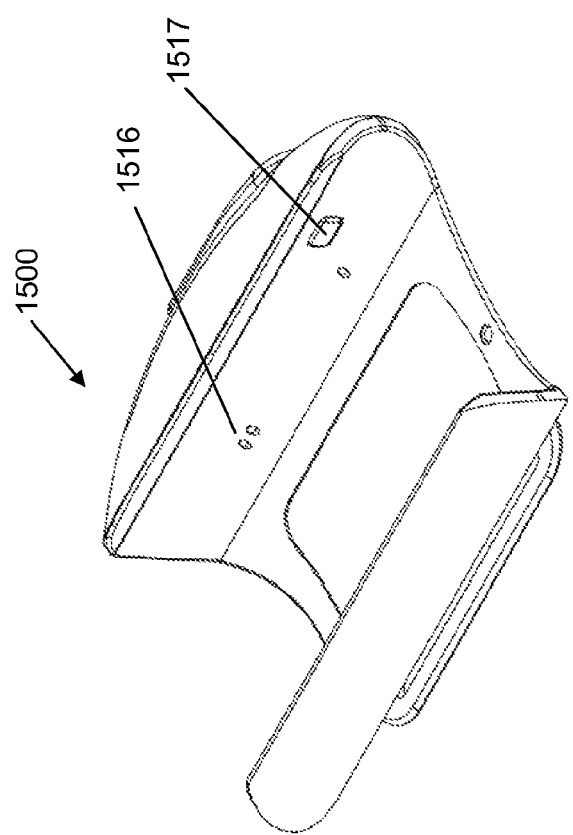
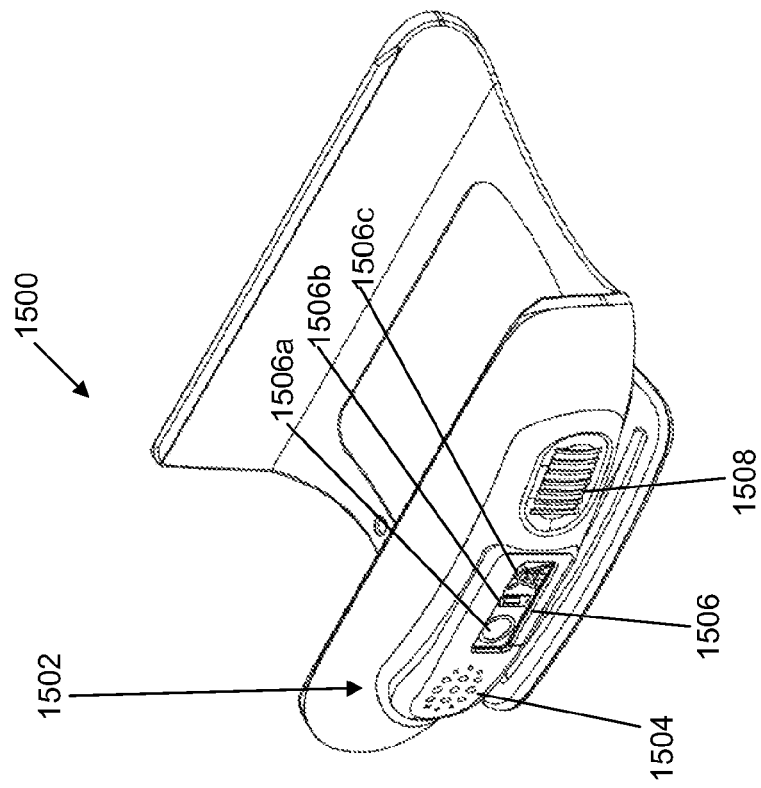
FIG. 15B
FIG. 15A

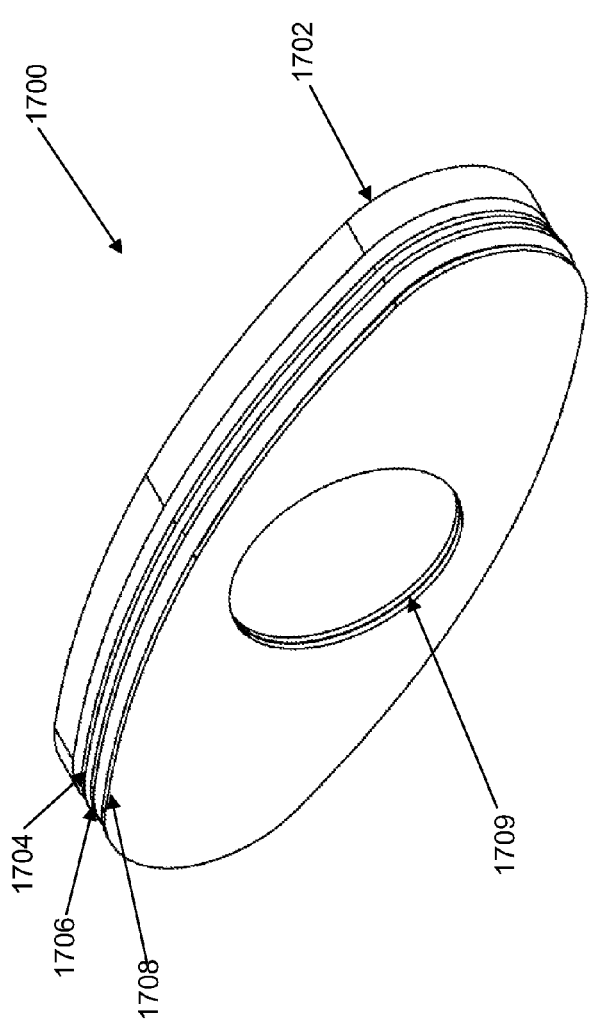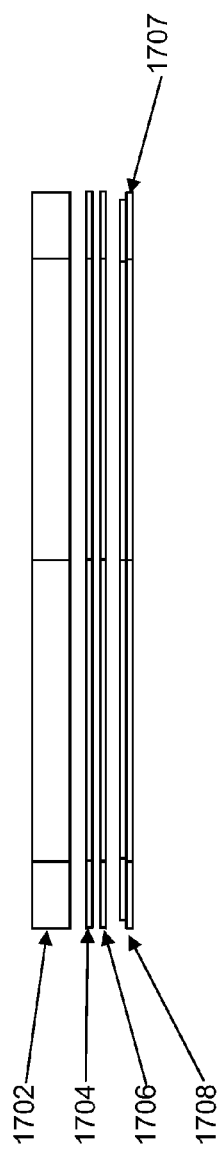
FIG. 17A
FIG. 17B

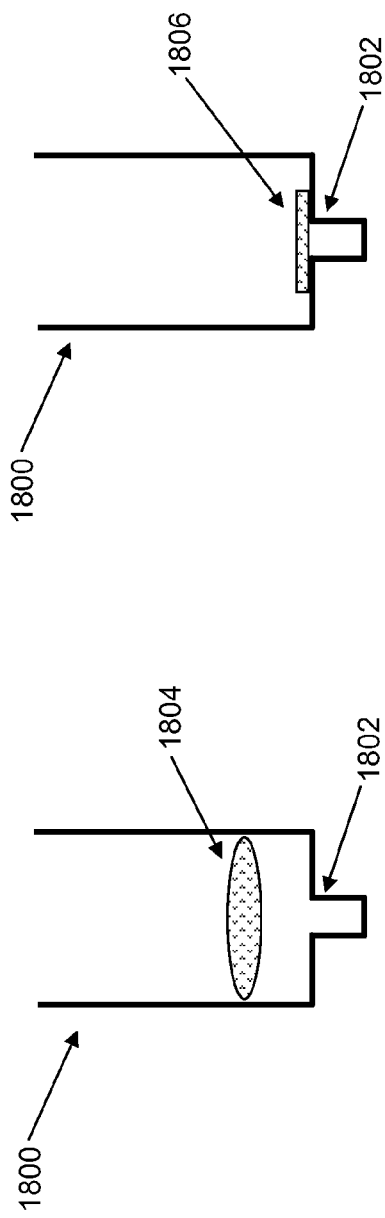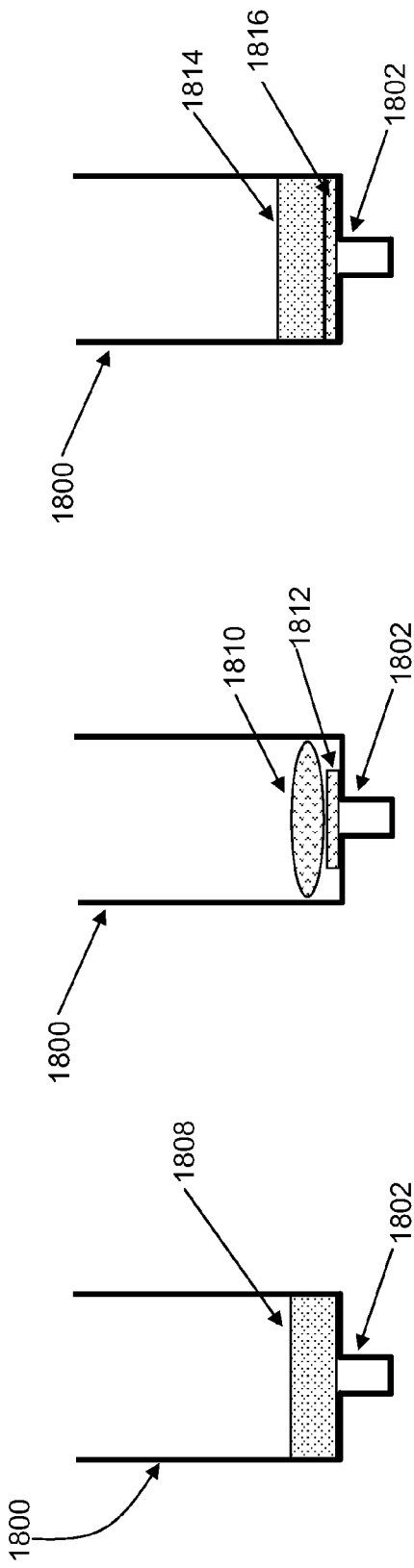

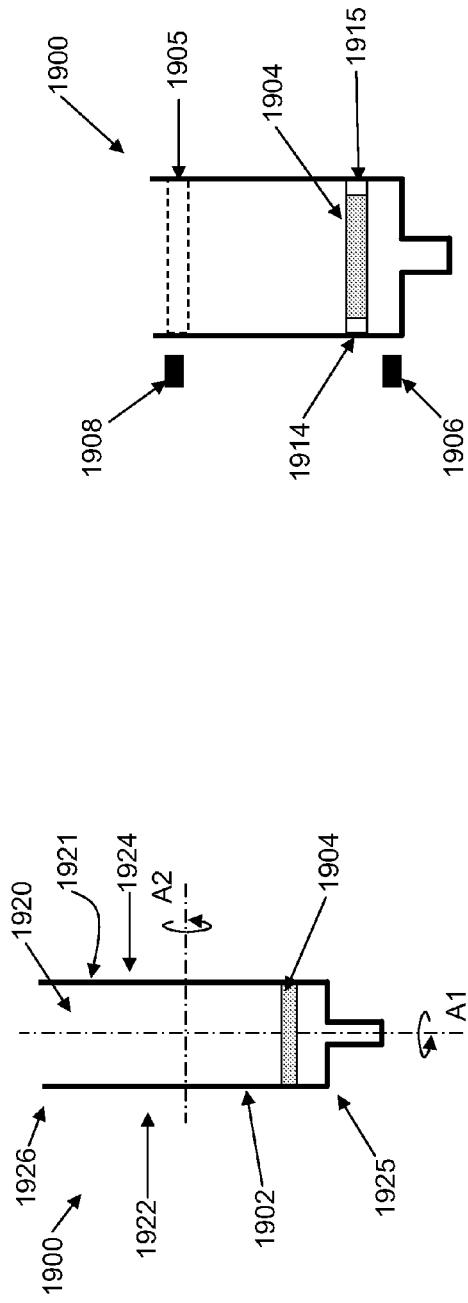
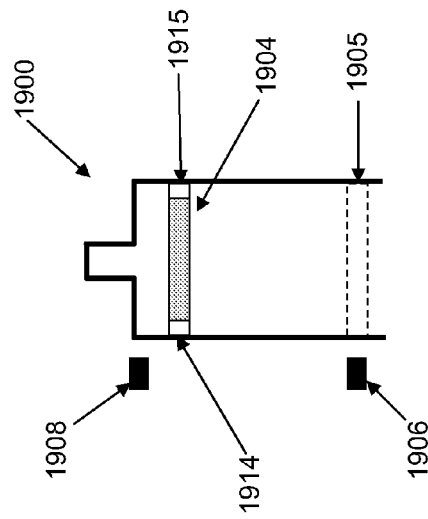
FIG. 19B
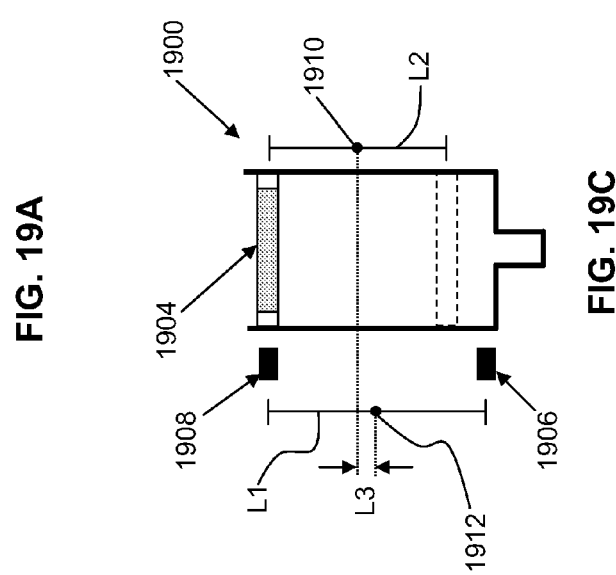
FIG. 19D
FIG. 19A
FIG. 19C

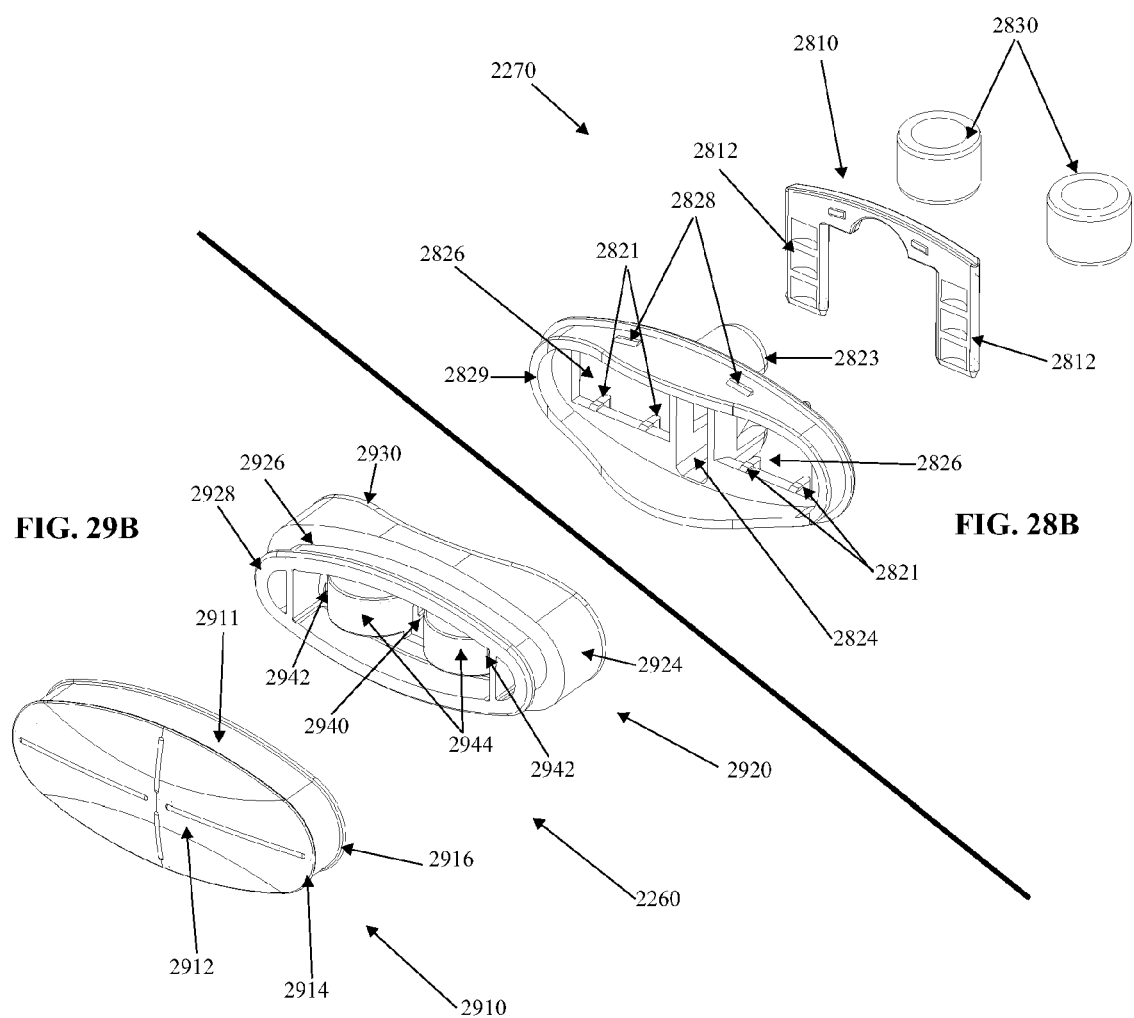

CONTROLLED NEGATIVE PRESSURE APPARATUS AND ALARM MECHANISM

CROSS-REFERENCE TO RELATED APPLICATIONS

This application is a continuation of U.S. application Ser. No. 13/207,360, filed Aug. 10, 2011, which a) claims benefit from U.S. Provisional Application Ser. No. 61/372,837, filed Aug. 11, 2010, and b) is a continuation-in-part of U.S. application Ser. No. 13/175,744, filed Jul. 1, 2011, which claims benefit from U.S. Provisional Application Ser. No. 61/372,419, filed Aug. 10, 2010, U.S. Provisional Application Ser. No. 61/372,843, filed Aug. 11, 2010, and U.S. Provisional Application Ser. No. 61/470,423, filed Mar. 31, 2011, each of which is hereby incorporated by reference in its entirety.

BACKGROUND

Research has shown that applying reduced pressure to a tissue wound may provide several beneficial effects. For example, applying sub-atmospheric pressure to a wound may lead to retraction of the damaged tissue edges and thus may expedite healing by facilitating wound contraction. Reduced pressure wound therapy may also provide mechanical stimulation to the damaged tissue, which may release growth factors to the wound bed to promote healing. In some cases, applying suction to a wound may remove necrotic tissue from the wound bed and may help to reduce bacterial load.

In the delivery of reduced pressure wound therapy, an airtight dressing is applied to a part of the body having a wound and a certain negative pressure is introduced to the wound area. It is desirable to maintain a substantially constant level of reduced pressure to the wound site. In such therapy, factors such as air leaks and fluid ingress contribute to the overall decrease in the magnitude of the reduced pressure; thus the reduced pressure tends to move towards atmospheric pressure. Except with the use of vacuum bottles, the source of the substantially constant reduced pressure may include some mechanism to compensate for the leaks or fluid ingress in order to maintain the pre-set negative pressure of the system. Examples of negative pressure sources that accomplish this are regulated by an electrically-powered pump, a pressure sensing means and a controller means to adjust the output of the pump. However, these systems require an electrical source, are bulky, noisy, and limit patient mobility.

In light of these and other benefits of reduced pressure tissue therapy, methods and devices that ensure a reliable application of reduced pressure to a wound may be desirable.

BRIEF SUMMARY

In one example, a reduced pressure therapy system is provided, comprising a suction device comprising a suction chamber and a slidable seal therein, a magnet coupled to the slidable seal, and an alarm device configured to retain the suction device, wherein the alarm device comprises a sensor configured to detect the location of the magnet within the suction chamber, and a notification mechanism configured to generate an alert according to the location of the magnet. The alarm device may be configured to be electrically activated when retaining the suction device. The suction device may further comprise a conductive element along an outer surface and the alarm device comprises two or more connectors, wherein the conductive element is configured to provide an electrical conduit between the two or more connectors to electrically activate the alarm device. The alarm device may further comprise a tactile power switch configured to be pressed when the alarm device retains the suction device. The suction device may further comprise a fluid absorption material retained by a carrier within the suction chamber. The fluid absorption material may be bonded to an outer surface of the carrier. The carrier may comprise a pouch configured to releasably retain the fluid absorption material. The suction device may further comprise a screen configured to sequester the expandable fluid absorbent material in a selected region of the suction chamber. The expandable fluid absorbent material may be sequestered in the selected region of the suction chamber that is independent of suction device orientation. The suction device may further comprise a screen located between the carrier and the distal portion of the suction chamber. The screen may be adhesively attached to the suction chamber, and/or to the carrier. The suction device may have a charged configuration and a depleted configuration, wherein in the charged configuration, the magnet is not detectable by the sensor and in the depleted configuration, the magnet is detectable by the sensor. The alarm device may be configured to detect the configuration of the suction device regardless of the orientation of the suction device as it is retained within the alarm device. The sensor may comprise a first reed switch at a first location and a second reed switch at a second location separate from the first location, and where the alarm device retains the suction device such that in the charged configuration, the magnet may be located between the first and second locations and not detectable by either reed switch, and in the depleted configuration, the magnet is detectable by at least one reed switch. The first and second locations may define a first line with a first midpoint, wherein the travel path of the magnet from charged to depleted configurations define a second line with a second midpoint, and wherein the first and second midpoints are offset from each other. The distance of the magnet to the nearest reed switch may be less in the depleted configuration than in the charged configuration. The suction device may be retained within the alarm device in two orientations, or in four orientations. The second orientation may be the first orientation rotated 180 degrees around a transverse axis of the suction device, or rotated 180 degrees around a longitudinal axis of the suction device. The reduced pressure therapy system may further comprise a reed switch at a proximal location of the alarm device, where the alarm device retains the suction device such that in the charged configuration, the magnet is not detectable by the reed switch, and in the depleted configuration, the magnet is detectable by the reed switch.

In another example, a reduced pressure therapy system is provided, comprising a suction device comprising a suction chamber with an inlet opening and a slidable seal therein, a expandable fluid absorbent material located within the suction chamber, and a screen configured to block displacement of the expandable fluid absorbent material out of the suction device. The screen may be located within the suction chamber. The expandable fluid absorbent material, prior to any fluid absorption, may have a fixed location in the suction chamber that is independent of suction device orientation. The expandable fluid absorbent material may be retained by a carrier structure, and may be bonded to a surface of the carrier structure, but may be releasably contained within the carrier structure. The carrier structure may comprise a permeable pouch. The red permeable pouch comprises two permeable layers sealed together.

In one example, a device for reduced pressure therapy, comprising a suction chamber with a longitudinal axis and a radial axis perpendicular to the longitudinal axis, a seal assembly located within the suction chamber, the seal assembly comprising a seal coupled to a seal mount, wherein the seal and seal mount are movable with respect to each other, and wherein the seal assembly is configured to slide along the longitudinal axis of the suction chamber. The seal may comprise a distal flange and a proximal flange, wherein the distal and proximal flanges are deflectable. The seal may further comprise a lumen with a proximal aperture, and a distal ledge, and wherein the seal mount comprises a protruding edge configured to engage the ledge. The seal and the seal mount may be coupled such that a portion of an inner wall of the lumen and the seal mount are separated by a gap. The protruding edge of the seal mount may not contact the lumen ledge when the seal assembly slides distally and wherein the protruding edge contacts the lumen ledge when the seal assembly slides proximally. The proximal flange of the seal is capable of greater radial compression than the distal flange. The side walls of the seal may be radially compressible, and/or may be configured to radially deflect when the proximal flanges are deflected. The device may further comprise a lubricant located along the inner walls of the suction chamber, which may be flowable. The lubricant may be characterized by a viscosity of greater than 1,000,000 cP, or 1,500,000 cP. The lubricant may comprise at least one silicone, and/or may comprise at least one member from the group consisting of fluorosilicone, dimethylsilicone, perfluoropolyether, mineral spirits, synthetic oils, and polyxylene. At least a portion of the seal assembly may be made of dimethylsilicone and lubricant comprises fluorosilicone and dimethylsilicone, in an amount wherein the viscosity of the lubricant is at least 1,500,000 cP. The lubricant may comprise 20 Mol % fluorosilicone fluid and 80 Mol % dimethylsilicone fluid. The lubricant may be substantially non-reactive with at least the surfaces the lubricant is in contact with, wherein the surfaces comprise at least the inner walls of the chamber and at least a portion of the seal assembly. The lubricant may be in simultaneous contact with at least a portion of the seal assembly and the inner surface of the suction chamber.

In another example, a method of treating a patient is disclosed, comprising providing negative pressure to a treatment site using a suction device comprising a suction chamber having a distal and proximal portion, a sliding seal assembly within the suction chamber, and a constant force spring attached to the sliding seal assembly and configured to move the sliding seal assembly across the suction chamber, wherein the distal portion of the chamber has a first cross-sectional area and the proximal portion of the chamber has a second cross-sectional area that is greater than the first cross-sectional area. The sliding seal assembly may comprise a seal coupled to a seal mount, wherein the seal and seal mount are movable with respect to each other as the sliding seal assembly moves between the distal and proximal portions. The suction device may further comprise a lubricant that is simultaneously in contact with at least a portion of the sliding seal assembly and an inner wall of the suction chamber.

In still another example, a method of treating a patient is disclosed, comprising providing suction to a treatment site using a suction device, and absorbing fluid from a treatment site using a fluid absorbent material, wherein the fluid absorbent, prior to fluid absorption, has a fixed location within the suction device. The method may further comprise blocking expulsion of the fluid absorbent material using a screen located within the suction device. The suction device may comprise a suction-generating chamber with a sliding seal, and wherein the fluid absorbent material and the screen are located within the suction-generating chamber.

Various embodiments herein disclose a suction device that can maintain a substantially constant pressure within a certain tolerance for pressure variations over a particular leakage or infusion rate. In particular, the suction device maintains the substantially constant pressure even during fluid or air ingress into the reduced pressure system. Furthermore, the suction device may achieve this by reducing the friction between the seal and the chamber wall. The disclosure describes suction devices that achieve narrow pressure tolerances by employing certain lubricants, spring assembly configurations, or seal designs. In addition, some embodiments are configured to provide containment of exudates from the wound that may enter the suction chamber.

In one embodiment, a suction device is configured to generate and substantially maintain a set reduced pressure for use in treating tissue of a subject, comprising a suction chamber, a ribbon spring, and a lubricant; wherein when a volume of at least air or exudate is introduced into the reduced pressure system, a plot of the reduced pressure of the system against the volume introduced into the system results in a substantially oscillating wave pattern, wherein the magnitude of the typical peak-to-peak amplitude, if any, is no greater than 20 mmHg. In some embodiments, the magnitude of the typical peak-to-peak amplitude is no greater than 10 mmHg. In some of the foregoing embodiments, the magnitude of the typical peak-to-peak amplitude is no greater than 5 mmHg. In some of the foregoing embodiments, the oscillating wave pattern is substantially a saw tooth wave or substantially flat over test conditions involving continuous constant rate infusion or leakage.

In some of the foregoing embodiments, the negative pressure generated by the suction device is reduced by less than 15 mmHg over a period of 10 hours from the time the set negative pressure is reached. In some of the foregoing embodiments, the negative pressure generated by the suction device is reduced by less than 20 mmHg over a period of at least 80 hours from the time the set negative pressure is reached.

These changes may be evaluated, for example, under test conditions involving a constant infusion or leakage rate of a liquid or gas, up to a certain volume. In one instance, the maximum variations occur during an infusion rate of up to 1 cc/hr, 2 cc/hr, 3 cc/hr, 4 cc/hr, 5 cc/hr, 6 cc/hr, 7 cc/hr, 8 cc/hr, 9 cc/hr 10 cc/hr, or 15 cc/hr or 20 cc/hr, up to a volume of 10 cc, 20 cc, 30 cc, 40 cc, 50 cc, 60 cc, 70 cc, 80 cc, 90 cc, 100 cc, 150 cc, 200 cc, 250 cc or 300 cc, for example. In some of the foregoing embodiments, a volume of at least a gas or liquid introduced into the suction chamber at a rate of 3 cc/hour for at least a duration of 16 hours. In a further embodiment, the average pressure in the suction chamber over the duration of time is 80±5 mmHg. In some of the foregoing embodiments, the temperature of the suction device varies by no more than 5° C. during test conditions.

In some of the foregoing embodiments, the reduced pressure generating assembly comprises a.) a suction chamber, wherein the suction chamber has a longitudinal axis and an inner surface; b.) a seal assembly comprising a sliding seal coupled to a seal mount, wherein the seal assembly is configured to slide in the suction chamber along the longitudinal axis; and c.) a lubricant, wherein the lubricant is in simultaneous contact with at least a portion of the sliding seal and the inner surface of the suction chamber. In some embodiments, the lubricant is characterized by a viscosity of greater than 1,000,000 cP.

In some of the foregoing embodiments, the lubricant comprises at least one silicone. In specific embodiments, the lubricant comprises at least one member from the group consisting of fluorosilicone, dimethylsilicone, perfluoropolyether, mineral spirits, synthetic oils, and polyxylene. In some of the foregoing embodiments, the lubricant comprises fluorosilicone and dimethyl silicone, in an amount wherein the viscosity of the lubricant is at least 1,500,000 cP.

In some of the foregoing embodiments, the lubricant is non-reactive with at least the surfaces the lubricant is in contact with, wherein the surfaces comprise at least the inner surface of the chamber and at least a section of the sliding seal assembly surface. In other embodiments, the lubricant composition and the seal material are selected to substantial reduce seal degradation that results in seal leaks for a minimum pre-specified period of time, which may be at least 6 months, 9 months, 12 months, 15 months, 18 months, 24 months, 30 months or 36 months or more.

In some of the foregoing embodiments, at least a portion of the sliding seal and at least a portion of the seal mount is separated by a gap. In some of the foregoing embodiments, the gap is configured to provide a space for the sliding seal to occupy when it is compressed by the inner surface of the suction chamber. The portion of the sliding seal may be a radially inward facing surface and the portion of the seal mount may be a radially outwardly facing surface, and the radially inward facing surface of the sliding seal may be configured to resiliently deflect inward toward, and even contact, the radially outward facing surface of the seal mount. The radially inward facing surface of the sliding seal may also be a radially inward facing surface with the smallest radial location compared to other radially inward facing surfaces of the sliding seal. The radially outward facing surface of the seal mount may also have the smallest radial location compared to other radially outward facing surfaces of the seal mount.

In some of the foregoing embodiments, at least a portion of the sliding seal has an inner and outer surface, wherein at least a portion of the outer surface of the sliding seal is in contact with at least the inner surface of the suction chamber and the inner surface of the sliding seal does not contact with a solid surface when the sliding seal travels along the longitudinal axis of the chamber. In some of the foregoing embodiments, the sliding seal is comprises a material selected from an elastomer compatible with the lubricant.

In another embodiment herein discloses a suction device for use in treating tissue of a subject, wherein the device is configured to generate and substantially maintain a set negative pressure of at least 50 mmHg, comprising at least two ribbon springs coupled to the sliding seal assembly, wherein the ribbon springs are configured to unwind in opposite direction relative to each other, and the springs are of different lengths relative to each other.

Various embodiments herein disclose a suction device for use in treating tissue of a subject, wherein the device is configured to generate and substantially maintain a set negative pressure of at least 50 mmHg, comprising a.) at least one ribbon spring comprising an interior end, and an exterior end; and b.) a sliding seal assembly coupled to the exterior end of the ribbon spring, wherein the sliding seal assembly comprises a seal, wherein the uncoiling of the spring permits a travel distance of the seal along the longitudinal axis of the interior of the suction chamber, and the spring has a diameter such that travel distance of the seal can be covered in less than one rotation of the spring; wherein the spring is configured such that during the coiling of the ribbon spring, the interior end of the ribbon spring does not transition from non load-bearing to load-bearing at any point.

Various embodiments herein disclose a suction device for use in treating tissue of a subject, wherein the device is configured to generate and substantially maintain a set negative pressure of at least 50 mmHg, comprising a.) at least one ribbon spring comprising an interior end and a top surface; and b.) a bushing, wherein the exterior surface of the bushing is configured with an indentation; wherein the interior end of the ribbon spring is mounted on the bushing to form a spring-bushing assembly, and the interior spring end is positioned in the indentation of the bushing, such that the top surface of the spring end is approximately flush with the exterior surface of the bushing adjacent to the indentation. In a particular embodiment, the depth of the indentation in the bushing is approximately the thickness of the spring end. In a more specific embodiment, the depth of the indentation is 6/1000 to 7/1000 of an inch.

Various embodiments herein disclose a suction device for use in treating tissue of a subject, wherein the device is configured to generate and substantially maintain a set negative pressure of at least 50 mmHg, comprising a suction chamber configured with a bio-hazard containment assembly, wherein the bio-hazard containment assembly comprises a superabsorbent material. In some embodiments, the bio-hazard containment assembly has a total volume of less than 4 cc prior to contact with a liquid. In some of the foregoing embodiments, the superabsorbent material absorbs an amount of liquid at least 10 times its weight. In some of the foregoing embodiments, the superabsorbent material is selected from at least a natural, synthetic, or modified natural polymers. In some of the foregoing embodiments, the superabsorbent material is selected from a silica gel or cross-linked polymers. In some of the foregoing embodiments, the amount of superabsorbent material is less than 2.5 g. In some of the foregoing embodiments, the superabsorbent material is contained in a liquid permeable layer. In some of the foregoing embodiments, the liquid permeable layer is selected from at least one of the members of the group consisting of polypropylene, nylon, rayon, and cellulose.

Various embodiments herein disclose a dressing for a wound bed, comprising a pressure sensor and a communication channel having a first and second end, wherein the first end is connected to the pressure sensor and the second end is positioned on or near the wound bed, wherein the dressing is configured such that the pressure sensor is in fluid communication with the wound bed. In some of the foregoing embodiments, the channel is a flexible catheter. In specific embodiments, the second end of the catheter comprises perforations. In some of the foregoing embodiments, the pressure sensor comprises a bellow. In some of the foregoing embodiments, the pressure sensor comprises a microelectronic pressure sensing device.

Disclosed herein is a reduced pressure therapy device that may comprise a suction device with a suction chamber and a slidable seal within the suction chamber, a magnet coupled to the slidable seal, and an alarm device comprising a sensor that is configured to detect the location of a magnet within the suction chamber. The alarm device may be configured to retain the suction device, and may also comprise a notification mechanism that is configured to generate an alert based on the location of the magnet. In some variations, the alarm device is configured to be electrically activated when retaining the suction device. The alarm device may comprise a conductive element along an outer surface and the alarm device comprises two or more connectors. The conductive element may be configured to provide an electrical conduit between the two or more connectors to electrically activate the alarm device. In some variations, the alarm device may comprise a tactile power switch configured to be pressed when the alarm device retains the suction device.

Optionally, a suction device may comprise a fluid absorption material retained by a carrier within the suction chamber. In some variations, the fluid absorption material may be bonded to an outer surface of the carrier. Alternatively or additionally, the carrier may comprise a pouch configured to releasably retain the fluid absorption material. A suction device may also comprise a screen located between the carrier and the distal portion of the suction chamber. In some variations, the screen may be adhesively attached to the suction chamber or may be adhesively attached to the carrier.

Disclosed herein is a reduced pressure therapy system that may comprise a suction device comprising a suction chamber with an inlet opening and a slidable seal within the suction chamber. The reduced pressure therapy system may also comprise an expandable fluid absorbent material located within the suction chamber and a screen configured to block displacement of the expandable fluid absorbent material out of the suction device. The screen may also be configured to sequester the expandable fluid absorbent material in a selected region of the suction chamber. The screen may be located within the suction chamber. In some variations, the expandable fluid absorbent material, prior to any fluid absorption, may have a fixed location in the suction chamber that is independent of suction device orientation. In some variations, the expandable fluid absorbent material may be retained by a carrier structure. The carrier structure may be retained at a selected region in the suction chamber. For example, the expandable fluid absorbent material may be bonded to the carrier structure, and in some cases, may be bonded on a surface of the carrier structure. Additionally or alternatively, the expandable fluid absorbent material may be releasably contained within the carrier structure. The expandable fluid absorbent material may be woven into the carrier structure. In some variations, the carrier structure comprises a permeable pouch. One variation of a permeable pouch may comprise two permeable layers sealed together. Optionally, the expandable fluid absorbent material may comprise one or more disinfecting agents.

In some variations of a suction device fluid retention assembly, the carrier structure may comprise an aperture therethrough, and may be located within the suction chamber such that the aperture is aligned with the inlet opening of the suction chamber. The screen of the fluid retention assembly may be interposed between the inlet opening and the carrier structure.

In some variations of a suction device fluid retention assembly, the carrier structure may comprise a permeable pouch. The permeable pouch may comprise two permeable layers sealed together, and may optionally be sealed together along the perimeter of each of the layers. The permeable pouch may be attached to the screen of the fluid retention assembly. In some variations, the expandable fluid absorbent material may be releasably contained within the carrier structure.

Methods of treating a patient using reduced pressure therapy are also described herein. One variation of a method for treating a patient may comprise providing suction to a treatment site using a suction device and absorbing fluid from a treatment site using a fluid absorbent material. Prior to fluid absorption, the fluid absorbent material may have a fixed location within the suction device. Some methods may further comprise blocking expulsion of the fluid absorbent material using a screen located within the suction device. In some variations, the method may use a suction device comprising a suction-generating chamber with a sliding seal, where the fluid absorbent material and the screen are located within the suction-generating chamber.

One variation of a method for treating a patient may comprise providing suction to a treatment site using a suction device comprising a suction-generating chamber, absorbing fluid from a treatment site using a fluid absorbent material, and blocking expulsion of the fluid absorbent material using a screen located within the suction-generating chamber. In some variations, the fluid absorbent material may have a fixed location within the suction-generating chamber.

Provided herein is a reduced pressure therapy system comprising a suction device comprising a suction chamber, a expandable fluid absorbent material located within the suction chamber; and a screen configured to sequester the expandable fluid absorbent material in a selected region of the suction chamber. The suction chamber may comprise an inlet opening at a distal portion of the chamber and a slidable seal therein. In some variations, the expandable fluid absorbent material may be sequestered in the selected region of the suction chamber that is independent of suction device orientation. For example, the screen may sequester the expandable fluid absorbent material at the distal portion of the suction chamber. Alternatively or additionally, the expandable fluid absorbent material may be retained by a carrier structure, wherein the carrier structure is retained at the selected region in the suction chamber. In some variations, the expandable fluid absorbent material may be bonded to the carrier structure, such as to a surface of the carrier structure. The expandable fluid absorbent material may alternatively or additionally be woven into the carrier structure. Optionally, the expandable fluid absorbent material may comprise one or more disinfecting agents.

In some variations, the carrier structure may comprise an aperture therethrough, and the aperture may be aligned with the inlet opening of the suction chamber. The screen may be interposed between the inlet opening and the carrier structure. In some variations, the expandable fluid absorbent material may be releasably contained within the carrier structure. The carrier structure may comprise a permeable pouch, and in some variations, the permeable pouch may be attached to the screen. The permeable pouch may comprise two permeable layers sealed together. The two permeable layers may be sealed together along the perimeter of each of the layers.

Another variation of a reduced pressure therapy system may comprise a chamber with a movable magnet and a magnet sensitive mechanism configured to detect a magnetic field of the movable magnet. The chamber may be a vacuum-generating chamber configured with a fixed wall and a movable wall. In some variations, the movable wall may comprise a slidable seal, while in other variations, the vacuum-generating chamber may comprise a bellows mechanism, where the magnet is located on the movable wall of the bellows. The chamber may also be a fluid trap chamber, and in some variations, may comprise a float, where the float is coupled to the movable magnet. In some variations of a reduced pressure therapy system, the magnet sensitive mechanism may comprise one or more reed switch, where the reed switch may normally have an open state. A plurality of reed switches may be provided along a movement axis of the movable magnet. Alternatively, the reduced pressure therapy system may comprise a Hall effect sensor. The magnet sensitive mechanism may be coupled to a clip configured to attach to the vacuum system. In certain variations, the reduced pressure therapy system may further comprise an indicator mechanism connected to the magnet sensitive mechanism and configured to provide at least one signal indicated of a position of the movable magnet. The at least one signal may be a visual, auditory, or tactile signal.

Another variation of a reduced pressure therapy system may comprise a non-electrically powered vacuum-generating chamber configured with a position element located on a movable region of the vacuum-generating chamber, and a circuit comprising a first state when the position element is at a first location and a second state when the position element is at a second location. The circuit may be configured to be detachably attachable to the vacuum-generating chamber. The circuit may also comprise an electrical power source and a signaling mechanism, where the signaling mechanism is configured to generate at least one signal that is an audio, visual, and/or tactile signal. In some variations, the signaling mechanism may be configured to generate a wireless signal, or may be configured to transmit an alarm signal to a remote monitoring display.

The position element of a reduced pressure therapy system may comprise an electrical pathway having a first end located about a first surface of the chamber and a second end located about a second surface of the chamber, and the first stat of the circuit is an open circuit and the second state of the circuit is a closed circuit state. In some variations, the first surface of the chamber may be an outer surface of the chamber, and in some cases, the chamber may be a bellows chamber. In other variations, the first surface of the chamber may be an inner surface of the chamber, and in some cases, the movable region of the vacuum-generating chamber may be a slidable sealing wall. The position element of a reduced pressure therapy system may be a magnet. In some variations, the circuit may be a Hall effect sensor circuit and/or a reed switch circuit.

Also described below are methods for treating a patient using a reduced pressure therapy system. One example of a method for treating a patient may comprise treating a patient with a reduced pressure therapy system comprising a non-electrically powered vacuum mechanism and an electrically powered alarm system, wherein the electrically powered alarm system comprises a magnetic sensitive mechanism, and using a magnetic sensitive mechanism to indicate a state of the vacuum mechanism. The magnetic sensitive mechanism may comprise a reed switch, where the reed switch has a sensitivity of about 10 to about 60 Ampere-Turns. The reed switch may be in a normally open state. The method may also comprise detaching the vacuum mechanism from the alarm system and attaching a new vacuum mechanism to the same alarm system. The method may also comprise activating the new vacuum mechanism.

Another variation of a reduced pressure therapy device may comprise a suction device with a suction chamber and a slidable seal within the suction chamber, where the slidable seal is oriented transversely to the longitudinal axis of the suction chamber, a magnet coupled to the slidable seal transversely to the longitudinal axis of the suction chamber, and an alarm device comprising one or more sensors that may be configured to detect the location of a magnet within the suction chamber. The alarm device may be configured to retain the suction device along the longitudinal axis. The alarm device may comprise a first sensor at a distal portion of the alarm device, and a second sensor at a proximal portion of the alarm device, where the first and second sensors are configured to detect the location of the magnet. Additionally, the alarm device may comprise a notification mechanism configured to generate an alert when the magnet is aligned with the second sensor.

Another variation of a reduced pressure therapy device with an alarm system using a magnetic sensor mechanism may comprise a suction device, the suction device comprising a suction chamber, a slidable seal within the suction chamber, and a central shaft coupled to the slidable seal, a magnet coupled along the longitudinal axis of the central shaft, and an alarm device configured to retain the suction device. The alarm device may comprise a sensor configured to detect the position of the magnet within the suction chamber, and a notification mechanism configured to generate an alert according to the position of the magnet.

Some variations of a reduced pressure therapy device with an alarm system may comprise a suction device comprising a suction chamber with a longitudinal axis from a proximal portion to a distal portion, a slidable seal disposed within the suction chamber transverse to the longitudinal axis, and a shaft fixedly attached to the slidable seal, wherein the shaft is oriented along the longitudinal axis, a magnet coupled to the shaft along the longitudinal axis, and an alarm device configured to retain the suction device. The alarm device may comprise a sensor configured to detect the position of the magnet within the suction chamber, and a notification mechanism configured to generate an alert according to the position of the magnet.

Certain variations of reduced pressure therapy devices with an alarm system may use an electrical switch mechanism. For example, a reduced pressure therapy device may comprise a suction device comprising a suction chamber and a slidable seal within the suction chamber, an electrical switch coupled to the slidable seal, and an alarm device configured to retain the suction device. The attachment feature may comprise a notification mechanism configured to generate an alert when aligned with the electrical switch.

Another variation of a reduced pressure therapy device may comprise a suction device comprising a suction chamber and a slidable seal transversely disposed within the suction chamber, an electrical current conduit coupled to the slidable seal, wherein the conduit extends across the entire transverse width of the slidable seal, and an alarm device configured to retain the suction device. The alarm device may comprise a notification mechanism with a first electrical contact and a second electrical contact opposite the first electrical contact, wherein the notification mechanism is configured to generate an alert when the first and second electrical contacts are connected by the current conduit.

Certain variations of reduced pressure therapy devices may comprise a suction device comprising a suction chamber and a slidable seal within the suction chamber, a magnet coupled to the slidable seal, and an alarm device configured to retain the suction device. The alarm device may comprise a magnetic field sensitive switch configured to activate a notification mechanism to generate an alert according to the location of the magnet. In some variations, the magnetic field sensitive switch may be a reed switch. Alternatively or additionally, the magnetic field sensitive switch may comprise a sensor to detect the location of the magnet within the suction chamber.

Other variations of reduced pressure therapy devices may comprise a suction device comprising a suction chamber and a slidable seal transversely disposed within the suction chamber, a magnet coupled to the slidable seal, and an attachment feature configured to retain the suction device along the longitudinal axis. The slidable seal may be oriented transversely to the longitudinal axis of the suction chamber. The attachment feature may comprise a reed switch at a proximal portion, where the reed switch is configured to be closed when the magnet is at or near the proximal portion. The attachment feature may also comprise a notification mechanism configured to generate an alert when the reed switch is closed.

Disclosed herein is another variation of a reduced pressure therapy device that may comprise a suction device with a suction chamber and a slidable seal within the suction chamber, a magnet coupled to the slidable seal, and an alarm device comprising a sensor that is configured to detect the location of a magnet within the suction chamber. The alarm device may be configured to retain the suction device, and may also comprise a notification mechanism that is configured to generate an alert based on the location of the magnet. The alarm device may optionally comprise a tactile power switch configured to be pressed with the alarm device retains a suction device therein. The suction device may have a charged configuration and a depleted configuration. In the charged configuration, the magnet may not be detectable by the sensor, while in the depleted configuration, the magnet may be detectable by the sensor. In some variations, the alarm device is configured to detect the configuration of the suction device regardless of the orientation of the suction device within the alarm device. In some variations, the sensor may comprise a first reed switch at a first location and a second reed switch at a second location separate from the first location. The alarm device may retain the suction device such that in the charged configuration, the magnet is located between the first and second locations and not detectable by either reed switch, and in the depleted configuration, the magnet is detectable by at least one reed switch. Optionally, the first and second locations may define a first line with a first midpoint, wherein the travel path of the magnet from charged to depleted configurations define a second line with a second midpoint. The first and second midpoints are offset from each other. In some variations, the distance of the magnet to the nearest reed switch is less in the depleted configuration than in the charged configuration. The suction device may be retained in the alarm device in two or more orientations, e.g., four orientations. In one embodiment, the suction device may be retained within the alarm device in a first orientation and a second orientation, where the second orientation is the first orientation rotated 180 degrees around a transverse and/or longitudinal axis of the suction device. In another variation of a reduced pressure therapy device, the alarm device may comprise a reed switch at a proximal location of the alarm device, where the alarm device retains the suction device such that in the charged configuration, the magnet is not detectable by the reed switch, and in the depleted configuration, the magnet is detectable by the reed switch.

Disclosed herein is another variation of a reduced pressure therapy device that may comprise a suction chamber with a slidable seal therein, a magnetic element or magnet coupled to the slidable seal, a first alignment protrusion at a distal portion, and a second alignment protrusion at a proximal portion. The suction device may have a charged configuration and a depleted configuration, wherein the distance of the magnet to the first alignment protrusion in the charged configuration is greater than the distance of the magnet to the second alignment protrusion in the depleted configuration. In another variation of a reduced pressure therapy device, the distance of the magnet to the distal end of the suction chamber in the charged configuration is greater than the distance of the magnet to the proximal end of the suction chamber in the depleted configuration.

BRIEF DESCRIPTION OF THE DRAWINGS

A better understanding of various features and advantages of the embodiments described herein may be obtained by reference to the following detailed description that sets forth illustrative examples and the accompanying drawings of which:

FIGS. 7A and 7B are schematic depictions of a reed sensor in an open and a closed configuration, respectively.

FIG. 9 is a block diagram of one variation of an alarm system that may be used with reduced pressure therapy devices.

FIG. 10A depicts a block diagram representation of another variation of an alarm system that may be used with reduced pressure therapy devices. FIG. 10B depicts one variation of an orientation circuit; FIG. 10C depicts one variation of a sensor circuit; FIG. 10D depicts one variation of an amplifier circuit.

FIG. 14B depicts a first orientation of the suction device of FIG. 14A; FIG. 14C depicts a second orientation of the suction device of FIG. 14A.

FIGS. 15A and 15B are perspective views of a variation of an alarm device that may be used with a suction device.

FIG. 17A is a perspective view of another variation of a fluid retention assembly comprising an absorbent pad and filter; FIG. 17B is a side view of the fluid retention assembly of FIG. 17A; FIG. 17C is top view of the filter of the fluid retention assembly of FIG. 17A.

FIG. 18A is a schematic depiction of a suction device with a fluid retention assembly comprising a pouch; FIG. 18B is a schematic depiction of a suction device with a fluid retention assembly comprising a mesh; FIG. 18C is a schematic depiction of a suction device with a fluid retention assembly comprising an absorbent pad; FIG. 18D is a schematic depiction of a suction device with a fluid retention assembly comprising a pouch and a mesh; FIG. 18E is a schematic depiction of a suction device with a fluid retention assembly comprising an absorbent pad and a mesh.

FIG. 19A is a schematic depiction of one orientation in which a suction device may be retained in an alarm device; FIGS. 19B and 19C are schematic depictions of the relative positioning between a suction device and an alarm device; FIG. 19D is a example of an alternate orientation in which a suction device may be retained in an alarm device.

FIGS. 28A and 28B are posterior and anterior component views of one embodiment of a spring assembly, respectively.

FIGS. 29A and 29B are posterior and anterior perspective component views, respectively, of one embodiment of a sliding seal assembly and spring assembly.

DETAILED DESCRIPTION

While embodiments have been described and presented herein, those embodiments are provided by way of example only. Variations, changes and substitutions may be made without departing from the invention. It should be noted that various alternatives to the exemplary embodiments described herein may be employed in practicing the invention. For all of the embodiments described herein, the steps of the methods need not to be performed sequentially.

Various types of reduced pressure therapy systems may be used depending on the severity of the tissue wound and the activity level of the patient. In some cases, reduced pressure tissue therapy systems may extract tissue exudates, e.g., wound exudates and interstitial fluids, while providing reduced pressure therapy. Some reduced pressure tissue therapy systems comprise a suction device with an open pressure supply, e.g., continuous electric pump. These systems typically are noisy, and their bulkiness and weight often restricts the mobility of a patient. Patients that desire greater mobility may use a reduced pressure tissue therapy system comprising a wearable suction device that does not rely on power from an electrical source, e.g., non-electrically powered.

Figure 1A:
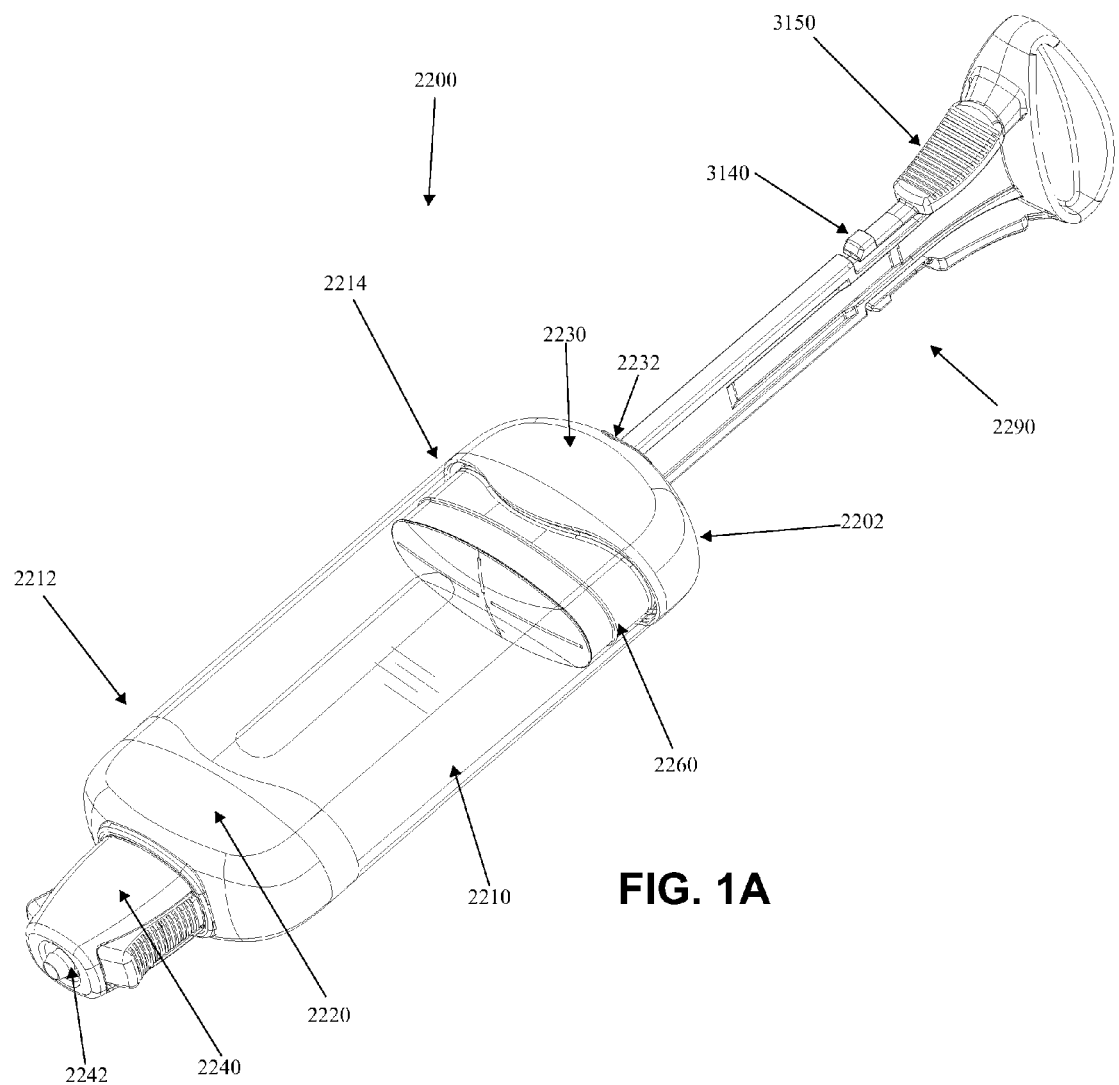
FIGS. 1A and 1B are perspective views of a variation of a reduced pressure therapy device in a mechanically uncharged and charged configuration, respectively.

FIG. 1A is a perspective view of one example of a wearable suction device 2200 that may be used in reduced pressure tissue therapy. As depicted there, the suction device 2200 may comprise a suction chamber 2210, a suction generating mechanism (not shown), and a sliding seal assembly 2260 that is movably retained in the suction chamber 2210. One variation of a suction generating mechanism of the suction device 2200 is depicted in FIGS. 1C and 1D, and may comprise one or more springs 2950, and the proximal side of the sliding seal assembly 2260 may be coupled to one or more springs 2950. The springs 2950 may be constant force springs, or any other type of springs that may be used to apply a force on the sliding seal assembly 2260 in a proximal direction. The suction device 2200 may also comprise a housing 2202 that may retain the suction chamber 2210. The housing 2202 may comprise a proximal cap 2230 with proximal opening 2232 and a distal cap 2220 with a distal port 2242. In some variations, the distal cap 2220 may comprise a fitting housing 2240 configured for interfacing with a tube (e.g., a tube connected to a dressing) such that the tube is in fluid connection with the suction chamber. In some variations, the fitting housing 2240 may be detachable from the distal cap 2220. Negative pressure generated in the suction chamber 2210 may be conveyed to a tissue site through a distal aperture in the suction chamber leading to the distal port 2242 of the fitting housing 2240. Tubing connected to the distal port 2242 may allow the negative pressure to be directed to the tissue site and/or dressing. The suction device may also comprise an activation tool 2290 that may be inserted through the proximal opening 2232, where the activation tool 2290 is configured to mechanically charge the suction device 2200, for example, by urging the sliding seal assembly to certain positions in the suction chamber. In some variations, the activation tool 2290 may be releasably snap-locked in the proximal opening 2232, which may help secure the sliding sealing assembly 2260 in a certain position within the suction chamber 2210. For example, the activation tool 2290 may comprise release buttons 3150 with 3140 latches such that when the release buttons 3150 are released, the 3140 latches may be engaged in one or more grooves in the proximal cap 2230 at or near the proximal opening 2232, thereby retaining the activation tool in the suction chamber. When the release buttons 3150 are pressed (e.g., squeezed), the 3140 latches may disengage from the grooves and allow the activation tool 2290 to be withdrawn from the proximal opening 2232. FIG. 1A depicts the configuration of the suction device 2200 before it is activated, where the sliding seal assembly 2260 is located at a proximal portion 2214 of the suction chamber, and where the activation tool 2290 is inserted into the proximal opening 2232 of the proximal cap 2230 but has not yet displaced the sliding seal assembly 2260. The suction chamber 2210 may comprise a translucent or optically clear material, or an opaque material with or without a translucent or optically clear window.

Figure 1B:
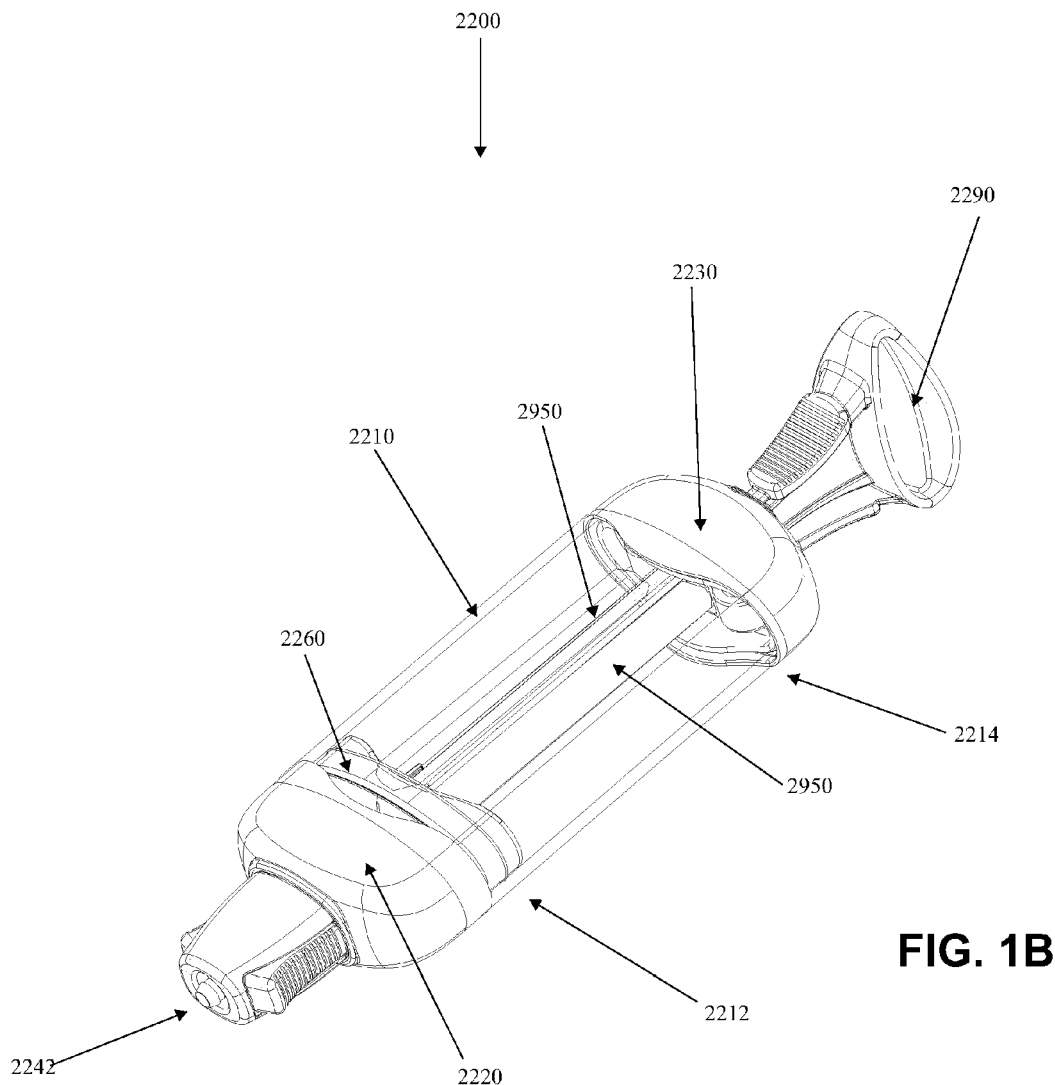
Figure 1C:
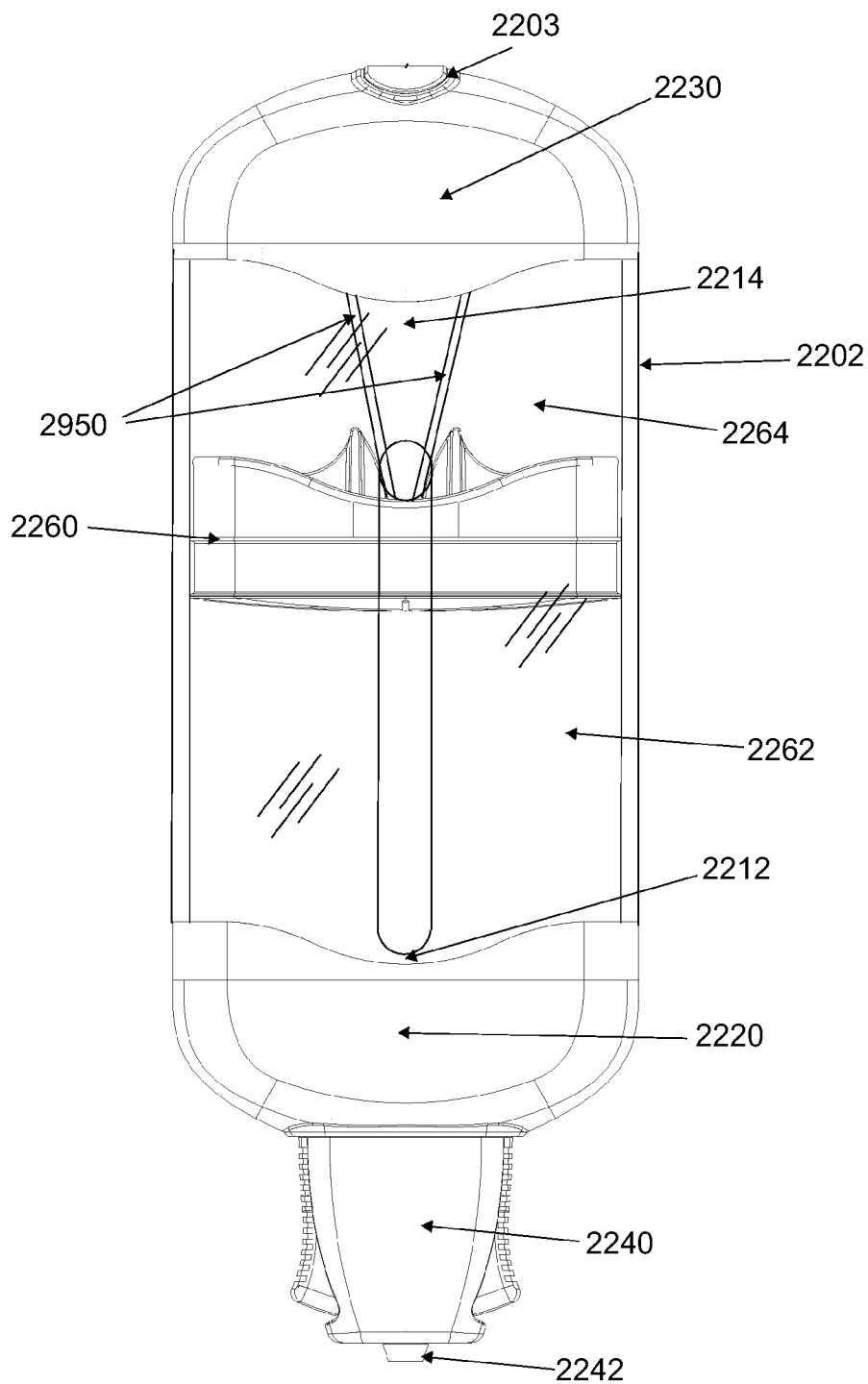
FIGS. 1C and 1D are superior and side elevational views of the device in FIGS. 1A and 1B in an activated and partially depleted state.
Figure 1D:
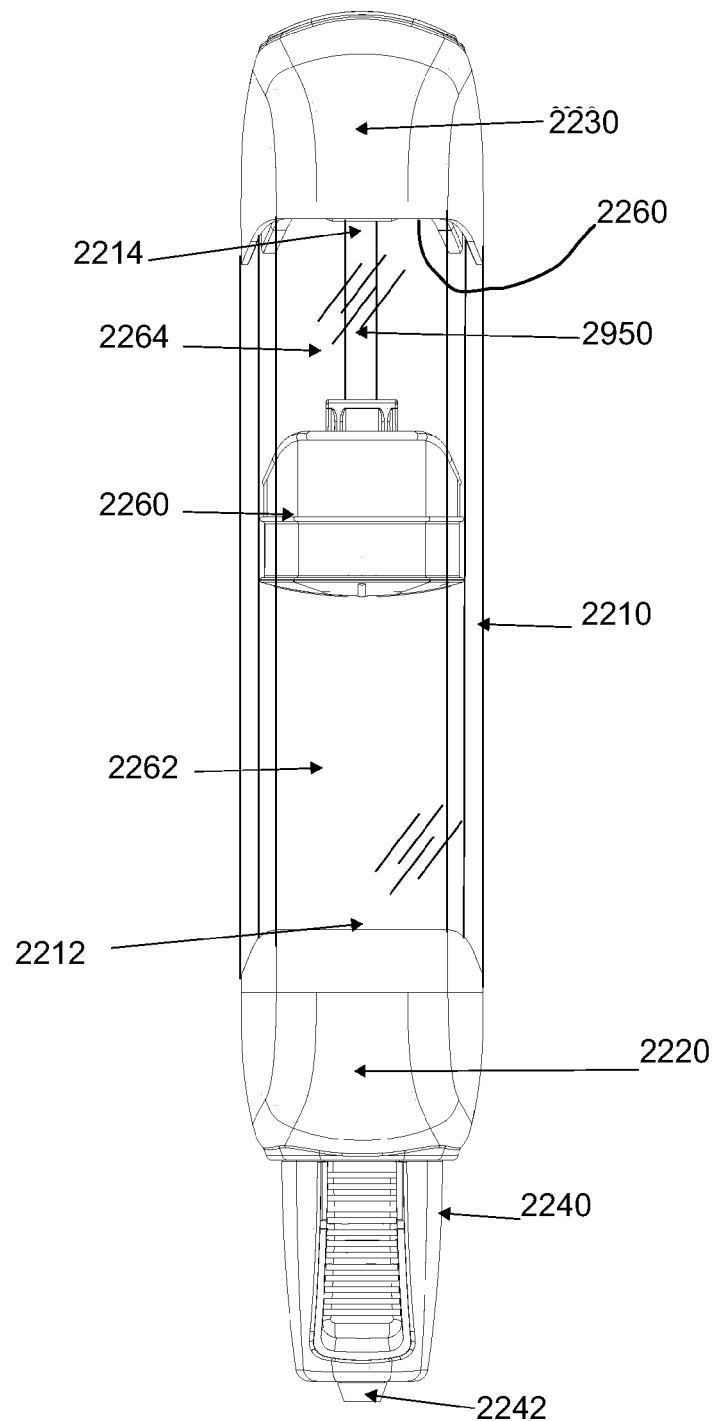

FIG. 1B depicts the suction device 2200 in a mechanically charged configuration. To mechanically charge the suction device 2200, the activation tool 2290 may be pushed through the proximal opening 2232 to extend or distally displace the sliding seal assembly 2260 from the proximal portion 2214 of the suction chamber 2210 to a distal portion 106 of the suction chamber 2210. Depending upon the particular configuration, the activation tool 2290 may be pushed until the sliding seal assembly 2260 contacts a wall of the distal cap 2220, until it is adjacent the distal end wall of the suction chamber 2210, until the springs 2950 are maximally extended, and/or until mechanical interference between the activation tool 2290 and the proximal cap 2230 resist further insertion. Urging the sliding seal assembly 2260 to the distal position 106 as depicted in FIG. 1B may in turn extend the springs 2950 that are attached to the proximal side of the sliding seal assembly. This may generate potential energy within the springs 2950. Other variations of wearable suction devices that may be used in a reduced pressure tissue therapy system, as well as methods of using the systems and devices, are described in U.S. patent application Ser. No. 12/372,661, filed on Feb. 17, 2009, which is hereby incorporated by reference in its entirety.

Upon removal of the activation tool 2290, the springs 2950 are able to exert a proximally directed force onto the sliding seal assembly 2260, which is capable of generating reduced pressure in the suction chamber 2210 and transmitting the reduced pressure to a sealed wound enclosure coupled to the device 2200. The reduced pressure is generated by expanding the volume of air initially located in a sealed enclosure or chamber of the device from a smaller volume of the chamber to a larger volume. Upon expansion of the air within the sealed enclosure, the density of the air molecules is decreased and the pressure within the sealed chamber is reduced to a sub-atmospheric level. As exudates and/or gaseous leakage occurs, the springs 2950 will retract the sliding seal assembly 2260, thereby maintaining the reduced pressure level within the collection chamber. In some variations, there may be a lubricant provided between the sliding seal assembly 2260 and the internal walls of the suction chamber 2210, which may help the sliding seal assembly to move smoothly and consistently across the suction chamber to generate negative pressure. As the sliding seal assembly 2260 returns to its maximum retracted state, the level of reduced pressure level will begin to decrease and may be replaced or recharged.

FIGS. 1C and 1D are superior and side elevational views of the device from FIG. 1A in an activated state and with the springs 2950 having partially expended the potential energy from the fully charged configuration. As can be seen when the sliding seal assembly 2260 is in a partially expended position, the suction chamber 2210 may be subdivided by the sliding seal assembly 2260 into a collection chamber 2262 and a working chamber 2264, where the collection chamber 2262 is the space between the sliding seal assembly 2260 and the distal end wall 2212 of the suction chamber 2210, and the working chamber 2264 is the space between the proximal end 2214 of the suction chamber 2210 and the sliding seal assembly 2260 which contain the springs 2950. When the suction device is in the charged configuration, the volume of the collection chamber may be about zero, or sometimes less than about 5 cc. In some instances, upon activation of the mechanically charged device, the collection chamber may increase in volume up to about 3%, sometimes about 5% and other times about 10% or even about 20% until the force exerted by the springs 2950 is counterbalanced by the force generated by the reduced pressure in the collection chamber 2262. In some variations, a suction device may be configured to apply a pre-determined amount of negative pressure. For example, the volume of the suction chamber and/or the spring constant of constant force springs may be selected in order to provide a pre-determined amount of pressure. Pre-determined pressure levels may range from −50 mmHg to −150 mmHg, e.g., −75 mmHg, −100 mmHg, −125 mmHg, etc.

Figure 1E:
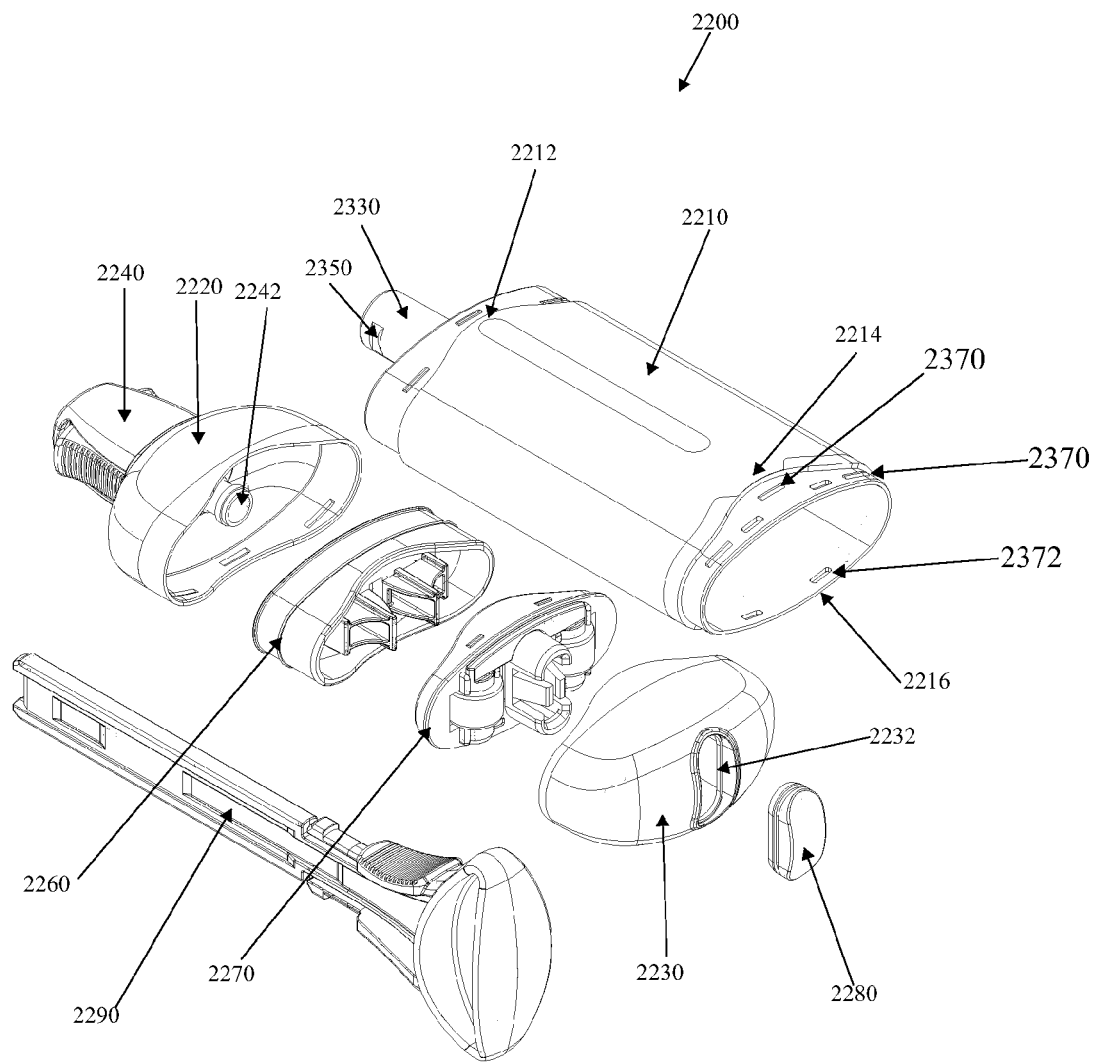
FIGS. 1E and 1F are posterior and anterior perspective component views of the embodiment from FIG. 1A.
Figure 1F:
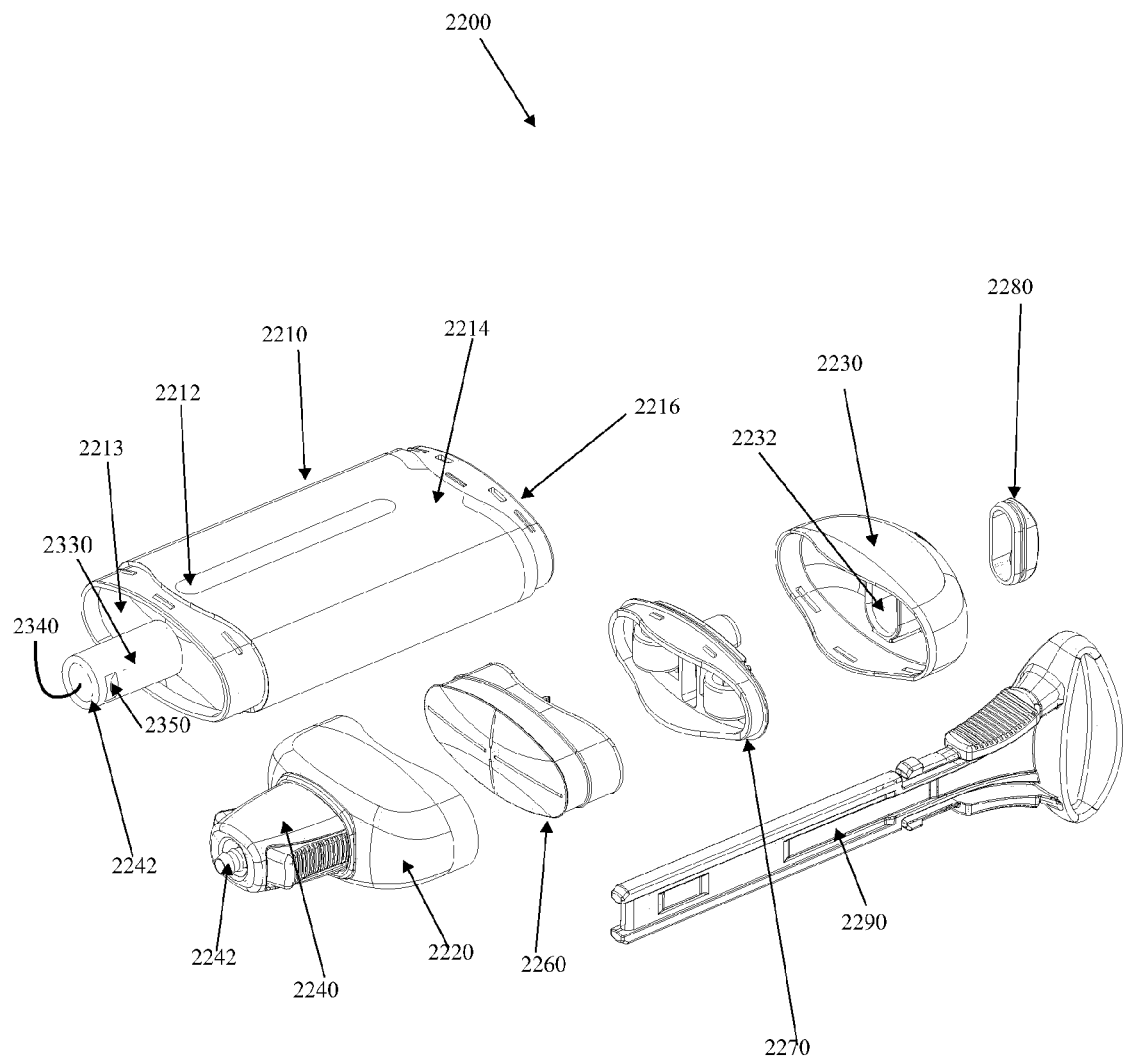

FIGS. 1E and 1F depict posterior and anterior component views of the suction device 2200. The distal cap 2220 and the proximal cap 2230 may be configured to be detachably secured to the distal end 2212 and the proximal end 2214 of the suction chamber 2210, respectively. The proximal end 2212 and/or the distal end 2214 of the suction chamber 2210 may also comprise notches 2360 and 2370, respectively, which may be configured to facilitate coupling to the proximal cap 2230 and/or distal cap 2220 of the device 2200, respectively. Notches 2372 or apertures may also be provided for attaching the spring assembly 2270 to the suction chamber 2210. A fitting housing 2240 may be coupled to the distal cap 2220, enclosing a distal port 2242 that may be configured to connect the suction chamber 2210 with another component of the therapy system (e.g., an extension tube or an attachment port on a sealant layer). The suction chamber may be fabricated from a rigid polymer adapted to maintain the external shape of the suction chamber shape under reduced pressure. In some embodiments, the entire body of the suction chamber may be transparent, thereby permitting visual inspection the quantity and quality of wound exudates contained therein. In other embodiments, the suction chamber may comprise a non-transparent body but with an inspection window.

As mentioned above, the fitting housing 2240 may be configured to removably detach from to the distal cap 2220, while in other examples, the fitting housing may be integrally formed with the distal cap 2220 or otherwise configured not to be detached once joined. A sliding seal assembly may be movably located within the suction chamber 2210. The sliding seal assembly 2260 may be coupled to a spring assembly secured to the proximal cap 2230 of the suction device 2200. In other embodiments, the spring assembly 2270 may also be secured about the proximal opening 2216 of the suction chamber 2210. An opening 2232 may be provided in the proximal cap 2230 to permit insertion of a priming or activation tool 2290 which is configured to prime the suction device 2200. Once the suction device 2200 is primed and activated, the activation tool 2290 may be removed, and the opening 2232 on the proximal cap 2230 may be closed by a proximal cap seal 2280. The proximal cap seal 2280 may be any type of seal that may prevent entry of undesired contaminants or other environmental agents (e.g. water during showering) into the suction chamber 2210. In other examples, the proximal cap seal may be attached to the proximal cap by a tether. In still other examples, the proximal cap seal may be configured with a passageway or slit and comprises a deformable material that permits insertion and/or removal of the activation tool and reseals upon removal of the activation tool. In the latter embodiments, the proximal cap seal need not be removed before priming or inserted back into the opening after removal of the activation tool.

In some embodiments, the reduced pressure therapy device comprises a non-circular suction chamber design which may provide the therapy device with a low or reduced profile. In some examples, the low profile permits placement of the reduced pressure system on the body near the wound, with or without the use of extension tubing. This ergonomic chamber design coupled with the integrated system configuration may permit discrete wearing of the devices to enhance life quality. In one particular example, the suction device comprises a variable volume chamber with an oval cross-sectional geometry that provides a substantial exudate handling capacity while also providing a low profile. In other examples, the cross-sectional shape (i.e. transverse shape to the longitudinal axis of the device) of the suction chamber may have any of a variety of other types of geometric configurations (e.g., circular, rectangular, triangular, octagonal (or other polygonal shapes), etc.). This permits improved mobility, discretion, flexibility, and/or comfort during treatment. The low-profile geometry may also streamline the workflow of using the reduced pressure therapy system by locating the suction device at or adjacent to the treatment site, rather than a remote site, and may also eliminate the use of extension tubing to maintain fluid communication between a treatment site and a separate suction device.

In some embodiments of the tissue therapy system the suction device is fabricated from a rigid polymer adapted to maintain the external shape of the suction chamber shape under reduced pressure. The suction chamber can be made of any suitable polymer such as, but not limited to polycarbonate, co-polyester, polyethylene, polypropylene, acrylic, ABS, glass, medical-grade polymers, or a combination thereof.

A suction device may be configured to provide negative pressure to a tissue region via a conduit (e.g., tubing) that is in communication with an enclosure that provides an airtight environment around the tissue region. For example, a tube may connect a suction device to a tissue cover structure or dressing comprising an occlusive cover sheet with an adhesive layer is applied over the tissue region (e.g., wound). The dressing may be able to enhance the functionality and/or usability of delivery of reduced pressure to body surfaces. In some examples, the tissue cover and/or dressing may be filled with a contact material such as gauze, foam or other porous materials, to provide cushioning and distribute the reduced pressure throughout the tissue region (e.g., wound bed). The adhesive sheet may serve as a dressing and create a substantially airtight enclosure which encompasses the tissue region. This enclosure is in fluid communication with a reduced pressure source. The reduced pressure source may comprise an electric vacuum pump, in-wall suction, or any of the suction devices described herein. The fluid communication between the vacuum source and the occlusive sheet is provided by a conduit which communicates with an opening in the occlusive sheet, or which passes through the tissue cover (e.g., through the dressing).

In one configuration of the device the tissue cover may comprise a dressing that is made of a hydrocolloid dressing having some or all of the properties mentioned above, and/or one or more breathability, moisture absorbent abilities, skin protective properties, and wound healing characteristics. This dressing may also provide for a moist wound healing environment and is an appropriate dressing for satellite wound lesions. In one embodiment, the adhesive dressing may be formulated such that it flows on application of body heat and/or pressure to the dressing surface to eliminate potential leak channels that may form during application. In other embodiments, the application of light energy may also initiate a softening phenomenon to allow the adhesive to flow more readily and fill gaps.

Figure 37:
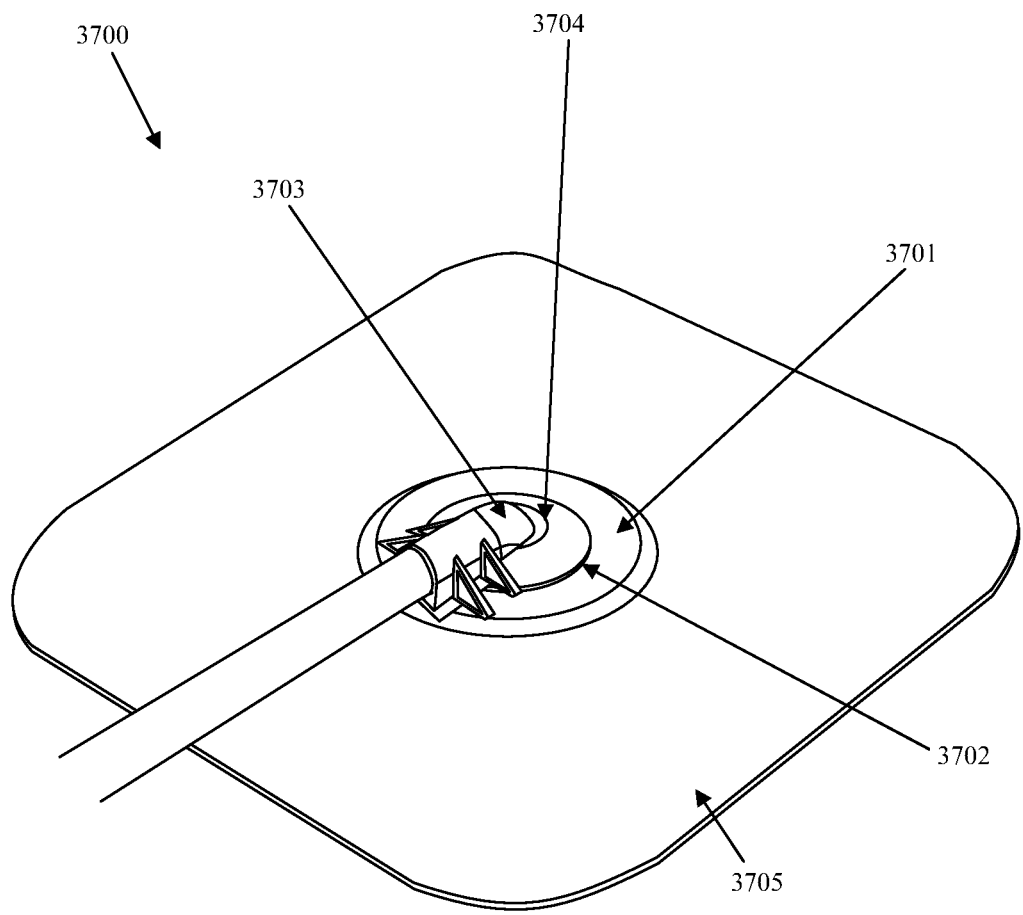
FIG. 37 depicts one variation of a tissue cover comprising a dressing that may be used with any of the suction devices described herein.

One example of a tissue cover comprising a dressing that may be used with any of the suction devices described herein as part of a reduced pressure therapy system is depicted in FIG. 37. A tissue cover 3700 may be attached to a suction device or vacuum source (not shown). The tissue cover 3700 may comprise a flexible, adhesive sheet which may be placed over a body surface. The tissue cover 3700 may further comprise release liners, carrier films or other features known in the art to facilitate application of the dressing 3700 to a treatment site. The tissue cover 3700 may also comprise a port member 3701 with an elastomeric membrane pressure indicator 3702 attached to a dressing 3705 of the tissue cover. In this example, the tubing attachment portion or connector 3703 of the port member 3701 is surrounded by a radial section 3704 of elastomeric membrane which deforms under pressure. Optionally, the tissue cover 3700 may comprise a port which allows passage of the fluid communication conduit from one side of the dressing 3705 to the other. The dressing 3705 may comprise at least one adhesive side which in practice may be adhered to a body surface to create a substantially airtight seal. The dressing and dressing adhesive may comprised polyurethane, hydrocolloid, hydrogel, silicone, acrylic, any other material or any combination thereof known in the art. Other variations of tissue covers and dressings that may be used in a reduced pressure tissue therapy system, are further described in U.S. patent application Ser. No. 12/626,426, filed on Nov. 25, 2009, and in U.S. patent application Ser. No. 12/683,987, filed on Jan. 7, 2010, which are hereby incorporated by reference in their entirety.

In some embodiments, a one-way flow mechanism may be interposed along the length of the fluid communication pathway between a dressing of a tissue cover and the vacuum source. In some mechanisms, the one way flow mechanism is located in or integrated into the body of the port member, while in some embodiments, the one-way flow mechanism may be integrated into the dressing or port-dressing interface. In still other embodiments, the one way flow mechanism may be located in or integrated into the tubing. In some embodiments, the one way flow mechanism may prevent or reduce the degree or risk of backflow of wound drainage (e.g., wound aspirate or exudates) collected by the reduced pressure source back to the wound. The one way flow mechanism may also permit detachment of the vacuum source without backflow of gas back into the treatment site. Multiple one way flow mechanisms may be provided along a flow pathway. In other embodiments, one way flow mechanism may be incorporated into port, or the vacuum source attached to the one way flow mechanism. In some embodiments, the one way flow mechanism may be a one way valve, such as a duckbill valve, a slit valve, a spring valve, an umbrella valve or any other suitable one way valve known in the art. In some embodiments, a plurality of one way flow mechanisms may be interspersed throughout the fluid communication conduit. In further embodiments, the one way flow mechanisms may have non-uniform opening or cracking pressures to account for fluid pressure differentials from pressure head or flow rate.

In order to produce substantially constant levels of reduced pressure within a certain tolerance range, there are several potential challenges. For instance, the sliding friction between the seal and the wall of the chamber, defects in the seal, variations in the force profile of the constant force springs, and the variability in the dimensions of the device components all contribute to fluctuations or perturbation in the reduced pressure level of the system.

For example, in a suction device comprising a constant force spring/sliding seal mechanism configured to deliver a substantially constant reduced pressure, there may be two main opposing forces acting on the sliding seal: the force exerted by the springs and the force created by the negative pressure in the suction chamber. Another force that contributes to the system may be frictional resistance. This force relates to the resistance of the relative motion between seal of the suction device and the wall of the chamber. In one way, this frictional force contributes to the variation in the reduced pressure of the system when, for example, a leak is introduced into the system.

A change in the pressure level may result from an air leak through the occlusive dressing, or by generation of exudate at the wound site, for example. Exudates are typically body fluids or mixed fluids and other cellular matter. When the magnitude of the reduced pressure within the system is lowered by a leak or by exudate generation, the force that the reduced pressure exerts on the sliding seal may decrease relative to the force exerted by the oppositional constant force springs. In a truly frictionless system, the constant force spring mechanism would immediately compensate for the imbalance of forces, pulling the seal and expanding the volume of the suction chamber, thus increasing the magnitude of the reduced pressure until the pull force from the reduced pressure equals the pull force of the constant force springs.

However, taking frictional forces into account, the friction from the contact of the sliding seal-chamber wall may add to the resistance of the reduced pressure and provides additional resistance for the oppositional springs. Thus, the magnitude of the reduced pressure may decrease until the force of the reduced pressure and frictional resistance is less than the opposing force of the constant spring. At this point, the constant force spring system engages and pulls the seal such that an increased volume is created in the suction chamber, thereby increasing the pull of the reduced pressure until a balance is restored between the opposing forces. This cycle repeats until the device is discharged, the seal travels the course of the device or the maximum volume of the suction chamber is reached.

If the pressure of the suction chamber is measured as a function of the volume of air introduced into the system by the leak, the resulting signal may be characterized by an oscillating pattern. The oscillating pattern may be described as a substantially regular, repetitive wave pattern with a peak and trough. In some embodiments, the peak-to-peak amplitude refers to the difference between the high and low values of adjacent peaks (peak and trough) in an oscillating wave. In some embodiments, the average peak-to-peak amplitude may be calculated over the course of the discharge of the suction device. Occasionally, there may be one or more variations in the signal where a substantially greater amplitude than the average amplitude is observed as a spike in the trace. The term "typical peak-to-peak" amplitude does not refer to these anomalies.

Figure 21:
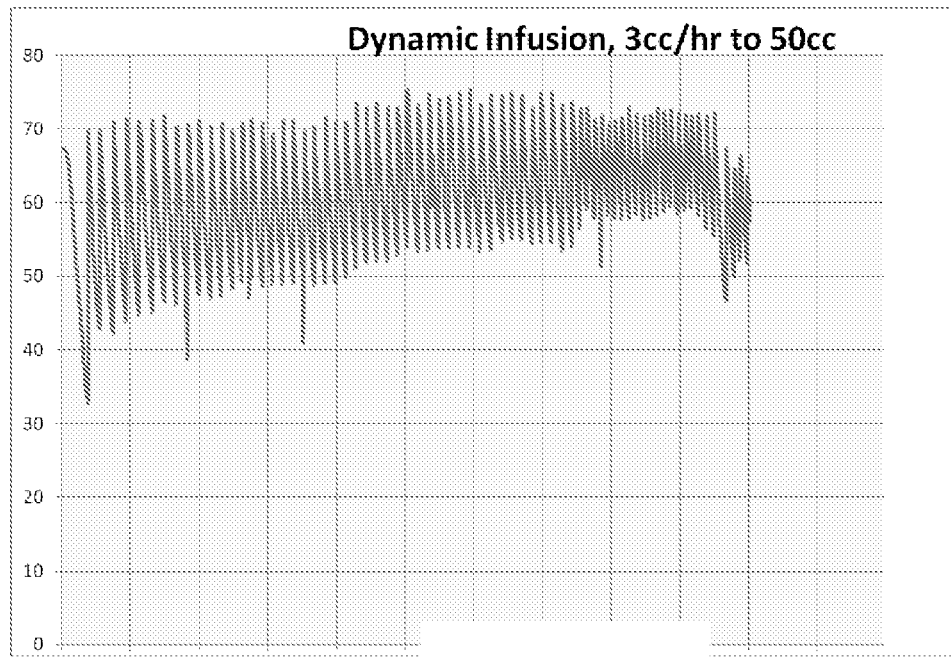
FIG. 21 is a plot of the measured pressure generated by the suction device over a period of 18 hours, wherein the device employs a non-optimized lubricant.

A non-limiting example of an oscillating pattern is a saw tooth wave. For instance, FIG. 21 shows a pressure signal having a saw tooth pattern. The portion of the wave that decreases from the peak to the trough corresponds to the decrease in the magnitude of the pressure as the leak progresses and the negative pressure is reduced. The pressure continues to decrease to a certain point, which point is determined, in part, by the amount of frictional resistance between the seal and the chamber wall, until the force exerted by the springs is greater than the sum of the frictional resistance and the force exerted by the reduced pressure. At this point, an inflection point in the signal may be followed by an increase in negative pressure and the signal begins the upward climb from the trough to the next peak. This increase corresponds to the sliding seal being pulled back by the springs, increasing the volume of the suction chamber and increasing the magnitude of the reduced pressure until the resistance of the springs is counterbalanced by the force of the reduced pressure and the frictional resistance. This is known as the slip/stick effect. In a frictionless system, a constant leak may result in the seal traveling at a constant rate to adjust from the decrease in negative pressure. In contrast, the frictional resistance of the sealing surfaces results in the periodic "sticking" of the sliding seal. In addition, the frictional resistance experienced by a seal at rest is higher than when the seal is in motion. Thus, the force required to move the seal at rest must overcome static frictional resistance which can be higher than the kinetic frictional resistance when the seal is in motion.

In order to reduce the oscillating pressure signal that results from this phenomenon, this disclosure provides a suction device that reduces the frictional resistance resulting from the contact of the sliding seal and the chamber wall. Various embodiments herein disclose a suction device configured to generate and substantially maintain a set negative pressure for use in treating tissue of a subject, comprising a suction chamber, a ribbon spring, and a lubricant; wherein when a volume of at least air or exudate is introduced into the reduced pressure system, a plot of the negative pressure of the system against the volume introduced into the system results in a substantially oscillating wave pattern, wherein the magnitude of the typical peak-to-peak amplitude is no greater than 20 mmHg. In some embodiments, the magnitude of the typical peak-to-peak amplitude is no greater than 10 mmHg. In some embodiments, the magnitude of the typical peak-to-peak amplitude is no greater than 5 mmHg. In some embodiments, the magnitude of the typical peak-to-peak amplitude is no greater than 1 mmHg. In some of the foregoing embodiments the volume introduced into the system is at least 50 cc. In some of the foregoing embodiments the volume introduced into the system is at least 25 cc. In some of the foregoing embodiments the volume introduced into the system is at least 10 cc. The magnitude of variation may also be characterized in relative terms as a percentage of variation from the nominal relative pressure reduction level. In some examples, the percentage of variation may be less than 25%, less than 20%, less than 15%, less than 10%, less than 8%, less than 6%, less than 5%. The maximum variation may be measured in a number of ways, e.g., under test conditions involving a constant infusion or leakage rate of a liquid or gas, up to a certain volume. In some instances, the maximum variations occur during an infusion rate of up to 1 cc/hr, 2 cc/hr, 3 cc/hr, 4 cc/hr, 5 cc/hr, 6 cc/hr, 7 cc/hr, 8 cc/hr, 9 cc/hr 10 cc/hr, or 15 cc/hr or 20 cc/hr, up to a volume of 10 cc, 20 cc, 30 cc, 40 cc, 50 cc, 60 cc, 70 cc, 80 cc, 90 cc, 100 cc, 150 cc, 200 cc, 250 cc or 300 cc, for example. In some of the foregoing embodiments, depicted in FIG. 21, a volume of at least a gas or liquid introduced into the suction chamber at a rate of 3 cc/hour for at least a duration of 16 hours for suction chamber nominally configured to generated a relative reduction in pressure level of 80±5 mmHg.

As mentioned previously, leaks in the system may involve the interfaces between the device, tubing, dressing and treatment site, or any non-continuous junction that forms the substantially closed system of the reduced pressure system. In some of the foregoing embodiments, the source of the leak originates from imperfections in the seal formed by the sliding seal and the chamber wall. In some of the foregoing embodiments, the source of the leak originates from where the sealing layer attaches to the body of the subject. In some of the foregoing embodiments, the source of the leak originates from any of the connection points between the suction device and the wound.

Some variations of suction devices may comprise lubricants that may be used to resist leaks in the interface between the seal and the suction chamber wall, and/or may an interface material to reduce static and/or dynamic friction effect such that the seal may move with respect to the chamber wall without sudden fluctuations in movement or direction. Lubricants may help the seal to slide with a gradual and/or constant speed along the suction chamber, thereby maintaining a substantially constant level of pressure within the chamber. Optionally, a lubricant may also be capable of flowing across the surfaces of the seal and/or chamber wall so that the lubricant is not displaced from the interface as the seal moves across the chamber. Lubricants may also help to decrease the frictional resistance between the seal and the chamber walls, which may help to mitigate the oscillating pattern pressure changes of the system. For example, lubricants may reduce the coefficient of friction between the seal and the suction chamber wall while still maintaining and airtight seal. In some variations, lubricants may be able to provide an interaction between the seal and the suction chamber such that the static coefficient of friction is substantially equal to, or similar to, the kinetic coefficient of friction. Optionally, lubricants may be non-reactive with the material of the seal and/or seal mount such that the lubricant is not absorbed into the seal or seal mount, and/or does not cause any deterioration of the seal or seal mount. Some variations of suction devices may not have any lubricants contacting the seal and/or suction chamber.

In some variations, the use of lubricants between the sliding seal assembly and the suction chamber wall may still result in an oscillating pattern of pressure changes as shown in the saw tooth wave of FIG. 21, where a fluorosilicone lubricant was used. While not bound by theory, it is believed that the force exerted by the seal against the chamber wall may displace the lubricant from the critical contact area or interface between the seal and the suction chamber wall, thus reducing the benefits of a lubricant. This behavior is similar to a "squeegee" effect. Lubricants may be selected with certain properties (e.g., viscosity, hydrophobicity, adhesion, cohesion, etc.) that enable it to remain substantially between the surface of the seal and suction wall. For example, the lubricant may be characterized by a high viscosity, however the viscosity of the lubricant should allow for the lubricant to flow across the surfaces of the sliding seal assembly and/or suction chamber wall and may have the ability to resist the "squeegee" effect of the sliding seal lips pushing the lubricant away from the sealing contact surfaces. For example, a lubricant with very high viscosity may help reduce the tendency of the lubricant to be pushed aside by the compression of the sliding seal lips.

A sufficiently viscous lubricant may also be able to fill in defects in the sealing surface. This may help provide a low-friction interface between the seal and the suction chamber walls, and may also help maintain an airtight interaction between the seal and the suction chamber wall. A viscous lubricant may have cohesive properties that may help ensure an even coating across the surfaces of the seal and/or suction chamber. For example, the molecules of the lubricant may mutually attract each other so that the lubricant maintains a continuous fluid coating across the chamber walls and/or seal. Alternatively or additionally, the lubricant may exert a weak adhesive and/or cohesive to the surface of the chamber walls and/or seal, which may allow the lubricant to fill in any micro-cracks or surface irregularities while allowing relative motion between the chamber walls and seal to occur. Such cohesive properties of a viscous fluid may also help the lubricant remain substantially localized to the contact area between the seal and the chamber walls, while still retaining a certain degree of flowability.

A lubricant's viscosity can be measured by techniques known in the art. In some of the embodiments, the lubricant is characterized by a viscosity of at least 1,000,000 cP. In some of the embodiments, the lubricant is characterized by a viscosity of at least 500,000 cP. In some of the embodiments, the lubricant is characterized by a viscosity of at least 1,500,000 cP. In some of the embodiments, the lubricant is characterized by a viscosity of between 750,000 and 1,750,000 cP, or between about 1,400,00 cP and about 1,600,000 cP. In some of the embodiments, the lubricant is characterized by a viscosity of between 500,000 and 1,500,000 cP. In some of the embodiments, the lubricant is characterized by a viscosity of between 1,000,000 and 2,500,000 cP. In some of the embodiments, the lubricant is characterized by a viscosity of between 1,000,000 and 2,000,000 cP.

In some of the foregoing embodiments the viscosity of the lubricant is not less than 100,000 cP. In some of the foregoing embodiments the viscosity of the lubricant is not less than 10,000 cP.

In some of the foregoing embodiments, the lubricant is a silicone. In some of the foregoing embodiments, the lubricant is at least one of the members of the group consisting of fluorosilicone and dimethylsilicone. In some of the foregoing embodiments, the lubricant comprises a 20% fluorosilicone and 80% dimethylsilicone by weight. In some of the foregoing embodiments, the lubricant is a silicone lubricant with a viscosity between 1,000,000 and 2,000,000.

Dry lubricants can be chemically cross-linked or otherwise bonded to the chamber wall or seal prevents the lubricant being displaced by the compressive force from the sliding seal lips. However, the use of a flowable lubricant has the advantage of sealing small physical defects or imperfections in the sliding seal or suction chamber, and reduces air leaks.

Since the overall friction experienced by the seal should be reduced or minimized, in some embodiments it is advantageous to design the sliding seal and the chamber such that there is a reduced amount of compression needed to create an airtight seal. Where a reduced amount of compression is used to create a seal, minor imperfections in the sealing surfaces have a greater chance of permitting air leaks. Thus, the ability of a flowable lubricant to fill in and correct these defects presents an advantage not available with dry lubricants.

Factors that influence the selection of an appropriate lubricant and material for the sliding seal material include the non-reactivity and compatibility between the two materials. For instance the sliding seal should have limited swelling from being in contact with the lubricant. More generally, the material of the sliding seal assembly and the lubricant material may be selected to limit undesirable interactions between these components (e.g., absorption of the lubricant into the seal, degradation of the seal by the lubricant, etc.). In one embodiment, fluorosilicone is combined with dimethylsilicone to form a lubricant that reduces swelling of the dimethylsilicone elastomer seal. In some of the foregoing embodiments, the sliding seal is an elastomer. In some of the foregoing embodiments, the sliding seal is dimethylsilicone elastomer.

In some variations, the static coefficient of friction between the sliding seal and the suction chamber wall is less than about 0.3, 0.2, 0.15, 0.12, 0.1, 0.08, 0.06 or 0.05. In some variations, the difference between the static coefficient of friction and the dynamic coefficient of friction between the sliding seal and the wall of the suction chamber may be less than 0.1, 0.08, 0.06, 0.05, 0.04, 0.03, 0.02 or 0.01, for example.

In some embodiments, the components of the system, such as the chamber, may be manufactured by thermoplastic injection techniques. This method may permit scalability of the component, reduces cost, and increases the dimensional consistency of the components. The chamber of the device has a long bore and to produce this part via injection molding, in some embodiments, requires the introduction of a slight draft to allow the injection mold tool to release the part. The draft causes the cross sectional area near the closed end of the chamber (i.e., the distal end, which may have a distal conduit or extension structure to which tubing may be attached) to be slightly smaller than the cross sectional area near the open end of the chamber (i.e., the proximal end). The cross-sectional area will typically increase linearly from the closed to the open side. In some embodiments, the draft across the longitudinal length of the chamber should be less than ½ of 1 degree per side, and in other embodiments, may be less than ¼ of 1 degree. In some variations, the draft may be such that the distal end may be smaller than the proximal end by about 0.014 inch. A chamber may have an elliptical cross sectional area with a major and minor axis, and the draft may vary differently along the major and minor axes. For example, the length of the minor axis may vary by about 0.01 inch across the longitudinal length of the chamber, and the length of the major axis may vary by about 0.0075 inch across the longitudinal length of the chamber.

The differences in cross-sectional area introduced by the draft may introduce variability in the amount of radial compression of the sliding seal. For instance, the smaller cross-section near the closed end of the chamber compresses sliding seal more than the larger cross-sectional area near the open end of the chamber. Greater radial compressive stress on the sliding seal may increase the amount of frictional resistance between the sealing surfaces. In one embodiment, the seal design reduces radial compressive stress of the sliding seal, especially when the sliding seal moves from an area of broader inner chamber dimensions to an area of narrower inner chamber dimensions. By reducing the compressive stress on the seal, the difference in the effective sliding friction between a less-compressed and a more compressed state may be reduced.

In some of the foregoing embodiments, the device comprises a sliding seal coupled to a seal mount, wherein the sliding seal has an inner surface and an outer surface and the seal mount has an outer surface. In some of the foregoing embodiments, at least a portion of the outer surface of the seal mount and at least a portion of the inner surface of the sliding seal is separated by a gap. In specific embodiments, the sliding seal undergoes radial compression as the seal slides to narrower portions of the chamber, wherein the compression of the sliding seal results in seal being displaced by a certain amount, wherein the gap is an amount equal to or greater than the amount of displacement of the sliding seal. In some of the foregoing embodiments, the sliding seal is free-floating.

In other embodiments of the reduced pressure system, the sliding seal may be fabricated from a material adapted to create an airtight separation between the portion of the suction device below it and the remainder of the suction device. The material may be elastomeric or non-elastomeric. The sliding seal can be made of materials such as: silicone, dimethylsilicone, fluorosilicone, nitrile, natural rubber, thermoplastic elastomer, thermoplastic urethane, butyl, polyolefin, polyurethane, styrene, polytetrafluoroethylene, any other suitable material, or a combination thereof.

Figure 23:
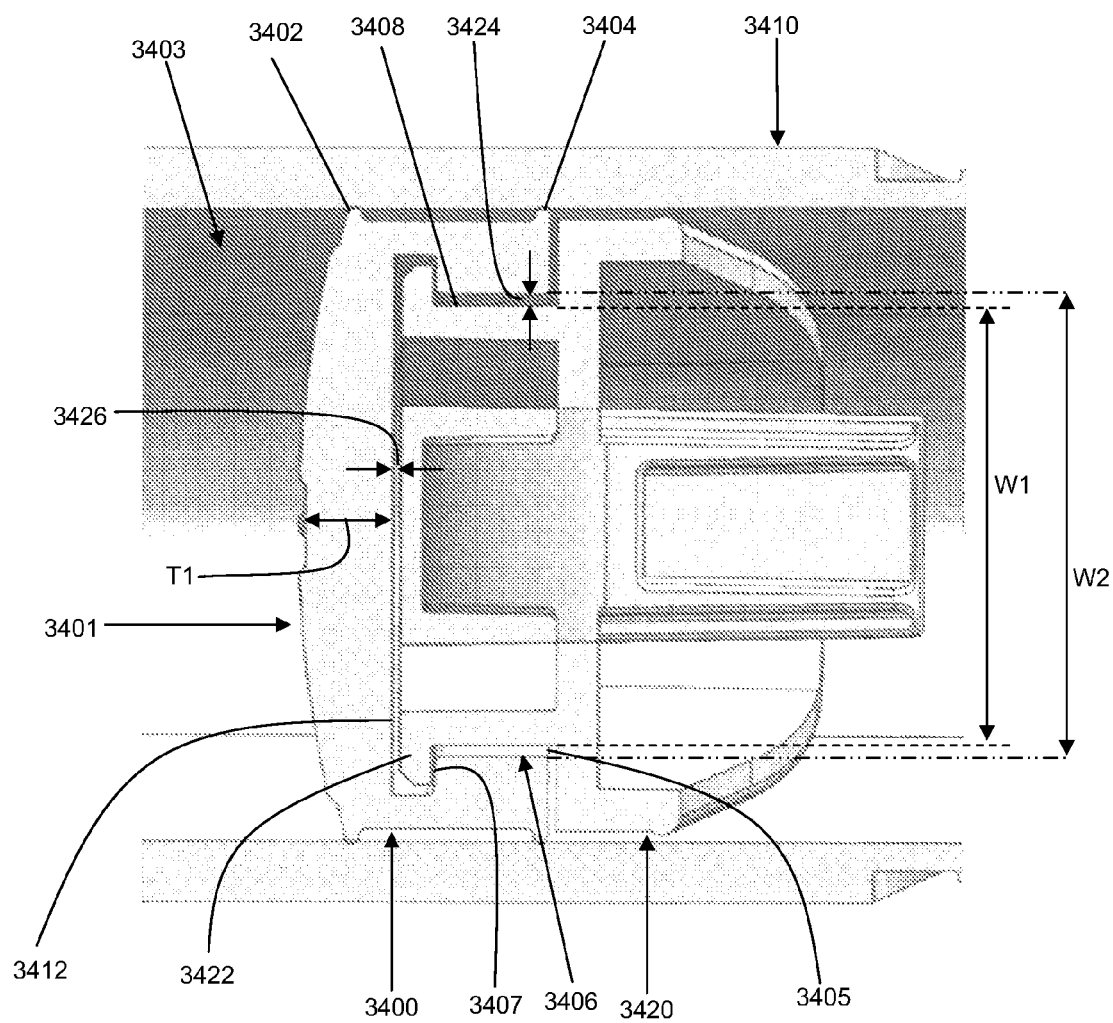
FIG. 23 is an image of a cross-section of a part of the suction device showing a section of the outer surface of the seal in contact with the inner surface of the suction chamber, and a gap between a section of the inner surface of the seal and the rigid piston.

Sliding seals may be made of a compressible material such that the sliding seal may be able to reversibly transition from a compressed state to an expanded state while still maintaining an airtight seal against the inner walls of the suction chamber. Examples of suitable materials for a sliding seal may include silicone, dimethylsilicone, fluorosilicone, nitrile, natural rubber, thermoplastic elastomer, thermoplastic urethane, butyl, polyolefin, polyurethane, styrene, polytetrafluoroethylene, any other suitable material, or a combination thereof. In some variations, a sliding seal may comprise one or more protruding edges (e.g., flanges) that may be capable of both radial compression and longitudinal deflection. For example, FIG. 23 depicts a sliding seal 3400 that may comprise a distal flange 3402 and a proximal flange 3404 which may be configured to longitudinally deflect as the sliding seal moves along the longitudinal axis of the suction chamber 3410 and/or in the presence of negative pressure within the chamber. The flanges 3402, 3404 may have a low deflection force, which may help the sliding seal to accommodate a draft in the chamber. The deflectable flanges 3402, 3404 may also help prevent angular deviations or displacement of the sliding seal 3400 within the chamber 3410. The distal flange 3402 and the proximal flange 3404 may have similar or different deflection forces. For example, the proximal flange 3404 may have a lower deflection force than the distal flange 3402.

Additionally or alternatively, a sliding seal may be coupled to a seal mount such that the sliding seal may yield under radial compression against the walls of the suction chamber. The interface between the sliding seal and the seal mount may allow additional radial compression of the seal, which may limit and/or reduce the frictional force on the seal as it moves longitudinally along the suction chamber (e.g., from a broader region to a narrower region of the suction chamber or vice versa). For example, the sliding seal 3400 may comprise a lumen 3406 with a proximal aperture 3405 and a distal ledge 3407. The distal ledge 3407 may be located proximally from the distal side 3401 of the sliding seal. A seal mount 3420 may comprise a protruding edge 3422 at a distal-most side that is configured to contact and/or engage the ledge 3407 of the sliding seal. The width W1 of the seal mount 3420 may be less than the width W2 of the lumen aperture 3406, such that there is a radial gap 3424 between the lumen walls of the sliding seal and the surface of the seal mount. Optionally, the lengths of the seal mount 3420 and sliding seal lumen 3406 may be such that there may be a longitudinal gap 3426 between the lumen walls of the sliding seal and the surface of the seal mount. The radial gap 3424 may provide additional space for the seal mount 3420 to yield to compressive forces, for example, by allowing the proximal flange 3404 to radially compress into the gap 3424. Compression of the proximal flange 3404 may also cause the side walls 3408 of the sliding seal to radially deflect as permitted by the radial gap 3424. The size of the radial gap 3424 may be at least partially determined by the draft of the suction chamber 3410. For example, the radial gap 3424 may be such that the sliding seal can accommodate the draft of the chamber without excessively increasing the frictional force experienced by the sliding seal (e.g., as the sliding seal moves from a broader to a narrower portion of the chamber). The longitudinal gap 3426 may provide some space for longitudinal expansion of the sliding seal 3400 as its side walls 3408 deflect into the radial gap 3424. In some variations, the size of the radial gap 3424 may be from about 0.005" to about 0.015", and the size of the longitudinal gap 3426 may be from about 0.005" to about 0.015". In some variations, there may not be a longitudinal gap between the sliding seal and seal mount, and the distal portion of the mount may abut with the distal wall of the lumen.

As the seal mount 3420 is moved by an activation tool or force-generating mechanism (e.g., constant force springs), the mount may move with respect to the seal because of the radial and longitudinal gaps. The contact between the seal mount 3424 and the sliding seal 3400 may vary. For example, when the seal mount 3420 is urged distally (e.g., towards the distal portion 3403 of the suction chamber as the suction device is being charged by an activation tool), the distal-most side of the seal mount 3420 may be contacting the distal wall 3412 of the lumen 3406. In some cases, the protruding edge 3422 may contact the distal-most portion of the lumen 3406, and may not be in contact with the distal edge 3407 when the seal mount is urged distally. When the seal mount 3420 is urged proximally (e.g., towards a proximal portion of the suction chamber by constant force springs during the generation of negative pressure), the protruding edge 3422 may contact the distal ledge 3407 and not the distal wall 3412 of the lumen. As the mount is urged proximally, the engagement between the protruding edge 3422 and the ledge 3407 may act to pull the sliding seal 3400 along with the seal mount. While the seal mount 3422 being urged either distally or proximally, the protruding edge 3422 of the seal mount 3420 may be pressed against either the distal wall 3412 and/or the distal ledge 3407 with sufficient force such that the seal and the mount may not move radially with respect to each other. This may help stabilize the sliding seal within the suction chamber and help reduce angular deviations. However, in cases, the seal mount 3422 may be urged distally with sufficient force so that the protruding edge 3422 is not contacting the distal ledge 3407, but is not yet contacting the distal wall 3412. Optionally, the seal and the mount may not be in contact at all. In this state, because of the radial gap 3424 and in the absence of frictional force between the seal mount and the sliding seal, the seal mount 3420 may move radially with respect to the sliding seal 3400.

The deflection force of the proximal and distal flanges 3402, 3404 may be different due to the differing distance between the flanges to the lumen 3406. For example, the proximal flange 3404 is in closer proximity to the lumen 3406 than the distal flange 3402, and this may allow the proximal flange to deflect and/or compress more readily than the distal flange. In other variations, the proximal and distal flanges 3402, 3404 may have substantially similar deflection forces, as may be desirable. The thickness T1 of the sliding seal 3400 at the distal side 3401 may be greater in the middle of the seal than towards the side of the seal. A thickened middle portion of a sliding seal may provide the necessary rigidity for generating and maintaining negative pressure in the distal portion 3403 of the chamber 3410, while thinner side portions may allow the flanges 3402, 3404 to deflect and/or compress as the seal moves along the chamber. In some variations, the thickness T1 of the sliding seal at the distal side 3401 may be in the range of about 0.2" to about 0.01", sometimes about 0.15" to about 0.05", other times about 0.125" to about 0.075". In one example, the thickness T1 of the sliding at the distal side 3401 may be 0.125" in the thickened middle portion, and may be 0.075" in the thinner side portions.

Various embodiments herein may comprise a reduced pressure wound treatment system that features the ability to contain and store exudates released into the system. Sources of the exudate generally originate from the tissue or wound of the patient to which the system is attached. Exudates are typically body fluids and contain bio-hazardous products. Exudates that enter into the reduced pressure system may collect in the suction chamber. A used suction device may contain biohazardous materials such as exudates from the wound bed and create a challenge in safely disposing of the spent device.

Various embodiments herein disclose a device wherein exudates which enter the suction chamber may be contained within the chamber without the ability to leak out of the suction device. In one embodiment, the device reduces the risk of contamination anyone in contact with the suction device and permits the suction device to be disposed of in solid waste disposal sites. The reduced pressure chamber of the suction device contains a fluid retention assembly (e.g., a biohazard containment assembly) comprising a superabsorbent material, wherein when the exudate comes into contact with superabsorbent material, it is absorbed by the material and unable to exit the suction device chamber. The liquid is stored in the superabsorbent material. The ideal superabsorbent material is able to absorb and contain an amount of liquid that is many times its own weight and has a high absorbance capacity. In addition, in some of the foregoing embodiments, a fluid retention assembly (e.g., a biohazard containment assembly) comprises anti-bacterial agents which can further reduce the risk of contamination and improve safety in handling the suction device.

Methods and devices for treatment of damaged tissue are disclosed, including treatment of wounds by employing non-electrically powered reduced pressure therapy devices. Maintenance and control of the sub-atmospheric pressure generated may be provided by such devices while reducing usage discomfort to the user. In some embodiments, a reduced pressure therapy system may comprise a suction device, and a tissue cover structure that comprises a sealant layer, a contact matrix and optional extension tubing. The suction device may be a non-electrically powered device, which may be configured to be silent and/or wearable. In some embodiments, the suction device may have a low-profile so that it may be worn inconspicuously under clothing. The sealant layer may create a substantially airtight enclosure over the damaged tissue to provide fluid communication between the suction device and the enclosure containing the damaged tissue. Fluid communication may be provided by a direct connection between the suction device and the sealant layer, or may be provided through extension tubing connecting the suction device and the attachment port. In some embodiments, the sealant layer may be flexible, but in other embodiments the sealant layer may be semi-rigid or rigid. In some examples, a semi-rigid or rigid sealant layer may facilitate handling or application of the sealant layer to a treatment site while reducing or eliminating the risk that the sealant layer may fold and adhere on itself. The extension tubing may be coupled to the sealant layer and/or suction device using a connector or fitting. The connector may optionally comprise a releasable locking mechanism to facilitate attachment and detachment of the extension tubing, and/or to prevent accidental disconnection. For example, the releasable locking mechanism may comprise a release button or other actuator which serves as a locking mechanism which may be manipulated during attachment and/or detachment of the tubing. In other embodiments, the suction device may be connected directly to the sealant layer attachment port, and may comprise a connector with the same or similar connector as the extension tubing, to permit both direct attachment of the suction device and remote attachment using the tubing.

In one embodiment, a system for reduced pressure therapy may comprise a tissue cover structure that comprises a contact layer matrix that is placed into or over the wound bed or other tissue defect. In some embodiments, the contact layer matrix may be used to distribute the reduced pressure more evenly through the wound bed, and may also provide a scaffold or contact surface which promotes healing. In another embodiment, the damaged tissue cavity, packed with the contact layer matrix, is then placed under a sealant layer to produce a sealed enclosure containing the contact layer and the wound bed. Fluid communication to the interior of enclosure is provided by an attachment port of the sealant layer.

In some embodiments of the device, the tissue cover structure may comprise a sealant layer made of a hydrocolloid material or any other material known to those skilled in the art. The hydrocolloid sealant layer may be semi-porous and breathable to absorb moisture from the wound while protecting the skin. In addition, the hydrocolloid sealant layer is typically thicker than other materials such as acrylic adhesives to allow for easier placement with less folding and wrinkling and to seal potential fluid leak paths.

In one embodiment of the device disclosed herein, the attachment port is directly mounted to a distal portion of the suction device. In other embodiments the attachment port is connected to the suction device via an extension tube. In some embodiments, the extension tube may be adapted to mitigate entanglement. The suction device and the extension tubing may have similar fittings and release buttons to resist accidental disconnection. In embodiments in which extension tubing is used, the proximal end of the extension tubing may be connectable to the distal end of the suction device with a complementary fitting that is similar to the fitting on the attachment port. Likewise, the distal end of the extension tubing may be connectable to the suction port with a complementary fitting that is similar to the fitting at the distal end of the suction device.

Various embodiments herein also disclose a device and method to detect a blocked base layer. During the application of negative pressure, it is possible for the path from the wound bed to the suction source to become blocked. Blockage of the path can occur for a variety of reasons, such as development of a clot, thick exudate ingression, crust, or other solid material from exudates. Kinks or compression of the extension tube or other portion of the reduced pressure pathway, for instance, may cause blockage. Such blockage can result in a difference in pressures below and above the blockage, such as at the wound bed level and at the suction device, respectively. Thus, although the suction device appears to maintain a desired negative pressure, the pressure at wound bed level may be closer to atmospheric pressure and any benefit of reduced pressure therapy would be lost. The ability to detect a loss of reduced pressure specifically at the wound bed level would give clinicians an opportunity to address potential blockages.

There are some existing solutions for detecting a loss of suction for powered pumps such as the disclosure of U.S. Pat. No. 7,438,705. However, detecting a loss of reduced pressure at the wound bed in a non-electrically powered device has yet to be seen.

Figure 36A:
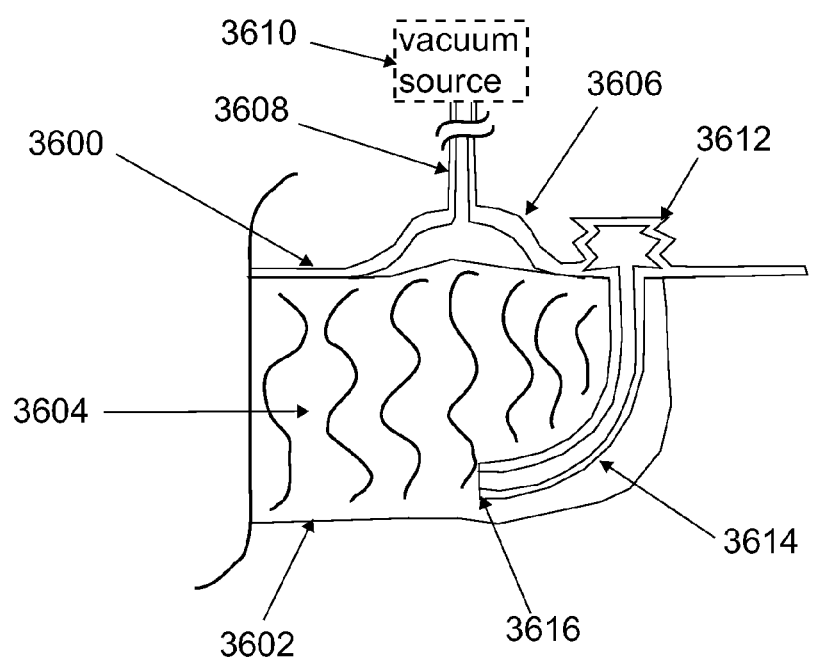
FIGS. 36A-36B are schematic illustrations of two embodiments comprising a sensor is in communication with a wound bed.
Figure 36B:
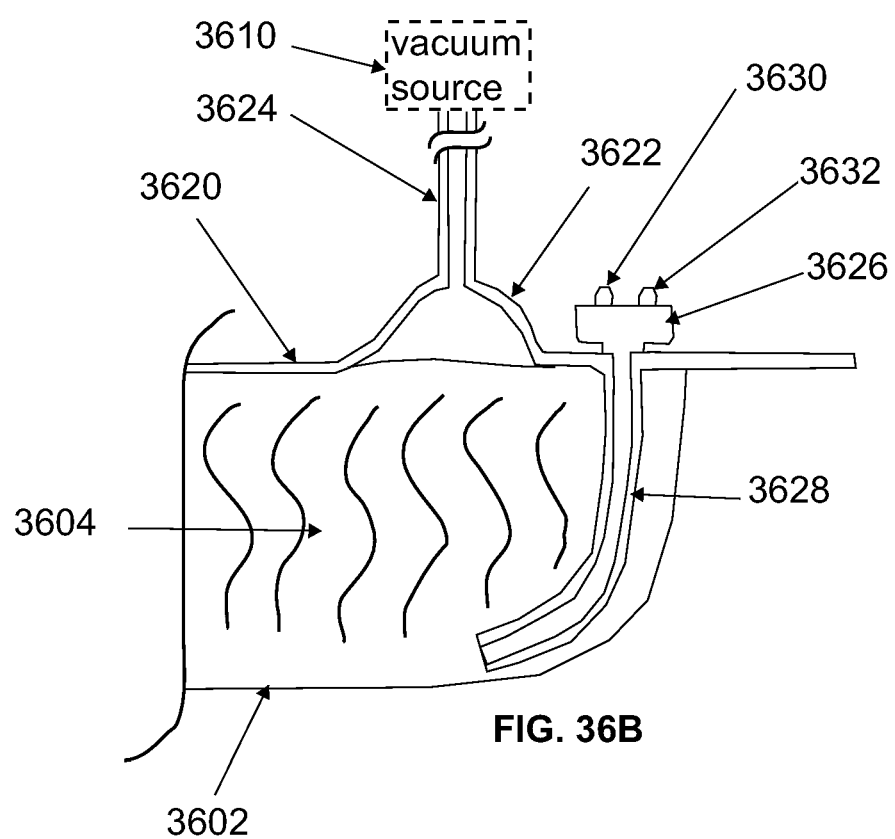

Various embodiments herein disclose a dressing for a wound bed capable of indicating decreased negative pressure at the wound bed, wherein the dressing comprises a sensor and a communication channel between the dressing and the wound bed. The sensor detects and indicates a reduction or lack of negative pressure at the wound bed site. Some embodiments of the device disclosed herein comprise a pressure gauge integrated into the attachment port or another component. The mounting of the pressure gauge into the attachment port enables accurate measurement of pressure level within the enclosure adjacent to the wound and formed by the sealant layer. The pressure gauge described herein may less susceptible to incorrect pressure readings that are typically caused by clots in the tubing connecting the reduced pressure source to the wound. Examples of a pressure sensor include a collapsible bellow or an electronic pressure sensor. Examples of these embodiments are illustrated in FIGS. 36A and 36B. However, other embodiments may not have a pressure gauge or sensor.

In FIG. 36A, a portion of a wound dressing 3600 placed over a wound bed 3602 and comprising an optional base layer or contact layer 3604 (e.g. gauze or foam) placed in the wound bed 3602. The dressing 3600 comprises a port 3606 that is attached (or integrally formed) with tubing 3608 used for attachment to a vacuum source 3610, and a pressure-sensitive structure 3612 that is in communication with the wound bed 3602 via an opening in the dressing, or an optional communication tube 3614. In FIG. 36A, the communication tube 3614 is depicted with its distal end 3616 located below the contact layer 3604, but in other examples, the distal end may be located within or above the contact layer 3604. In still further examples, the communication tube may be fenestrated along its length or may comprise multiple tubes. In the example in FIG. 36A, the pressure-sensitive structure 3612 comprises a bellows structure that is normally expanded at atmospheric pressure but collapses at certain relative reduced pressure levels that are used with negative pressure wound therapy (e.g. −50 mm Hg, −75 mm Hg, −100 mm Hg, −125 mm Hg, or −150 mm Hg, or greater).

In sensors or indicators utilizing a bellow design, the bellow is collapsed under negative pressure, and upon loss of negative pressure, the bellow expands. Thus, expansion of the bellow provides the clinician an indication that reduced pressure at the site of the wound bed is lost. The bellow is in fluid communication with the wound bed site. The bellow shape or conformation should change in response to the reduction of negative pressure at the wound bed site. For instance, if the wound bed site has adequate negative pressure, the bellow appears collapsed. As the negative pressure at the wound bed level is reduced, the bellow changes from a collapsed to an expanded state. In some embodiments, the fully expanded bellow indicates that the wound bed is at atmospheric pressure. In some embodiments, the bellow volume is at least 0.5 cc. In some embodiments, the bellow volume is at least 1 cc. In some embodiments, the bellow volume is at least 2 cc. In some embodiments, the bellow volume is at least 3 cc. In some embodiments, the bellow volume is between 1-5 cc. In some embodiments, the bellow volume is between 1-3 cc. In some embodiments, the bellow volume is less than 10 cc.

The bellow material is flexible and permits the bellow to change shape in response to changes in pressure. In some embodiments the material may stretch. In other embodiments the material has a low stretch characteristic. The bellow material may comprise, for example, silicone or polyurethane. In some embodiments the bellow has "accordion" shaped folds to accommodate the collapsed and expanded states. In other embodiments, the bellow is smooth without folds. Moreover, the bellow is designed to change appearance to indicate to a person having ordinary skill in the art if there is a change in negative pressure. In some embodiments, the sensor does not rely on any electronic circuitry or electrical impulse to indicate a change in negative pressure.

In alternative embodiments, the sensor comprises an electrical component, such as MEMS technology to communicate the information of a change in negative pressure to the clinician. Microsystem Technology or MEMS Technology is the integration of miniaturized components of sensor applications using newly developed miniaturization techniques. Microsystems combine microelectronic components (Integrated Circuits) with micromechanical or micro-optical components. The microelectronic element employs standard semiconductor technology to analyze and manage the output data of the micromechanical or optical element. One of the first microsystem applications, the pressure sensor, uses the combination of mechanical sensing elements and electronic circuitry. The micromechanical components are produced on silicon wafers, a material well known in chip manufacturing.

In FIG. 36B, the wound bed 3602 may also be treated with an optional base layer or contact layer 3604 (e.g. gauze or foam). The dressing 3620 likewise may also comprise a port 3622 that is attached (or integrally formed) with tubing 3624 used for attachment to a vacuum source 3610, but an electronic sensor 3626 may attached to the dressing 3620 or otherwise in communication with an opening in the dressing to measure the pressure in the wound bed 3602. An optional communication tube 3628 may also be provided for the electronic sensor to isolate and sample pressure at locations remote from the electronic sensor. In other variations, the electronic sensor 3626 may comprise an elongate sensor lead with a sensor mechanism at its tip. This sensor lead may be located in the communication tube 3628, which may protect the sensor lead from damage or interference from wound bend exudates. The electronic sensor may be configured with any of a variety of functions, including indicators of battery power, and/or adequate levels of pressure reduction. The indicator may be a light 3630, and the sensor may also include a on/off mechanism 3632.

The sensor, including the responder coil and the pressure sensitive capacitor may be enclosed and/or encapsulated suitable for attachment to or embedding in the wound dressing. The enclosure and encapsulation materials are biocompatible. To facilitate the functioning of the present invention, the dressing comprises a connection between the pressure sensitive capacitor and the wound bed.

Examples of pressure sensors include, for instance, the disclosure U.S. Pat. No. 6,840,111 entitled "Micromechanical Component And Pressure Sensor Having A Component Of This Type." This patent discloses a micromechanical component for mounting on a carrier as well as a pressure sensor.

The dressing and wound bed is in communication via a channel. An example of a communication channel is a flexible catheter tube, comprising a first and second end, wherein the first end is connected to the dressing and the second end is located at the wound bed, below the base layer. Moreover, any type of flexible tubing that permits the sensor to indicate the pressure level at the wound layer is appropriate. In specific embodiments, the first end of the communication channel is in communication with the sensor. The tubing should be flexible to allow for positioning to the wound bed, yet the tubing should be able to have the mechanical strength to maintain fluid communication between the sensor and the wound bed and avoid collapsing or kinking.

The sealant layer may also comprise an attachment port to facilitate attachment and/or detachment of the suction device or extension tubing to the sealant layer. In some examples, the attachment port may have a variety of relative configurations and/or relative positions with respect to the sealant layer and the suction device. In some instances, the attachment port may be articulated and/or flexible. For example, an attachment port may be configured with a swivel base, which may permit the attachment port to rotate. An articulated and/or flexible attachment port may also reduce the transmission of torsion or other forces that may be transmitted between the suction device and the sealant layer. The attachment port may be integrally formed with sealant layer at the point of manufacture, or may be provided separately and attached to the sealant layer at the point of use. The latter embodiments may permit clinician flexibility or customization of the relative location of the attachment port with respect to the sealant layer. The attachment port configuration may also provide improved patient comfort as the attachment port design reduces communication of torsion forces to the wound bed, which may be caused by the suction device movements, while allowing quick integration. Furthermore, ability to bend and/or rotate allows independent placement of the sealant layer with respect to the attachment port orientation. The flexibility of the attachment port may also reduce the risk of pressure point induced injury. The attachment port may allow for simple snap-in attachment of the vacuum source. The connection of the attachment port nozzle to the dressing interface may have a small footprint and/or a low profile to reduce the possibility of pressure point injury. In some embodiments, the swivel base of the attachment port may have a thin elastomeric base which is integrated into the sealant layer. The swivel base is configured to allow maximal sealant layer moldability while maintaining integration with the more rigid system elements to form a seal around body surfaces. In some embodiments, a reduced pressure therapy device with an attachment port may reduce or eliminate one or more steps that are used to attach the reduced pressure source to the sealant layer and to create fluid communication between the wound and reduced pressure source. Unlike existing reduced pressure therapy systems, the attachment port may be configured to attach the vacuum source without adhesives and/or without cutting the sealant layer.

In some embodiments, the reduced pressure therapy device may be configured with one or more actuators to facilitate activation of the suction device and/or release of the suction device from the skin or tissue. For example, the suction device may comprise an activation mechanism. In some embodiments, the suction device contains a button or other actuator which initiates the application of reduced pressure at the treatment site. The activation mechanism may be provide with indicia, such as the word "ACTIVATE" or a color green, or any other word or coding with similar meaning, is provided thereon or nearby. Pressing the said button may open a valve and allow fluid communication between the enclosure formed adjacent to the wound bed and the suction chamber, or may unlock a sliding seal to permit movement. More specifically, the activation may cause constant force springs to retract in order to expand the combined volume of the space below the sliding seal and within the wound enclosure. The reduced pressure created therein may exert a force on the sliding seal substantially equal to that of the springs.

In some embodiments, the reduced pressure therapy device may further comprise an additional button or actuator which is configured to close the valve and/or decouple the suction device from the extension tubing or sealant layer enclosing the wound. Pressing the additional button may allow detachment of the suction device from the attachment port or the extension tubing and activate a one way valve which traps the exudates within the suction chamber or otherwise closes any pathway out of the suction chamber. The tubing to the dressing may have a one way valve such that air and/or exudates may move in one direction (e.g., away from the wound bed) and not the other (e.g., towards the wound bed).

In some embodiments, the therapy device may be primed or charged prior to applying the reduced pressure. In some configurations of the device, the charging and activating method may be performed in a single continuous step. While in other configurations, the charging and the activating method may be performed in distinctly separate steps. In one example, the sliding seal within the suction device may be primed by being positioned at the distal end of the suction device. The positioning of the sliding seal may be performed by any of a variety of priming mechanisms, such as a slider or push rod, for example. In some embodiments, the sliding seal may automatically begin to slide back to generate a pressure differential in the reduced pressure chamber after priming. In other embodiments, the suction device may comprise an activating mechanism which is actuated separately from a priming mechanism to initiate the generation of the pressure differential. In some configurations, the activating mechanism may directly block or restrict movement of the sliding seal, while in other configurations, the activating mechanism may restrict or limit flow of fluid and/or materials into the chamber of the suction device. In one example, the release mechanism may comprise a separate button or lever that is configured to alter communication or flow through a valve coupled to the reduced pressure chamber. The valve may be a blade valve or rotatable valve, for example. Pressing the activation button may lift a blade valve or turn the lever of a rotatable valve to permit fluid flow into the reduced pressure chamber.

In certain embodiments, the priming mechanism comprises a priming key or activation tool configured extend the force mechanism or displace the sliding seal into its primed position. In some examples, the activation tool comprises an elongate rigid member that is configured to be positioned in an opening in the body of the suction device and may be used as a lever or push rod to prime the reduced pressure generation mechanism. In some embodiments, the activation tool can be used to mechanically press the sliding seal towards the distal end of the suction device until a latch, embedded within the shaft of the activation tool, locks into place. In some embodiments the activation tool is integrated into the body of the suction device and may also serve as a cap to close the suction device. In some embodiments, the activation tool may be configured to hold and maintain the suction device in a non-charged state. For example, the activation tool may be releasably locked to the body of the suction device to provide safe storage of noncharged suction device, with the locked activation tool preventing or limiting a non-charged spring mechanism from retracting during storage and/or handling. In some instances, without the activation tool in place, retraction from storage and/or handling may occur, due to micro-leaks out of the suction chamber that may cause the springs to lose the energy stored in them, for example. In other embodiments, the activation tool enables re-charging of the spring or other force mechanism that has been depleted or otherwise lost some charge. For example, recharging may be performed when accidental discharge or an undetected leak causes the springs to lose the energy stored in them, or after emptying the collection chamber.

In another embodiment, a method for treating a patient is provided where the method comprises steps of (a) detaching a non-electrically powered and non-circular reduced pressure generating device from a wound covering, (b) charging the reduced pressure generating device with potential energy without generating a reduced pressure, (c) attaching the recharged reduced pressure generating device to the wound cover, and (d) activating the recharged reduced pressure generating device to generate reduced pressure in an enclosure underneath the wound covering.

Further provided herein is a method for treating a patient, where the method comprises steps of (a) sealing a wound cover to a body site, and (b) reducing the pressure level at the body site using a vacuum generating device that has an elongate length and a non-circular cross-sectional shape transverse to the elongate length. In some embodiments, the vacuum generating device may be configured to maintain substantially constant reduced pressure level at the wound site without changing its external dimensions and independent of its orientation with respect to the body site. In such an embodiment, the method may further comprise a step of sliding a non-circular seal along a movement axis in a non-circular reduced pressure chamber, wherein the seal and the suction chamber have non-circular configurations transverse to the movement axis.

In one embodiment of the reduced pressure system, the suction chamber comprises an ellipsoidal cylinder having a sliding seal concentrically disposed therein. The chamber has a variable effective volume defined by the distance between the distal end of the chamber, which is located adjacent to the opening connected to the sliding blade valve and a current position of the sliding seal. In the primed state, the seal is closest to the distal end of the suction device, and the effective volume of the chamber is zero or nearly zero. The sliding seal may be connected to one or a series of springs which may be used to bias the seal towards an activated state where the effective volume of the chamber is the maximum. The springs may have any of a variety of configurations, including ribbon springs. The ribbon spring may be a substantially constant force spring or a variable force spring. In some examples, a combination of spring types may be used. In still other examples, a single ribbon may be configured with a coil at each end and attached to a slidable seal at a middle region of the single ribbon. In one embodiment of the device, the spring(s) may exert a force of less than 0.5 pounds. In other embodiments of the present invention the constant force spring(s) may exert a force of less than 1 pound. In some embodiments of the reduced pressure system the constant force spring(s) may exert a force of less than 5 pounds. In other embodiments of the device disclosed herein the substantially constant force spring(s) may exert a force of less than 20 pounds. In other examples, the force per square inch exerted across the collection volume of the device may be in the range of 0.1 psi to 15 psi, in some examples 0.5 to 10 psi, and in other examples 1 psi to 5 psi, or 0.5 psi to 2.5 psi, or 1.5 psi to 2.5 psi. This pressure may be exerted by a single force member or may be the aggregate pressure from two or more force members. The force or pressure may be selected based on the type, size, location, or another suitable characteristic of the wound being treated.

In some embodiments, the suction device may be configured to generate a reduced pressure which may be generally characterized by the absolute pressure level and/or by a pressure level reduction relative to the atmospheric pressure. In some embodiments, the device is configured to generate a level of reduced pressure between 0 and 760 mmHg. In some embodiments, the generated amount of reduced pressure in the enclosure formed by the sealant layer and treatment site is more than 10 mmHg, 20 mmHg, 50 mmHg, 80 mmHg, 100 mmHg, 150 mmHg, 200 mmHg, 500 mmHg, 700 mmHg, or even 750 mmHg or more. The device may generate an absolute reduced pressure underneath the sealant layer where the reduced pressure is anywhere between 0 and 760 mmHg. In some embodiments, the generated level of reduced pressure in the enclosure formed by the sealant layer is less than 700 mmHg, sometimes less than 600 mmHg, other times less than 400 mmHg, or even less than 250 mmHg, 125 mmHg, 75 mmHg, 50 mmHg, less than 25 mmHg, or less than 10 mmHg. In some embodiments, the sealant layer generally follows the perimeter of the area of tissue being treated. The tissue therapy devices may have different collection chamber sizes which allow for treatment of larger, more exudative wounds while maintaining the smallest configuration possible for enhanced usage comfort. This may be particularly advantageous for small wounds or treatment sites, as a smaller reduced pressure source can be partially or fully integrated into the dressing or sealant layer. In some embodiments, the cavity of the suction device is 50 cc or less in volume, while in other embodiments, the cavity may be 100 cc in volume. In other embodiments, the collection chamber is less than 150 cc in volume. In some embodiments, the collection chamber is less than 200 cc in volume. In other embodiments, the collection chamber is smaller than 300 cc in volume. In some embodiments, the collection chamber is less than 500 cc in volume. In other embodiments, the collection chamber is less than 1000 cc in volume. In other embodiments, the cavity of the suction device may be at least 50 cc, 100 cc, 150 cc, 200 cc, 300 cc, 500 cc or 1000 cc or more.

Figure 25A:
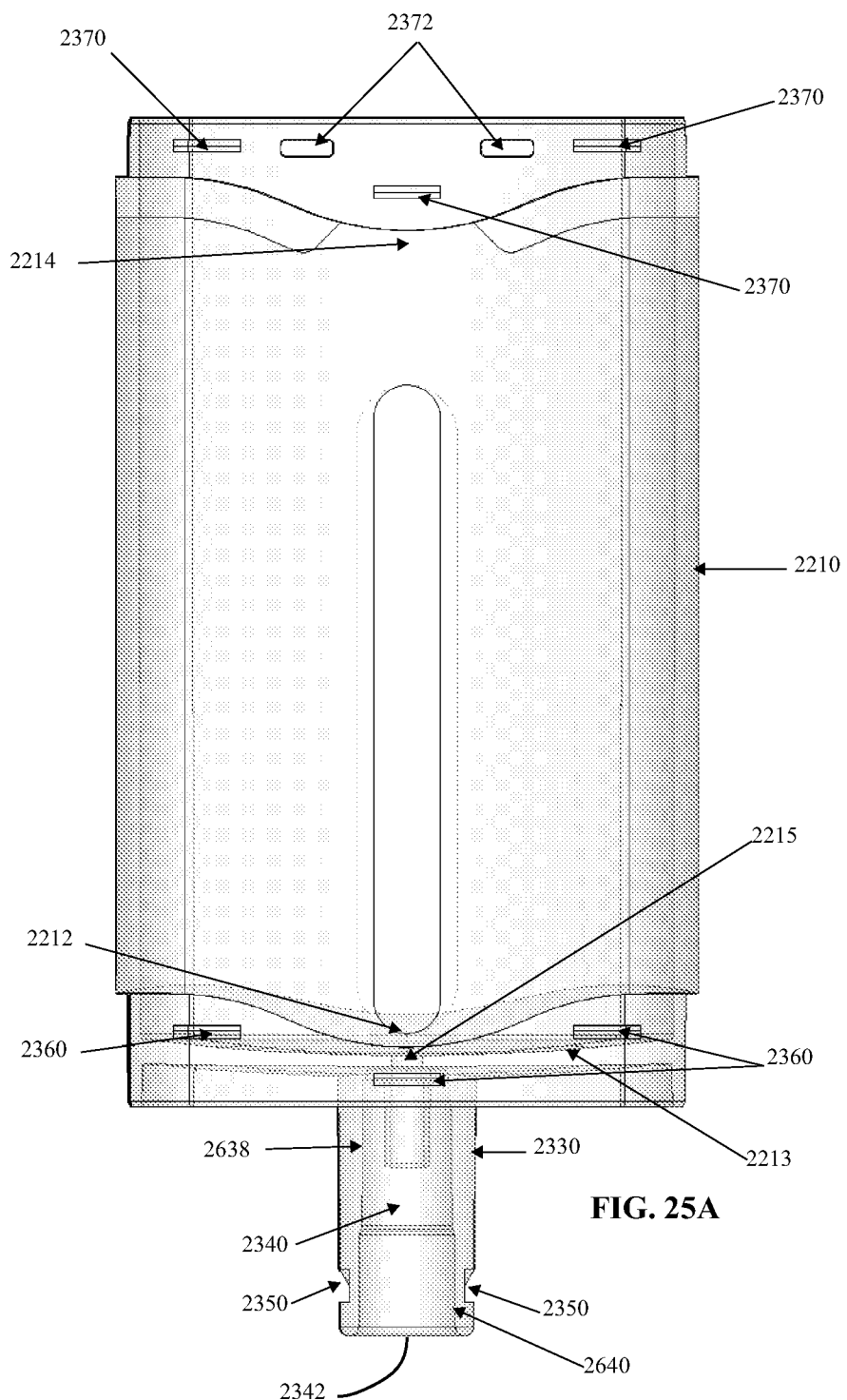
FIG. 25A is a superior elevational view of the suction chamber.
Figure 25B:
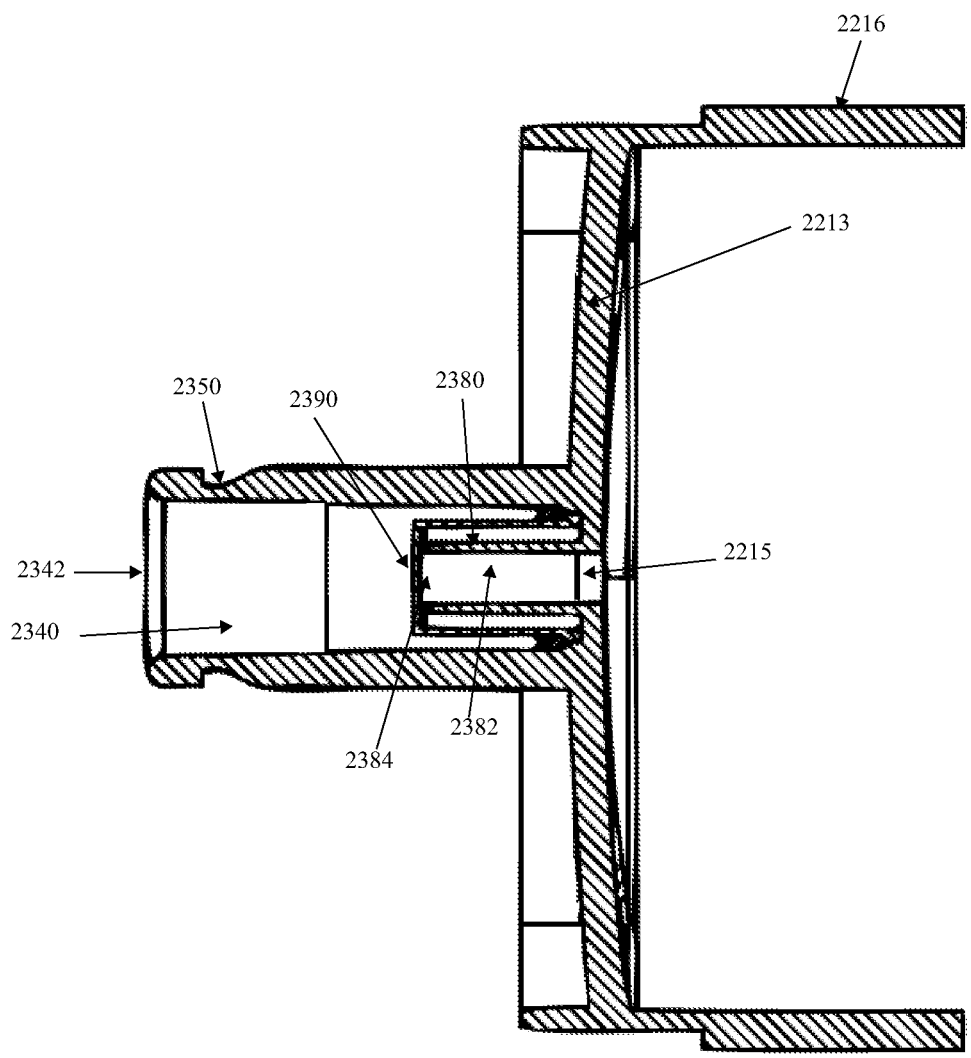
FIG. 25B is a cross-sectional view of the distal end of the suction chamber.

To convey negative pressure to a desired tissue region, a suction device may comprise a distal port with a conduit lumen. For example, FIG. 25A provides a detailed superior view of the suction chamber 2210 and FIG. 25B provides a cross-sectional view of the distal portion of the suction chamber 2210 from FIG. 25A. The distal end wall 2213 of the suction chamber 2210 may further comprise a distal opening to permit communication with the suction chamber. The distal end wall 2213 of the suction chamber 2210 may further comprise a conduit 2330 or other extension structure. The conduit 2330 comprises a conduit lumen 2340 with a conduit opening 2342 which are in fluid communication with the collection chamber 2310 of the suction chamber via the distal opening 2215 of the distal end wall 2213. The conduit 2330 may comprise any of a variety of notches 2350, grooves or flanges, which may facilitate attachment of the conduit 2330 to one or more components associated with the fitting housing 2240.

Although a user-controlled valve may be provided in some embodiments to open or close fluid communication with the suction chamber, in some examples, the fluid communication may be controlled automatically by the coupling and/or decoupling of the device components. For example, the conduit 2330 of the device 2200 may also comprise an inner conduit 2380 located in the main conduit lumen 2340, the inner conduit 2380 comprising an inner conduit lumen 2382 and an inner conduit opening 2384. Referring to FIG. 25B, a chamber slit seal 2390 may be located about the inner conduit opening 2384. In its base configuration, the chamber slit seal 2390 may be configured with a normally closed configuration to block fluid communication through the conduit 2330. In some examples, a chamber slit seal 2390 may be opened by inserting a structure through the seal to deform it and maintain the patency of the opening formed in the seal. As will be explained in greater detail below, in other examples, such as the slit seal 2390 in FIG. 25B, the slit seal 2390 may be configured to be pushed over, around, and/or down toward the base of the inner conduit 2380 when a complementary structure is inserted into the main conduit lumen 2340.

Figure 26A:
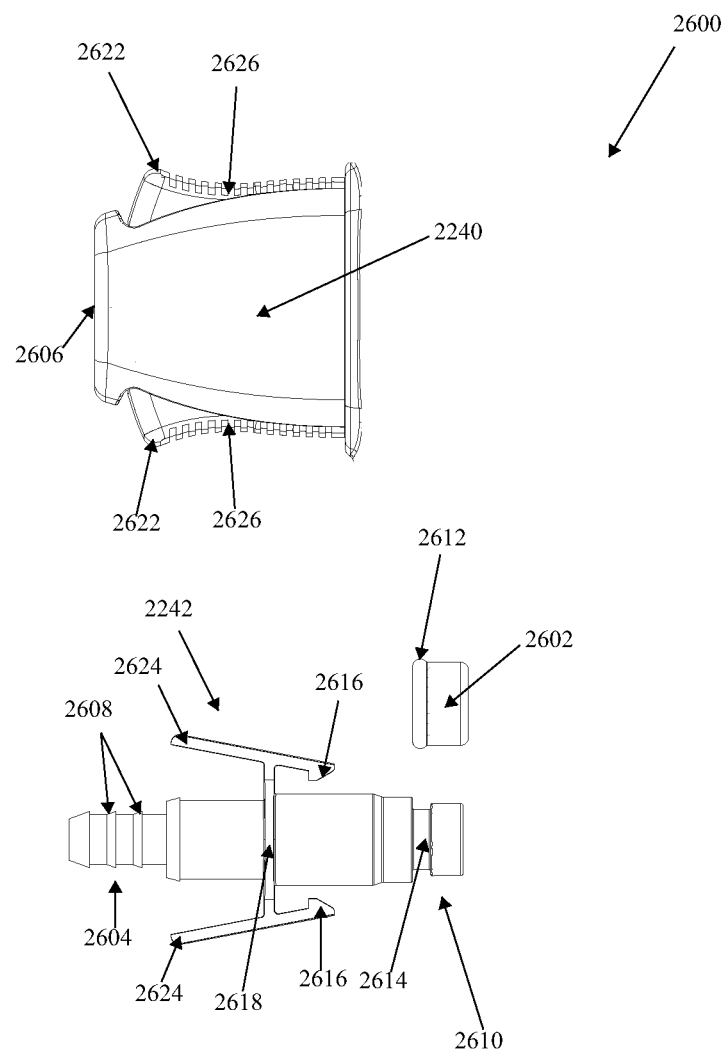
FIG. 26A is a component view of a fitting assembly.

FIG. 26A is a top component view of a fitting assembly 2600, comprising the fitting housing 2240, a distal port 2242 and a fitting slit seal 2602. As mentioned previously, the fitting housing 2240 may be configured to permanently or detachably couple to the distal cap 2220 of the device 2200, or may be integrally formed with the distal cap. In the embodiment shown in FIG. 26A, fitting 2610 comprises a connector section 2604 that is accessible through an opening 2606 in the fitting housing 2240 and permits a complementary fit with the connector of another component. For example, connector section 2604 may be coupled to a connector of an extension tube or the attachment port of a sealing layer with a snap fit or an interference fit. In the specific example in FIG. 26A, the connector section 2604 comprises multiple flanges 2608 which may be used to provide a resistance fit with tubing, but may also be used with a complementary connector to form a complementary interfit.

Figure 26B:
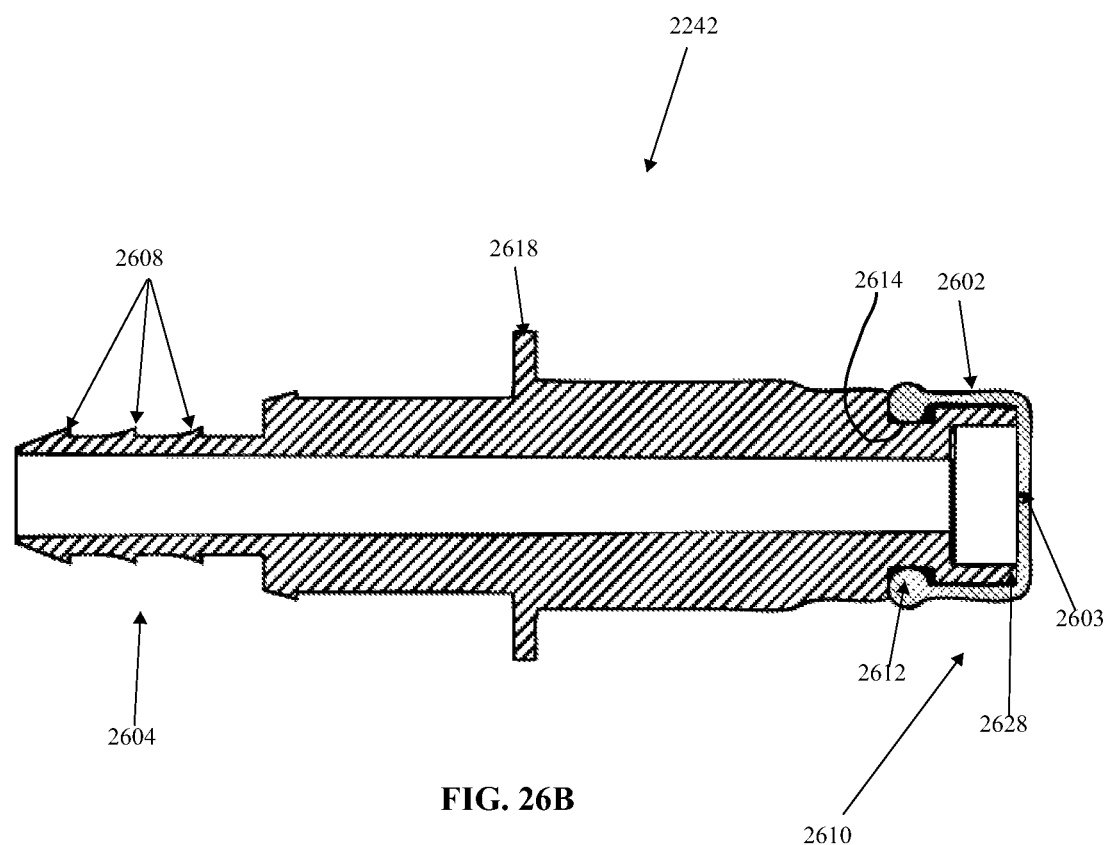
FIG. 26B is a cross-sectional view of the fitting of the fitting assembly from FIG. 26A.

Referring to FIGS. 26A and 26B, the distal port 2242 may also comprise a chamber connector 2610 with a fitting slit seal 2602. When the device is assembles, the chamber connector 2610 may be located within the distal cap 2220 of the device 2200, but the particular location may vary with the particular embodiment. The fitting slit seal 2602 may comprise a distal ring 2612 with an inner profile configured to engage a groove 2614 on the chamber connector 2610 of the distal port 2242. The outer profile of the seal 2602 and/or the distal ring 2612 may be configured to seal against the inner surface main conduit lumen 2340. The fitting slit seal 2602 may also comprise a slit that provides a deformable passageway through the seal 2602. Thus, in some embodiments, the fitting slit seal 2602 may be configured to both form an airtight seal between the chamber connector 2610 and the conduit lumen 2340 of the suction chamber 2210 and also to control fluid communication through the fitting assembly 2600. FIG. 26B illustrates a side cross sectional view of fitting 2610 coupled to the fitting slit seal 2612 at the fitting's proximal end.

Referring back to FIG. 26A, fitting assembly 2600 may also comprise an interlocking structure that comprises at least one resilient tab 2616 that is disposed on and project outwardly from a base member 2618 coupled or integrally formed with the distal port 2242. When the fitting assembly 2600 is coupled to the suction chamber 2210, the tabs 2616 are configured to engage complementary recesses (2350 in FIGS. 25A and 25B) on the conduit 2330 of the suction chamber 2210. An interlocking mechanism may resist or prevents inadvertent decoupling of the distal port 2242 from the suction chamber 2210. The fitting housing 2240 may further comprise one or more release structures or buttons 2622 that are coupled to or interface with the levers 2624 of the projecting tabs 2618. Depressing the buttons 2622 will release the interlocking mechanism by displacing the tabs 2616 from the notches 2350 on the suction chamber 2210 and permit decoupling of the distal port 2242 and fitting housing 2240 from the distal cap 2220 and the suction chamber conduit 2330. The release buttons 2622 may comprise one or more textured gripping surfaces 2626 that may facilitate manual connection or disconnection of the distal port 2242.

Figure 27A:
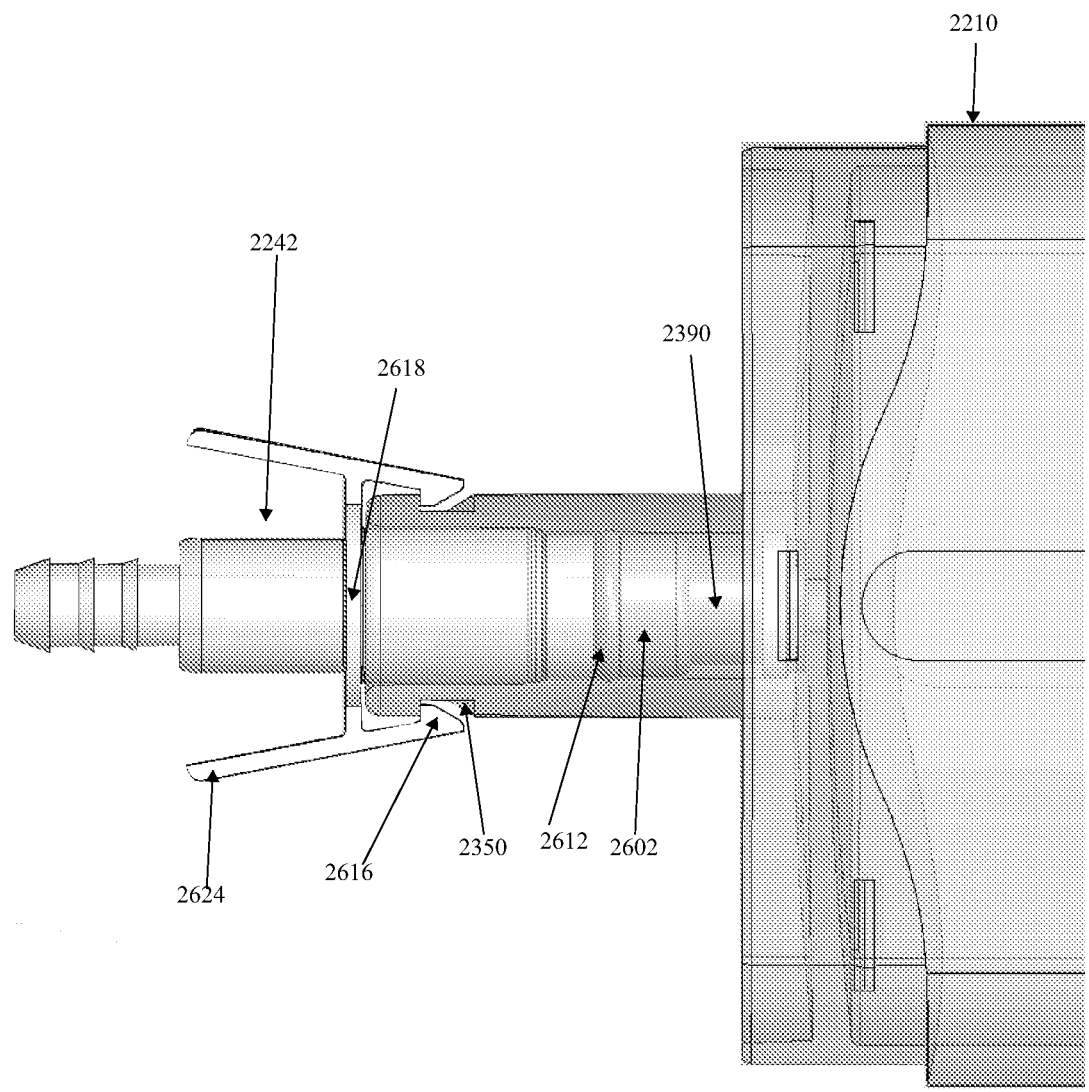
FIG. 27A is a schematic cut-away view of one embodiment of a connecting mechanism between a fitting and a suction chamber connector.
Figures 27B, 27C:
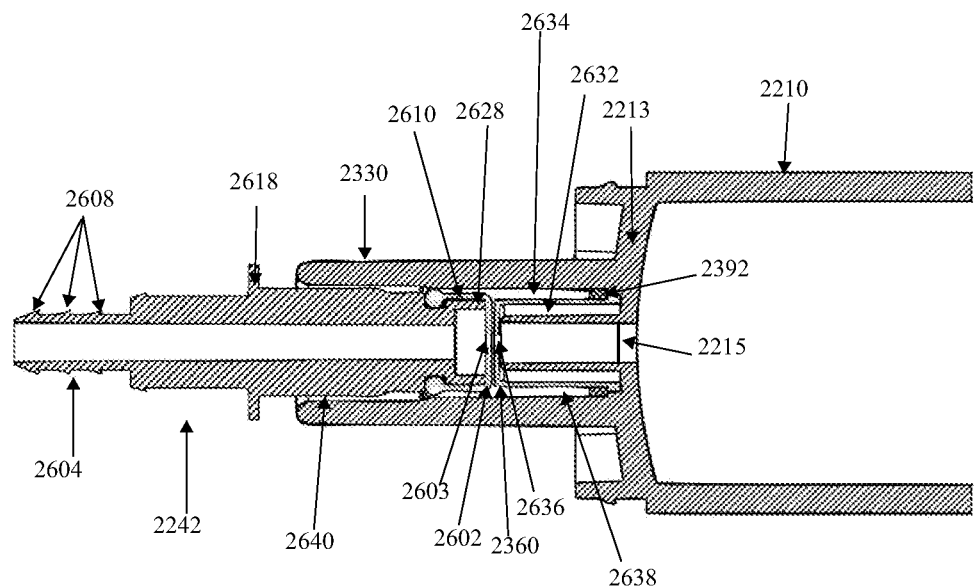
FIGS. 27B and 27C are cross-sectional views of the connecting mechanism from FIG. 27A.

FIG. 27A is a schematic superior cut-away view of the suction chamber 2210 and the distal port 2242 of the fitting assembly 2600 when the distal port 2242 is fully inserted into the conduit 2330. As illustrated, the tabs 2616 projecting from the base member 2618 of the distal port 2242 form an interfit with the notches 2350 on the surface of the suction chamber conduit 2330. FIGS. 27B and 27C are side cross sectional views of a portion of the suction chamber 2210 and the distal port 2242, before and after the distal port 2242 has been fully seated into the conduit 2330. FIGS. 27B and 27C further illustrate the connecting mechanism between chamber slit seal 2390 on the inner conduit 2380 and fitting slit seal 2602 of the distal port 2242. In FIG. 27B, when distal port 2242 is inserted into the conduit 2330, the fitting slit seal 2602 initially contacts chamber slit seal 2390, which is mounted on a seal base 2392. As illustrated in FIG. 27C, further insertion causes the edge 2628 of the chamber connector 2610 to exert a force along the perimeter 2660 of the chamber slit seal 2390. An inner gap 2632 and/or an outer gap 2634 about the chamber slit seal 2390 provide space for the chamber slit seal 2390 to deform or compress away from the edge 2628 of the chamber connector 2610. This results in the enlargement of the opening or slit 2636 of the chamber slit seal 2390 as it is pushed proximally away from the inner conduit opening 2384. In some examples, the inner and outer gaps 2632 2634 may also reduce the frictional resistance of the chamber slit seal 2390 against the inner conduit 2380 or the surface of the conduit lumen 2340, respectively. As the distal port 2242 is further inserted into the conduit lumen 2340, the exposed inner conduit 2380 penetrates through the slit 2603 of the fitting slit seal 2602, thereby opening fluid communication from the suction chamber 2210, through the distal opening 2215 of the suction chamber 2210, through the inner conduit 2380 and through the distal port 2242. In the embodiment depicted in FIGS. 27A to 27C, the tabs 2616 and the notches 2350 of the locking mechanism may be used to provide rotational alignment of the between the fitting slit seal 2602 and the chamber slit seal 2390, if needed. This may be useful where the slits of the seals 2602 and 2390 are single linear slits. In other configurations where the slits are multiple radial slits, rotational alignment may or may not affect the patency of the fluid communication.

When distal port 2242 is decoupled from the suction chamber conduit 2330, of the withdrawal of the inner conduit 2380 from the fitting slit seal 2602 results in closure of the fluid passageways to the sealed wound and may limit air entry into the wound during decoupling. As the distal port 2242 is further separated, the edge 2628 of the chamber connector 2610 is withdrawn and the chamber slit seal 2380 is able to elastically revert back to a closed position to seal the suction chamber 2210. In some embodiments, chamber slit seal 2380 is able to elastically revert back to a closed position with the aid of a coaxially mounted coil spring. Although both seals 2602 and 2390 are closed, the outer surface of the fitting slit seal 2602 continues to form a seal with the conduit lumen 2340 until further separation occurs. As may be seen in FIGS. 27B and 27C, the conduit lumen 2340 of suction chamber 2210 has a non-uniform diameter along it longitudinal length, and may comprise a proximal segment 2638 having a reduced diameter relative to the distal segment 2640. The transition in diameter between the proximal and distal segments 2638 and 2640 may be gradual or stepped. The conduit lumen 2340, for example, comprises at least one step transition region 2642 between the segments 2638 and 2640. In some examples, step transition region may provide different tactile feedback compared to gradual transitions.

The slit seal may be fluid impervious and may be fabricated from any of suitable resilient materials, such as, but not limited to, synthetic elastomer, silicone rubber, or natural rubber. The seal material may be compatible with wound exudates that may be collected by the suction chamber during a reduced pressure treatment. The seal material may be sterilized by treatment of radiation, steam, ethylene oxide or other suitable techniques known to those skilled in the art.

Figures 28A, 29A:
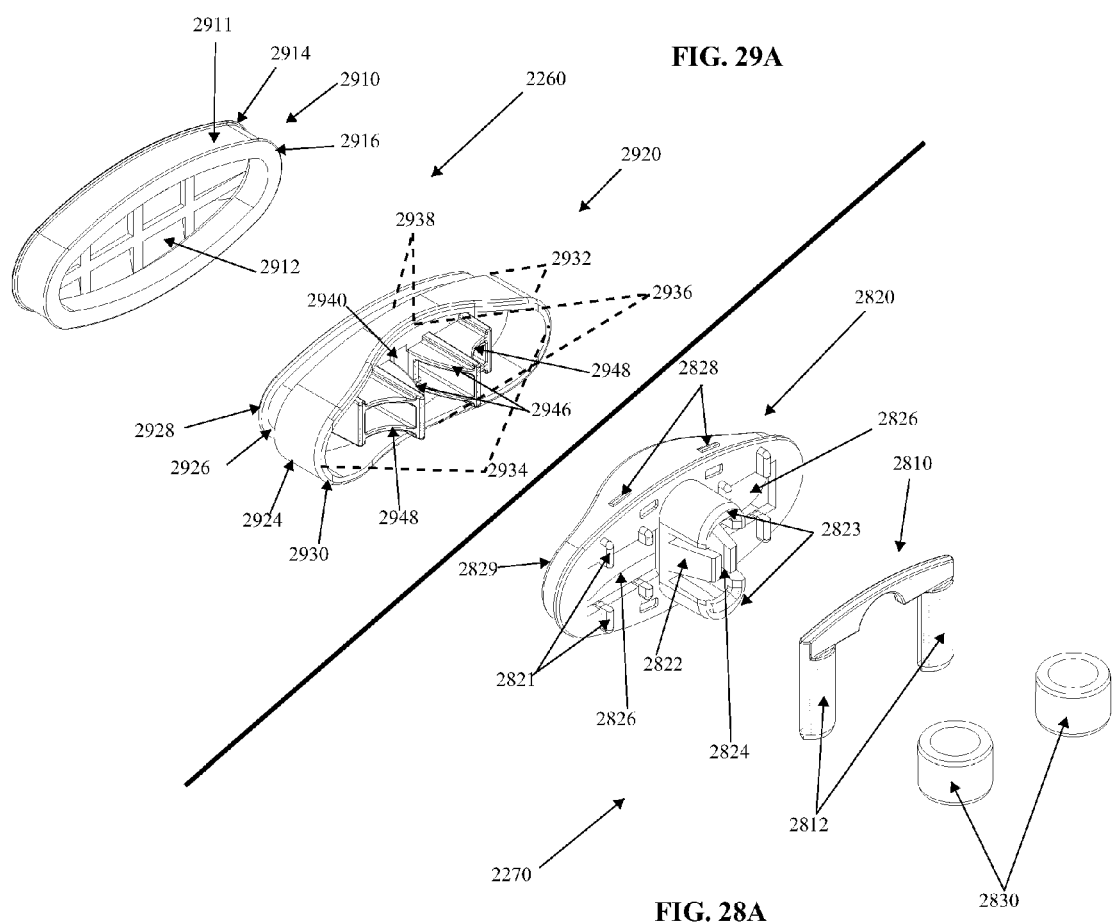

Turning to FIGS. 28A and 28B now, the spring assembly 2270, which is mounted at the proximal end of the suction chamber and covered by the chamber proximal cap, comprises a spring carrier 2820 and a U-shaped spring retainer 2810 containing two bushings 2830 mounted on the two vertical rails 2812 of the spring retainer 2810. Two substantially constant force springs (not shown in this figure) may each comprise a coiled body coupled to and wrapped around bushing 2830 and a free end distally extended and attached to the sliding seal assembly. The springs may or may not be constant force springs. The spring attachment mechanism will be discussed in greater detail below. The spring carrier 2820 comprises a central opening 2824 and two side openings 2826. The central opening 2824 is configured to permit passage of the activation tool to access and displace the sliding seal assembly. The side openings 2826 are configured to house the bushings 2830 and the springs when the spring retainer 2810 is coupled to the spring carrier 2820. As shown in this figure, multiple ridges 2821 may be located adjacent the side openings 2826 to limit the movement of the bushings 2830 and springs coiled around bushings 2830, thereby reducing deflections or deformations of the springs during operation of the suction device. The spring carrier 2820 may also comprise resilient tabs 2822 that may slidably engage one or more grooves on the activation tool shaft, which may reduce angular deviations of the activation tool with respect to the longitudinal movement axis of the seal. The spring carrier 2820 may also comprises two interlocking structures 2823 configured to releasably lock the activation tool in place after the suction device is primed. The interlocking mechanism will be described in detail later. Fixation structures 2828 may be provided to form a snapfit or other type of interfit with complementary structures on the suction chamber.

FIGS. 29A and 29B are component views of the sliding seal assembly 2260 that comprises a piston seal 2910 and a piston 2920. The sliding seal assembly 2260 may be configured to traverse between the distal end and the proximal end of the suction chamber while maintaining a substantially airtight seal. As mentioned previously, the sliding seal assembly 2260 provides an airtight separation the suction chamber between a collection chamber and a working chamber. In the depicted embodiment, the piston seal 2910 has a non-circular, elliptical cross-sectional shape with respect to its movement axis in the suction chamber, but in other embodiments, other shapes as described herein may be used. The piston seal 2910 may comprise a side wall 2911 and a distal end wall 2912. The side wall 2911 of the piston seal 2910 further comprises a distal perimeter ridge 2914 and a proximal perimeter ridge 2916, the dimensions of which may be larger than that of the side wall 2911 of piston seal 2910. The ridges 2914 and 2916 may be configured to be in a sliding contact with the interior surface of the suction chamber. They may provide a sealed contact while limiting sliding friction. The exterior surfaces of the piston seal and/or the interior surfaces of the suction chamber may comprise a friction-reducing lubricant or a lubricious coating material.

The piston seal 2910 may be detachably coupled to the piston 2920 or in some embodiments, the piston seal 2910 and the piston 2910 may be integrally formed. In the depicted embodiment, the piston 2920 may comprise an elliptical frame with a side wall 2924. The distal portion of side wall 2924 may comprise a recess 2926 and a raised edge or flange 2928 configured form a complementary interfit with the piston seal 2910. The proximal perimeter edge 2930 of side wall 2924 may have a complementary shape to the distal edge 2829 of the spring carrier 2820. In the depicted embodiment, both the proximal edge 2930 of the piston side wall 2924 and the distal perimeter edge 2829 of the spring carrier have a curved, non-planar configuration. As mentioned previously, the seal and/or seal mount (e.g. piston 2920) may have a variable longitudinal length along its perimeter. In some instances, an increased longitudinal dimension may provide additional stability to the seal along a dimension of the seal. In some examples, the side length along a section of the perimeter of the piston 2920 may be related to the transverse dimension intersecting a) that side length of the perimeter and b) the central movement axis of the seal and/or piston. In the example in FIG. 29A, the lateral longitudinal surface of the piston 2920 may have a longitudinal length 2932, based upon the increased width 2934 of the piston 2920 relative to the height 2936 of the suction chamber 2210 (corresponding to the increased width and reduced height of the suction chamber 2210). In comparison, the superior longitudinal surface of the piston 2920 may have a longitudinal length 2938 that is smaller than the longitudinal length 2932 of the lateral longitudinal surface from the reduced height 2936 of the piston 2920.

Figure 29C:
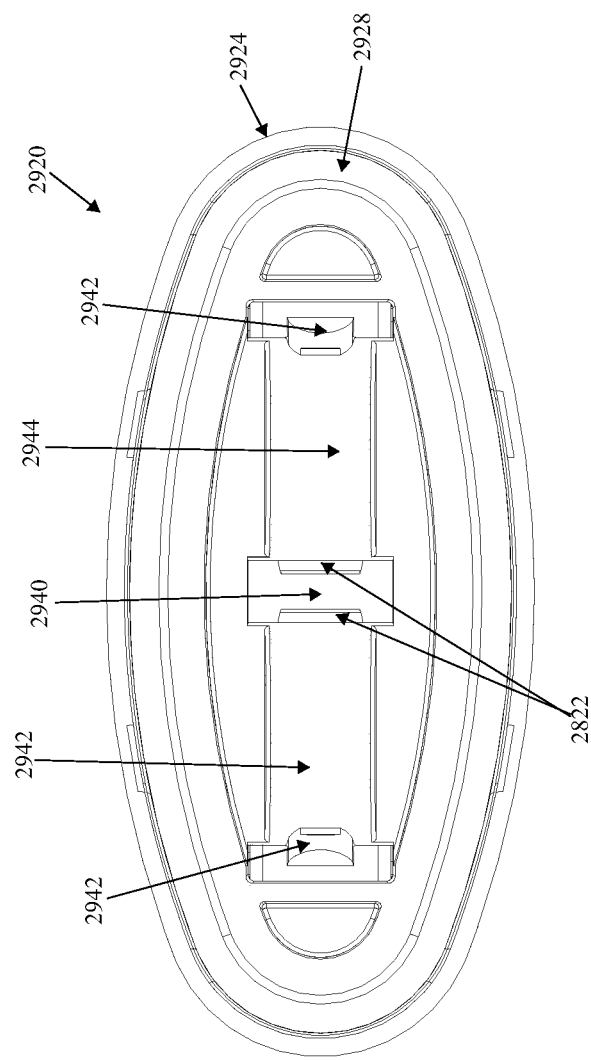
FIG. 29C is a front elevational view of the sliding seal assembly.
Figure 30:
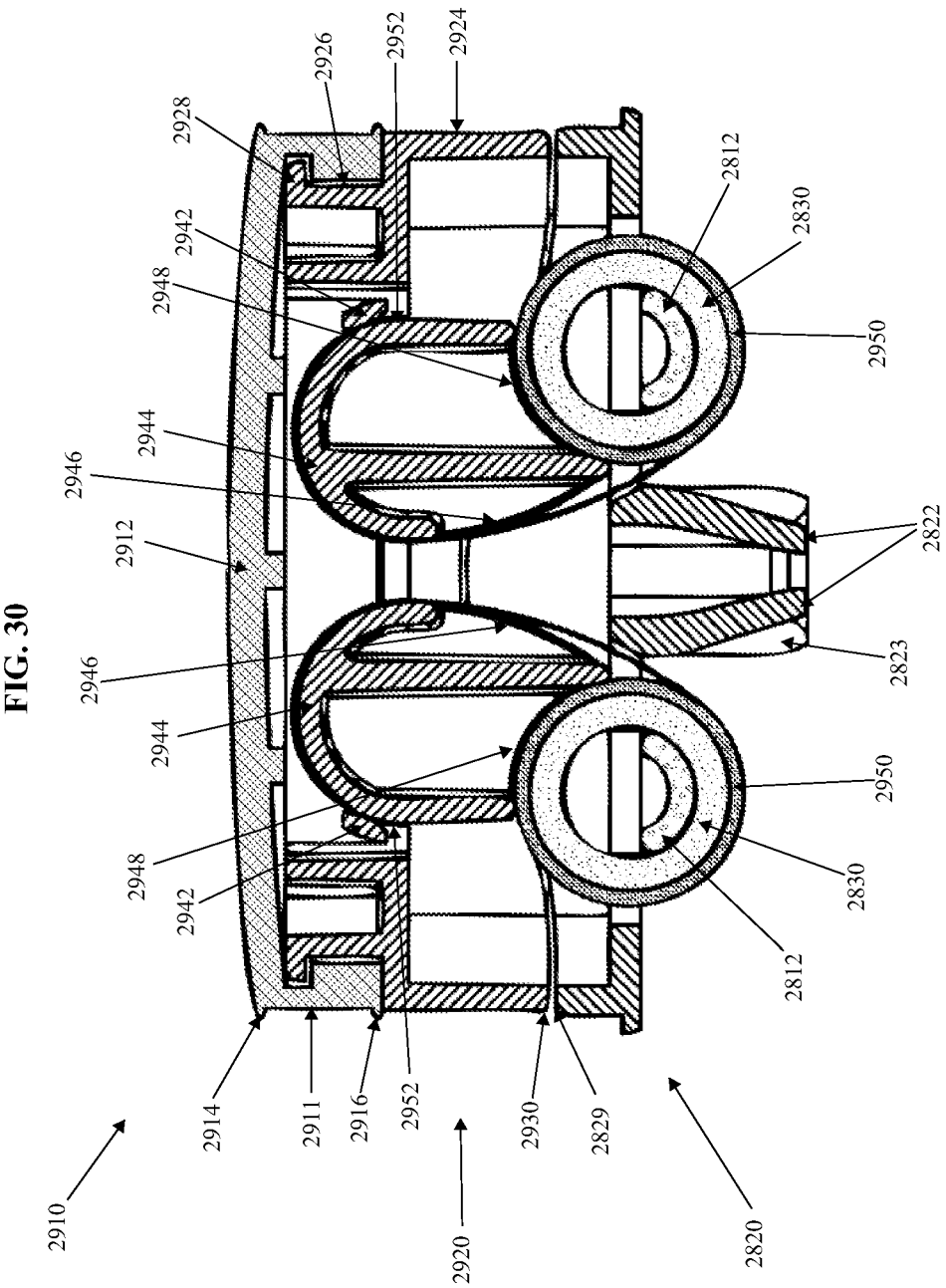
FIG. 30 is a cross sectional view of one embodiment of a sliding seal assembly coupled to a spring assembly.

Referring to FIGS. 29A, 29B and 30, the piston 2920 may also comprise a central opening 2940 which may be aligned with the central opening 2824 of spring carrier 2820. The piston central opening 2940 may be configured to provide passage of the distal ends of the constant force springs. FIG. 29C provides a frontal elevational view of the piston 2920. The distal regions 2952 of the constant force springs 2950 (depicted only in FIG. 30) may extend through the central opening 2940 and are coupled to a pair of spring retaining structures 2942 disposed on the front surface of piston 2920. In this particular embodiment, the retaining structures 2942 are configured to be inserted into apertures provided on the springs and may or may not maintain their coupling using residual spring force that may be present in the springs in the retracted configuration. The retaining structure and the springs may have any of a variety of other coupling configurations, however (e.g. the retaining structures may comprise posts which block displacement of T-shaped spring ends). Between the central opening 2940 and the retaining structures 2942 are curved support surfaces 2944 which are configured to push against the springs. In some examples, the length of the curved support surfaces 2944 between the central opening 2940 and the retaining structures 2930 may be at least one or one and a half times the width of the springs, while in other examples may be two or three times or four times the width of the springs. In some examples, the curved support surfaces 2944 provide a substantial surface area to distribute the pushing forces and may reduce the risk of damage to the springs. Referring back to FIG. 29A, the piston 2920 may further comprise convex supports 2946 adjacent to the central opening 2940, which may also support the springs as the springs converge into the central opening 2940. The convex supports 2946 may have a curved length of at least about the width of the springs, but in other examples may be at least two or three times the width of the springs. Referring to FIGS. 29A and 30, the convex supports 2926 may also comprise a concave region 2948, which may accommodate the coils of the spring and the spring carriers 2830 when the sliding seal assembly 2260 is in a retracted configuration. Although the sliding seal assembly 2260 and the spring assembly 2270 depicted in FIGS. 28A to 29B utilized two springs, in other examples, one spring, three springs, four springs, or five or more springs may be used. The number of springs, the type of springs, and the width and length of the springs may be varied, and in other examples, non-spring bias members may be used (e.g. sealed pneumatic shocks).

Figure 31A:
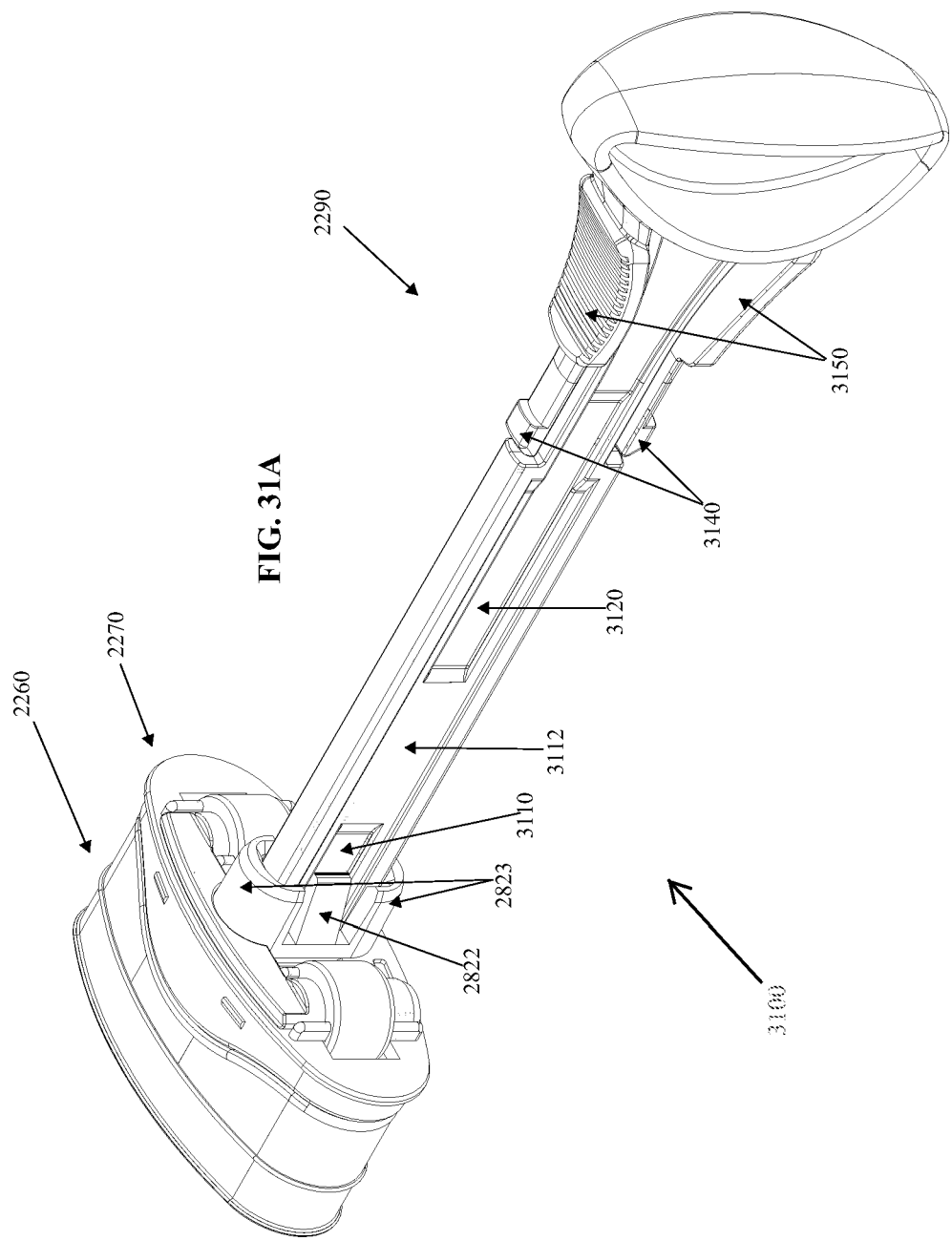
FIGS. 31A to 31C are schematic perspective views depicting one example of a priming procedure using a activation or priming tool.
Figure 31B:
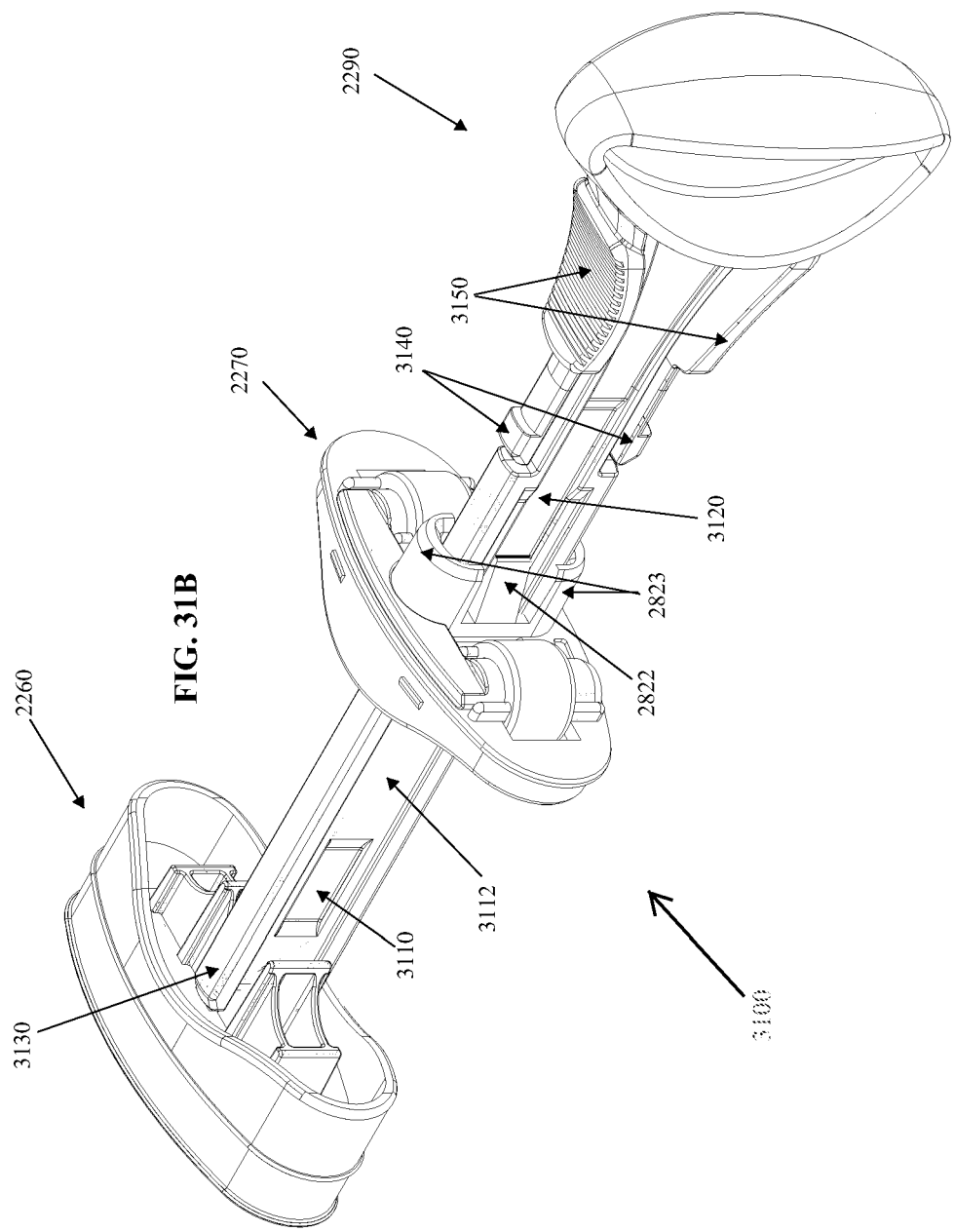
Figure 31C:
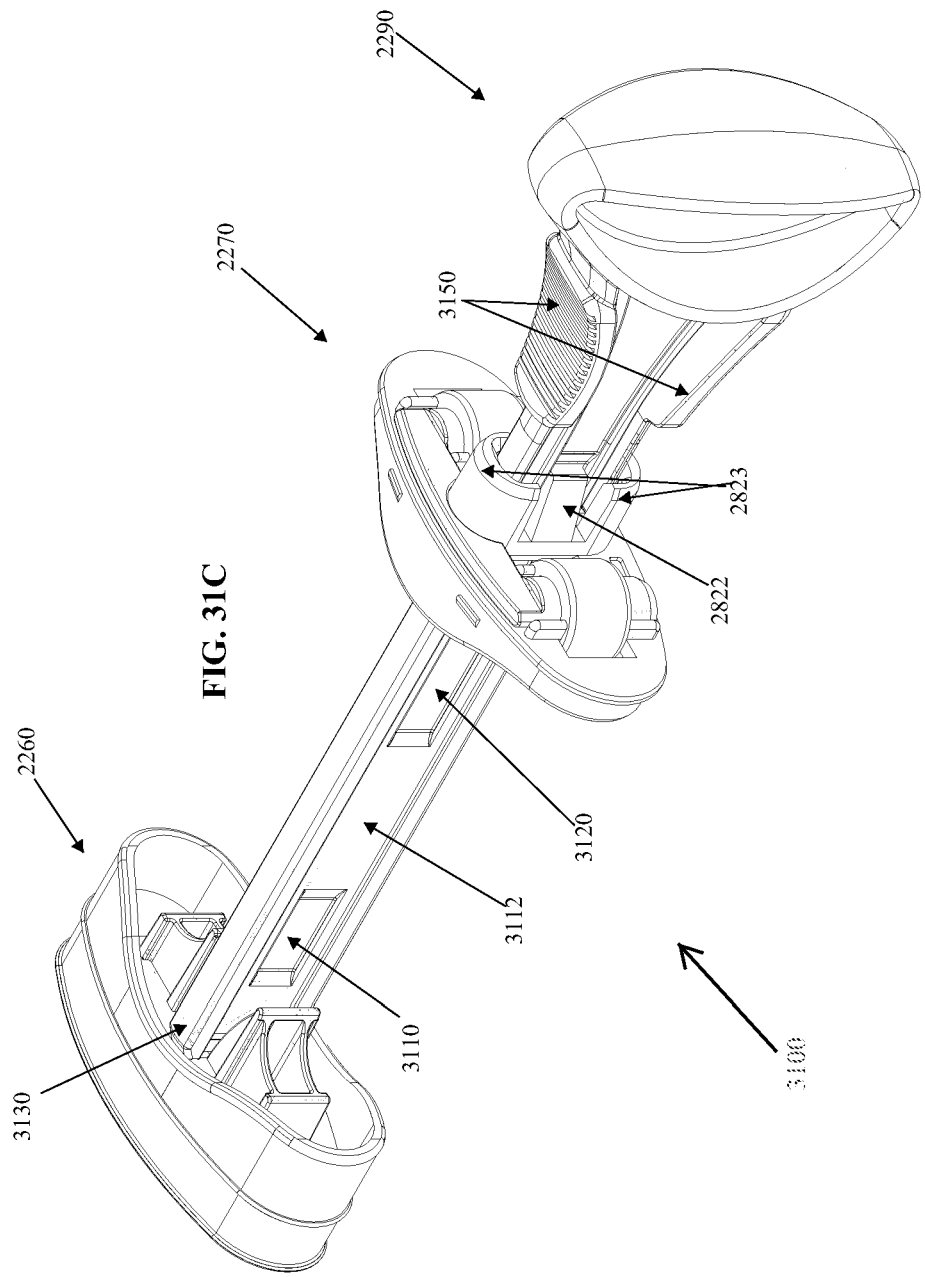

FIGS. 31A to 31C schematically illustrate one example of a priming procedure of the suction device 2200 with a activation tool 2290 from FIGS. 23A and 23B, where the springs have not been shown to better illustrate the interactions between the sliding seal assembly 2260, spring assembly 2270 and the activation tool 2290. The activation tool 2290 comprises a tool shaft 3100 with a distal recess 3110 and a proximal recess 3120 on each side of the shaft 3100. Located between the recesses 3110 and 3120 is a non-recessed portion 3112 of the shaft 3100. The distal end 3130 of the activation tool 2290 is has a cross sectional shape and size that is able to pass through the central opening 2824 of the spring assembly 2270 to contact the piston 2920 of the sliding seal assembly 2260. During the priming procedure, the activation tool 2290 may be pushed against the piston 2920 but is not configured to couple or attach to the piston 2920. In other embodiments, however, the distal end 3130 of the activation tool 2290 and the piston 2920 may be configured to form a complementary interlocking fit or interference fit. Before priming, the springs will pull and maintain the sliding seal assembly 2260 into a proximal or retracted position against the spring assembly 2270. As the activation tool 2290 is inserted into the suction device, the resilient tabs 2822 on the spring assembly 2270 will slidably engage the distal recess 3110 on the tool shaft 3100. As the activation tool 2290 is further inserted, the user may receive tactile feedback of increased resistance as the tabs 2822 are resiliently displaced out of the distal recesses 3110. Further insertion may provide additional tactile feedback from increased frictional resistance by the tabs 2822 against the non-recessed portion 3112 of the shaft 3100. As the activation tool 2290 is further inserted, the sliding seal assembly 2260 is separated from the spring assembly 2270 and the constant force springs or bias members attaching the assemblies 2260 and 2270 will elongate and generate potential energy. As sliding seal assembly 2260 is further displaced distally, the tabs 2822 will then engage the proximal recess 3120 on the prime tool shaft 3100. The position and length of the of the non-recessed portion 3112 and the recesses 3110 and 3120 of the shaft 3100 may be configured to provide the user with tactile feedback indication, or may be provided to resist ejection of the activation tool 2290 out of the suction device. For example, if the wound or fluid communication to the wound is incompletely sealed, or if there is an excessive volume of air or exudates the wound, upon activation of the suction device, the sliding seal assembly 2260 may retract suddenly. The non-recessed portion 3112 of the activation tool 2290 may provide at least partial retention of the tool 2290 so that the user can reprime the suction device. The recesses 3110 and 3120 may be configured with ramped proximal and distal surfaces movement of the tabs 2822 in and out of the recesses 3110 and 3120.

Upon full priming of the suction device, latches 3140 located on the prime tool shaft 3100 may engage the interlocking structures 2823 on the spring assembly 2270 to locks the activation tool 2290 into place, as depicted in FIG. 31C. The activation tool 2290 may be left in the locked configuration in the suction device, and may even be stored and/or distributed in a primed position. The locking mechanism also permits the suction device to be primed without requiring that the suction device be already coupled to the sealant layer. Thus, the user need not be concerned about uncoupling the suction device or unsealing the sealant layer during the priming procedure, and may handle or orient the suction device in any manner, e.g. abutting the connector surface of the suction device against a table or wall to provide leverage when pushing the priming tool.

To activate the primed suction device, the user may depress the release buttons 3150 located at the proximal end of the prime tool 2290. Pressing the release buttons 3150 disengage the latches disengages latches 3140 from the interlocking structures 2823, thereby permitting the removal of the activation tool 2290 out of the suction chamber. The release buttons 3150 may also comprise one or more textured gripping structures or materials to facilitate latch release. Although the embodiment depicts in FIGS. 31A to 31C comprises a activation tool 2290 with two latches 3140 and two release buttons 3150, in other embodiments, a different number latches and/or buttons may be provided, or a different configuration of a locking mechanism may be provided (e.g. a locking pin that may be inserted and removed by the user).

As described previously, once the activation tool 2290 is proximally withdrawn, the sliding seal assembly will be retracted by the charged constant force springs. Such movement will expand the combined volume of the space below the sliding seal assembly and the sealed wound enclosure, and reduce the pressure level therein. Where there has been an inadvertent leak in the system or excessive air or exudates in the wound, the activation tool 2290 may be used to reprime the device. In these embodiments, the method for using the suction device may further comprise resealing the wound and/or reseating one or more connectors of the reduced pressure therapy device, and repositioning the slidable seal or sliding seal assembly to the extended or primed position and reactivating the device.

In some embodiments, the method of treating an area of damaged tissue may comprise affixing a sealant layer around an area of tissue to be treated; creating a sealed enclosure around the area of the tissue with the sealant layer, inserting a collection chamber into a housing chamber and priming the collection chamber; creating a fluid communication between the collection chamber and the sealed wound enclosure; activating the collection chamber to create a reduced pressure level within the sealed wound enclosure; if the collection chamber is filled up with wound exudates, terminating the fluid communication between the collection chamber and the wound seal and releasing the collection chamber from the wound site; withdrawing the collection chamber from the housing chamber and replacing it with a new collection chamber; and repeating the steps as appropriate to continue a reduced pressure treatment.

EXAMPLE 1

Reduced Variation in Pressure with High Viscosity Lubricant

In this example, the use of a high-viscosity liquid lubricant is shown to reduce pressure fluctuations in the suction device with a simulated leak.

Cartridge A: A suction device (SNaP suction device), wherein a non-optimized lubricant (fluorosilicone; 100,000 cP) was used to reduce friction between the seal and inner surface of the suction chamber was primed. A simulated air leak of 3 cc/hour was introduced into the apparatus. A total of 50 cc of air was allowed into the suction chamber over a period of about 16.7 hours. The pressure was measured over the duration of the experiment.

Cartridge B: The same conditions described above were applied to a different suction device, wherein a lubricant of a higher viscosity (20:80 fluorosilicone/dimethylsilicone, 1,500,000 cP) was employed.

Figure 22:
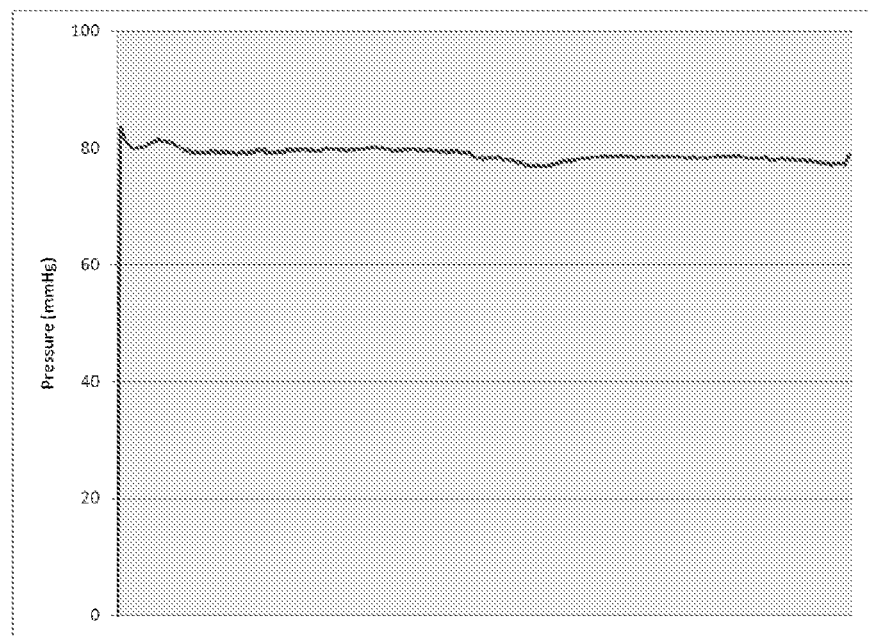
FIG. 22 is a plot of the measured pressure generated by the suction device over a period of 18 hours, wherein the device employs a high viscosity lubricant of 1,500,00 cP.

FIGS. 21 and 22 show the plots of the pressure over time for each of the apparatuses, respectively.

The pressure variation of cartridge A results in a saw tooth wave. The magnitude of peak-to-peak amplitude appears to range from about 15 to over 25 mmHg, with the majority of peak-to-peak difference of over 20 mmHg. In contrast, the peak-to-peak amplitude is significantly reduced in cartridge B at the observed resolution, resulting in a smoother line. Although there is overall variations in pressure, the peak-to-peak amplitude appears to be less than or close to 1 mmHg. Thus, the higher viscosity lubricant in cartridge B was more effective in reducing the frictional resistance of the sealing surfaces (the surface of the seal lips in contact with the chamber wall surfaces), resulting in a reduced pressure that is characterized by a tighter, narrower tolerance.

EXAMPLE 2

Seal to Seal Mount Configuration

This example provides a description of a free-floating sliding seal that can accommodate radial compression from narrowing of the inner diameter of the chamber. FIG. 23 is a cross-sectional view of a seal assembly positioned within the suction chamber. The elastomer seal is supported by a seal mount. A gap exists between the portion of the seal closer to the chamber wall and structures of the seal mount. As the inner dimensions of the chamber narrows, the walls of the chamber applies a force to the contact areas of the sliding seal, which in turn are displaced into the small gap. The gap, therefore, absorbs deformation of the sliding seal and any increase in frictional resistance between the seal lips and the chamber wall is reduced. If instead the design incorporated a line-to-line fit between the sliding seal inner surface and seal mount, upon narrowing of the chamber, the seal lips would exert a force against the chamber wall and the frictional force would increase.

EXAMPLE 3

Modified Bushing-Spring Assembly

This example describes a modified bushing design which reduces rotational resistance variations in the spring.

Another factor which hinders the ability to deliver constant pressure throughout the length of the seal travel relates to the construction of the springs. Ribbon springs are constructed from thin strips of metal, such as 301 Stainless steel, which are coiled tightly. The springs extend by unwinding, and as they are unwound, their coiled state provides resistance. Because the local geometry at the point of unwinding remains relatively unchanged regardless of the length of spring that has been unwound, the resistance, and therefore force, remains constant. If, on the other hand, the local geometry was disturbed, the resistance of the spring and subsequently the force it exerts changes.

Figure 24A:
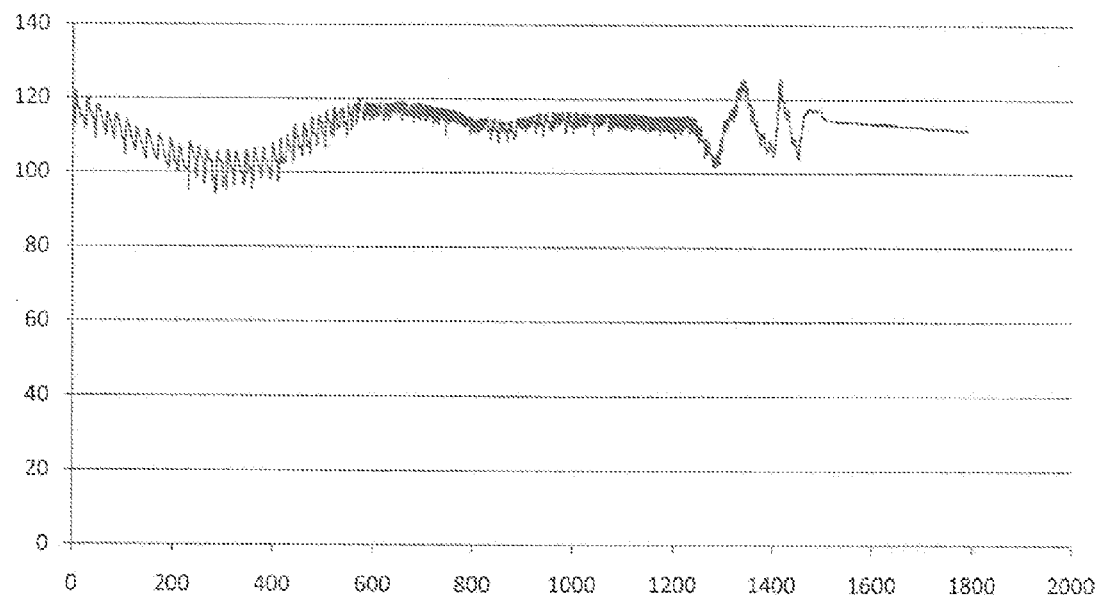
FIG. 24A is a plot of the pressure exerted by a suction device with a simulated leak of 9 mL/hr over a period of 3 hours.

Because of the coiled construction of the ribbon spring, there will always be one end of the spring which will be present on the inside diameter of the coil. The unwinding, and therefore extension of the springs causes rotational motion of the coil, which can be modulated by a radial bushing or bearing surface. The load of the spring is born by the upper half of the bearing surface, regardless of the rotational position of the spring coil. As the spring coil rotates, at some point the interior end of the ribbon spring will transition from the non load-bearing area to the load-bearing area. Because of the additional thickness of the spring end, subsequent layers of spring on top of the spring end are slightly deformed. Thus, the local geometry in that region is different from the other points around the circumference of the coiled spring. The slight deformation results in additional resistance to rotation at the transition point, resulting in a drop in the force exerted and a reduction of negative pressure in the system. The drop in negative pressure corresponds to a trough observed in FIG. 22 as well as in FIG. 24A around 300 minutes.

The additional resistance of rotation when the interior spring end transitions from non-load bearing to the load-bearing area can be mitigated by reducing or eliminating the thickness introduced by the interior spring end. The exterior diameter of a bushing is configured with an indentation which accepts the interior end of the springs. This indentation can be a notch, cut-out or other depression which accommodates the thickness of the spring end. As the interior end of the springs reaches the transition point from non-load bearing area to load-bearing area, no additional thickness is introduced because the spring end surface is flush with the bushing surface, and the force trough is mitigated.

Figures 24B, 24C:
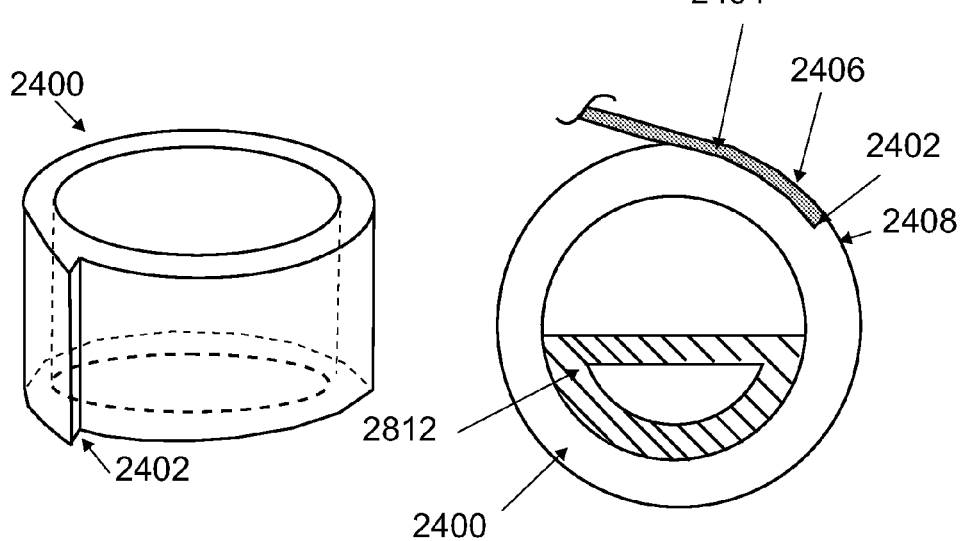
FIG. 24B is a perspective drawing of a bushing comprising an axial indentation in the outer surface of the bushing.
FIG. 24C is a cross-sectional view of the bushing-spring assembly.

FIG. 24B and is a perspective drawing of a bushing 2400. The indentation 2402 has a depth corresponding to approximately the thickness of the spring. FIG. 24C shows a cross sectional view of the bushing 2400 mounted on the vertical rails 2812 of the spring retainer 2810 in FIG. 28A, for example. The section of the bushing 2400 shown has an indentation 2402, the depth of the indentation 2402 corresponds to the thickness of the spring ribbon 2404, which is the darkened area, such that the top surface 2406 of the ribbon 2404 is approximately flush with the adjacent outer surface 2408 of the bushing 2400.

EXAMPLE 4

Comparison of Lubricant Performance in Suction Device

This example compares the difference in pressure performance of different viscosity lubricants in a suction device with and without introduced leaks.

Figure 32:
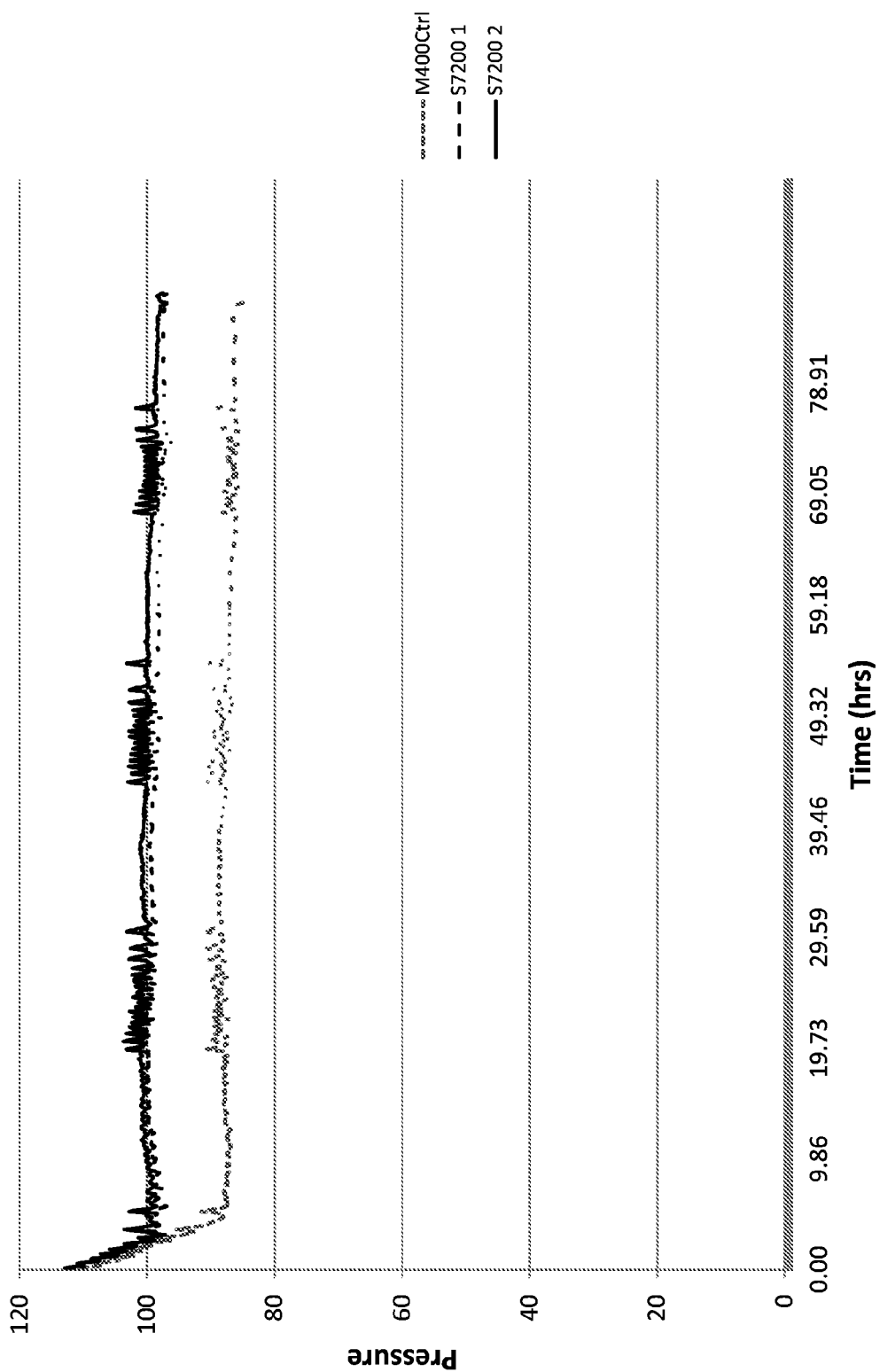
FIG. 32 is a plot comparing pressure exerted by low and high viscosity lubricated devices over a time period of 4 days.

FIG. 32 is a graph which shows the plots the pressure exerted by the suction device against a time period of over 4 days without any leaks into the system. The top two traces represent units that are lubricated with a 20/80% fluorosilicone/dimethyl silicone mixture having a viscosity of 1,500,000 cP (e.g., a 20 Mol. % fluorosilicone fluid from Nusil Technologies, Carpinteria, CSM-420-7). The bottom traces, shows the unit employing a lubricant having a viscosity of 100,000 cP.

A constant pressure of about 100 mmHg is maintained in the apparatuses employing the higher viscosity lubricant. The effect of the lower viscosity lubricant results in over a 10 mmHg reduction in the average pressure.

EXAMPLE 5

Biohazard Containment Assembly

Figure 33A:
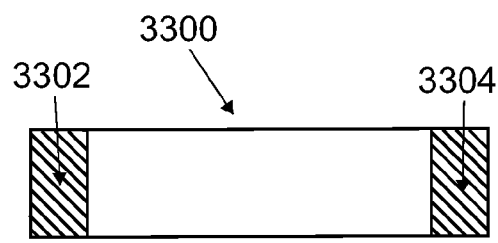
FIGS. 33A and 33B are schematic front and back elevational views of a liquid permeable pouch containing superabsorbent materials.
Figure 33B:
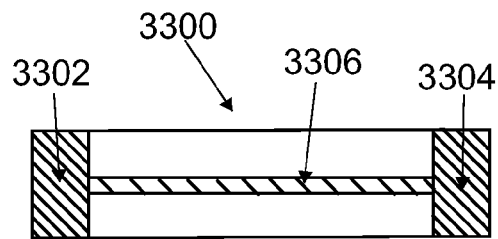
Figure 34A:
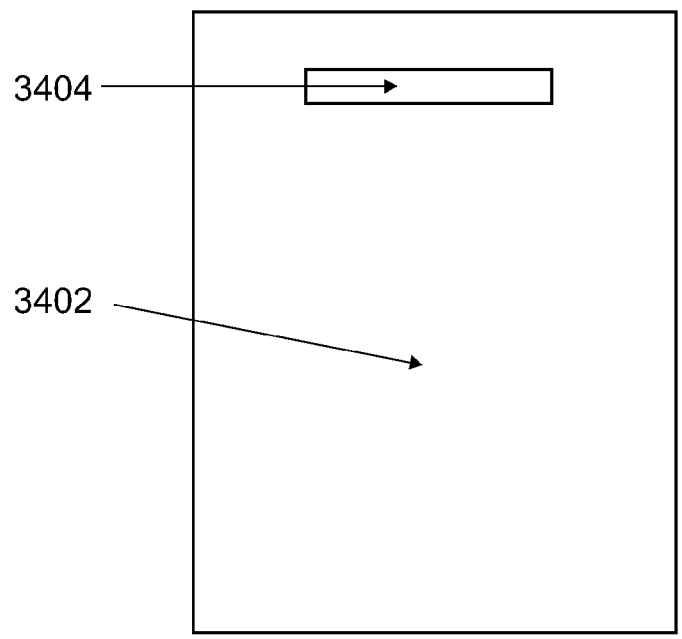
FIG. 34A is a schematic illustration of a first layer of material with an opening cut out of the layer, wherein the opening is smaller than the profile of the pouch.
Figure 34B:
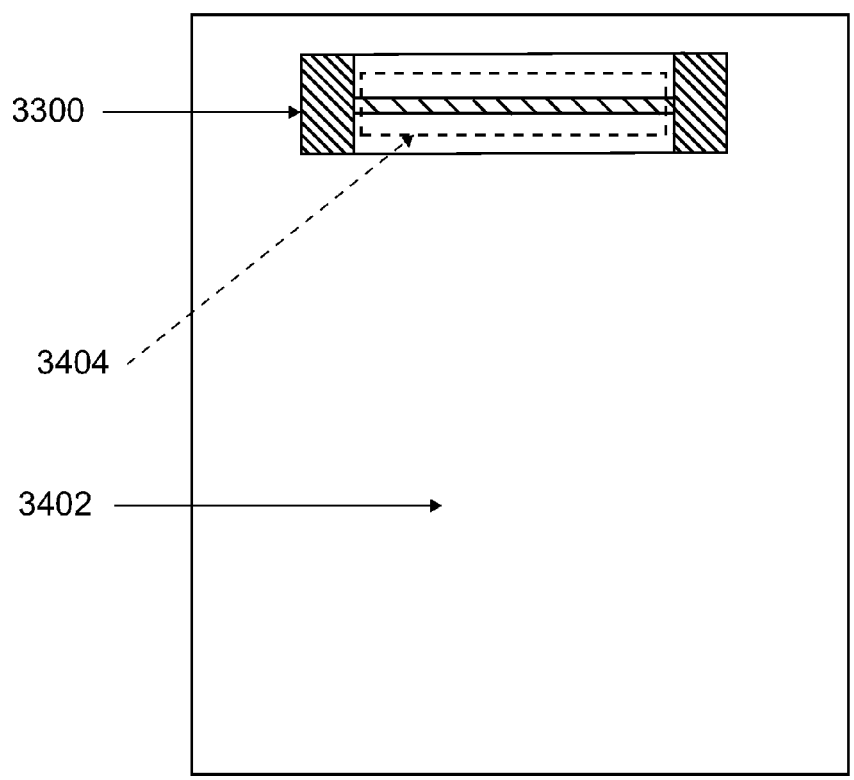
FIG. 34B schematically depicts the front-side of the liquid-permeable pouch secured over the opening of the first layer.
Figure 34C:
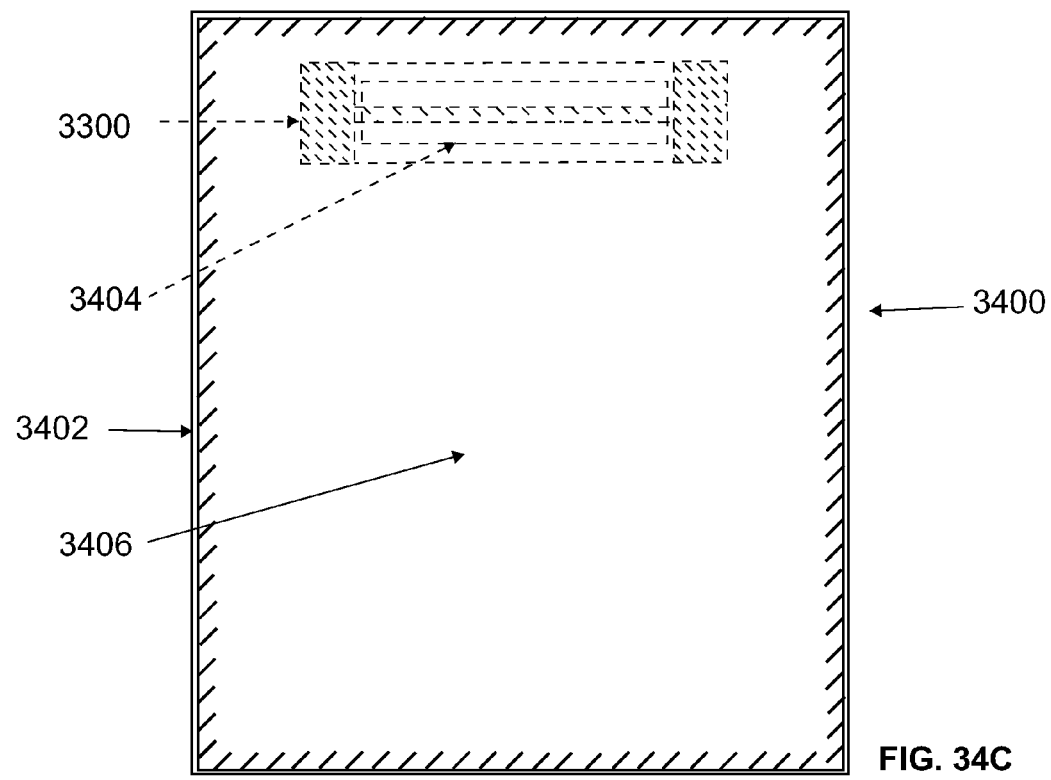
FIG. 34C schematically depicts a second layer covering the pouch and the first layer, wherein the first and second layers are sealed around the perimeter.
Figure 35:
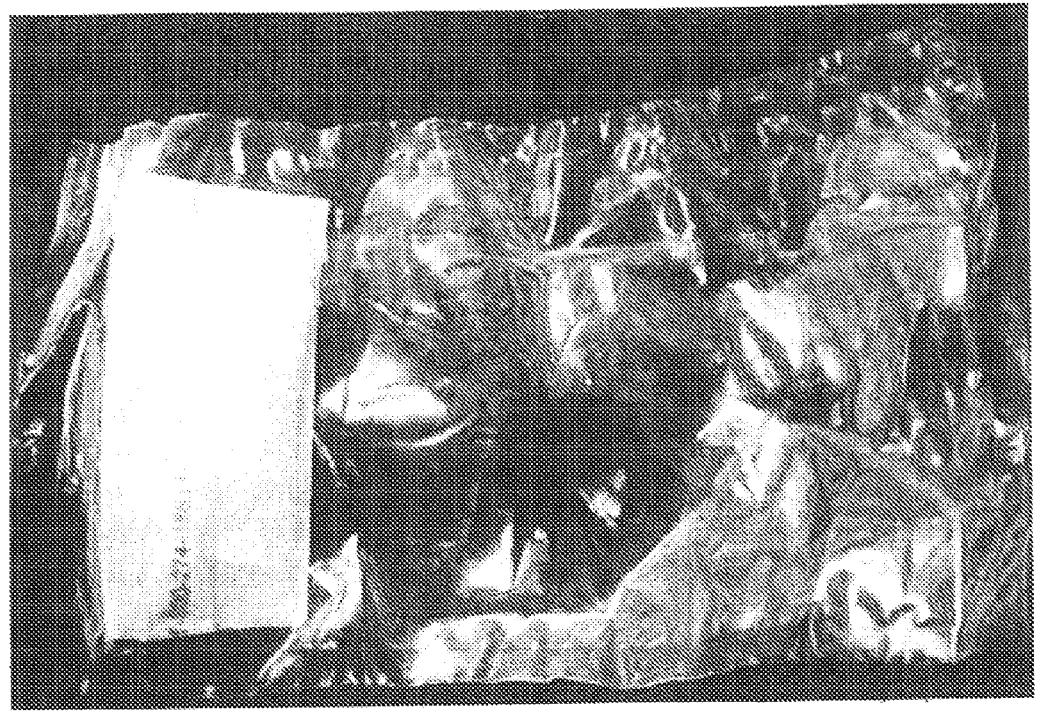
FIG. 35 shows an image of the pouch sandwiched between two layers that are sealed together around the perimeter of the bag.

This example describes a biohazard containment assembly capable of retaining exudates that enter the suction chamber. In one embodiment, the assembly is positioned in the distal region of the interior of the suction chamber. FIGS. 33A and 33B are schematic illustrations of a sealed liquid permeable pouch 3300 containing superabsorbent materials with front-side and rear-side views shown respectively. The pouch 3300 may manufactured using a single layer of material that is folded over itself and sealed at its side seams 3302 and 3304 and end seam 3306. Of course, the pouch may also be manufactured using multiple layers or materials sealed together, and in some variations, different materials may be used and/or materials of different shapes may be fused to together. Also, multi-laminate materials may be used in one or regions of the pouch or container. The seals of the pouch, and/or the walls of the pouch, may be configured to rupture, tear or separate as the pouch contents expand with liquid contact. To resist contamination or issues relating to dispersal of the pouch contents into the suction device, the pouch may be placed in a containment bag of sufficient size to accept the expanded superabsorbent pouch material. FIG. 34A is an illustration of a layer 3402 of a bag with an opening 3404 cut out or otherwise formed in the layer 3402, wherein the area of the opening 3404 is smaller than the profile of the pouch. FIG. 34B is an illustration of front-side of the liquid-permeable pouch 3300 placed over the opening of the layer 3402 of the bag and secured in place (e.g. using an adhesive, head melting, stitching, or combinations thereof). FIG. 34C is an illustration of a second layer 3406 of the bag 3400 positioned over the first layer 3402 and the pouch 3300. The first and second layers 3402 and 3406 are sealed to each other around the perimeter 3408 of the bag 3400. In FIG. 34C, the second layer 3406 is schematically depicted as slightly smaller than the first layer 3402, but in other examples the second layer may have the same size and/or shape as the first layer, or may be larger and/or have a different shape than the first layer. The containment bag may also be prefabricated with an opening cut out and one or more sides sealed prior to assembly of the superabsorbent pouch into the containment bag. FIG. 35 is a superior elevational photograph of the liquid-permeable pouch sandwiched between two layers that are sealed together around the perimeter of the bag. The back surface of the pouch is oriented superiorly, while the front surface of the pouch is exposed to the opening bag layer, which is oriented inferiorly.

Some variations of a reduced pressure therapy system may be configured to remove and store exudates located at the treatment site. Exudates are typically body fluids or mixed fluids and other cellular matter. In some variations, the device may be configured with a fluid retention mechanism to resist or prevent leakage of the exudates that have been suctioned into the suction chamber. For example, some fluid retention mechanisms may be configured to sequester exudates within a certain portion of the suction device, regardless of the orientation of the suction device. This may help to reduce the risk of contamination to users or healthcare personnel and their surroundings during use and/or disposal. In some variations, the fluid retention mechanism may be configured to prevent exudates that have been drawn into the suction device from flowing out of the suction device. For example, a fluid retention mechanism may be configured to allow exudates to flow in one direction (e.g., into the suction device), but not in the opposite direction (e.g., out of the suction device). In some variations, a suction device may have a fluid retention assembly in its suction chamber, where the fluid retention assembly may comprise an absorbent material so that when the exudates come into contact with the absorbent material, it is absorbed by the material and retained and/or sequestered within the suction chamber. Optionally, the fluid retention assembly may also comprise a screen or mesh that may be used to sequester the absorbent material in a certain portion of the suction chamber. The screen or mesh may also help to prevent the absorbent material from moving around and/or exiting the suction chamber, and in some variations, may also help to prevent exudates collected in the suction chamber from exiting the chamber through the distal port or inlet. While some suction devices may have one or more fluid retention assemblies, some suction devices may not.

Absorbent materials that may be used in a fluid retention assembly may be selected according to the expected viscosity (or other liquid characteristic) and/or quantity of the exudates. Certain absorbent materials may also be selected based on the desired absorption capacity. The absorption capacity of the material may be maintained under negative and/or positive pressure conditions. Some variations of an absorption material may hygroscopic, and may be able to absorb vapor. The fluid absorption material may be permeable to air, such that the negative pressure generated by the suction device may be conveyed to the wound without substantial hindrance. Suitable absorbent materials may be selected from natural, synthetic, and modified natural polymers and materials. Absorbent materials may be inorganic or organic materials, such as sodium acrylic-based polymers, silica gels, cross-linked polymers, etc. Other examples of absorbent materials may include gauze, pulp, sponges, foams, desiccated hydrogels, and cross-linked polyprotic resins. Suitable absorbent materials may be available from various commercial vendors, such as Dow Chemical Company located in Midland, Mich., U.S.A., and Stockhausen GmbH & Co. KG, D-47805 Krefeld, Federal Republic of Germany. Other examples of absorbent materials may include starch-acrylonitrile co-polymers, carboxy methyl cellulose (CMC), acrylic acid, polyvinyl alcohol (PVA) and isobutylene maleic anhydride (IMA), as well as various foams, including XTRASORB™. Some variations of a fluid retention assembly may use a superabsorbent material, which may be capable of retaining an amount of water equal to at least 100% of its dry weight (e.g., as measured by the test of Intrinsic Absorbent Capacity). As used herein, "absorbent capacity" refers to the total mass of water that a specified quantity of absorbent material can hold, and is simply the Intrinsic Absorbent Capacity multiplied by the dry mass of the absorbent material. Thus 10 g of material having an Intrinsic Absorbent Capacity of 5 has an absorbent capacity of 50 g (or 50 ml of fluid). For example, a superabsorbent material may have an Intrinsic Absorbent Capacity of at 1 or greater. The ability for a material to absorb a relatively large amount of liquid compared to its own weight permits a larger capacity of liquid to be contained in the suction chamber than the same amount of material having a lower absorbance capacity. In some of the foregoing embodiments, the superabsorbent material may be Isolyser™ by Microtek Medical. Other examples of absorbent materials that may be used with a fluid retention assembly for a suction device may include sodium polyacrylate with sodium dichloro-S-triazinetrione dihydrate, cellulose based substrates, AQUA KEEP® polymer products, etc. More generally, the absorbent materials used in the absorbent members of the present disclosure may have an Intrinsic Absorbent Capacity of 2 or greater. In some embodiments the intrinsic absorbent capacity is 4 or greater. In some embodiments the intrinsic absorbent capacity is 7 or greater. In some embodiments the intrinsic absorbent capacity is 10 or greater. In some embodiments the intrinsic absorbent capacity is 3 to 30. In some embodiments the intrinsic absorbent capacity is 4 to 25. In some embodiments the intrinsic absorbent capacity is 12 to 40.

In some variations, the fluid absorbent material may have a first non-hydrated state and a second hydrated state, where in the non-hydrated state the absorbent material may occupy a smaller volume than when in the hydrated state. For example, the absorbent material may expand as it absorbs fluids and transitions from the non-hydrated to hydrated configuration. In some variations, the absorbent material in the non-hydrated state may be powder-like, and in the hydrated state, the absorbent material may be gel-like, or may be a solid or a semi-solid. In other variations, the absorbent material may be a planar sheet or pad that thickens or expands as it absorbs fluid. The fluid absorbent material may be a porous material (e.g. a sponge, foam, textile, etc), and may be a planar or three dimensional porous matrix. An absorbent material that is a planar pad may have a first thickness in the non-hydrated state, and a second thickness in the hydrated state, where the second thickness is greater than the first thickness. Alternatively or additionally, the absorbent material may comprise loose components such as pellets, spheres, granules, clusters, powder, and the like. The particle sizes may range from about 20 μm to about 500 μm, for example, about 20 μm to 30 μm, or about 200 μm to 300 μm, or about 350 μm to 390 μm in the non-hydrated state. The absorbent material may also take the form of a collapsed woven material, such as a textile, or compressed polymer or sponge or porous matrix in its non-hydrated state. In the expanded hydrated state, the absorbent material may expand, and may be enlarged pellets or clusters, an expanded textile or sponge or porous matrix. In some cases, the absorbent material in the hydrated state may be a solid, a semi-solid, or a gel. Some variations of absorbent materials may decompose as it absorbs fluids. In some examples, the fluid absorbent material may be a volume neutral material, wherein the total volume of the separate fluid and separate absorbent material is approximately the same volume of the fluid and absorbent material when intermixed. For example, the separated total volumes and the intermixed volume may be equal, or at least within 5% or 10% of each other. In other examples, the fluid absorbent material may be a volume increasing material, wherein the intermixed volume is at least 15% or 25% or more than the total separated volumes.

The amount of absorbent material that is provided in the suction chamber may be limited by the dimensions of the collection chamber of a charged suction device. Thus, when the seal is moved to the distal end of the chamber, it reduces the volume of space available in the suction chamber. In some embodiments, the absorbent material may occupy a volume of less than about 10 cc, about 5 cc or about 4 cc. In some embodiments, the biohazard containment assembly occupies a volume of less than 5 cc. In some embodiments, the biohazard containment assembly occupies a volume of less than 4 cc. In other embodiments, the volume of the absorbent material may be characterized by the maximum volume of the chamber in which it resides. For example, the absorbent material may less than about 25%, about 20%, about 15%, or about 10% of the chamber volume. In some embodiments, the amount of absorbent material may be between 0.5 g to 4 g. In some embodiments, the amount of absorbent material may be between 0.5 g to 2.5 g. In some embodiments, the amount of absorbent material may be between 0.5 g to 1.75 g. In some embodiments, the amount of absorbent material may be about 1.5 g. In some embodiments, the amount of absorbent material may be at least 1 g. In some embodiments, the amount of absorbent material may be at most 2 g. In some embodiments, the amount of absorbent material may be at most 3 g. In some embodiments, the amount of absorbent material may be at most 4 g.

Optionally, some variations of a fluid retention assembly may comprise a disinfectant, which may help to sanitize exudates that enter the collection chamber. For example, the disinfectant may be attached to, bonded to, embedded in, cross-linked with and/or otherwise incorporated with the absorbent material. In other examples, the disinfectant may be freely disposed within the collection chamber, or may be attached to other structures, such as the slidable seal assembly. The disinfectant may be anti-bacterial (e.g. bacteriostatic or bacteriocidal), anti-viral, anti-fungal, and/or anti-parasitic. Some examples of disinfectant compounds that may be used in a fluid retention system may include chlorhexidine, sodium hypochlorite, sodium dichloro-s-triazinetrione dehydrate (or other chlorine-based disinfectant), a sulfonamide, silver sulfadiazine, polyhexanide. In some variations, the absorbent material itself may also act as a disinfectant. For example, a fluid retention assembly may use a liquid medical waste solidifier, such as Isolyser LTS-Plus® Solidifier or Isosorb® Solidifier by Microtek Medical. Optionally, the fluid retention assembly may also comprise a deodorizer, such as zeolite, activated charcoal, silica gel, or hydrogen peroxide. In some variations, the disinfectant treat the collected exudates such that the expended device may be disposed as regular trash, rather than as biohazardous waste.

A fluid retention assembly may be installed in the suction chamber of a suction device in a variety of configurations. Fluid retention assemblies may comprise an absorbent material that may be sequestered in a portion of the suction chamber, temporarily or permanently. For example, a fluid retention assembly may comprise an absorbent pad or sheet that may be attached to the walls of the suction chamber so that it does not move within the suction chamber as the suction device changes orientation. Alternatively or additionally, a fluid retention assembly may comprise a screen (e.g., a mesh, filter, etc.) that may be attached at a distal portion of the suction chamber. For example, the screen may be attached within the distal portion of the suction chamber, just proximal to a distal portion leading to the distal port of the suction device. In some fluid retention assemblies, the absorbent material may be retained by a carrier structure, e.g. bonded to a surface of a supporting sheet or other structure, or enclosed in a pouch or other container. The pouch may freely move within the suction chamber, or may be attached to any desired region of suction chamber such that it remains at the desired region despite any changes in the orientation of the suction device. A fluid retention assembly may comprise a combination of one or more of the above described components, as may be desirable. For example, a fluid retention assembly may comprise absorbent materials enclosed in a pouch, where the pouch is sequestered to a portion of the suction chamber by one or more screens. A fluid retention assembly may comprise an absorbent pad or sheet that may be temporarily or permanently secured within the suction chamber using adhesives and/or one or more screens. Various examples of fluid retention assemblies are described below.

In some variations, the absorbent material of a fluid retention assembly may be retained by a carrier structure, such as a pouch. In some variations, the absorbent material may be enclosed in an internal pouch made of a semi-permeable membrane. This internal pouch may help to prevent the fluid absorption material from obstructing or clogging the various valve and/or conduits of the suction device. A pouch 1804 may be temporarily or permanently attached to any portion of the suction device, for example, in a distal portion of a suction chamber 1800 (toward the distal port 1802), as depicted in FIG. 18A. In some variations, the pouch may be located adjacent to the internal opening of the distal port 1802. The absorbent material may be surrounded by and enclosed in a liquid permeable membrane to form an absorbent bag. The membrane may be a mesh, filter, screen, molecular sieve, and the like. Non-limiting examples of suitable materials for the liquid permeable membrane may include woven and nonwoven polyester, polypropylene, nylon, rayon or the like, particularly in the form of formed or apertured thermoplastic films, including those described in U.S. Pat. No. 4,324,246 issued to Mullane and Smith on Apr. 13, 1982 and U.S. Pat. No. 4,342,314 issued to Radel and Thompson on Aug. 3, 1982. Other known semi-permeable membrane materials can be employed, including those made from textured cellulosic basesheets with hydrophobic matter added to selected portions of the basesheet, particularly the most elevated portions of the basesheet, as described in commonly owned copending U.S. application, "Dual-zoned Absorbent Webs", Ser. No. 08/997,287, filed Dec. 22, 1997. In some of the foregoing embodiments, an outer surface of the liquid permeable membrane may be treated with a surfactant to improve liquid penetration, and may have gradients in wettability created having different chemical treatments on the two surfaces of the topsheet, such that fluid is preferentially absorbed in targeted intake regions and repelled by other regions. In some of the foregoing embodiments, the liquid permeable membrane may comprise at least one seam wherein at least two sections of the membrane are joined together. In some embodiments, the expansion of the absorbent material within the liquid permeable membrane may result in the rupture of the liquid-permeable membrane. In certain embodiments, the absorbent material may be expelled upon rupture of at least one seam of the liquid-permeable membrane.

In some of the foregoing embodiments, at least a portion of the liquid permeable layer is enclosed in a secondary enclosure, such as a plastic bag. In some of the foregoing embodiments, expansion of the superabsorbent material ruptures the liquid-permeable layer and is expelled into the secondary enclosure. The secondary enclosure prevents the superabsorbent material from contacting the interior surfaces of the suction chamber. The secondary enclosure is designed to permit liquid to enter the liquid permeable layer.

In some of the foregoing embodiments, a semi-permeable membrane of a fluid retention assembly may contain the absorbent material and help to isolate the material from contacting the suction device. The semi-permeable membrane may allow fluids to cross the membrane in one direction, but not in the other direction. For example, a semi-permeable membrane pouch containing absorbent material inside may allow exudates to be drawn by the absorbent material into the pouch, while the semi-permeable membrane prevents the exudates from flowing out of the pouch. The membrane may be permeable to air, as may be desirable. In some variations, a fluid retention assembly may comprise a pouch made of a fluid impermeable material that is directly connected to the distal portion of the suction device. Negative pressure may be generated in the pouch and conveyed to the tissue site. Any exudates collected by the pouch during reduced pressure therapy may be retained such that exudates do not contact the walls of the suction chamber. When the suction device is depleted, the pouch may be removed from the suction device and discarded.

Optionally, some variations of a fluid retention assembly may comprise a screen or mesh positioned near the distal end of the suction chamber to retain the absorption material within a certain region of the suction device. The screen or mesh may prevent or resist the extrusion or release of the absorbent material from the suction chamber, which may occur during patient movement and/or recharging of the device. For example, a screen or mesh may be semi-permeable, which may allow exudates to be collected in a suction chamber, but may prevent the exudates from exiting the distal port of the suction chamber. In some variations, the screen or mesh may be air and fluid permeable, but not fluid absorbent. FIG. 18B schematically depicts a suction chamber 1800 with a distal port 1802, and a screen 1806 proximal to the distal port 1802. In some variations, a fluid retention assembly may comprise a plurality of screens or meshes, arranged such that the absorbent material is constrained between two screens. In some variations, the screen or mesh may block movement of particles of a certain size and/or liquid or semi-solid of a certain viscosity, while allowing smaller particles and liquids to pass therethrough. The screen or mesh may be provided over the distal portion of the suction chamber, for example, the screen may be attached over a distal valve of the suction device leading to the tissue treatment area. Suction devices that use an absorbent material that has discrete components in its non-hydrated state, such as powder, pellets, loosely associated particles, may have such a screen or mesh to help prevent the material from exiting the suction chamber.

The screen or mesh may have a sieve size large enough to permit the fluid exchange of liquid and air through the mesh, but small enough to not allow solids or semi-solids to pass through. The mesh may have two sides, a proximal and a distal side. The proximal side faces the sliding seal assembly while the distal side faces the distal end of the chamber. In some embodiments, the sieve size of the mesh may be less than 5 mm. In some embodiments, the sieve size of the mesh may be less than 2 mm. In some embodiments, the sieve size of the mesh may be less than 1 mm. In some embodiments, the sieve size of the mesh may be less than 0.5 mm. In some embodiments, the sieve size of the mesh may be less than 10 mm. The mesh may comprise any of a variety of materials, including a metal (e.g. steel, copper), a ceramic, or a plastic (e.g. polypropylene, polyethylene, polyester, polyamide or other thermoplastic.

Some fluid retention assemblies may use a screen or mesh made of a woven or a fibrous material. For example, the screen may be made from random-laid fibers (e.g., from wood pulp) using water or air to transfer the fibers. After the fibers have been air or liquid laid, synthetic resin bonding agents may be applied to the pulp web using a spray process. Meshes that may be used in a fluid retention assembly may be made of Airtex® airlaid fabrics, which may be obtained from Georgia-Pacific (Neenah, Wis.).

Other variations of fluid retention assemblies may comprise an absorbent material that has a self-contained form (e.g., a porous matrix, sponge, gauze, pad, foam, etc.). The absorbent material may be permeable to air, as may be desirable. In some examples, the absorbent material may be woven or non-woven sponges or gauze, and/or may be made of a porous material. In some variations, the absorbent material may be permeable to air, as may be desirable. The absorbent material may be made of any of the materials previously described. In some variations, the absorbent material may be retained by a carrier structure. For example, the absorbent material may be immobilized in a substrate (e.g., impregnated or woven into a matrix, adsorbed to a porous matrix, etc.). In some variations, the absorbent material may be bonded to the carrier structure and/or integrated with the substrate matrix. The absorbent material may or may not be sterile. Fluid retention assemblies comprising such absorbent materials may or may not include a screen or mesh to prevent movement of the absorbent material as the suction device changes orientation. An absorbent material, e.g., an absorbent pad 1808, may be temporarily or permanently attached at any desirable portion of the suction device, for example, at a distal portion of the suction chamber 1800, as depicted in FIG. 18C. The self-contained absorbent material may be retained in the suction chamber by adhesion, friction fit, and the like, and/or may conform to the cross-sectional geometry of the suction chamber (e.g., form fit).

Fluid retention assemblies may comprise any combination of the features described above. For example, a fluid retention assembly may comprise a screen 1812 attached at a distal portion of the suction chamber 1800 (e.g., covering the distal port 1802) and a pouch 1810 comprising an absorbent material enclosed in a semi-permeable membrane, as depicted in FIG. 18D. The screen 1812 may have a smaller cross-sectional area than that of the suction chamber 1800. In other variations, a fluid retention assembly may comprise a screen 1816 attached at a distal portion of the suction chamber 1800 just proximal to the distal port 1802 and a porous matrix 1814 attached to the walls of the suction chamber 1800, just proximal to the screen, as illustrated in FIG. 18E. The screen 1816 may have a similarly sized cross-sectional area as compared to the suction chamber 1800. In still other variations, a fluid retention assembly may comprise a porous matrix attached to the side walls of the suction chamber at a distal portion of the chamber, and a pouch comprising an absorbent material enclosed in a semi-permeable membrane proximal to the porous matrix. Alternatively, the porous matrix may be located proximal to the absorbent pouch. The components of the fluid retention assemblies described here may be arranged in any order, as may be suitable (e.g., the pouch or porous matrix may be distal to the screen). While retention assemblies comprising a single screen or filter have been described here, in some variations, there may be more than one screen. Additional screens may be helpful for sequestering the absorbent material in one or more selected regions of the suction chamber, and may provide for additional filtration of exudates, as may be desired.

Figure 16A:
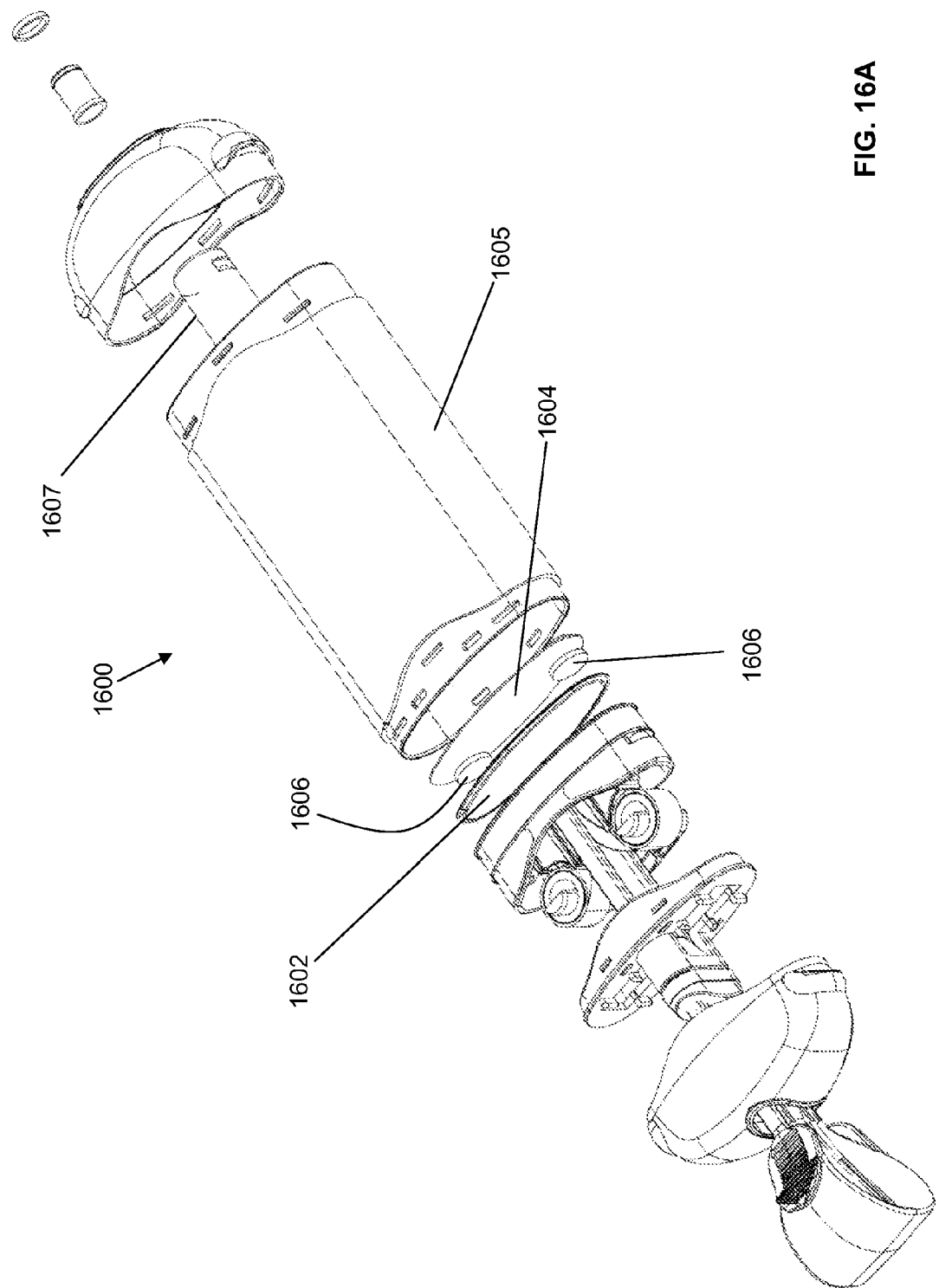
FIG. 16A is an elevational component view of one variation of a suction device for reduced pressure wound therapy.
Figure 16B:
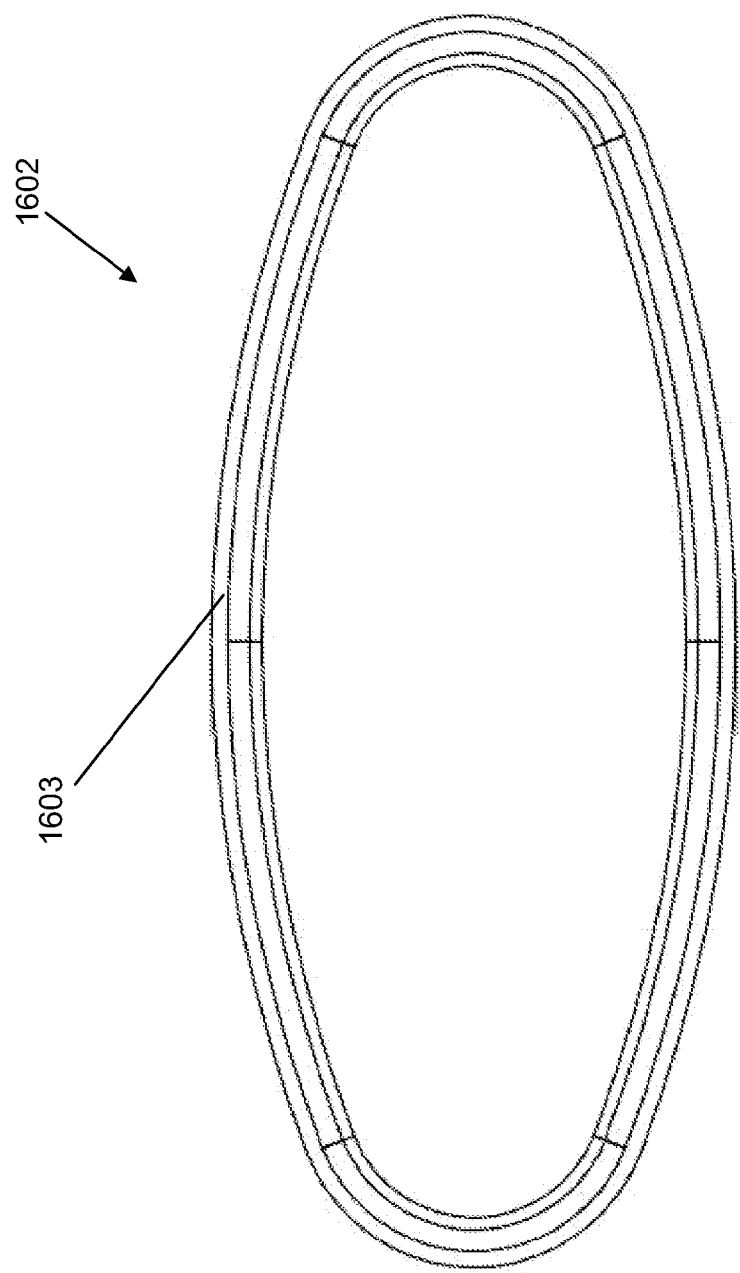
FIG. 16B is a superior view of one variation of a fluid retention assembly comprising a pouch that may be used with the suction device of FIG. 16A.

One example of a suction device with a fluid retention assembly is depicted in FIGS. 16A and 16B. Suction device 1600 may have a fluid retention assembly comprising a pouch 1602 configured to retain a fluid absorbent material, an air and liquid-permeable screen or mesh 1604 between the pouch 1602 and a distal port 1607, and optionally one or more adhesive tabs 1606 to attach the pouch 1602 to the mesh, and/or to attach the mesh 1604 to the distal portion of the suction chamber 1605. The pouch 1602 may comprise a semi-permeable membrane (e.g., an air and liquid permeable membrane) so that the absorbent material in the pouch may draw exudates into the pouch. In some variations, the semi-permeable membrane may be configured to help reduce leakage of exudates out of the pouch. The absorbent material in the pouch may be any of the materials previously described. The pouch and mesh may or may not have a shape that corresponds to the cross-sectional shape of the suction device (e.g., the cross-section of the suction chamber). FIG. 16B depicts an enlarged view of the pouch 1602, which has an elliptical shape corresponding to the elliptical shape of the suction chamber 1605. The pouch 1602 may comprise a sealed opening, or a perimeter seal 1603 between two layers of the pouch, which may help to retain the fluid absorbent material in the pouch prior to use. In some variations, upon absorption of a sufficient amount of fluid into the pouch, the sealed opening or the perimeter seal 1603 may be configured to open or separate, permitting expansion and/or release of the fluid absorption material into the rest of the suction chamber. In some other variations, the sealed opening or the perimeter seal 1603 may also be used to help temporarily or permanently secure the pouch 1602 to a location in the suction chamber, e.g., the proximal or distal side, so that the pouch 1602 does not move within the suction device chamber. Optionally, the fluid retention assembly may comprise additional meshes, which may be used to secure the pouch and/or to filter exudates. For example, an additional mesh may be provided on other proximal side of pouch 1602, across from the mesh 1604, where the two meshes may act to retain the pouch 1602 between them. Additional descriptions of suction devices and fluid absorption materials that may be used within a suction device are provided in U.S. Pat. Appl. No. 61/372,837, filed on Aug. 11, 2010, which is hereby incorporated by reference in its entirety. In some of the foregoing embodiments the pouch may be placed in the suction chamber in contact with the proximal side of the mesh in a way that permits air and liquid to fluidly exchange from one side of the mesh to the other.

Figure 17C:
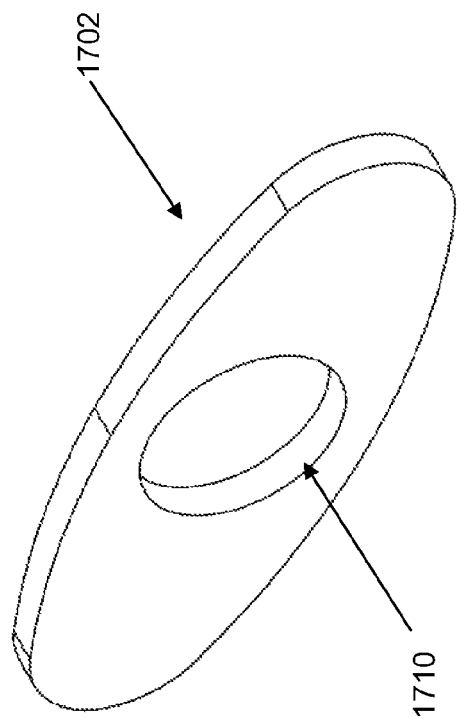
FIG. 17C is a perspective view of the absorbent pad of the fluid retention assembly of FIG. 17A.

Another example of a fluid retention assembly 1700 is depicted in FIGS. 17A-17C. The fluid retention assembly 1700 may comprise an absorbent pad 1702 at a proximal location, a first adhesive layer 1704, a mesh or screen 1706, and a second adhesive layer 1708 at a distal location. The absorbent pad may be made of any of the absorbent materials described previously. The fluid retention assembly 1700 may be located towards a distal portion of the suction device, such that the absorbent pad 1702 faces the suction chamber, and the second adhesive layer faces the distal-most portion of the suction device. For example, the fluid retention assembly 1700 may be placed at a distal portion of the suction chamber, over the internal aperture of the distal port of the suction device. The first and second adhesive layers 1704, 1708 may be made of any suitable adhesive, such as pressure sensitive adhesives, and may have adhesive properties on both sides. The first adhesive layer 1704 may be used to attach the absorbent pad 1702 to the screen 1706. The second adhesive layer 1706 may be used to attach the screen 1706 to a distal surface of the suction device. As depicted in the side view of FIG. 17B, the second adhesive layer 1708 may optionally have an additional release liner layer 1707, which may allow the fluid retention assembly 1700 to be manufactured separately from the suction device, and then subsequently attached to the device prior to use. The screen 1706 may be made from any air or liquid permeable material, such as the screen materials described above.

Figure 17D:
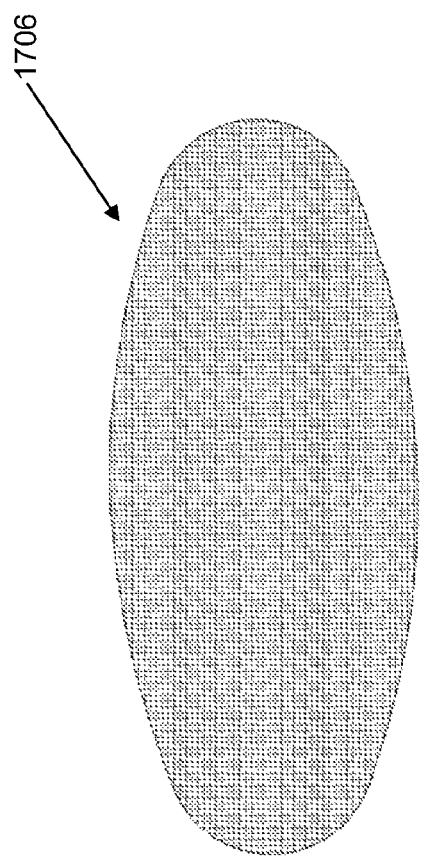
FIG. 17D is a top view of a mesh of the fluid retention assembly of FIG. 17A.

The second adhesive layer 1708 may have an aperture 1709 (and the first adhesive layer 1704 may have a corresponding aperture which is not shown). In some variations, the aperture 1709 may facilitate the flow of suction through the fluid retention assembly 1700. In other variations, one or more adhesive structures or regions may be provided that need not attach the entire distal surface or entire perimeter of the fluid retention assembly to the suction chamber. The one or more adhesive structures may or may not be located over an opening of the suction chamber. As depicted in FIG. 17C, the absorbent pad 1702 may also have an aperture 1710 that is aligned with the adhesive layer aperture 1709. As shown in FIG. 17D, the screen 1706 may not have an aperture, and therefore, the screen 1706 spans across the adhesive and absorbent pad apertures 1709, 1710. However, since the screen may be made of an air and liquid permeable material, the negative pressure generated in the suction chamber may be conveyed to a distal wound bed. The mesh size of the screen 1706 may be selected such that particles larger than the mesh size may not pass between the wound and the suction chamber. For example, wound exudates with blood material that is substantially liquid may pass from the wound to the suction chamber, but after the blood has clotted in the suction chamber, it cannot pass from the chamber back to the wound bed. Optionally, one or more additional screens may be provided to provide additional filtration of exudates and/or to secure the absorbent pad 1702, as may be desirable. For example, an additional screen may be provided on a proximal side of the absorbent pad 1702, thereby retaining the absorbent between the additional screen and the screen 1706. Other variations of a fluid retention assembly may not have any screens, which may allow for the exchange of materials between the wound bed and the suction chamber.

While some suction devices described herein may have fluid retention assemblies (e.g., biohazard containment assemblies), it should be understood that other variations of suction device may not have a fluid retention assembly.

Some variations of suction devices may comprise one or more indicators to inform a patient and/or practitioner when the device needs to be replaced (e.g., when the suction device is in a depleted state and no longer able to generate negative pressure). Visual indicators may be provided to indicate the state of the suction device, i.e., fully charged, at least partially charged or depleted, or fully depleted. Visual indicators may allow the position of the sliding seal assembly within the suction chamber to be readily identified. For example, the suction device may display a certain color to indicate that it is fully charged or at least partially charged or partially depleted, and a different color to indicate that it is fully depleted. In one variation, the sliding seal assembly may have a first portion that is colored green, and a second portion that is colored red. The suction chamber may comprise opaque and transparent portions that reveal certain portions of the sliding seal assembly as the suction device generates negative pressure. In some variations, the suction chamber may comprise an opaque material with one or more translucent or optically clear windows that may be used to view the location and/or colors of the sliding seal assembly within the suction chamber. For example, when the suction device is fully or partially charged, the green portion of the sliding seal assembly may be visible in an optically clear window, while the red portion is obscured by the opaque portion of the suction chamber. The green portion of the sliding seal assembly may allow a patient and/or practitioner to readily determine the depletion state of the suction device based on the location of the sliding seal assembly in the suction chamber. When the suction device is depleted and no longer able to generate any negative pressure, the red portion of the sliding seal assembly may become visible while the green portion may be obscured. In other variations, the sliding seal assembly may have additional colors to indicate intermediate levels of depletion. For example, the sliding seal assembly may have a first green portion, a second red portion, and a third yellow portion. The suction chamber may comprise opaque and transparent portions that reveal only the green portion of the sliding seal when the suction device is fully charged, only the yellow portion when the suction device is partially charged or partially depleted, and only the red portion when the suction device is fully depleted. Alternatively, the sliding seal assembly may have a single color or pattern that is readily visible through the suction chamber (e.g., having bright intensity, high contrast, highly noticeable visual attributes including contrasting edges, patterns, stripes, etc.). In some variations, the sliding seal assembly may have arrows or other symbols that may be used in combination with indicia on the suction chamber to indicate capacity of the device to generate negative pressure. Examples of suction devices with such visual indicators are described below.

Additionally or alternatively, certain variations of a suction device may comprise an alarm system to inform a patient and/or practitioner when the device needs to be recharged or replaced. For example, an alarm system may generate an alert to inform a patient and/or practitioner that a suction device is exhausted or nearly exhausted of its ability to provide negative pressure to a wound, and may prompt the patient to recharge the device, empty or replace the collection chamber, and/or replace the suction device. Once the suction device has been recharged, emptied, or replaced, the alert generated by the alarm system may be deactivated and/or reset. An alarm system may also provide confirmation to the patient and/or practitioner that the suction device has been properly initialized or charged.

In some examples, the alarm systems for use with a suction device may comprise a sensor mechanism and a notification mechanism. The sensor mechanism may directly or indirectly detect the capability of a suction device to continue to provide negative pressure, and may signal the notification mechanism to generate an alarm. For example, an alarm system may directly measure the pressure that is applied to the wound, while other sensor mechanisms detect indirect device configurations that are related to the pressure that is applied to the wound. Examples of sensor mechanisms that directly measure the pressure applied to the wound, and/or directly measure the capability of the suction device to provide negative pressure may include pressure transducers or gauges. Examples of sensor mechanisms that indirectly measure the pressure applied to the wound may include position detectors, proximity detectors, or mechanisms that are otherwise sensitive or responsive to the location of a slidable seal of the suction device. These may include, for example, linear encoders, rotary encoders, liquid sensors, volume sensors, and movement sensors, and the like. Some variations of sensor mechanisms may be configured to detect the configuration of the suction generating mechanism. For example, sensors may be used to measure the tension and/or coil state of the constant force springs of a suction mechanism. In some variations, sensor mechanisms may provide a binary output, i.e., indicating that the suction device is either charged or depleted, while in other variations, sensor mechanisms may provide a graded output, i.e., indicating that the suction device is 100%, 80%, 50%, 30%, 10%, 0%, charged or depleted. Examples of binary type sensor mechanisms may include a variety of switches, such as electrical or magnetic switches. Examples of graded type sensor mechanisms may include various encoders, such as linear or rotary encoders.

One or more types of notification mechanisms may be used in an alarm system for use with a suction device. Notification mechanisms may comprise visual alerts, audio alerts, electronic alerts, and/or tactile alerts. Examples of notification mechanisms may include LED activation, buzzers, tones, e-mail messages, text messages, vibratory mechanisms, etc. An alarm system may comprise a plurality of sensors, which may each drive one or more notification mechanisms. For example, an alarm system may comprise a first sensor to detect that the suction device is properly charged, where the first sensor is configured to trigger a first notification mechanism, e.g., LED activation. The alarm system may comprise a second sensor to detect that the suction device is depleted (or depleted beyond a pre-determined threshold), where the second sensor is configured to trigger a second notification mechanism, e.g., a buzzer. An alarm system may comprise any number of sensor mechanisms and/or notification mechanism as may be desirable to inform a patient and/or practitioner of the use and configuration of the suction device.

The components of an alarm system may be located on one or more components of a suction device, e.g. on the suction device, and/or may be located on a strap, clip or housing of an attachment device that may be used to attach the suction device to the patient. The location(s) of the alarm system components on the suction device and/or attachment device may be selected such that the components work in combination when the suction device is coupled to the attachment device. The alarm system may be integrated with the suction device and attachment device, or may be detachably coupled to the suction and attachment devices. In some cases, the location of the alarm system components may be determined in part by the location of the alarm system power source, as well as by the frequency with which the suction device or the attachment clip are replaced. For example, if the suction device is replaced more frequently than the attachment device, then it may be desirable for the reusable components of the alarm system (e.g., notification mechanism, sensor mechanism, battery pack, etc.) to be located on the attachment device. An alarm device may comprise an attachment device with an alarm system. Any alarm system components that may come in contact with body fluids may also be separated from the other components to prevent contamination of the other components. For example, portions of the sensor mechanism may contact exudates collected in the suction chamber, and may be segregated and/or detachable from the notification mechanism. In some variations, portions of both the sensor and the notification mechanisms may be located on the suction device and the attachment device. For example, alert component(s) of the notification mechanism may be located on the attachment device while a trigger component of the notification mechanism may be located on the suction device, where the trigger component activates the alert component when the suction device attains a certain configuration. In some variations, the sensor and/or notification mechanisms of an alarm system may be detachably coupled to the suction device and/or attachment device. This may allow the alarm system to be removed after the suction device is depleted. The alarm system may then be used with a new suction device (e.g., a charged suction device). The configuration of the alarm system and its arrangement with respect to the suction device and/or attachment device may be varied according to the needs of the patient and/or the practitioner.

Examples of alarm system mechanisms that may be used with a suction device for reduced pressure wound therapy are described below. While the components of the alarm system may be described in certain locations and configurations, it should be understood that the components may be in alternate locations and configurations as desired.

Some variations of alarm systems may comprise a magnetic sensor that is able to detect the position and/or location of a magnetic component. A magnetic component may itself generate a magnetic field, and/or may be any material that is capable of causing a detectable flux in a magnetic field (e.g., a wire carrying a changing an electric current), and/or may be any material that responds to the presence of a magnetic field (e.g., a ferromagnetic material). The movement and/or location of a magnetic component may activate a sensor by causing a potential difference in the sensor, which is known as the Hall effect. Magnetic sensors may comprise Hall effect detection elements that measure the potential difference caused by a moving magnet to determine the position of the magnet. The potential difference may indicate the precise location of the magnet with respect to the location of the magnetic sensor. One or more components of a suction device may comprise a magnetic component, and the position and/or location of the magnetic component may be detected by a magnetic sensor on the suction device or an alarm device. For example, a sliding seal assembly of a suction device may comprise a magnetic component, and a magnetic sensor on the alarm device may determine the location of the sliding seal assembly by detecting the location of the magnetic component. Alternatively, an alarm device may comprise one or more magnetic components at certain locations and the suction device may comprise a magnetic sensor. For example, an alarm device may comprise a magnetic component (e.g., along or embedded in an attachment clip or side wall), and a sliding seal assembly of a suction device may comprise a magnetic sensor. As the sliding seal assembly moves along the suction device, the sensor detects the location of the sliding seal assembly with respect to the magnetic components in alarm device. The position of the magnetic component relative to the sensor may be determined based on the magnetic characteristics of the magnetic component and a measured potential difference in a sensor caused by the movement of that magnetic component. The sensor voltage may be amplified and activate a notification mechanism on the alarm device to generate an alarm that informs the patient and/or practitioner of the status of the suction device. In some variations, the notification mechanism may comprise a thresholding function that converts an output from a graded type sensor into a binary alert, e.g., generating an alert only when the device is depleted past a certain threshold.

Figure 2A:
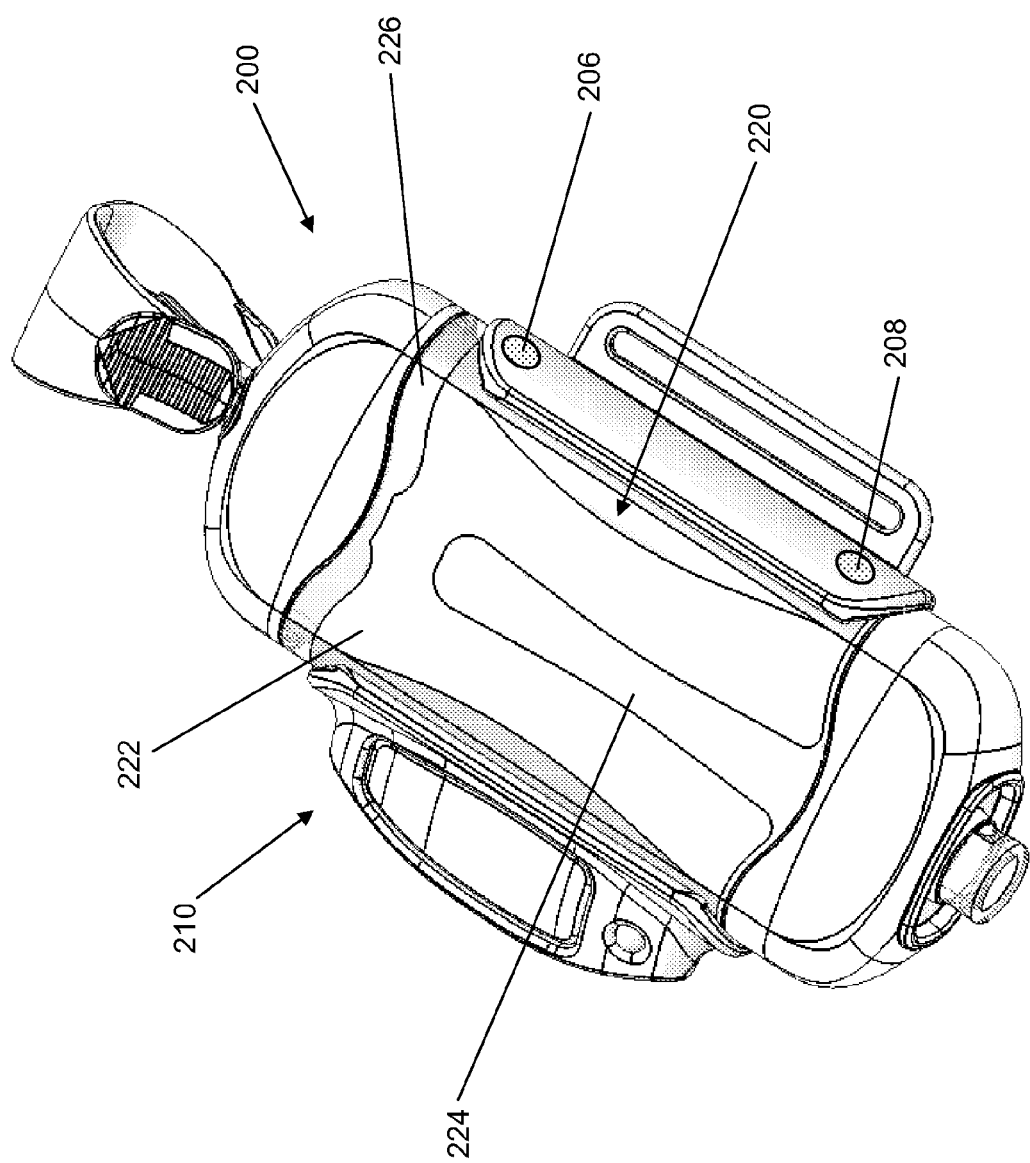
FIG. 2A is a perspective view of another variation of a suction device for reduced pressure therapy comprising a magnetic alarm system and an alarm device.
Figure 2B:
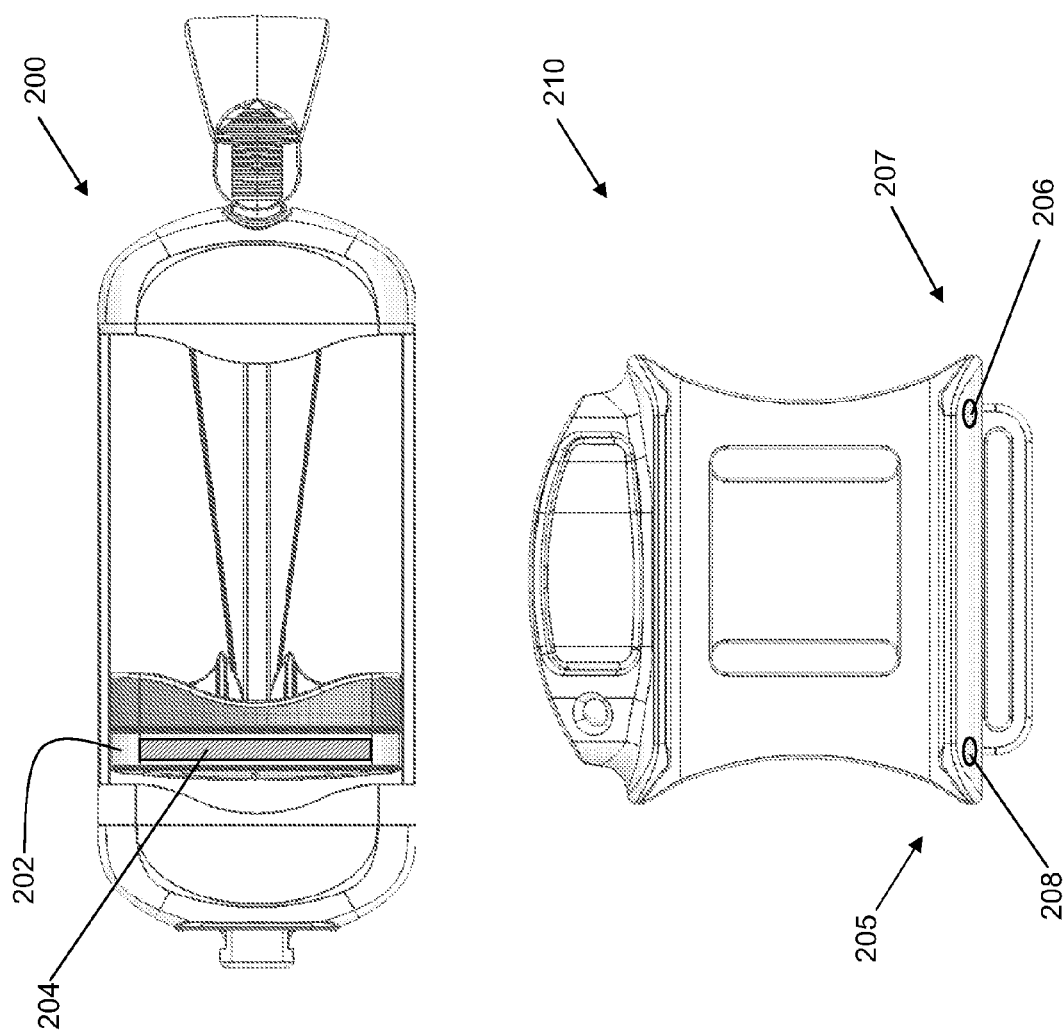
FIGS. 2B and 2C are superior component views of the suction device and alarm device, in charged and depleted states, respectively.
Figure 2C:
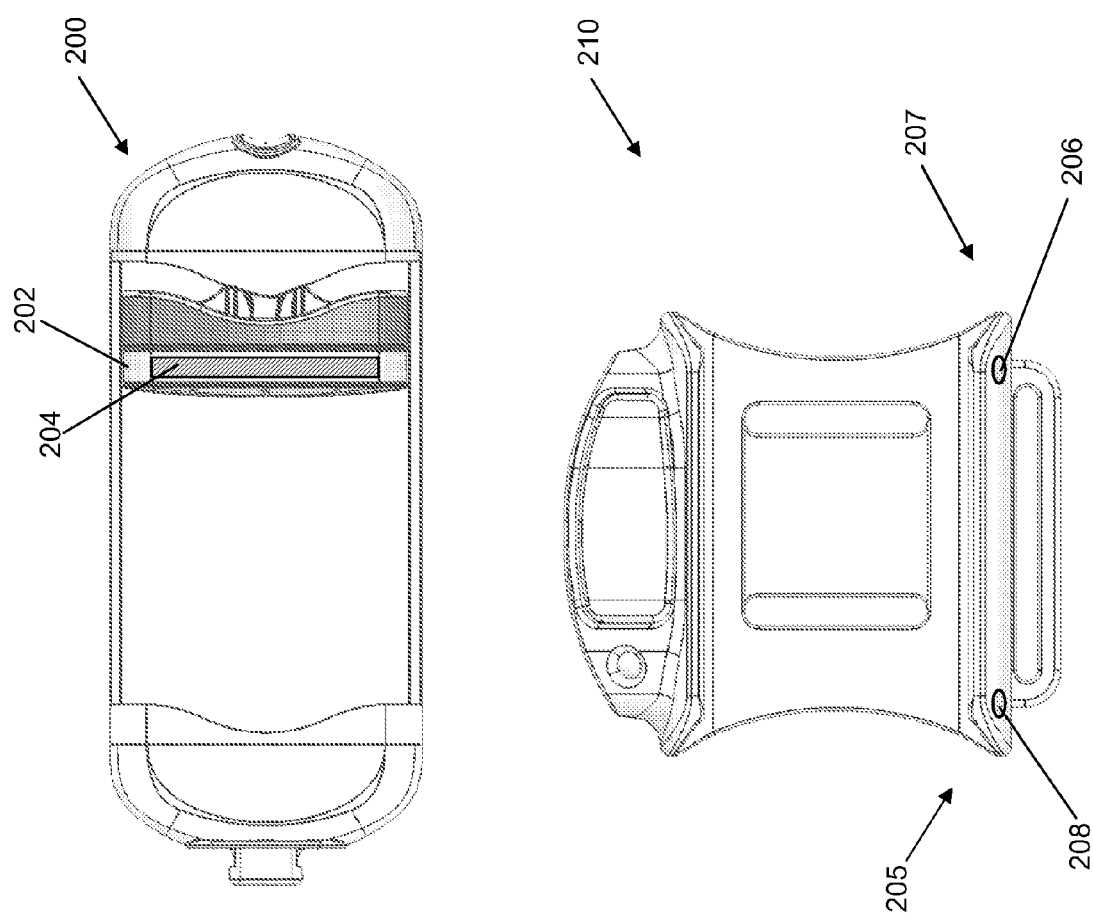

One variation of a suction device 200 with an alarm system using a magnetic sensor mechanism is depicted in FIGS. 2A-2C. The suction device 200 is configured to be retained by an alarm device comprising a clip 210 and a strap (not shown). As depicted in FIG. 2B, the sliding seal 202 of the suction device 200 may comprise a magnetic material 204. One or more magnetic sensors 206 and 208 may be provided to detect the location of the sliding seal 202 using the magnetic material 204. The location of the magnetic sensors 206 and 208 may be configured to facilitate detection of one or more states. For example, as illustrated in FIG. 2B, the first magnetic sensor 206 may be located at a proximal portion 207 of the clip 210 to detect when the sliding seal 202 is in a retracted position, which is indicative of the exhaustion or near exhaustion of the suction device 200. Another sensor 208 may be located in a distal portion 205 of the clip 210, for example, to detect that the sliding seal 202 has been adequately displaced by the activation tool, e.g., during the mechanical charging process. The magnetic sensors 206, 208 may be configured to detect the presence of absence of the magnetic material 204, and may be configured to provide a binary output to indicate the position of the magnetic material. Alternatively, the magnetic sensors 206, 208 may be configured to detect the proximity of the magnetic material 204, and may be configured to provide a graded output to indicate the position and proximity of the magnetic material to the sensors. The power source for the magnetic sensors 206, 208 may be a battery embedded within the clip 210.

Optionally, the suction device 200 may comprise a visual indicator such that a patient and/or practitioner can determine the depletion state of the suction device by visual inspection. For example, the sliding seal 202 may have a first region that is colored green and a second portion that is colored red. As illustrated in FIG. 2A, the suction chamber 220 of the suction device 200 may comprise an opaque portion 222, a first transparent portion 224, and a second transparent portion 226. The first transparent portion 224 may extend longitudinally from a distal portion to a proximal portion along the suction chamber 220. The width of the first transparent portion 224 may be such that the green region of the sliding seal 202 is exposed, while the red region of the sliding seal is obscured by the opaque portion 222. As the sliding seal 202 moves from a distal portion to a proximal portion of the suction chamber 220 (i.e., as the suction device transitions from a fully charged or partially charged state to a depleted state), the location of the green region as seen along the first transparent portion 224 may indicate the degree to which the suction device is depleted. When the suction device 200 is fully depleted, the sliding seal 202 may be co-localized with the second transparent portion 226, such that the red region of the sliding seal is visible in the second transparent portion 226 while the green region of the sliding seal is obscured. As depicted in FIG. 2A, the first transparent portion 224 may be longitudinally disposed with an oblong geometry and the second transparent portion 226 may be transversely disposed with a curved elongated geometry. However, it should be understood that the transparent portions may be located anywhere on the suction device and may have any size or shape as suitable for cooperating with the markings on the sliding seal to provide a visual indicator of the state of the suction device. Such a visual indicator mechanism may be used alone or in combination with any of the alarm systems described herein.

The output of an indicator or sensor mechanism may be used to generate an alert. In some variations, the output voltage of a magnetic sensor may be amplified in order to drive notification mechanisms and/or circuits. For example, the magnetic sensor may comprise a Hall effect sensing mechanism whose output voltage or current may be amplified to drive one or more notification mechanisms. Each magnetic sensor may activate independent notification mechanisms, and/or may signal a shared notification mechanism. As an example, the first magnetic sensor 206 may activate a first notification mechanism when the magnetic component 204 of the sliding seal 202 is located at or near the proximal portion 207 of the clip, and the second magnetic sensor 208 may activate a second notification mechanism that is distinct from the first notification mechanism when the sliding seal 202 is located at or near the proximal portion 207 of the clip. In some variations, the voltage outputs of the first and second magnetic sensors 206 and 208 may be inputs to a logic circuit that computes the location of the sliding seal 202 when it is between the distal portion 205 and the proximal portion 207 of the clip. The result of this logic circuit may be used to activate a third notification mechanism. For example, when a fully charged suction device 200 is attached to the clip 210, the first notification mechanism may be activated by the first magnetic sensor 206, and issue a first visual and/or audio alert. As the suction device 200 is used to apply negative pressure to a tissue region, the third notification mechanism may be activated by the first and second magnetic sensors 206 and 208, and issue a second visual and/or audio alert when the sliding seal 202 is halfway between the distal portion 205 and the proximal portion 207 of the clip 210. When the suction device 200 is exhausted or depleted, the second notification mechanism may be activated by the second magnetic sensor 208, and issue a third visual and/or audio alert. Some magnetic sensors may provide a binary output that indicates whether or not the sliding seal is at the location of the sensor or not, while other magnetic sensors may provide a graded output that indicates how far away the sliding seal is from the sensor. In some alarm systems, a plurality of binary type sensors may approximate the functional output of a graded type sensor. For example, while clip 210 is shown to have two magnetic sensors, it should be understood that other variations of alarm devices may have any number of magnetic sensors, e.g., there may be 1, 3, 4, 5, 6, 10, 12 or more magnetic sensors to detect the position of the sliding seal.

One example of a binary type sensor is a magnetic field sensitive switch, which may be configured to activate a notification mechanism in the presence of a magnetic field. Such binary type magnetic field sensitive switches change between an open and closed configuration according to the proximity of magnet. One example of a magnetic field sensitive switch is a reed switch, which is schematically depicted in FIGS. 7A and 7B. A reed switch 700 comprises a first electrical contact 702 on a first ferrous metal reed 706, and a second electrical contact 708 on a second ferrous metal reed 710. In the absence of a magnetic field, e.g., when a magnet 712 is some distance away from a central region 701 of the reed switch 700, the ferrous metal reeds 706, 710 and the associated electrical contacts 702, 708 may be in an open configuration such that the electrical contacts 702, 708 are separated by a distance, i.e., not touching or contacting each other. In the presence of a magnetic field, e.g., when the magnet 712 is in proximity of or within the central region 701 of the reed switch 700, the ferrous metal reeds 706, 710 may move according to the field and cause the electrical contacts 702, 708 to touch, thus closing the reed switch 700. In other variations, reed switches may be in a closed configuration in the absence of a magnetic field, and transition to an open configuration in the presence of a magnetic field. While a reed switch is described here, other examples of binary magnetic field sensitive switches may include proximity switches, speed switches, and the like. Any type of binary type magnetic field sensitive switches, as well as graded type magnetic field sensitive detectors, may be used to detect the presence of a magnet, as appropriate.

Figure 8:
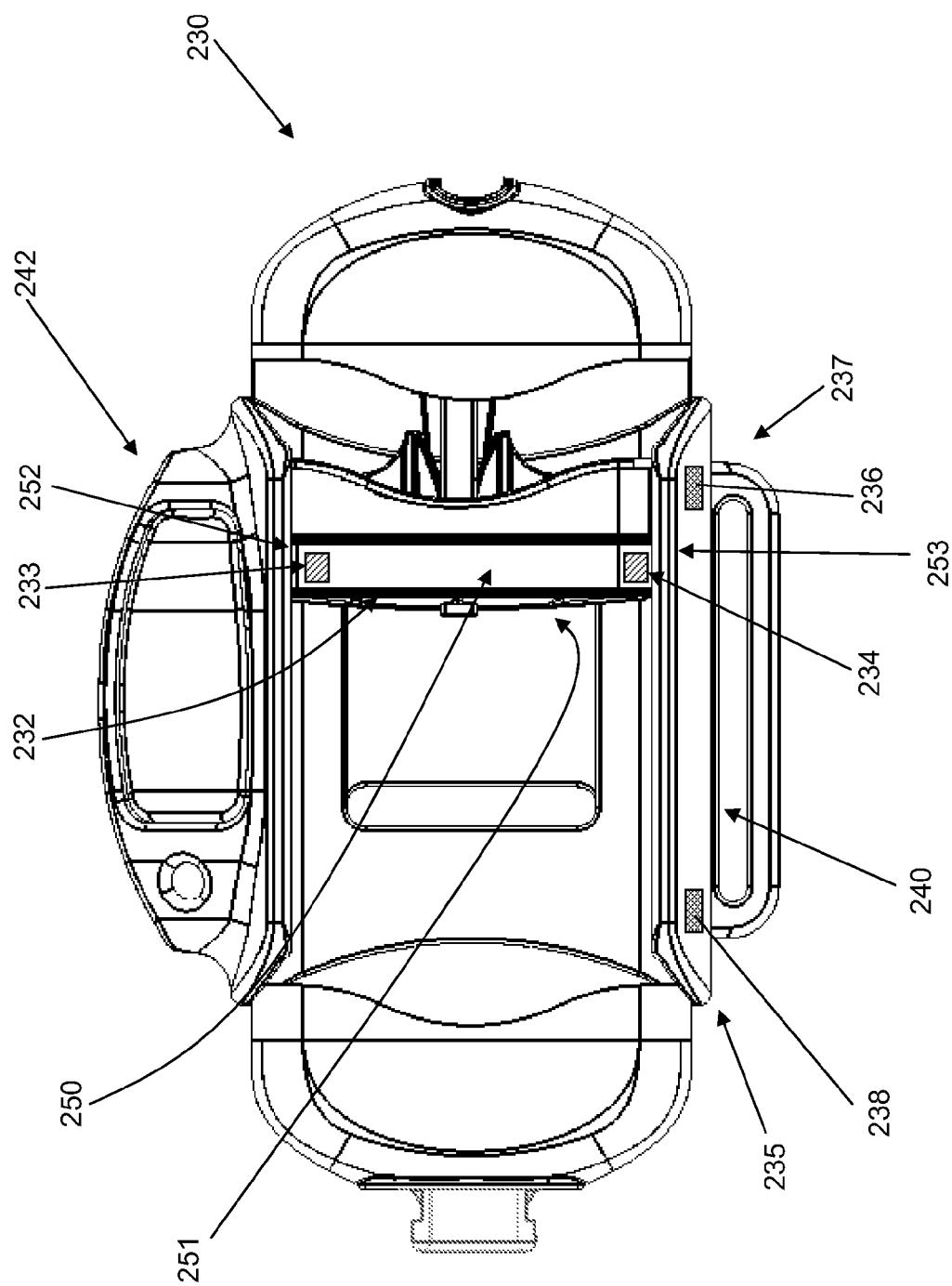
FIG. 8 depicts another variation of a suction device for reduced pressure therapy comprising an alarm system with one or more reed sensors, where the slidable seal of the suction device comprises one or more magnets.

One example of a suction device 230 with an alarm system using a magnetic field sensitive switch is depicted in FIG. 8, which illustrates the suction device 230 in a depleted configuration, e.g., just prior to charging with a key. As depicted there, the sliding seal 232 of the suction device comprises a magnet 234. The magnet 234 may be located on one side of the sliding seal 232 (e.g., the right side 253), but may also be located in the center of the sliding seal, or may extend along the entire length of the sliding seal, for example, similar to the magnetic component 204 depicted in FIGS. 2A to 2C. The magnet may be located on the superior portion 250 of the sliding seal (as depicted in FIG. 8), on the inferior portion 251, and/or the left side 252 and/or right side 253 (e.g., the left or right edge) of the sliding seal. In some variations, the magnet may be embedded within the sliding seal. Alarm device 242 may comprise one or more clips 240 for retaining suction device 230 and a strap coupled to the one or more clips (not shown). A first reed switch 236 may be provided at any location on the alarm device 242, for example, at a location that is close to the position of the sliding seal 232 when the suction device 230 is depleted, e.g., at a proximal portion 237 of the clip 240. When the magnet 234 is sufficiently close to the proximal portion 237, the magnetic field from the magnet 234 may affect the first reed switch 236 such that it transitions from an open configuration to a closed configuration. Closing the first reed switch 236 may activate any of the notification mechanisms described below to generate an alert to indicate that the suction device is depleted. Optionally, a second reed switch 238 may be provided at a distal portion 235 of the clip 240 which may be configured to activate the same or different notification mechanism as the first reed switch 236. For example, the second reed switch 238 may be transitioned from an open configuration to a closed configuration when the sliding seal 232 is a distal portion of the suction device 230, which may activate a notification mechanism to indicate that the device has been successfully charged. In some variations, as discussed in further detail below, a second reed switch may be provided to permit the coupling of the suction device to the alarm device in either orientation. Any number of locations on the alarm device may have one or more reed switches according to where the practitioner and/or patient desires to be informed of the location of the sliding seal 232. The sensitivity of the reed switch may be configured depending upon the particular configuration of the suction device and magnetic shielding provided, if any, to protect other surrounding electronic devices. In some variations, greater magnetic shielding may be provided for use in the intensive care unit or hospital setting, or with patients with implantable devices such as a defibrillator or pacemaker. In some examples, non-magnetic MRI-compatible units may be provided in addition to magnetic variants of the device, and the clip may be configured with two or more detector mechanisms to accommodate multiple types of devices.

In some variations, the sliding seal 232 may comprise a second magnet 233 that is located on the left side 252 of the sliding seal 232. The additional magnet may allow the suction device 230 to be retained in the alarm device 242 in an alternate orientation. For example, the suction device 230 may be retained in the alarm device in an orientation that is rotated 180° around the longitudinal axis from the orientation depicted in FIG. 8 (e.g., such that the relative position of the superior portion 250 of the suction device is interchanged with the inferior portion 251, and the left side 252 is interchanged with the right side). Suction and alarm devices with alarm systems that are configured to accommodate a plurality of retention orientations will be described in detail below.

Figure 3A:
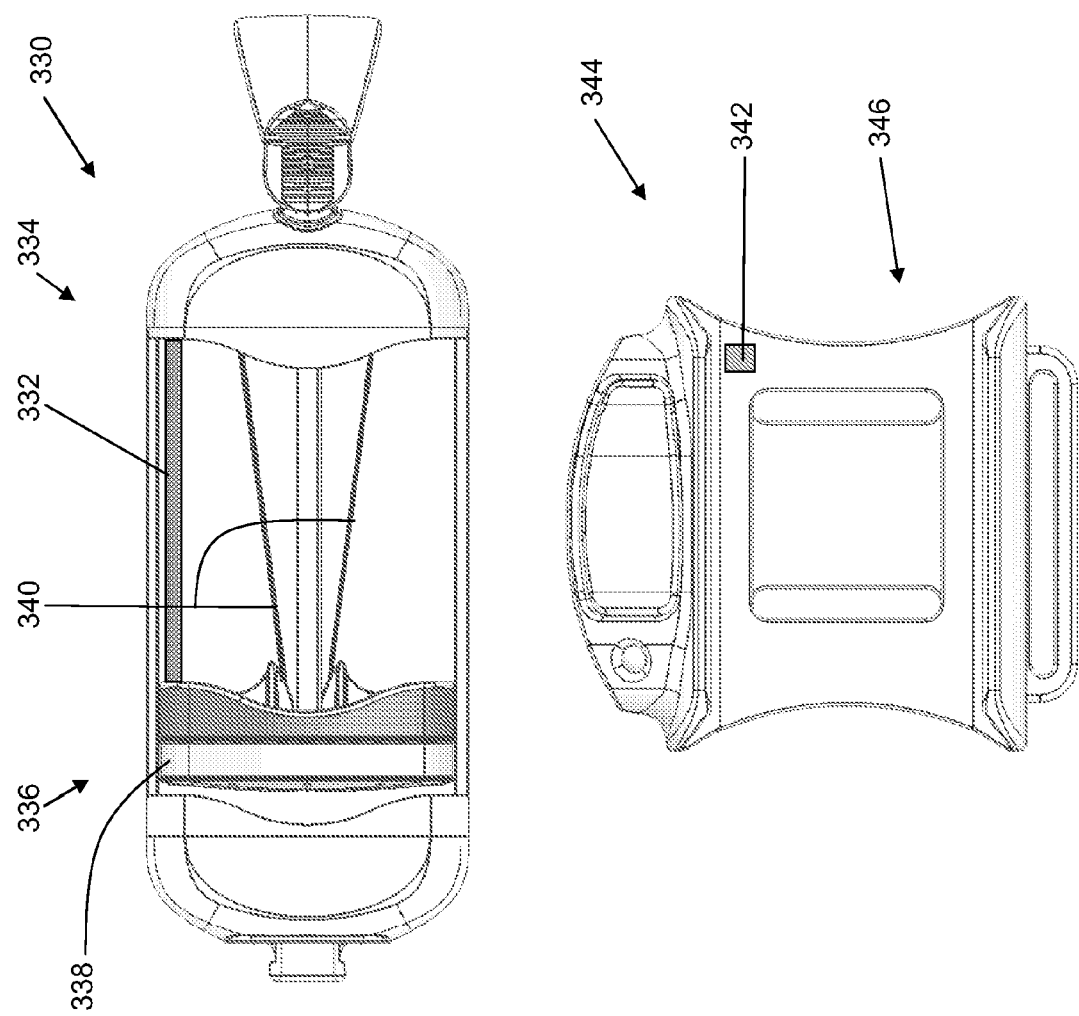
FIG. 3A is a superior component view of another variation of a suction device in a mechanically charged configuration, comprising an alarm system with a magnetic sensor mechanism.

One variation of a suction device 330 with an alarm system using a graded type magnetic sensor mechanism is depicted in FIG. 3A. Suction device 330 is configured to be retained within alarm device 344, which may comprise a clip with a magnetic linear encoder 342 at a proximal portion 346 of the alarm device 344. Optionally, the alarm device 344 may comprise a strap that may be coupled to the clip to attach it to a patient. The power source for the linear encoder 342 may be a battery embedded within the alarm device 344. Suction device 330 comprises a multi-pole flexible magnetic strip 332 that spans along a longitudinal length of the device, from a proximal portion 334 to a distal portion 336 of the device, and aligned over the magnetic linear encoder 342. The distal end of the flexible magnetic strip 332 may be fixedly attached to the base of a sliding seal 338 of the suction device 330, and rotatably attached to the proximal portion 334 of the suction device. The relative motion due to the longitudinal shortening of the magnetic strip during the application of negative pressure may be detected by the magnetic linear encoder 342. In some variations, the magnetic strip 332 may be coupled to a portion of the springs 340. In the charged configuration, the magnetic strip 332 is extended, as depicted in FIG. 3A. As the springs 340 recoil and shorten during the course of negative pressure therapy, the magnetic strip may recoil and shorten similarly (as the magnetic strip 332 may be at least partially coiled at the proximal portion 334). In other variations, as depicted in FIG. 3A, the magnetic strip 332 may be coupled to a non-central region of the sliding seal 338, and as the suction device 330 is used to apply negative pressure, the magnetic strip 332 shorten and form a coil around a rotatable pin that is separate from the coil of the springs 340. Alternatively or additionally, the magnetic strip 332 may be wrapped around a first rotatable pin at the proximal portion 334, and coupled to a second slidable and/or rotatable pin that retains the magnetic strip within the housing of the suction device 330. For example, the second pin may be slidable on a side slit in the housing of the suction device 330, and may be coupled to the sliding seal 338 such that its movement across the suction device corresponds to the movement of the sliding seal. The rotation of the pin and/or the movement of the magnetic strip 332 across the magnetic linear encoder 342 may be detected and used to trigger an alarm when the suction device 330 is exhausted or depleted. The second pin may be made of a magnetically detectable material (e.g., a magnet or ferromagnetic metal, etc.), which may allow its location along the suction device to be detected by any suitable proximity detector (e.g., any of the sensors described above).

In other variations, a multi-pole magnetic strip may be located along a longitudinal length of the clip, and the magnetic linear encoder may be embedded in the slidable seal of the suction device, in alignment with the magnetic strip. As the slidable seal with the linear encoder moves across the magnetic strip, the linear encoder detects the relative movement between the seal and the magnetic strip, which may be used to compute the location of the slidable seal within the suction device. In this variation, a power source such as a battery may be provided on the suction device, where the power source may be mechanically or electrically recharged and/or may be replaced when depleted.

Figure 3B:
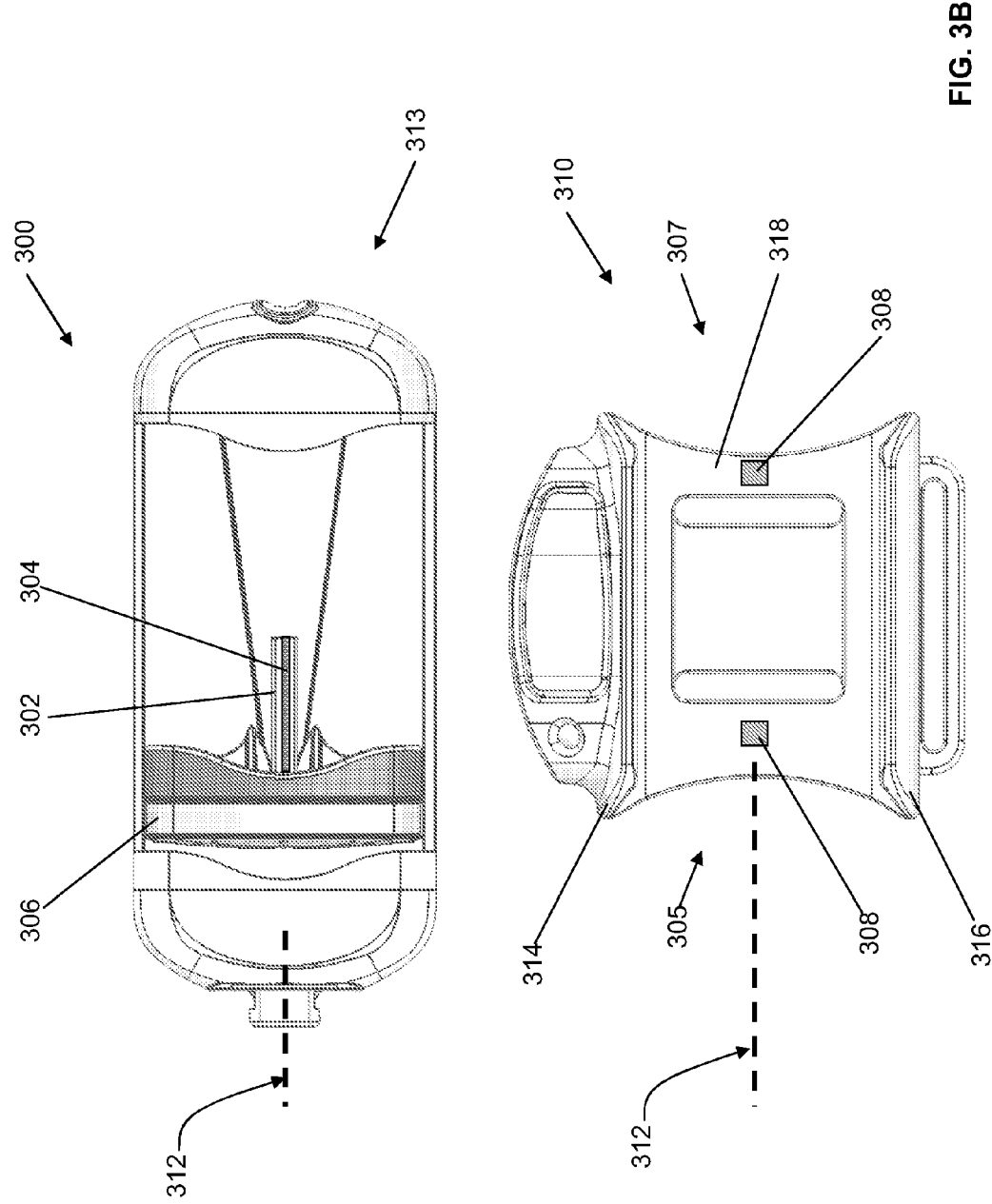
FIG. 3B is a superior component of another variation of a suction device in a mechanically charged configuration with a magnetic sensor mechanism.

Another variation of a suction device 300 with an alarm system using a graded type magnetic sensor mechanism with an alarm device 310 is illustrated in FIG. 3B. The suction device 300 comprises a shaft 302 that is fixedly attached to a sliding seal 306. The shaft 302 may comprise an elongate magnetic component 304 that may be embedded along a substantial length of the shaft. The alarm device 310 may comprise a clip having one or more magnetic linear encoders 308 to detect the movement of the elongate magnetic component 304 embedded in the shaft 302. A magnetic linear encoder located at the proximal portion 307 of the clip 310 may detect when the suction device 300 is depleted and trigger a notification mechanism to generate an alert.

The elongate magnetic component 304 may be embedded over 30% to about 100% of the total length of the shaft 302. The shaft 302 may have a length such that it does not protrude from the body of the suction device 300. For example, the shaft length may be is less than or equal to the distance between the sliding seal 306 and the proximal portion 313 of the suction device 300 in the depleted configuration. For example, the distance between the sliding seal 306 and the proximal portion 313 of the suction device in the depleted configuration may be from about 30 millimeters (mm) to about 200 mm, e.g., 90 mm. Accordingly, the length of the shaft 302 may be from about 10 mm to about 60 mm, e.g., 30 mm. Alternatively, certain suction devices may have a shaft with an elongate magnetic component that has a length that may protrude from the body of the suction device in the depleted configuration. Optionally, the shaft 302 may have a lumen therethrough configured to retain a key to mechanically charge the device.

In some variations, the elongate magnetic component 304 may be a multi-pole magnetic strip, where the pole length may be about 1.00 millimeter (mm). The location of the sliding seal 306 may be determined by the location of the elongate magnetic component 304 embedded within the shaft 302. The location of the elongate magnetic component may be detected by one or more magnetic linear encoders located on an alarm device 310. In some variations, the magnetic linear encoders may comprise an array of magnetic sensors, e.g., an array of Hall effect sensors.

Referring again to FIG. 3B, the alarm device 310 may have a first device retaining structure 314 and a second device retaining structure 316 that is directly opposite the first device retaining structure. The alarm device 310 also comprises a back panel 318 that is attached to the first and second retaining structures 314 and 316 on either side. When the suction device 300 is retained by the alarm device 310, the shaft 302 may move longitudinally across the length of the back panel 318. The one or more magnetic linear encoders 308 may be located anywhere on the alarm device 310 such that the longitudinal axis 312 of the shaft 302 passes over the linear encoder as the shaft moves. For example, in the alarm device 310 depicted in FIG. 3B, magnetic linear encoders 308 are located at a distal portion 305 and proximal portion 307 of the back panel 318 that overlaps with the longitudinal axis 312. In other variations of alarm devices, the magnetic linear encoder may be located anywhere on the alarm device that overlaps with the longitudinal axis of the suction device shaft, e.g. any location between the proximal 307 and distal portion 305 along the longitudinal axis of the shaft.

Additionally, the location of magnetic linear encoder 308 with respect to the elongate magnetic component 304 may be determined by the specification of the particular magnetic linear encoder selected. For example, the alignment of the elongate magnetic component over the magnetic linear encoder, the distance between the elongate magnetic component and the magnetic linear encoder, and other such positional details may be described in the specification of the magnetic linear encoder selected. Examples of elongate magnetic components and magnetic linear encoders that may be used here may include the MS10-10 magnetic multipole strip (pole length 1.0 mm, 10 poles) and the AS5311 high resolution magnetic linear encoder (Austria-Microsystems AG). Other suitable types of magnetic components and magnetic sensors and encoders may also be used with the suction and alarm devices described above.

While the magnetic components described above may be embedded or fixedly coupled to the sliding seal or shaft of the suction device, in other variations, the sliding seal or shaft may be itself magnetic, i.e., made of magnetic materials. The sliding seal and/or shaft may comprise an integral magnetic component, or may comprise a plurality of magnetic components throughout its length. Examples of magnetic materials that may be used in an alarm system comprising magnetic sensors include but are not limited to neodymium, iron, boron, samarium cobalt, alnico, ceramic, ferrite, various alloys (such as an alloy of neodymium, iron and boron) and the like. Alternatively or additionally, the magnetic components may be electromagnetic. The magnetic components may have any size or shape as may be suitable for attaching to the suction device and/or alarm device. For example, the magnetic components may be magnetic sheets or strips. Magnetic components may also be shaped as a disc, rectangular block, cylinder, etc.

The output of the magnetic linear encoder 308 may activate a notification mechanism that informs the patient and/or practitioner about the status of the suction device 300. The notification mechanism may be configured or programmed to issue certain indicators or alerts depending on the positional output of the magnetic linear encoder 308. For example, the magnetic linear encoder 308 may activate the notification mechanism to issue a first alert when the suction device 300 is fully charged and installed in the alarm device 310 as depicted in FIG. 3B. When the shaft 302 has moved to a position where the suction device 300 is partly depleted (e.g., about 30% depleted) the magnetic linear encoder 308 may activate the notification mechanism to issue a second alert. Any desired number of alerts may be issued according to the position of the shaft 302 as detected by the magnetic linear encoder 308. When the shaft 302 has moved to a position where the suction device 300 is nearly or fully depleted, the magnetic linear encoder 308 may activate the notification mechanism to issue another alert. More generally, the magnetic linear encoder and the notification mechanism may be configured or programmed to provide alerts at any frequency as desired by the patient and/or practitioner. While an encoder that detects longitudinal or linear movement is described above, other types of graded sensors will be described below.

In addition to a magnetic field sensitive reed switch described above, electrical switches that are triggered by certain configurations of the suction device may be used to activate (e.g. by closing or opening) a circuit of a notification circuit to generate an alert. Such electrical binary type switches may be triggered to particular configurations of the suction device, and may be used to activate a notification mechanism. One variation of a suction device 400 using a binary type electrical switch mechanism is depicted in FIGS. 4A-4E. The suction device 400 may comprise a slidable seal 420, where the slidable seal is attached or coupled to one or more springs 422 or a shaft 428 of a activation tool 426, as previously described. Suction device 400 also comprises a circuit conduit 410 embedded in the slidable seal 420. A notification mechanism as described below may be activated when the slidable seal 420 and the circuit conduit 410 are at a certain location in the suction device. For example, when the slidable seal 420 seal is in the location depicted in FIG. 4A, the notification mechanism may not be activated, but when the slidable seal 420 is in the location depicted in FIG. 4B, the notification mechanism may be activated.

Figure 4A:
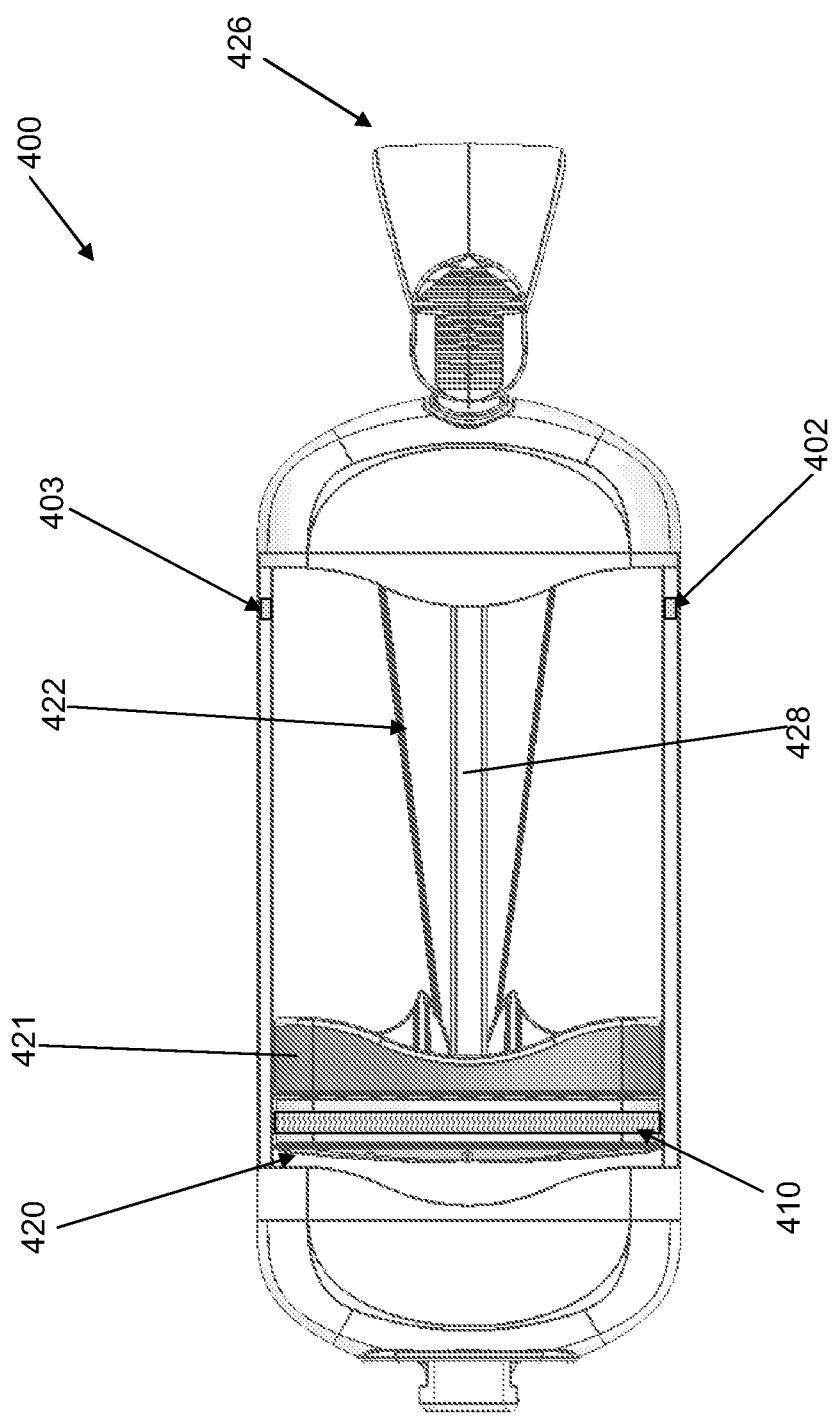
FIG. 4A depicts one variation of a suction device for reduced pressure therapy comprising an alarm system with an electric switch mechanism in a mechanically charged configuration.
Figure 4B:
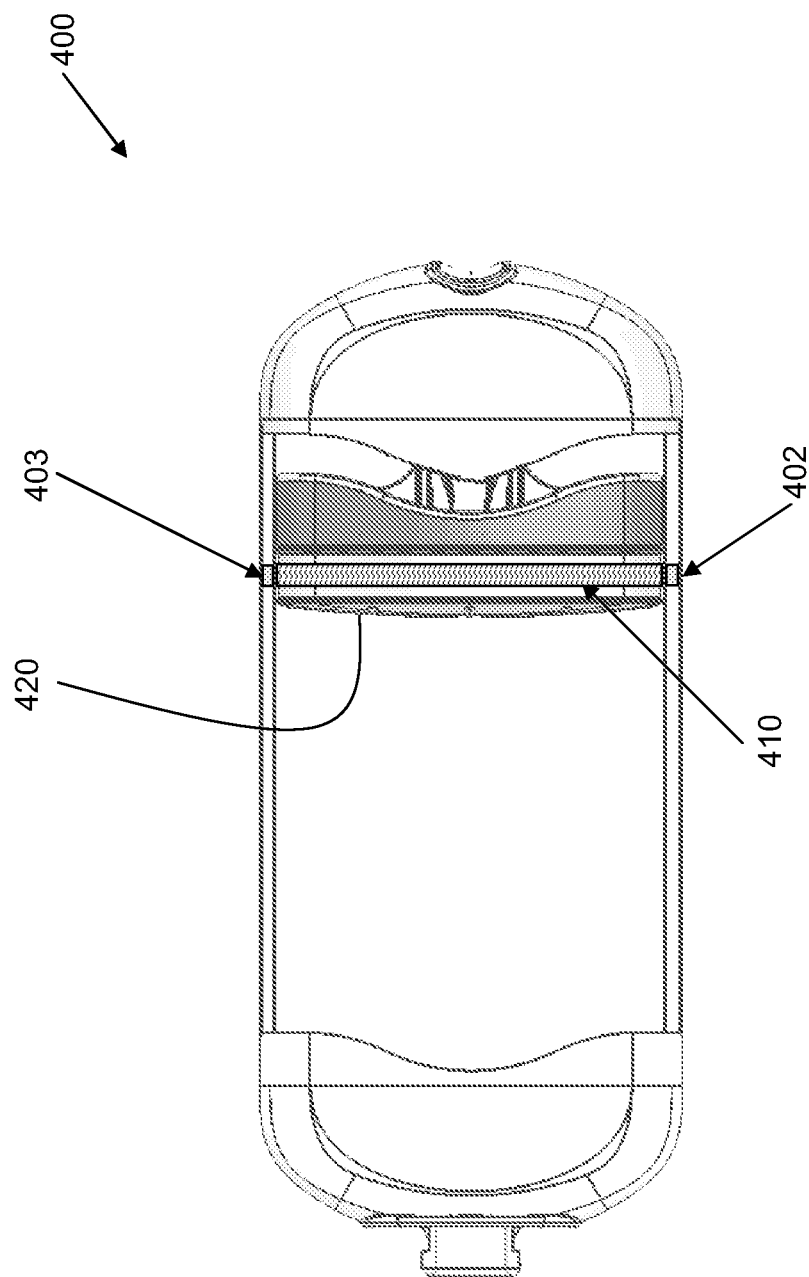
FIG. 4B is a depiction of the suction device of FIG. 4A in a depleted configuration.
Figure 4C:
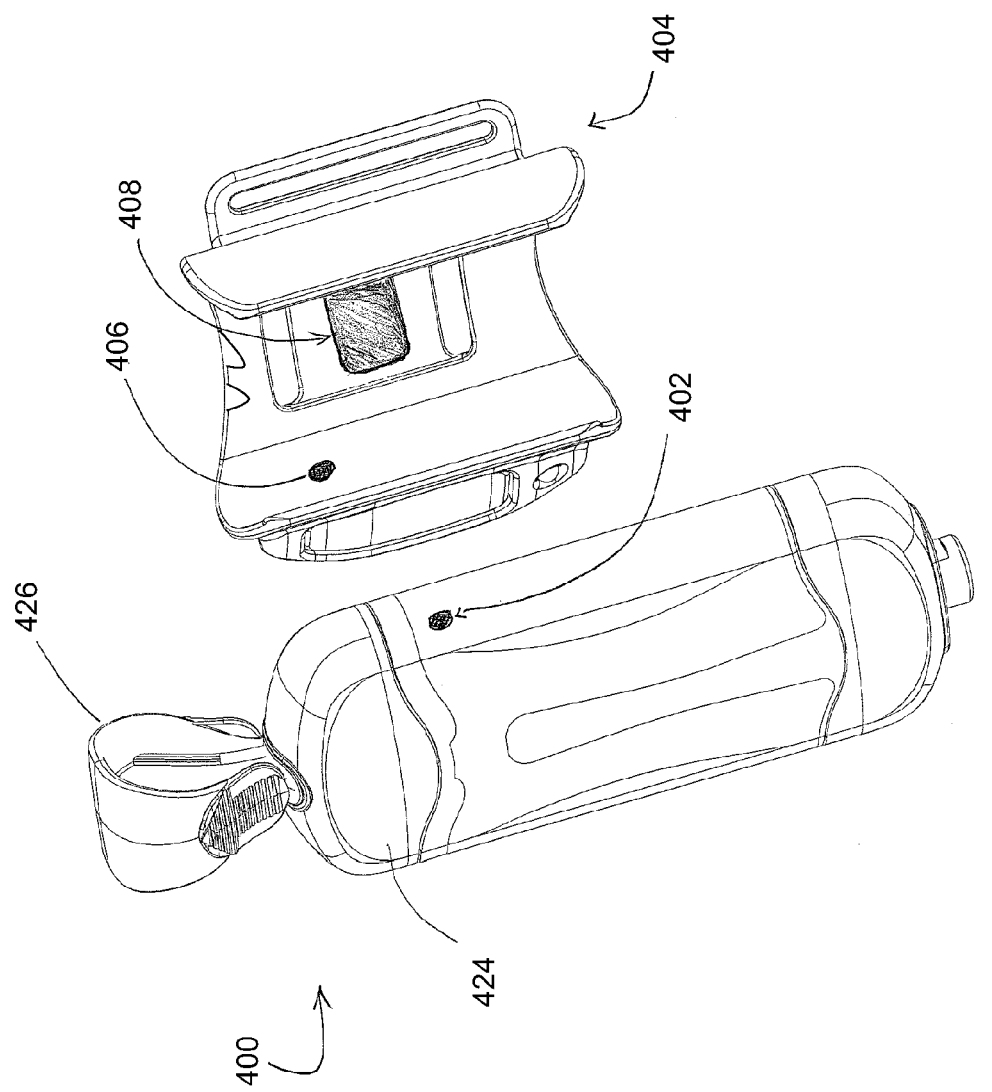
FIG. 4C is an anterior perspective component view of the suction device and an alarm device of FIG. 4A.
Figure 4D:
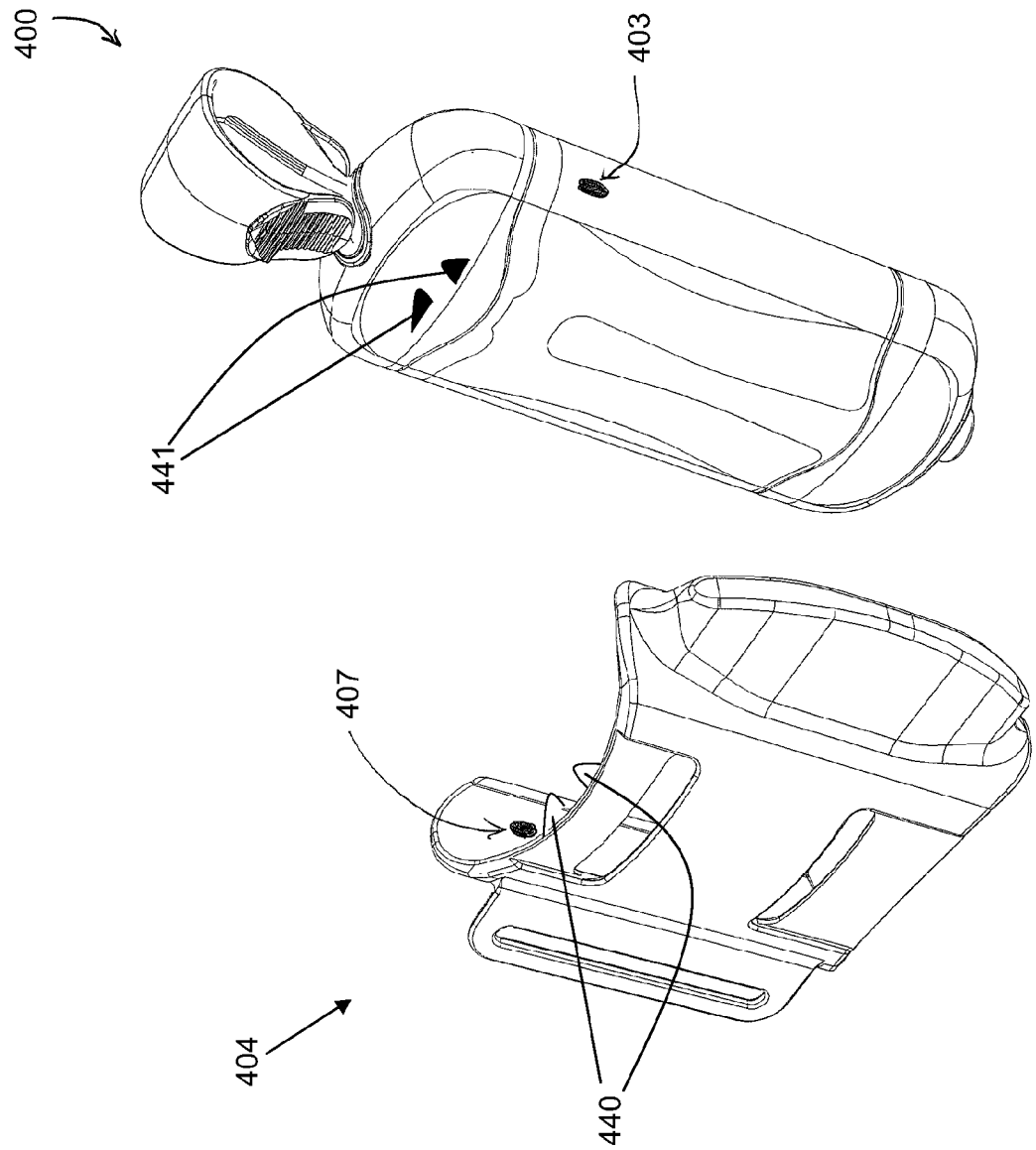
FIG. 4D is a posterior perspective view of the suction device and alarm device of FIG. 4A with an alarm device.
Figure 4E:
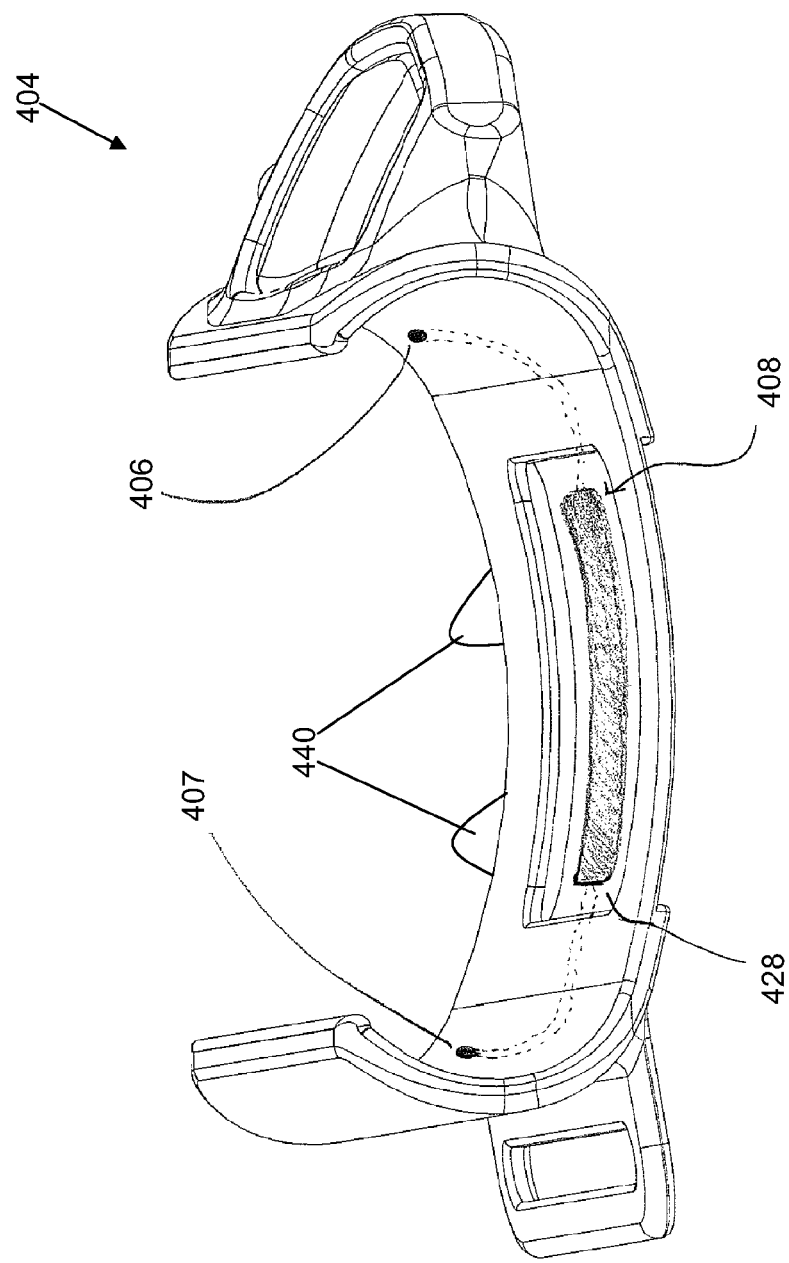
FIG. 4E is a side elevational view of the alarm device of FIG. 4C.

FIGS. 4C-4E illustrate one variation of a notification mechanism that may be activated closing a switch when the suction device attains a certain configuration. For example, a notification mechanism may be configured to generate an alert when the position sensor mechanism detects that the slidable seal is in a proximal position, i.e., the suction device 400 is depleted or exhausted. The notification mechanism may comprise a first activation contact 402 on one side of a proximal portion of the suction device housing 424, and a second activation contact 403 that may be directly across from the first activation contact. The activation contacts may extend through the entire thickness of the housing 424. The first activation contact 402 may be electrically coupled to the second activation contact 403 via an activation element in the sliding seal 420, e.g., the circuit conduit 410. When the circuit conduit 410 is not aligned with both the activation contacts 402 and 403, i.e., the suction device 400 is in the configuration depicted in FIG. 4A, the activation contacts are electrically isolated. When the circuit conduit 410 is aligned with both the activation contacts 402 and 403, i.e., the suction device 400 is in the configuration depicted in FIG. 4B, the activation contacts are electrically coupled, and current may flow between the activation contacts. There may be several pairs of activation contacts along the length of the suction device 400, which may sense various locations of the slidable seal 420 as desired. For example, the activation contacts 402 and 403 are located so that they may be aligned with the circuit conduit 410 of the slidable seal 420 when the suction device is depleted or exhausted. When the suction device 400 is in the depleted configuration shown in FIG. 4B, the activation contact 402, the circuit conduit 410, and the activation contact 403 may be aligned to form an electrical pathway therebetween.

The notification mechanism may comprise a circuit configured to generate an alert. For example, the notification mechanism may comprise a notification circuit 408, where the notification circuit 408 may comprise an open circuit which may be activated when the circuit is closed. The notification circuit 408 may be located on an alarm device 404 that is configured to retain the suction device 400, as illustrated in FIGS. 4C and 4D. The alarm device may comprise a clip, sheath, case, etc. that may have one or more grooves, protrusions, high-friction surfaces, etc. that are arranged to reliably retain and align the suction device within the alarm device. The alarm device may also have one or more bands, clips, belts, straps, etc. that may couple the suction device to a patient, e.g., an arm or wrist band, leg strap or brace, waist belt, and the like.

The notification circuit 408 may be attached to a back panel 428 of the alarm device 404, which is illustrated in FIG. 4E. The notification circuit 408 may comprise a first alarm contact 406 on one side of the alarm device, a second alarm contact 407 that may be opposite the first alarm contact 406, and a battery (not shown). The alarm contacts 406 and 407 may be the terminal nodes of an open circuit of the notification mechanism. In the open circuit configuration depicted in FIG. 4E, the notification circuit is in an inactivated state. Activation of the notification circuit 408 may require an electrical conduit between the alarm contacts 406 and 407. The alarm contacts 406 and 407 may be located such that when the suction device 400 is retained within the alarm device 404, the activation contacts 402 and 403 are aligned and touch each other. The connection between the alarm and activation contacts may be sufficiently intimate such that an electrical current may pass between them. Optionally, the engagement between the alarm and activation contacts may help to retain the suction device 400 within the alarm device 404. In some variations, the alarm contacts and the activation contacts may be complementary structures, such that they engage or mate when the suction device 400 is retained by the alarm device 404. For example, the alarm contacts and the activation contacts may be engaged by snap-fit, friction-fit, mechanical interfit, magnetic attraction, and the like.

As described above, a notification mechanism may comprise an electrical circuit with an open circuit where the termination nodes correspond to two or more alarm contacts. A notification circuit may be held in an inactivated state by the open circuit, and activated when the open circuit is closed, i.e., when one or more conductive pathways are provided between the alarm contacts. The alarm contacts may be electrical switch contacts and/or reed switch contacts that respond when a magnetic field is present.

In the variation of the suction device 400 described above, the alarm system is configured to alert the practitioner when the suction device is depleted of its ability to provide reduced pressure to a tissue. FIG. 4B depicts the location of the slidable seal 420 when the suction device is nearly depleted, where the activation contacts 402 and 403 are connected via the circuit contact 410. As described previously, when the suction device 400 is retained in the alarm device 404, the activation contacts 402 and 403 engage and connect with the alarm contacts 406 and 407. When the suction device 400 is in the configuration shown in FIG. 4B, the open circuit 432 of the notification circuit 408 is closed, and the tone generator 434 is activated. While the open circuit 432 has been described as being closed by circuit conduit 410, in other variations, the open circuit may be closed by other switch mechanisms. For example, the open circuit 432 may be closed by a spring-loaded button or knob that may be depressed when the slidable seal attains a certain position. In some variations, the slidable seal may have a protrusion that depresses the spring-loaded button to close the open circuit and activate the tone generator. As described previously, the alarm contacts of the notification circuit 408 may be closed by a reed switch. For example, when the magnet coupled to the slidable seal is in the vicinity of the reed switch, the reed switch may change to a closed configuration and activate the notification circuit.

The activation contacts, alarm contacts, and circuit conduit may be made of any electrically conductive material, such as copper, gold, silver, etc. Other types of electrically conductive materials may be used in to activate the notification circuit.

Figures 6A, 6B:
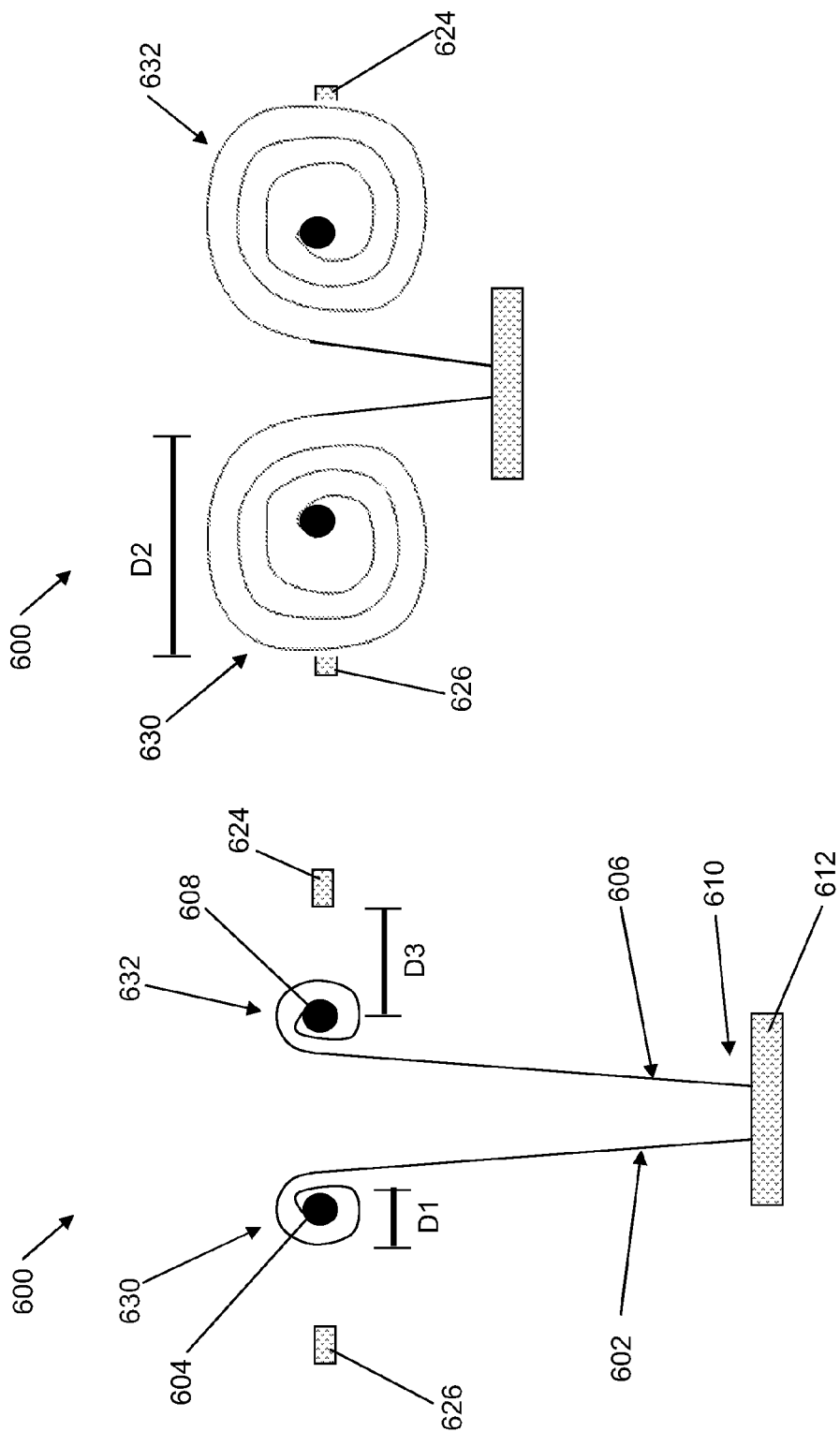
FIG. 6A is a schematic representation of a spring assembly in an extended configuration with a rotary sensor that may be used in a suction device.
FIG. 6B depicts the spring assembly of FIG. 6A in a retracted configuration.

While some suction devices may comprise alarm systems with sensor and/or notification mechanisms that track the position of the sliding seal assembly in the suction chamber of the device, alternatively or additionally, other suction devices may comprise alarm systems that track other moving components, such the one or more components of the suction generating mechanism. As described previously, a suction device may use one or more constant force springs to provide reduced pressure to a tissue region. The constant force springs may be extended using a shaft and/or an activation tool to push the slidable seal distally. As the constant force springs retract (e.g., as the ability to provide reduced pressure decreases), they may form a coil in a proximal portion of the suction device. In some variations, the retraction of the constant force springs as the suction device is depleted may rotate an axle around which the springs are wound. When the springs retract as the suction device is depleted, it may form a coil with increasing diameter as the springs retract. An alarm system may comprise a sensor mechanism that is triggered by the coiling of the constant force springs. FIGS. 6A and 6B schematically depict one example of a sensor mechanism that detects the coil size of a suction device spring assembly, and may be used to trigger a notification mechanism based on the degree to which the springs are coiled. FIG. 6A depicts the configuration of a spring assembly of a suction device when the suction device is charged. FIG. 6B depicts the configuration of the spring assembly when the suction device is depleted, where a notification mechanism may be triggered to generate an alert. The spring assembly 600 comprises a first spring 602 wrapped around a first rotatable axle 604 to form a first coil 630, and a second spring 606 wrapped around a second rotatable axle 608 to form a second coil 632. The distal portions 610 of the springs are attached to a slidable seal 612. During the use of the suction device, the springs retract to apply negative pressure to a tissue site, and rotate the first and second rotatable axles 604, 608. A rotary encoder, which may provide either a binary or graded type output, may be used to measure the rotation of the axles 604, 608 as the spring is extended or retracted, as well as the size of the coils 630, 632. Examples of how rotary encoders may be used are described below.

The rotary encoder (not shown) may measure the rotation of the axle 604 and map the measured rotation of the axle 604 to a particular sliding seal location. For example, the rotary encoder may maintain an internal count of the number of clockwise and counterclockwise rotations of the axles 604, 608. The linear movement of the springs may be computed based on the number of rotations in both directions. The linear movement of the springs may be mapped to the location of the sliding seal 612. According to the sliding seal location, the rotary encoder may generate a graded output that drives a notification mechanism, e.g., notification circuit 408, to generate an alert to the patient and/or practitioner.

Additionally or alternatively, the location of the sliding seal 612 may be determined using sensors that are configured to detect the diameter of the coils 630, 632, which may vary as the suction device is used. The constant force spring assembly 600 may also comprise a first sensor 626 and a second sensor 628, where the first and second sensors are configured to general a signal to the notification mechanism when the coils 630 and 632 are sufficiently large. The first and second sensors 626, 628 may be located at a distance D3 away from the respective axles 604, 608, such that the sensors are not activated when the suction device is charged, and activated when the suction device is depleted. For example, when the suction device using the constant force spring assembly 600 is fully charged (e.g., the slidable seal is in a distal position), the springs are fully extended as depicted in FIG. 6A, and a first coil 630 formed by the first spring 602, and a second coil 632 formed by the second spring 606 may have a diameter D1, where 0.5(D1)<D3, and may be from about 0 mm to about 16 mm, e.g. D1 may be from about 0 mm to about 30 mm, or from about 14 mm to about 17 mm, or from about 15.7 mm to about 15.9 mm. When the suction device is fully depleted (e.g., the slidable seal is in a proximal portion), the springs may be fully coiled, as depicted in FIG. 6B, and the first and second coils 630, 632 may have a diameter D2, where 0.5(D2)>=D3, and D2 may be from about 0.2 mm to about 35 mm, or from about 14.3 mm to about 17.3 mm, or from about 16.0 mm to about 16.2 mm. While the variation of the spring assembly described here may have two sensors, other variations of spring assemblies may have three or more sensors as desired, e.g., 3, 4, 5, 6, 8, 10 or more. Each of the sensors may drive individual notification mechanisms, or may drive two or more notification mechanisms. The sensors 626, 628 may also be used to detect when one or both the springs 602, 606 break, which may result in the sudden increase in coil diameter.

Additionally or alternatively, the springs 602, 606 may have a plurality of stripes oriented transversely to the length of the springs, where the spacing between the stripes may vary along the length of the springs (e.g., the spacing between stripes is directly related to the location of the stripes on the length of the spring). One or more optical sensors, e.g., a barcode scanner or laser backscatter sensor, may be provided to detect the stripe spacing of the springs at a reference location, which may map to slidable seal location. Optical sensors may be at a proximal location, e.g. longitudinally adjacent to the sensors 626, 628, or may be located anywhere along the length of the springs. The rotary encoders described above may provide graded type outputs that not only indicate a charged or depleted configuration, but also provide outputs that indicate intermediate configurations, e.g., suction device is about 100%, about 80%, about 50%, about 30%, about 10%, about 0%, charged or depleted. The notification mechanism may be adapted and/or configured to generate an alarm based on one or more intermediate configurations as desired.

Alarm systems with optical sensor mechanisms may also be used to detect the position of the slidable seal. For example, an optical sensor may be located at a proximal location (i.e., in proximity to the location of the slidable seal when the suction device exhausted or nearly exhausted, or at any location along the length of the suction device) that is configured to detect a certain optical cue on the slidable seal. For example, the slidable seal may have markings with a certain color, pattern (e.g., striped, dotted, zig-zag, etc.), reflectance or absorbance property that may be detected by an optical sensor, which may drive a notification mechanism to indicate that the slidable seal is at the location of the optical sensor, i.e., the suction device is exhausted or depleted. Examples of optical sensors that may include infrared sensors, photodiodes, CCD devices, and the like.

Some optical sensors may be configured to detect an optical interference. For example, the housing of a suction device may be substantially transparent or translucent, while the slidable seal may be substantially opaque. An interference sensor located at a proximal portion of the clip, at the location where the slidable seal may be when the suction device is exhausted or depleted. The interference sensor may detect an occlusion or blockage of light that may result from the movement of the opaque slidable seal when the device is exhausted, and trigger the notification mechanism accordingly. An alarm system comprising an optical sensor may be detachably coupled to the suction device, such that they may be removed from a depleted suction device and attached to a different (e.g., newly charged) suction device. In this way, the alarm system may be reused for multiple sessions of reduced pressure therapy.

Certain variations of suction devices may comprise a pressure transducer that may directly measure the pressure in the suction chamber, and signal a notification mechanism according to the measured pressure. The pressure transducer may be located at a distal portion of the suction chamber. Optionally, there may be a display or monitor that indicates the exact pressure being applied to a tissue region. Notification mechanisms may be configured to generate alerts according to certain pressure levels, as desired.

Certain variations of suction devices may also comprise liquid sensors that detect the presence of any fluids within the suction chamber. An alarm device may comprise a liquid sensor interface that receives the signal from the suction device liquid sensor, and drives a notification mechanism to notify the patient and/or practitioner when there is liquid in the suction chamber. Some types of liquid sensor mechanisms may also provide data about the quantity of liquid in the suction chamber, which may trigger an alert for the patient and/or practitioner to empty or replace the suction device. For example, some liquid sensor mechanisms may sense the location of a float within the suction device chamber, where the float moves according to the quantity of air and/or fluids in the chamber. In some variations, the float may comprise one or more magnetic components that may be detected by any of the magnetic field sensitive mechanism described above. The detected location of the float may activate the notification mechanism to generate an alert.

Suction devices may be retained in an alarm device in a particular orientation. Various features on the housing of the suction device may correspond to and/or be aligned with features on the alarm device to help ensure a certain alignment and/or orientation when the suction device is coupled to the alarm device. For example, one or more surface structures of the suction device housing and the alarm device may be configured to help ensure precise positioning of the suction device with respect to the alarm device. The interface between the suction device housing and the alarm device may also comprise features that secure the suction device in a desired alignment with the alarm device. In some variations, the suction device and/or alarm device may be configured such that the suction device may be retained in the alarm device in a plurality of orientations, as described further below. Examples of surface structures that may retain the alignment and position between two surfaces may include interlocking flanges or hooks, interlocking slits or seals, hook and loop engagement, a protrusion and a recess coupled by friction-fit, snap-fit structures, and the like. Examples of suction and/or alarm devices with features for alignment are described below.

In some variations, the suction device housing may have one or more protrusions or grooves that are complementary to one or more grooves or protrusions on the alarm device, e.g., form a mechanical interfit. For example, as depicted in FIG. 4D, the alarm device 404 may have one or more protrusions 440 that fit into recesses 441 on the housing of the suction device 400. In some variations, the suction device housing may also have curved grooves along its surface to accommodate the portions of the alarm device that contact the suction device. Alternatively or additionally, the suction and alarm devices may have snap latches and snap grooves at corresponding locations.

Suction and alarm devices with different sensor mechanisms may have different surface structures. This may help to ensure that only suction and alarm devices with compatible sensor mechanisms may be coupled together. For example, attachment clips with magnetic sensors may have alignment features that form an interfit with the alignment features of suction devices with a magnetic component in the sliding seal, but do not interfit with the alignment features of suction devices without a magnetic sliding seal. For example, the alignment features of the suction device 200 may not be compatible with the alignment features of the alarm device 310.

In other variations, suction and alarm devices may have electrical components that correspond to each other to help ensure that devices with compatible sensor mechanisms are coupled together. For example, the suction device may have a conductive element with a particular shape that corresponds to the location of one or more electrical pins on the alarm device. When the conductive element of the suction device is in alignment with the one or more pins on the alarm device, an electrical signal is provided to a microcontroller of the alarm system to indicate that the suction and alarm devices are compatible and/or are properly assembled together. In some variations, power is provided to the microcontroller only when certain pins on the alarm device are shorted together by the conductive element of the suction device. In some variations, the alarm device may comprise one or more electrical contacts configured to align with corresponding conductive elements on the suction device such that the alarm device is powered only when a suction device is placed within the alarm device such that the conductive elements are aligned with the one or more electrical contacts. Additionally or alternatively, the alarm device may comprise a power switch that is configured to be depressed by a suction device that is retained within the alarm device. Depressing the power switch may complete a circuit and connect a power source to an alarm system microcontroller that may be included with the alarm device. When the suction device is removed from the alarm device, the pressure on the switch may be released, thereby disconnecting the power source to the alarm system microcontroller. The power switch may be a tactile switch, or any suitable mechanical or electrical switch mechanism. For example, an alarm device may comprise a tactile switch located on the inside of the device (e.g., a back panel of the alarm device that is to receive a suction device). Insertion of a suction device into the alarm device may push on the tactile switch to power the alarm system on, and removal of the suction device from the alarm device may release the pressure on the switch to power the alarm system off. Such power switch mechanisms may be used to reduce power consumption of the reduced pressure therapy system by helping to ensure that the alarm device does not draw any power from the power source in the absence of a suction device.

Figure 14A:
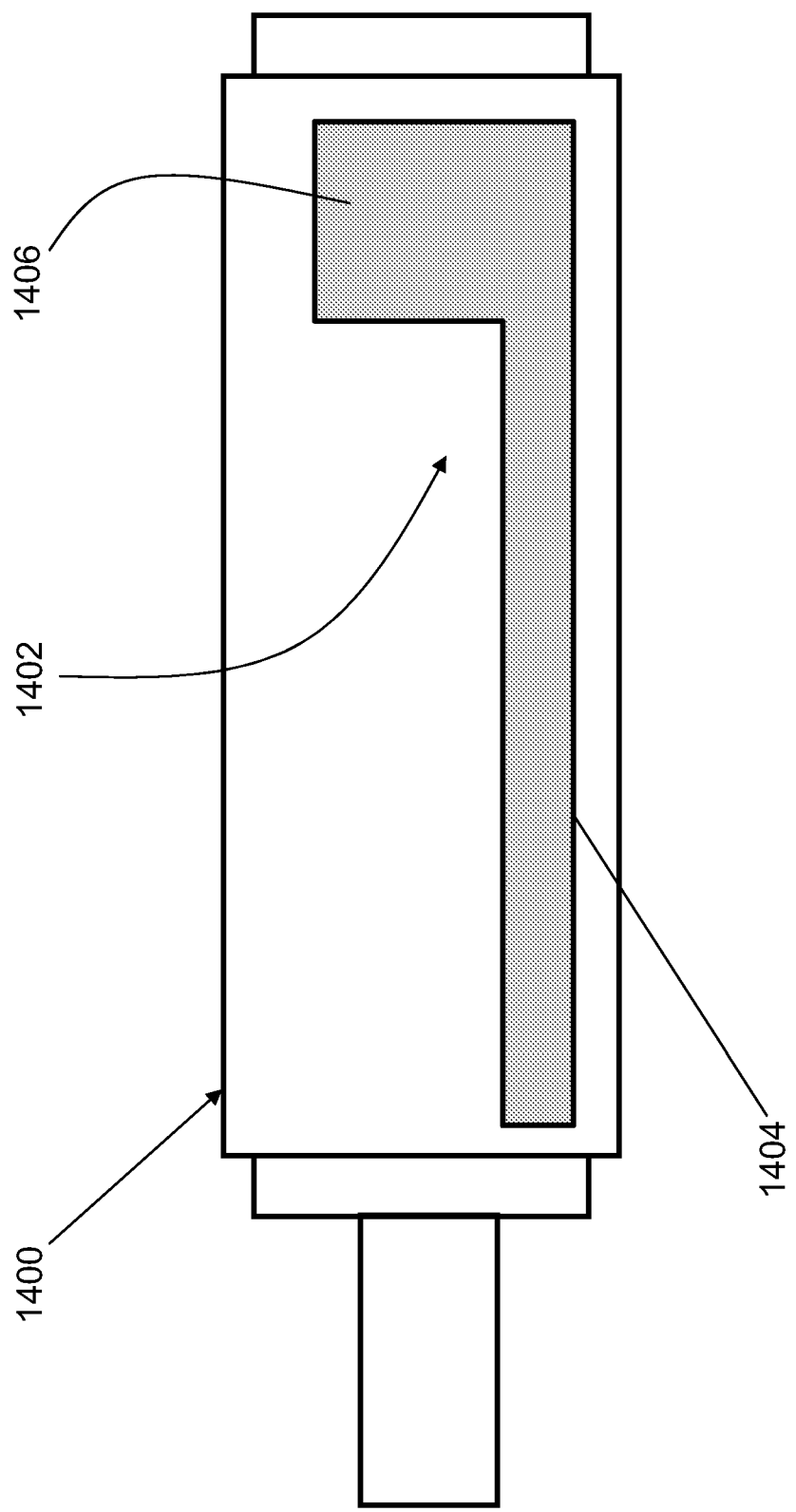
FIG. 14A is a schematic representation of a suction device with a conductive element.

FIGS. 14A-14C schematically depicts one example of an electrical mechanism that may be used to ensure that suction and alarm devices are compatible. Such an electrical mechanism may also be used to indicate the orientation of the suction device with respect to the alarm device so that a microcontroller on the alarm device may activate the appropriate sensors for depletion detection. In some variations, this mechanism may also be used to power the alarm system only when the suction device is retained in the alarm device. A suction device 1400 may comprise a conductive element 1402 that is accessible to an alarm device. The conductive element 1402 may have any geometry that is suitable for alignment purposes. For example, the conductive element 1402 may have an elongate portion 1404 along a length of the suction device 1400, and may also comprise an end portion 1406 that substantially extends from the elongate portion 1404. The conductive element may be located along a central axis of the suction device, or may be offset from the center. The overall geometry of the conductive element 1402 may be asymmetric or symmetric, depending on the configuration of electrical pins or pads on the alarm device. FIG. 14B schematically illustrates the positioning of suction device 1400 with respect to a plurality of pins on an alarm device. In some cases, the pins may be electrically isolated until coupled by a conductive element on the suction device. The pins 1410, 1412 and 1414 are schematically depicted, but for the sake of simplicity, the alarm device is not shown. FIG. 14B depicts a first orientation 1420 of the suction device, where the conductive element 1402 on the suction device electrically couples a first pin 1410, a second pin 1412, and a third pin 1414 together. Shorting these three pins together may send a first electrical signal to an alarm system microcontroller to indicate that the suction device is in the first orientation 1420. FIG. 14C depicts a second orientation 1422 that is a 180 degree rotation from the first orientation 1420. In the second orientation 1422, the first pin 1410 and the second pin 1412 are electrically coupled, however, the third pin 1414 is electrically isolated from the first and second pins. Shorting the first and second pins but not the third pin may send a second electrical signal to the microcontroller to indicate that the suction device is in the second orientation 1422. In some variations, power may be supplied to the microcontroller only when the suction device 1400 is in the first orientation 1420 or second orientation 1422, but not in the other orientation. While the conductive element 1402 on the suction device and the pins 1410, 1412, 1414 on the alarm device are configured to indicate two orientations, other suction devices may have one or more conductive elements with different geometries that correspond to three or more pins on the alarm device to indicate any number or orientations.

Figure 14D:
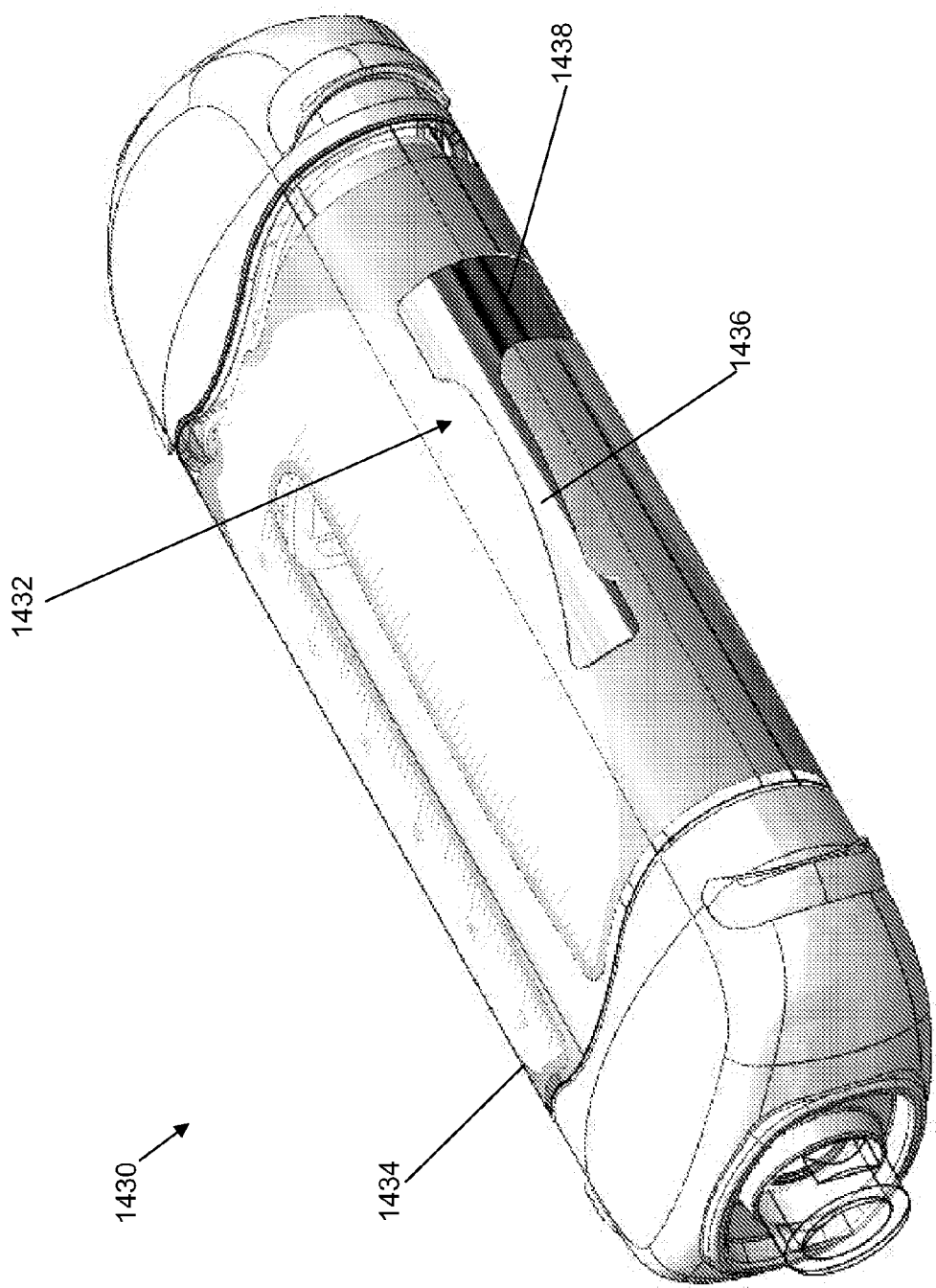
FIG. 14D is a perspective view of a variation of a suction device with a conductive element.
Figure 14E:
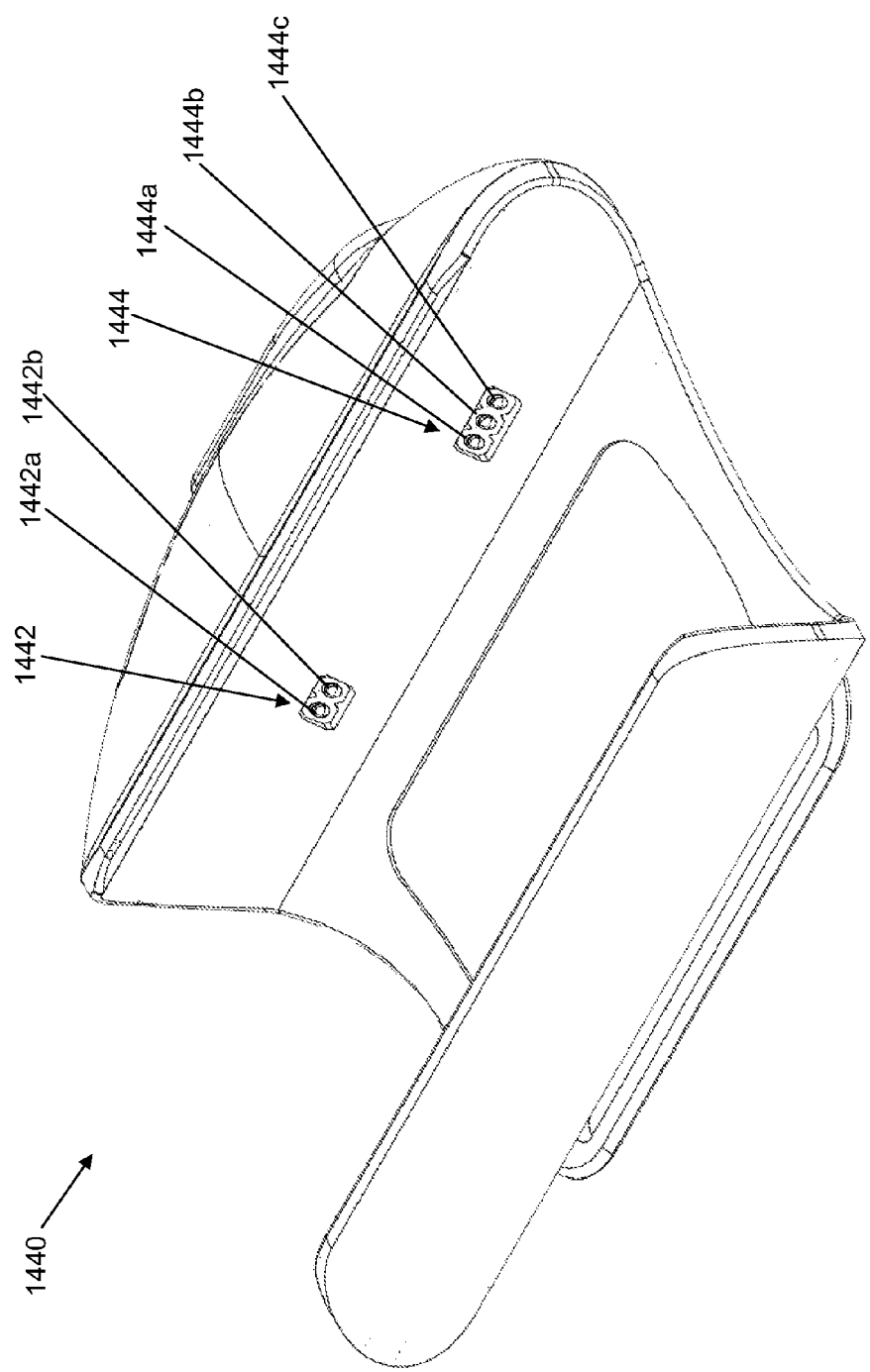
FIG. 14E is a perspective view of an alarm device with one or more connectors.

FIGS. 14D and 14E depict one example of a suction device 1430 and an alarm device 1440 that have an electrical mechanism that may be used for orientation identification, and/or to ensure that suction and alarm devices are compatible. The electrical mechanism may also be used as a power switch such that alarm device 1440 is not powered on until the suction device 1430 is retained therein. The suction device 1430 may comprise a conductive element 1432, and the alarm device 1440 may comprise a first pin connector 1442 and a second pin connector 1444 located such that the conductive element 1432 and the pin connectors contact each other when the suction device 1430 is placed within the alarm device 1440. As illustrated in FIG. 14D, the conductive element 1432 is located along a side portion of the housing 1434 of the suction device. The conductive element 1432 may have any suitable geometry, for example, it may have an elongate portion 1436 that extends along a longitudinal axis of the suction device, and an end portion 1438 that extends transversely to the elongate portion 1436. Portions of the conductive region 1432 may have any number of tapered, curved, rounded, etc. regions, as may be desirable. The location of the first connector 1442 and the second connector 1444 of the alarm device 1440 may correspond to the location of the conductive element 1432 of the suction device when retained in the alarm device. As illustrated in FIG. 14E, the first connector 1442 may comprise two pins 1443a, 1443b, and the second connector 1333 may comprise three pins 1445a, 1445b, 1445c, however, it should be understood that an alarm device may have any number of connectors, and each connector may have any number of pins. The connectors on the alarm device may correspond to the pin pads of an alarm system circuit, such as the alarm system circuit of FIG. 11, which will be described below. The number of pins on a connector may or may not match with the number of pins on the pin pad corresponding to that connector. The number of pins on each connector or pin pad may vary according to the alarm system circuitry.

While alarm devices may have connectors configured to be shorted by a conductive element on a suction device have been described above, alternatively or additionally, suction devices may have an alarm system with connectors, and the alarm device may have a conductive element configured to short the suction device connectors. For example, in variations where the suction device is electrically powered or has an alarm system that is electrically powered, the suction device may have electrical connectors that interface with a conductive element on the attachment feature. These electrical connectors may act as a power switch for the suction device, and/or an orientation and/or a compatibility interface between the suction device and alarm device, such that the suction device is not electrically activated until retained within the alarm device.

Various types of visual, audio, and tactile alerts generated by various notification mechanisms may be used with any of the sensor and/or detection mechanisms described above. In some examples, the alert may be an audio signal (e.g. a buzzer or ringing sound), a visual signal (e.g. flashing colored light) or a tactile signal (e.g. vibration from an asymmetric weight attached to a rotary motor), or a combination thereof. Other signals may include data signals that may be connected wirelessly or by wired connection to one or more displays and/or electronic healthcare/nursing record databases. These displays and/or electronic databases may be local (e.g. in the clip or a pocket-sized mobile device) to the user, or remote (e.g. the nursing station of the treatment facility, online electronic healthcare record database or the user's personal computer), and utilize any of a variety data transmission modalities (e.g. cellular networks and/or internet).

Figure 5:
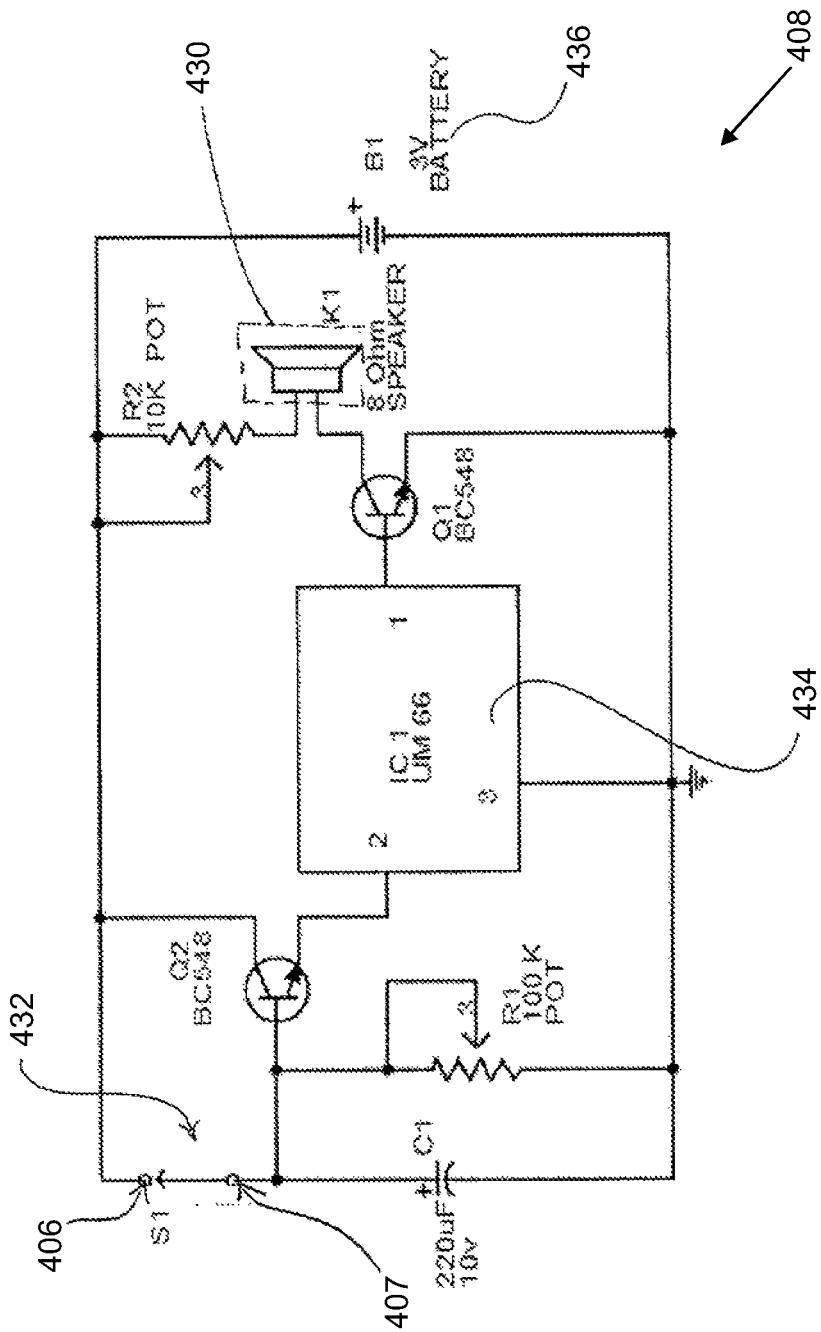
FIG. 5 depicts one example of a notification circuit that may be used an alarm system for reduced pressure therapy devices.

One example of a notification circuit 408 is depicted in FIG. 5. The notification circuit 408 may comprise an open circuit 432 with alarm contacts 406 and 407 as terminal nodes, and a tone generator 434 configured to drive speakers 430. All the components may be powered by a battery 436, which may provide a DC voltage that is appropriate for selected tone generator 434, e.g., from about 1.5 V to about 4.5 V. The tone generator 432 may be activated depending on the connectivity of the open circuit 432. Additional features may be included with the notification mechanism 408 to adjust the sound produced by the tone generator 434, the volume of the sound, and the duration that the sound is produced, etc. Variations of notification mechanisms may be used to activate different notification circuits to generate an alarm (e.g., visual or tactile alarms, as well as wireless signal generators), and may be included as separate modes that may be activated by the practitioner and/or patient. Notification circuits may also comprise memory components that may be configured to retain information about past alarm events, pre-programmed instructions, snooze functions, and the like. Notification circuit 408 may be located on the alarm device or on the suction device, as desired.

Additionally or alternatively to visual and/or audio alerts, notification mechanisms may issue electronic messages, such as text messages, e-mails, pages, etc., to indicate the state of the suction device, and whether or not the device needs to be replaced or emptied. The alerts may be provided to local monitors, such as the patient and/or attending medical practitioner, and/or may be provided to remote monitors, such as a medial practitioner who may be at a removed location. In some variations, the remote monitor may send a command to the suction device alarm system to issue an alert to prompt the patient to check on the suction device.

FIG. 9 depicts a block diagram representation of one variation of an alarm system 900. The alarm system 900 may comprise a microcontroller module 908 that has a microcontroller chip that may be programmed to accept sensor and/or user inputs and drive indicator outputs. For example, the microcontroller module 908 may receive input signals from a suction device orientation module 902, a sensor module 904, and a user input module 906. The orientation module 902 may provide information to the microcontroller module 908 regarding the position and/or orientation of the suction device with respect to the alarm device. The sensor module 904 may have one or more sensor mechanisms as described above, and may have, for example, one or more reed switches. The user input module 906 may comprise switches (e.g., power switch, toggle switches, etc.), buttons, dials, keyboards, and the like which may provide patient-specific information to the microcontroller 908, as well as to regulate the state of the alarm system 900. In addition to these inputs, the microcontroller module 908 may drive any number of output modules. For example, the microcontroller module 908 may drive a light-emitting diode (LED) module 910 that may be used as optical notifications to the patient, and/or may be used to backlight a display, such as a monitor. Outputs from the microcontroller may also be used to drive an indicator module 912 comprising notification circuits such as the ones previously described. In some variations, the indicator module 912 may comprise amplifiers that may augment the notification signal, whether audio, optical, tactile, electronic or otherwise, to help ensure that the patient and/or practitioner is made aware of the status of the alarm system. For example, the microcontroller may provide a signal to an audio amplifier that may in turn drive a speaker to generate an audible alert.

The various modules depicted in FIG. 9 may be located on either or both the suction device and alarm device. For example, the microcontroller module 908, optical notification module 910, user input module 906, and indicator module 912, may be located on the alarm device, while the sensor module 904 and the orientation module 902 may be located on the suction device. Alternatively, the components of both sensor module 904 and the orientation module 902 may be located on both the suction and alarm devices. The optical notification module 910 and the user input module 906 may also be on the suction device, as may be desirable. In other variations, all the modules depicted in FIG. 9 may be located only on the alarm device or only on the suction device. In still other variations, the modules depicted in FIG. 9 may be detachably coupled to the suction and alarm devices.

One variation of a system that comprises two reed sensors and generates an alarm based on signals from the reed sensors is depicted in FIG. 10A. The alarm system 1000 may comprise a first reed switch module 1004 and a second reed switch module 1006 that detect the position of the sliding seal within a suction device, and provide electrical signals, e.g., voltage or current signals, that correlate with the position of the sliding seal to a microcontroller module 1012. The microcontroller module 1012 may comprise a voltage sensor 1010. In some cases, the microcontroller module may comprise a programmable microcontroller or microprocessor with an embedded voltage sensor, for example, a system-on-a-chip microcontroller unit (MCU), such as any MCU in the C8051F93x-C8051F92x MCU family (Silicon Labs Inc of Austin, Tex.), for example. Any microcontroller with the appropriate power consumption (i.e., low power consumption), size (i.e., small size), and programmability (i.e., flexible software programming interface, compatibility with a variety of electronic components) may be used. The microcontroller module 1012 may receive inputs from a suction device orientation module 1002 which may be used to interpret the inputs from other modules in the alarm system 1000. The alarm system 1000 may also comprise a user switch module 1008 which may allow the patient to activate or deactivate the system, as well as to provide patient-specific data to the alarm system. The microcontroller module 1012 may drive a number of output modules, such as a LCD sense indicator module 1014, a LCD battery indicator module 1016, a LCD alarm indicator module 1018, a LED backlight module 1020, and an amplifier module 1022. In some variations, the microcontroller module may drive the LCD sense indicator module 1014 or a LCD segment to indicate that a suction device/cartridge is properly installed in the alarm device and/or that the alarm system is powered. For example, the LCD sense indicator module 1014 may be turned on or activated to indicate that there is a valid and/or compatible suction device coupled to the alarm device, and may be turned off or deactivated to indicate that there is no valid and/or compatible suction device coupled to the alarm device. Additionally or alternatively, the microcontroller module 1012 may drive radiofrequency transmitters or other electronic messaging devices to provide an e-mail or a text to a patient and/or practitioner to alert them of the state of the suction device.

Figure 10B:
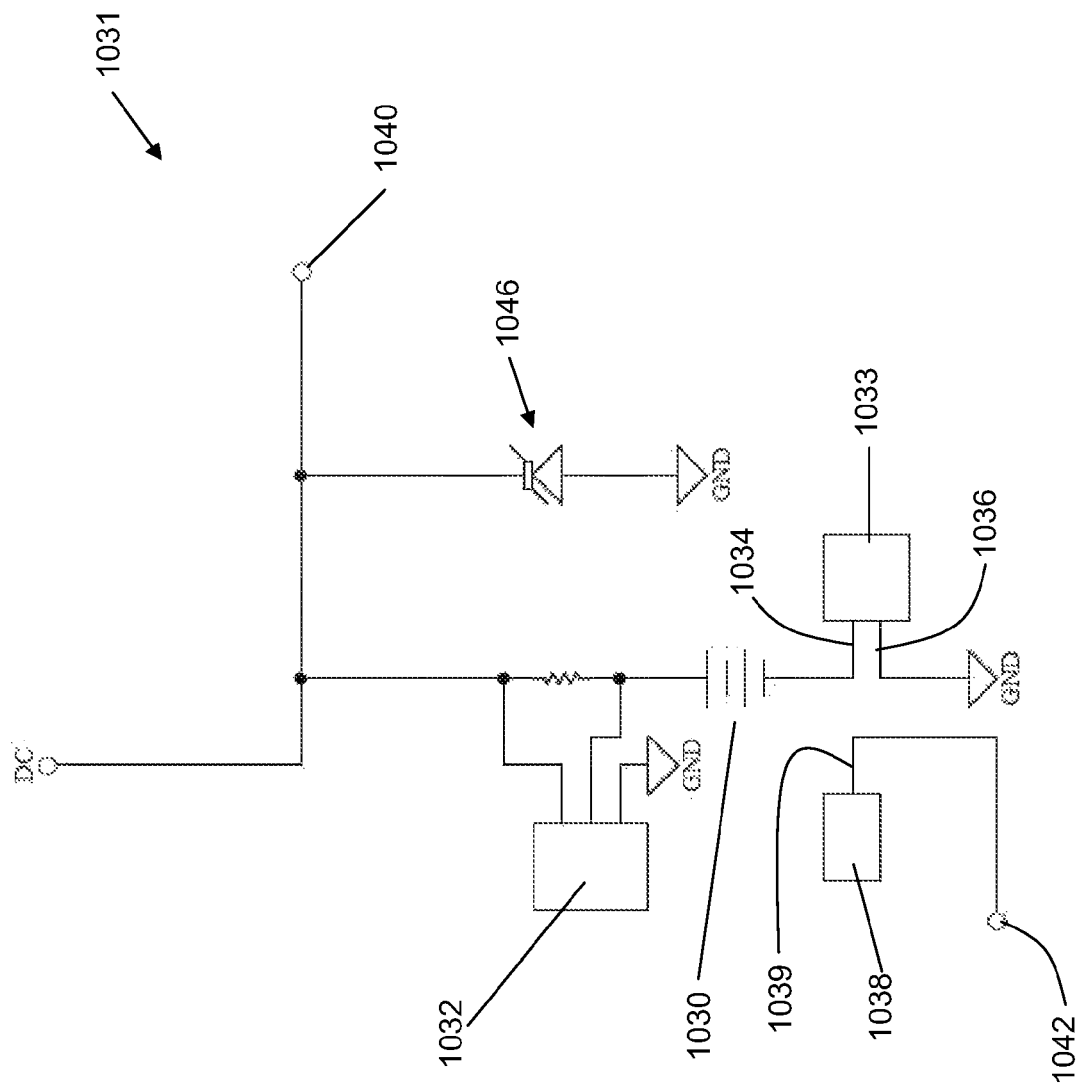
FIGS. 10B to 10D depict examples of circuits that may be implemented in the alarm system of FIG. 10A.

One example of an orientation circuit that may be used with an alarm device orientation module is depicted in FIG. 10B. Orientation circuit 1031 may comprise a first pin pad 1033 and a second pin pad 1038, where each pin pad may comprise one or more pins in any arrangement that corresponds to a conductive element in a suction device, as previously described. The first pin pad 1033 has a first pin 1034 and a second pin 1036, where electrically shorting them together may indicate a first suction device orientation. The first pin pad 1033 may be connected as a switch to a battery 1030 that may be configured to supply power to the alarm system, e.g., via a connection to the microcontroller module at the first terminal 1040. When the first pin 1034 and the second pin 1036 are electrically isolated, the first pin pad 1033 may be as an open circuit, and the battery 1030 may be disconnected from the electrical components of the alarm system. Shorting the first pin 1034 and second pin 1036 together may act to close the circuit such that the battery 1030 may provide power to the alarm system, e.g., by turning on the microcontroller module, etc. An optional LED diode 1046 connected to the first terminal 1040 may be activated when the first and second pins are shorted, which may provide a visual indication to the user that power is provided to the alarm system. The second pin pad 1038 may have a third pin 1039, where electrically shorting all three pins 1034, 1036, and 1039 may indicate a second suction device orientation. The connectivity of the second pin pad 1038 may be indicated to the microcontroller module via a second terminal 1042. Other variations of orientation circuits may have different a different number of pin pads and pins in a variety of arrangements. The battery 1030 may store sufficient energy to power the one or more electronic components of the alarm system, and may be selected according to the desired shelf life, service life, size, voltage, compatibility with other alarm system components, and/or discharge capacity. Any suitable batteries may be used with the orientation circuit 1031, for example, a battery with a shelf life of 10 years, service life of at least 8 weeks, such as the 3V CR2032 battery. Optionally, the orientation circuit 1031 may have a battery sensor 1032 that may provide an indication of how much energy is stored in the battery 1030, and activate a LED that may prompt the patient and/or practitioner to replace the battery or the alarm system. In certain variations, the alarm system may be powered by plugging into a wall socket instead of, or in addition to, using a battery.

Figure 10C:
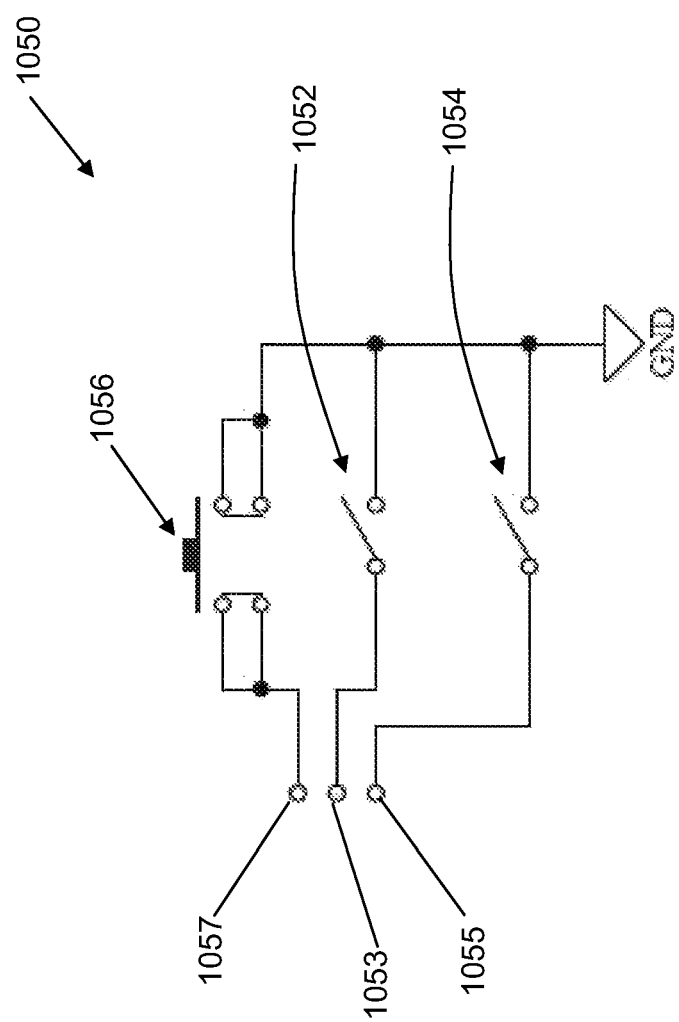

One example of a sensor circuit that may be used with an alarm device sensor module is depicted in FIG. 10C. The sensor circuit 1050 may comprise any number and types of sensors and/or switches, as previously described, for example, a first reed switch 1052 and a second reed switch 1054. When the slidable seal of a suction device is in proximity to the first reed switch 1052, it will close the switch and communicate the proximity of the slidable seal to the microcontroller module via a connection through a first terminal 1053. When the slidable seal of the suction device is in proximity to the second reed switch 1054, it will close the switch and communicate the proximity of the slidable seal to the microcontroller module via a connection through a second terminal 1055. Based on the data from the orientation module, the microcontroller module will make a determination as to the depletion state of the suction device. The sensor circuit 1050 may also comprise a user-activated switch 1056 that when closed, will activate the first and second reed switches. For example, the third terminal 1057 that is connected to a node of the user-activated switch 1056 may be connected to the microcontroller module, which may provide a certain voltage or current level that may only be conveyed to the first terminal 1053 and/or second terminal 1055 if the user-activated switch 1056 is closed and either or both the reed switches 1052, 1054 are closed. Other mechanisms for activating and/or deactivating the sensor circuit 1050, e.g., ON-OFF switches, may be used as appropriate.

Figure 10D:
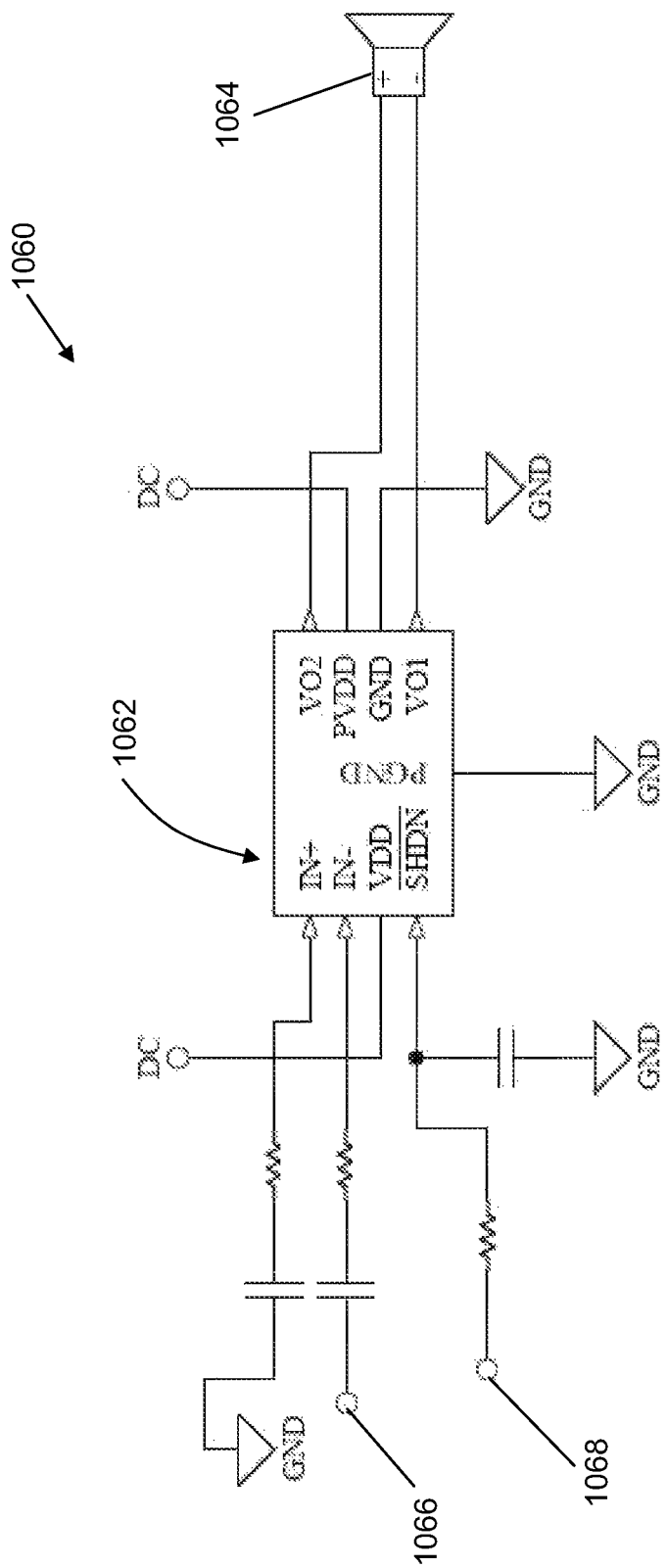

One example of an amplifier circuit that may be used with an alarm device orientation module is depicted in FIG. 10D. The amplifier circuit 1060 may comprise an amplifier chip 1062, which may receive signals from the microcontroller module via a first terminal 1066 and/or a second terminal 1068, and drive a speaker 1064 according to the microcontroller signals. Any suitable amplifier chip may be used in the amplifier circuit 1060, for example, the LM4675 amplifier. Amplifiers may be used with any desirable type(s) of indicators, including auditory, vibratory, visual, electronic, etc. to augment the activity of the indicators.

LED circuits that may be used with an alarm device alarm system may comprise a LED array with one or more LEDs driven by an input bus from the microcontroller module. Each LED in the LED array may represent the status of a component in the alarm system and/or the state of the microcontroller. For example, individual LEDs in the LED array may represent the status of the battery, activation of the microcontroller, orientation of the suction device with respect to the alarm device, the depletion or charging of the suction device, alarm mode, sleep or active mode, power mode, etc. The LED array may also be used as a LCD backlight, as appropriate. Optionally, the LED circuit may also comprise a zener diode array that may be used as a shunt voltage regulator to prevent sudden voltage surges. Alternatively, certain alarm systems may comprise an array of LCD segments or other electronic devices that may be used to represent the status of one or more components in the alarm system.

Figure 11:
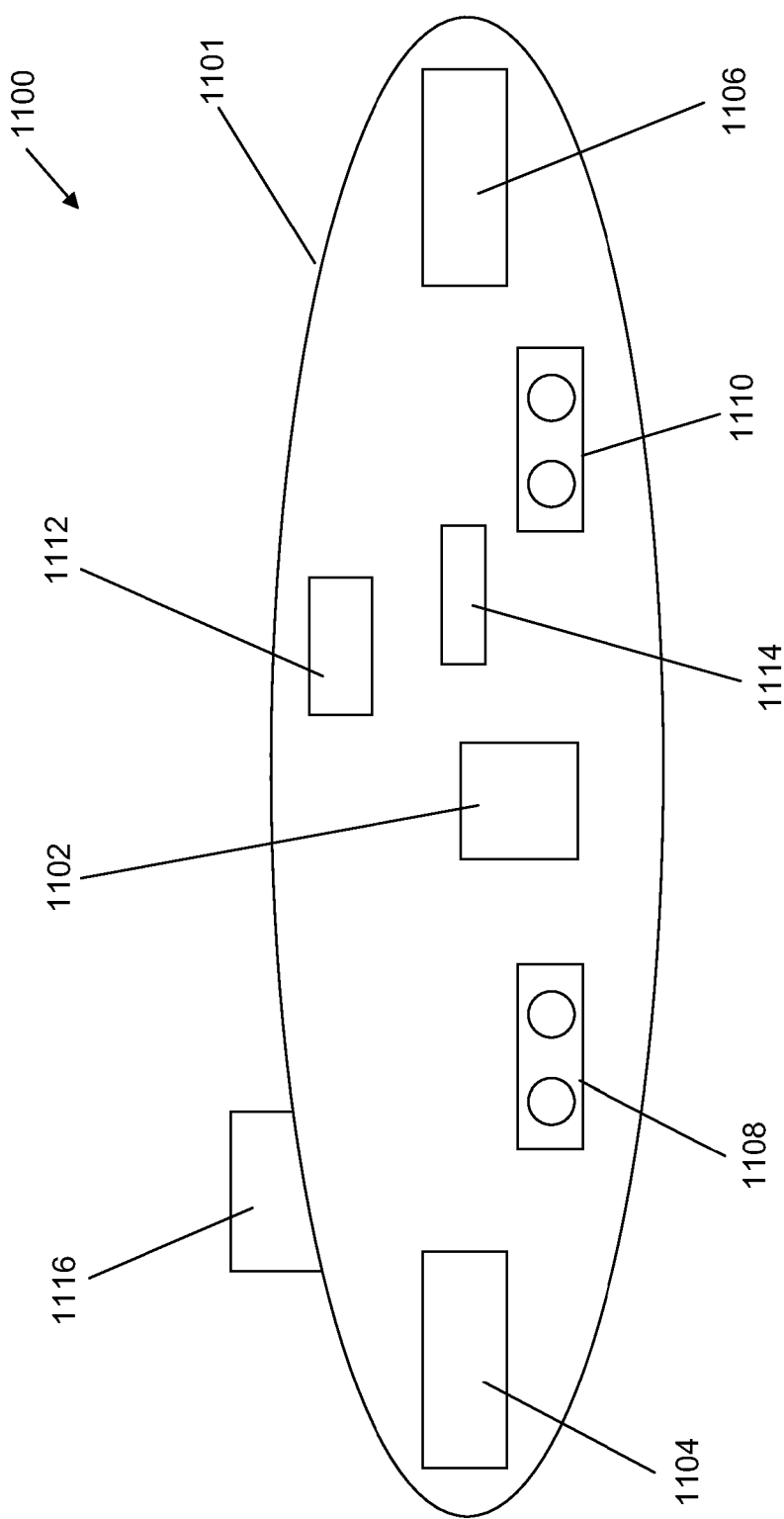
FIG. 11 is a schematic of exemplary alarm system components as arranged on a printed circuit board.

The components of any of the alarm systems described above may be mounted on a printed circuit board in accordance with their desired position on the alarm device. For example, the sensor mechanisms that are triggered to the location of the slidable seal of a suction device coupled to the alarm device may be positioned to correspond to the location of the seal in the charged and/or depleted configuration. FIG. 11 depicts one example of an alarm system 1100 with its components mounted on a printed circuit board 1101. The alarm system 1100 may comprise a microcontroller 1102 that receives signals from a first sensor mechanism 1104 located on a first side of the printed circuit board 1101 and a second sensor 1106 located on a second side of the board, where the second side is opposite the first side. The alarm system 1100 may also comprise a first pin pad 1108 and a second pin pad 1110 that may be used to determine the orientation of the suction device with respect to the alarm device. For example, the first connector 1442 depicted in FIG. 14E may correspond to the first pin pad 1108, and the second connector 1444 of FIG. 14E may correspond to the second pin pad 1110. The microcontroller 1102 may use the inputs from the first sensor mechanism 1104, second sensor mechanism 1106, first pin pad 1108, and second pin pad 1110 to determine the depletion or charge state of the suction device. The state of the suction device as determined by the microcontroller 1102 may be used to drive an amplifier module 1112 to generate any of the indicators descried above. The microcontroller 1102 may also be used to drive a LCD-LED array 1114 that may provide information to a patient and/or practitioner, e.g., by providing backlighting to a monitor, binary encoding of the suction device state, etc. While the printed circuit board 1101 is an oblong elliptical shape, it should be understood that it may have any geometry as suitable for the alarm device or clip.

Figure 12A:
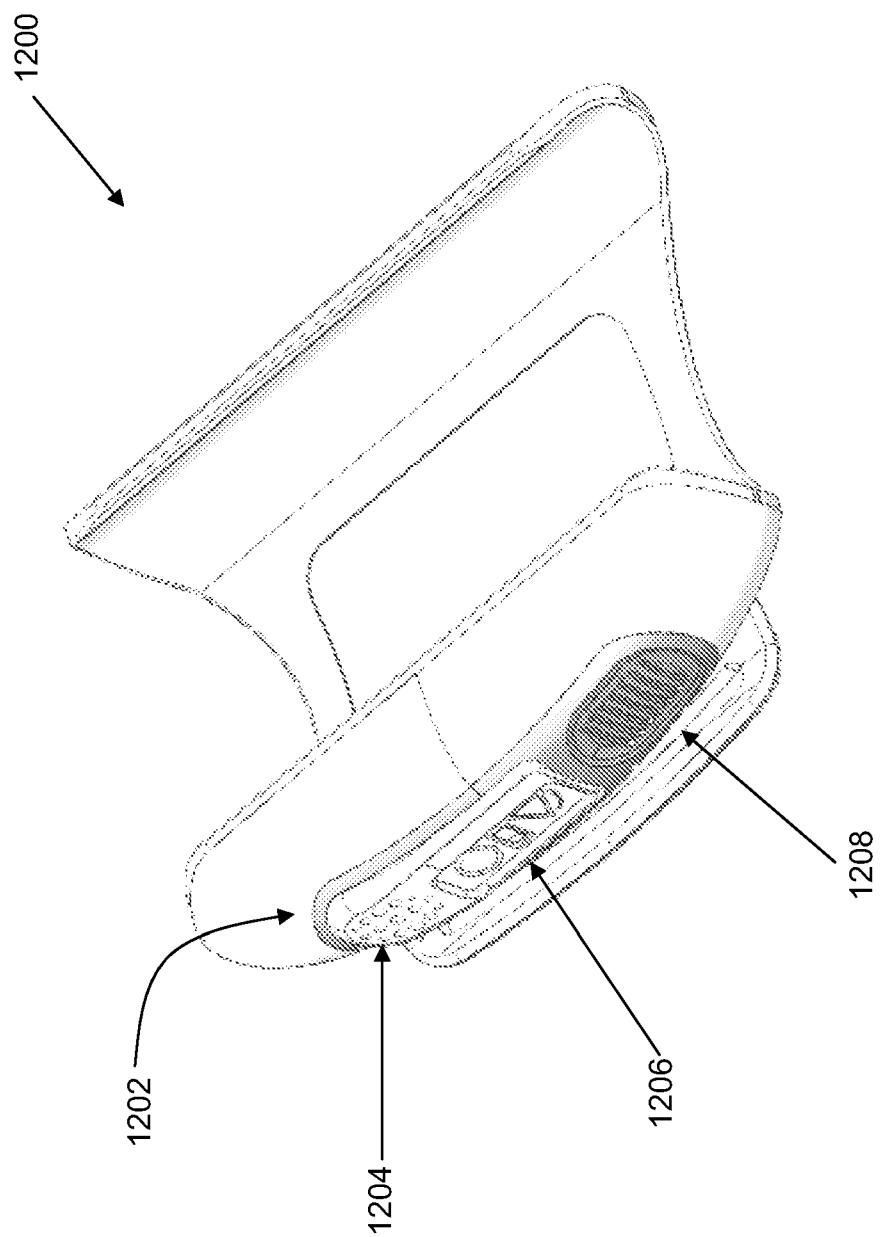
FIG. 12A is a perspective view of one variation of an alarm device.
Figure 12B:
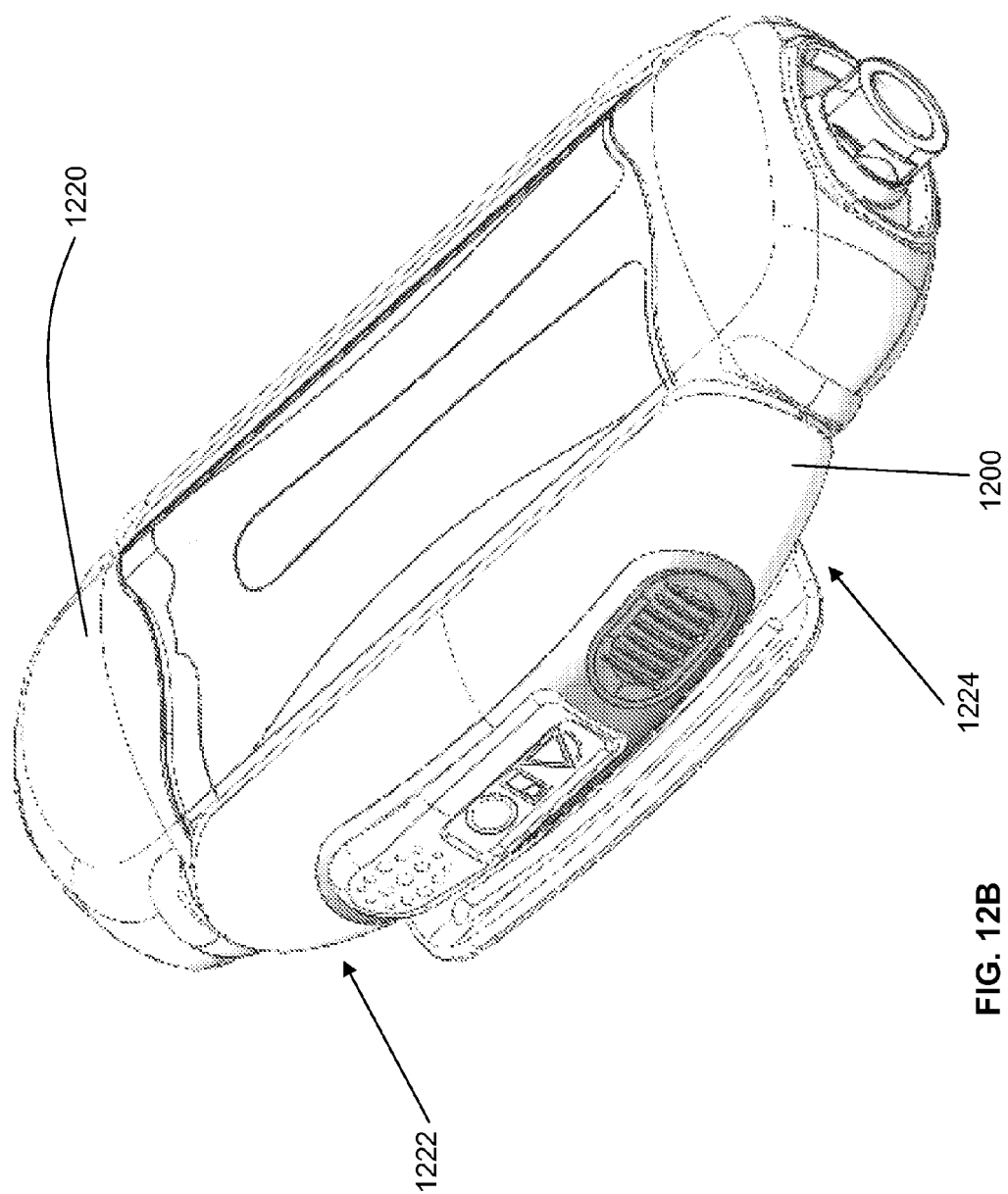
FIG. 12B is a perspective view of a suction device coupled to the alarm device of FIG. 12A.

One example of an alarm device 1200 that may use the alarm systems described above is depicted in FIG. 12A. The alarm device 1200 may have an alarm system 1202 embedded along a portion of the alarm device to detect the position of the slidable seal within a suction device. For example, the alarm system 1100 may be embedded along the longest dimension, e.g. its length, of the alarm device 1200. The alarm system 1202 embedded within the alarm device 1200 may comprise an audio speaker 1204, indicators 1206, and a user-activated switch 1208. The indicators 1206 may be configured to signal the state of the alarm system (e.g., active or inactive), the state of the suction device (e.g., depleted or charged, etc.), the state of the battery (e.g., charged or drained, etc.), and the state of any of the components in the alarm system. The user-activated switch 1208 may be a press-button or slide-button that may be used to activate backlight illumination for the indicators 1206 or to snooze an activated indicator or alert. FIG. 12B depicts an example of a suction device 1220 that may be retained within the alarm device 1200. In this example, a first sensing mechanism of the alarm system (e.g., a first reed switch) may be located at a proximal portion 1222 of the alarm device 1200 while a second sensing mechanism (e.g., a second reed switch) may be located at a distal portion 1224. The suction device 1220 may comprise a conductive element as previously described so that the alarm system microcontroller may determine the orientation of the suction device 1220 with respect to the alarm device 1200.

Another example of an alarm device 1500 that may use the alarm systems described above is depicted in FIG. 15A. The alarm device 1500 may have an alarm system 1502 embedded along a portion of the alarm device to detect the position of the slidable seal within a suction device. The alarm system 1502 embedded within the alarm device 1500 may comprise an audio speaker 1504, a display 1506, and a user-activated switch 1508. The display 1506 may comprise, for example, light bulbs, or an LED, LCD, OLED or other type of optical display. The display 1506 may be configured to signal the state of the alarm system (e.g., active or inactive), the state of the suction device (e.g., depleted or charged, etc.), the state of the battery (e.g., charged or drained, etc.), and the state of any of the components in the alarm system. For example, display 1506 may present an indicator 1506*a* may be in the shape of a circle and used to indicate that the system is powered on and active, i.e. that the suction device has been properly inserted and seated, and that there is adequate battery power to perform its detection and alarm functions. In other examples, the indicator 1506*a* may be configured to identify the current suction capacity of a suction device retained within the alarm device. The indicator 1506*b* may be used to indicate the status of the battery. The battery status may indicate a binary state (powered/unpowered), or may be configured to indicate multiple battery states, with three or more levels of battery power. The indicator 1506*c* may be used to indicate the alarm mode (e.g., alarm frequency, pre-programmed modes, snooze mode, etc.). The user-activated switch 1508 may be a press-button or slide-button that may be used to activate backlight illumination for the indicators 1506 or to snooze an activated indicator or alert (e.g., by silencing an audible alarm for a pre-selected period of time). An alarm device may also comprise one or more side connectors and/or one or more panel connectors. As depicted in FIG. 15B, the alarm device 1500 comprises a clip comprising one or more side connectors 1516 and a power supply button 1517. These connectors may be used as described above, for example, as a power switch, and/or orientation and/or compatibility verification mechanism. The power supply button 1517c may be depressed when a suction device is retained in the alarm device, thereby closing an open circuit and supplying power to the alarm system.

Figure 15C:
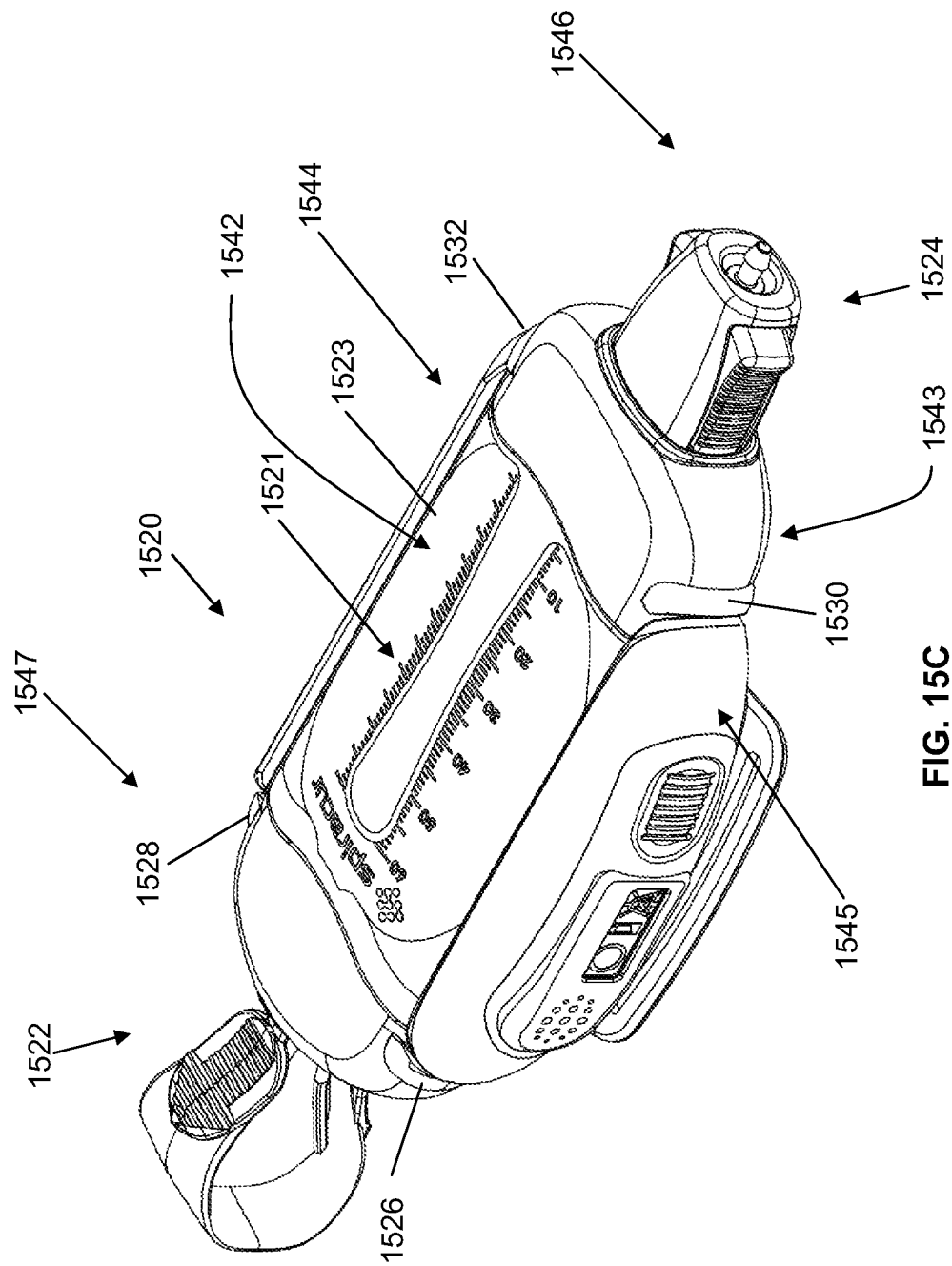
FIG. 15C is a perspective view of one variation of a suction device that may be retained within the alarm device of FIGS. 15A and 15B.
Figure 15D:
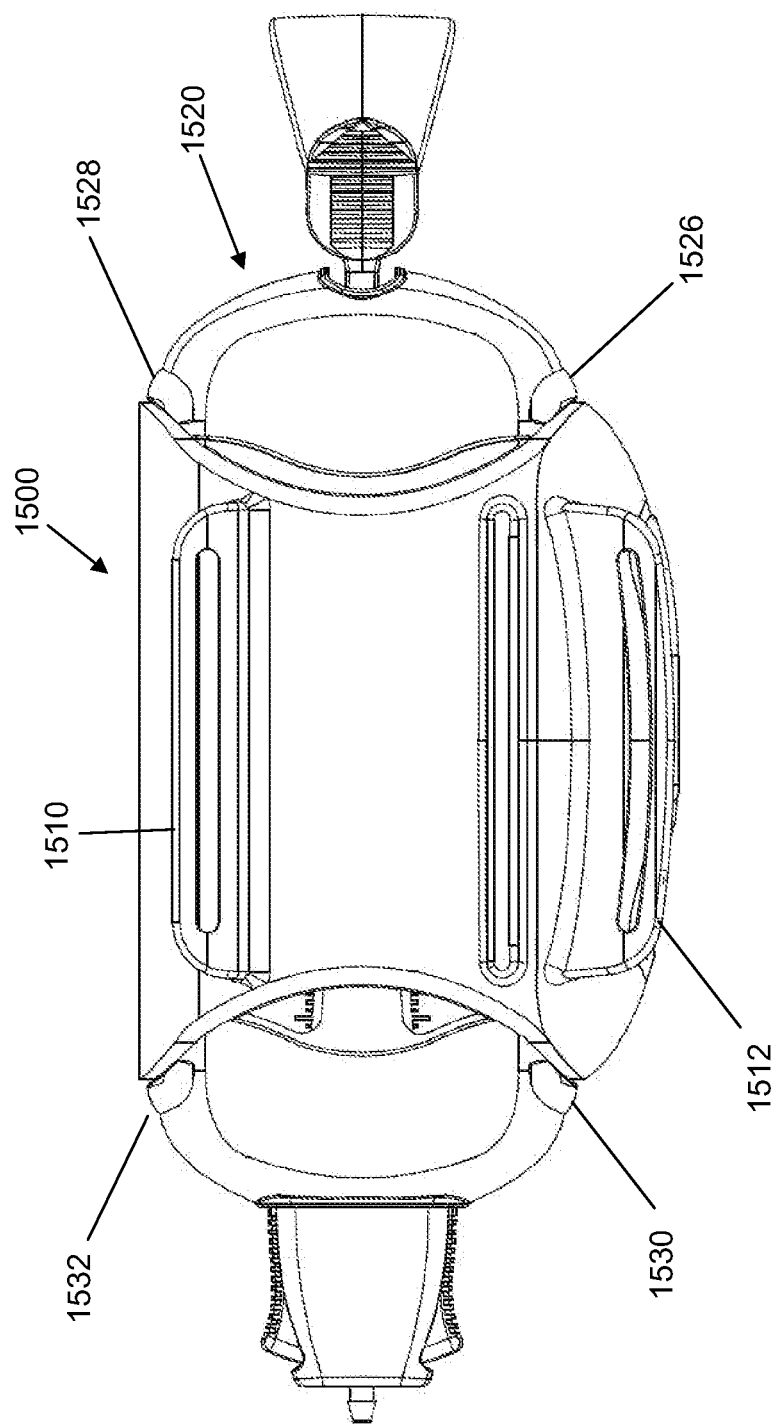
FIG. 15D is a superior view of the back of the attachment and suction devices of FIGS. 15A-15C.

FIG. 15C depicts an example of a suction device 1520 that may be retained within the alarm device 1500. The suction device 1520 may comprise measurement markings 1521 on a transparent portion of the suction chamber 1523 that may be used to quantify the position of a piston, and/or the quantity of a fluid, or volume of a solid or gel contained in the chamber. The suction device 1520 may also comprise one or more protrusions configured to engage with the alarm device, i.e., by snap-locking, such that an electrical connection may be made between a conductive element on the suction device and connectors on the alarm device. The protrusions may also help the alarm device retain the suction device with a certain alignment. For example, first and second protrusions 1526, 1528 may be located at a proximal portion 1522, while third and fourth protrusions 1530, 1532 may be located at a distal portion 1524 to retain the position of the suction device 1520 within the alarm device. In other variations, a suction device may comprise one or more recesses that correspond to one or more protrusions on the alarm device. The protrusions may be symmetrically arranged on the suction device (e.g., along a longitudinal and/or transverse axis) or asymmetrically arranged, as may be suitable. The protrusions may help ensure that a suction device retained in the alarm device does not move or change configuration during reduced pressure therapy. The location and geometry of the protrusions of the suction device may be configured such that the suction device may be retained in the alarm device in a variety of orientations, as described further below. Additionally or alternatively, engagement mechanisms such as magnetic, adhesive, hook-and-loop, etc. may be used to couple the suction and alarm devices, as described previously. A back panel of the alarm device 1500 retaining the suction device 1520 is depicted in FIG. 15D. The alarm device 1500 may optionally comprise a first loop portion 1510 and a second loop portion 1512, which may be used for coupling the alarm device to a belt or strap. In some variations, the alarm device 1500 may be coupled to a belt or strap by hook-and-loop engagement, snap-lock, buttons, clasps, adhesives, and the like. The suction device 1520 may comprise a conductive element as previously described so that the alarm system microcontroller may determine the orientation of the suction device 1520 with respect to the alarm device 1500.

In some variations, the suction device may be configured to be retained by the alarm device in a plurality of orientations, and the alarm device may be configured to detect the depletion state of the suction device (e.g., fully charged, partially charged/depleted, or fully depleted) regardless of the orientation in which the alarm device retains the suction device. For example, the suction device may be retained in the alarm device as shown in FIG. 15C, where the superior portion 1542 is facing up and the left side 1545 is closest to the alarm system 1502. The suction device 1520 may also be retained in an orientation where the inferior portion 1543 is facing up and the right side 1544 is closest to the alarm system 1502. Optionally, the suction device 1520 may also be retained in an orientation where the relative position of the distal end 1546 and the proximal end 1547 are switched.

FIG. 19 schematically illustrates the various orientations that a suction device 1900 may be retained in an alarm device. For example, the suction device 1900 comprising a suction chamber 1902 and a sliding seal assembly 1904 may be configured to be retained such that the superior portion 1920 is facing up. The alarm device may also be configured to retain the suction device 1900 in an orientation that is rotated around longitudinal axis A1 (e.g., 180°, such that the relative positions of the superior 1920 and inferior 1921 portions are switched, and the relative positions of the left 1922 and right 1923 sides are switched). The alarm device may also be configured to retain the suction device 1900 in an orientation that is rotated around transverse axis A2 (e.g., 180°, such that the relative positions of the distal 1925 and proximal 1926 portions are switched, and the relative positions of the superior 1920 and inferior 1921 portions are switched). The alarm device may be configured to retain the suction device 1900 in an orientation that is rotated around both axes A1 and A2 (e.g., rotated 180° around axis A1 and rotated 180° around axis A2 such that the relative positions of the superior 1920 and inferior 1921 portions, distal 1925 and proximal 1926 portions, and left 1922 and right sides 1924 are interchanged with each other, etc.). Accordingly, the alarm device may be configured to detect when the suction device 1900 is in a fully depleted state (e.g., sliding seal assembly 1904 has moved to a proximal portion of the suction chamber) in some or all of these retention orientations. For example, some alarm devices may be configured to detect the depletion state of a suction device in two retention orientations (e.g., in a first orientation and in a second orientation, where the second orientation is a front-to-back rotation of the first orientation). Some alarm devices may be configured to operate with a device that may be retained in three or more orientations (e.g., in a first, a second, a third, and a fourth orientation, where the second orientation is the first orientation rotated 180° around axis A1, the third orientation is the first orientation rotated 180° around axis A2, and the fourth orientation is the first orientation rotated 180° around axis A1 and rotated 180° around axis A2).

Suction devices may also be configured to be retained in the alarm device in a plurality of orientations. For example, suction devices may comprise protrusions similar to those described and depicted in FIGS. 15C-15D that can accommodate a plurality of retention orientations. Suction device may also comprise a sliding seal assembly with two or more magnetic elements, so that the location of the sliding seal assembly may be detected by the alarm device regardless of the retention orientation. Alternatively, alignment protrusions on a suction device may constrain the retention orientation of the suction device, such that the suction device may be retained in the alarm device in one or two orientations. In some variations, the alarm device is configured to only detect the depleted state of the suction device. For example, a suction device 1900 may have a first magnetic element 1914 on the left side 1922 of the sliding seal assembly and a second magnetic element 1915 on the right side 1924 of the sliding seal assembly, as schematically depicted in FIGS. 19B-19D. The alarm device may comprise a first reed switch 1906 at a first location and a second reed switch 1908 at a second location separate from the first location (e.g., the second reed switch 1908 may be proximal to the first reed switch). The suction device may be retained by the alarm device such that the location of the sliding seal assembly 1904 in the fully charged state is proximal to the location of the first reed switch 1906 of the alarm device, as depicted in FIG. 19B. The suction device 1900 may comprise a tab, shoulder, or any suitable stop structure (e.g., a wall of a distal cap) that may prevent the sliding seal assembly 1904 from moving to the distal-most portion of the suction chamber. When the suction device is this fully charged state, the location of the magnetic elements 1914, 1915 is such that they are undetected by the first reed switch 1906. When the suction device is fully depleted, the sliding seal assembly may be at the location 1905 depicted in FIG. 19C, and at least one of the magnets 1914, 1915 may be close enough to be detected by the second reed sensor 1908, thereby triggering an alert. The suction device 1900 may comprise a proximal tab, shoulder, or any suitable stop structure (e.g., a wall of a proximal cap) that may prevent the sliding seal assembly 1904 from moving further in the proximal direction. This particular arrangement of the alarm device with the suction device allows for the detection of the depleted state regardless of the orientation with which it is retained in the alarm device. For example, when the retention orientation of the suction device 1900 depicted in FIG. 19B is rotated 180° around axis A2, the device may be oriented as depicted in FIG. 19D. In this retention orientation, the magnetic elements 1914, 1915 of the sliding seal assembly in the fully charged configuration may be undetectable by the second reed switch 1908, but when the suction device is in the fully depleted configuration where the sliding seal assembly is at location 1905, the magnets 1914, 1915 may be detected by the first reed switch 1906. Such an arrangement of reed switches in the alarm device and magnets in the suction device may help to reduce patient confusion when installing the suction device in the alarm device, and may help to ensure that the alarm system is able to alert a patient when the suction device is depleted, regardless of the suction device orientation in the alarm device.

As described previously, the attachment protrusions of a suction device may help to ensure that the reed switches and magnetic elements are situated in a specific configuration with respect to each other (e.g., such that the alarm system may detect the depleted state of the suction device regardless of the retention orientation). For example, the location of the first and second reed switches 1906, 1908 may define a line segment L1 with a midpoint 1912. The position of the sliding seal assembly 1904 in the fully charged state and the position of the sliding seal assembly in the depleted state may define a travel path along a line segment L2 with a midpoint 1910, as depicted in FIG. 19C. The travel path may extend along the entire length of the suction chamber, or may extend along a portion thereof (e.g., ½, ⅔, ¾, of the length of the suction chamber, centered or offset from the center of the suction chamber). The attachment protrusions may be positioned such that the midpoint 1910 of the sliding seal assembly travel path is offset proximally from the midpoint 1912, for example, by an offset amount L3. Shifting the midpoint 1910 by offset L3 from the midpoint 1912 may help to ensure that when the suction device 1900 is in the fully charged state, the magnetic elements 1914, 1915 are not detectable by either reed switch, and when the suction device 1900 is in the fully depleted state, the magnet elements 1914, 1915 are detectable by at least one reed switch, regardless of the retention orientation of the suction device. For example, FIG. 19B depicts the location of the sliding seal assembly 1904 when the suction device 1900 is in the fully charged state. In such a location, the sliding seal assembly 1904 is not detectable by reed switch 1906. When the suction device 1900 transitions to the depleted configuration, the sliding seal assembly may be at location 1905, as depicted in FIG. 19C, and may be detectable by reed switch 1908. FIG. 19D depicts the suction device 1900, but retained in the alarm device after it has been rotated 180° around the axis A2 from the configuration shown in FIG. 19B. In the fully charged state and/or partially depleted intermediate states, the magnetic elements 1914, 1915 are not detectable by either reed switch 1908 or reed switch 1906. However, in the depleted configuration, the sliding seal assembly may be at location 1905, where it may be detectable by reed switch 1906.

The suction device may be configured to be retained in the alarm device such that the distance of magnetic elements of the sliding seal assembly to the nearest reed switch is less in the fully depleted state than in the fully charged state. As such, the alarm device may detect when the suction device is in the fully depleted state and generate an alert, but may not detect when the suction device is in the fully charged state. In some embodiments, the travel of the sliding seal assembly within the suction device may be such that the distance of the magnetic elements to the distal protrusions (e.g., protrusions 1530, 1532 of FIG. 15C) in the fully charged state may be greater than the distance of the magnetic elements to the proximal protrusions (e.g., protrusions 1526, 1528). Variations of these arrangements may be contemplated to ensure that regardless of the orientation of the suction device in the alarm device, the alarm system is able to detect when the suction device is depleted and to generate a signal to the patient.

In other variations, the suction device may be configured to be retained in the alarm device such that the distance of magnetic elements of the sliding seal assembly to the nearest reed switch is greater in the fully depleted state than in the fully charged state. In this variation, the alarm device may detect when the suction device is in the fully charged state, but not when it is in the fully depleted state, which may help signal that the suction device is properly installed.

Figure 20:
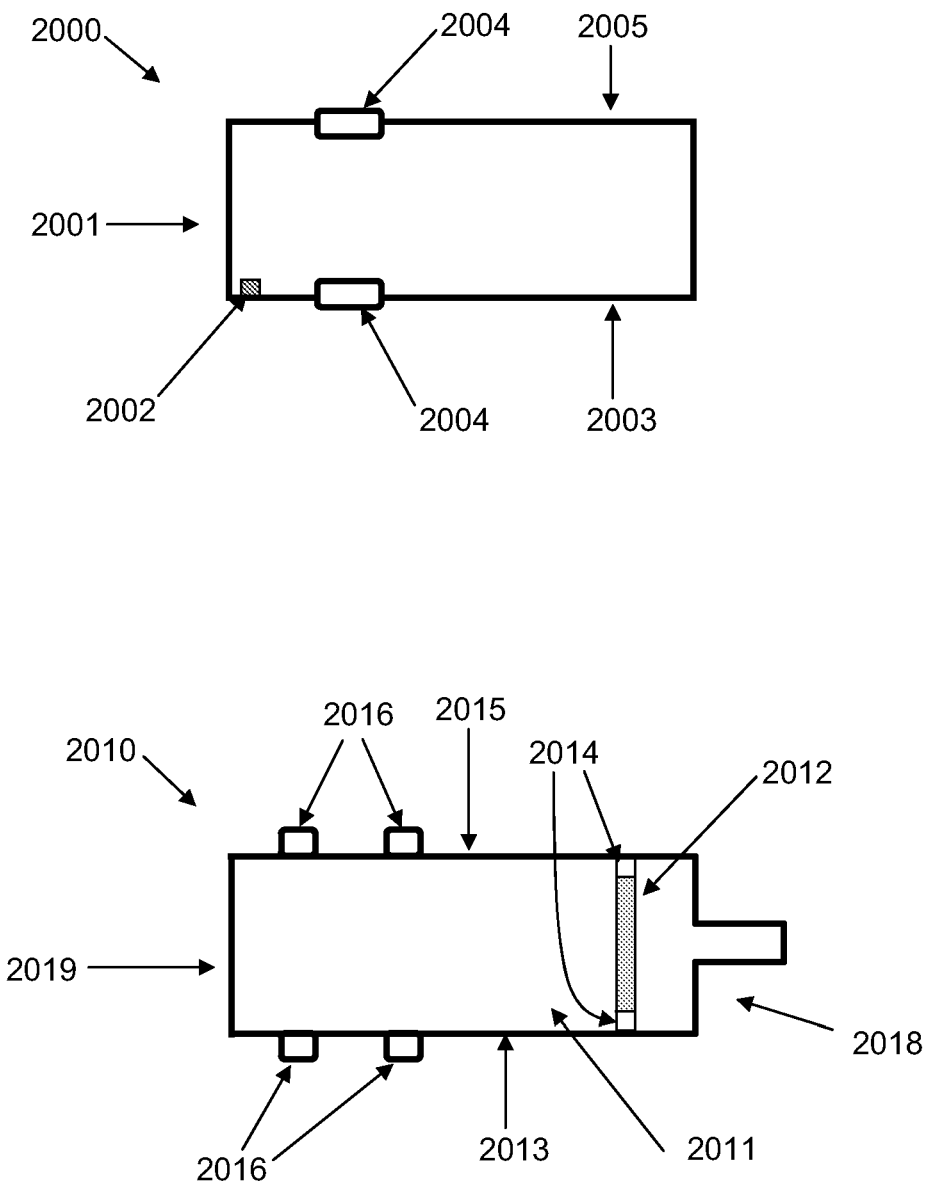
FIG. 20 is a schematic depiction of another variation of an alarm device comprising a single sensor and a suction device.

While alarm devices comprising two reed switches have been described and depicted herein, it should be understood that some variations may have only one reed switch. For example, one variation of a reduced pressure therapy system may comprise a suction device comprising a sliding seal assembly with two magnetic elements and an alarm device comprising only one reed switch, as depicted schematically in FIG. 20. The alarm device 2000 may be configured to detect the depleted state (and not the charged state) of the suction device 2010. The alarm device 2000 may comprise a reed switch 2002 located at a proximal portion 2001, and one or more alignment tabs 2004 (e.g., one located on the left 2003 and right 2005 side of the alarm device). The suction device 2010 may comprise a suction chamber 2011 with a sliding seal assembly 2014 in the suction chamber, and one or more alignment protrusions 2016 along the left 2013 and right 2015 sides. The alignment tabs 2004 may be located towards the proximal portion 2001. The alignment protrusions 2016 may be located in positions that correspond to the location of the alignment tabs 2004, and may interlock with each other (e.g., by snap lock, etc.). Placement of the alignment features in an offset position (e.g., towards the proximal or distal end of the devices) may help a patient and/or practitioner to install the suction device in a desired orientation with respect to the alarm device. The suction device 2010 may be retained in the alarm device 2000 such that the left 2013 and right 2015 sides of the suction device are aligned with the left 2003 and right 2005 sides of the alarm device. The suction device 2010 may also be retained in the alarm device 2000 such that the right 2015 and left 2013 sides of the suction device are aligned with the left 2003 and right 2005 sides of the alarm device (e.g., rotated 180° around the longitudinal axis). Optionally, the suction device 2010 may be retained by the alarm device 2000 in an orientation where the relative position of the distal portion 2018 and the proximal portion 2019 is interchanged (e.g., rotated 180° around a transverse axis from the orientation depicted in FIG. 20). The alignment tabs 2004 may be configured to interlock with the alignment protrusions 2016 in this transversely-rotated orientation. In such an orientation, the alarm device 2000 may be able to detect the depleted state of the suction device 2010. In some variations, suction devices may comprise a sliding seal assembly having only have one magnetic element, and may be retained in an alarm device in two or fewer orientations.

In alternative variations, the alarm device may comprise three or more reed switches, which may allow for the detection of additional suction device configurations and orientations. Optionally, suction devices may comprise sliding seal assemblies that have two or more magnetic elements in various locations. The number and locations of reed switches and magnetic elements on the suction device and alarm device may be varied in accordance with the desired retention orientation of the suction device, as well as the number of suction device configurations that are to be detected.

Figure 13:
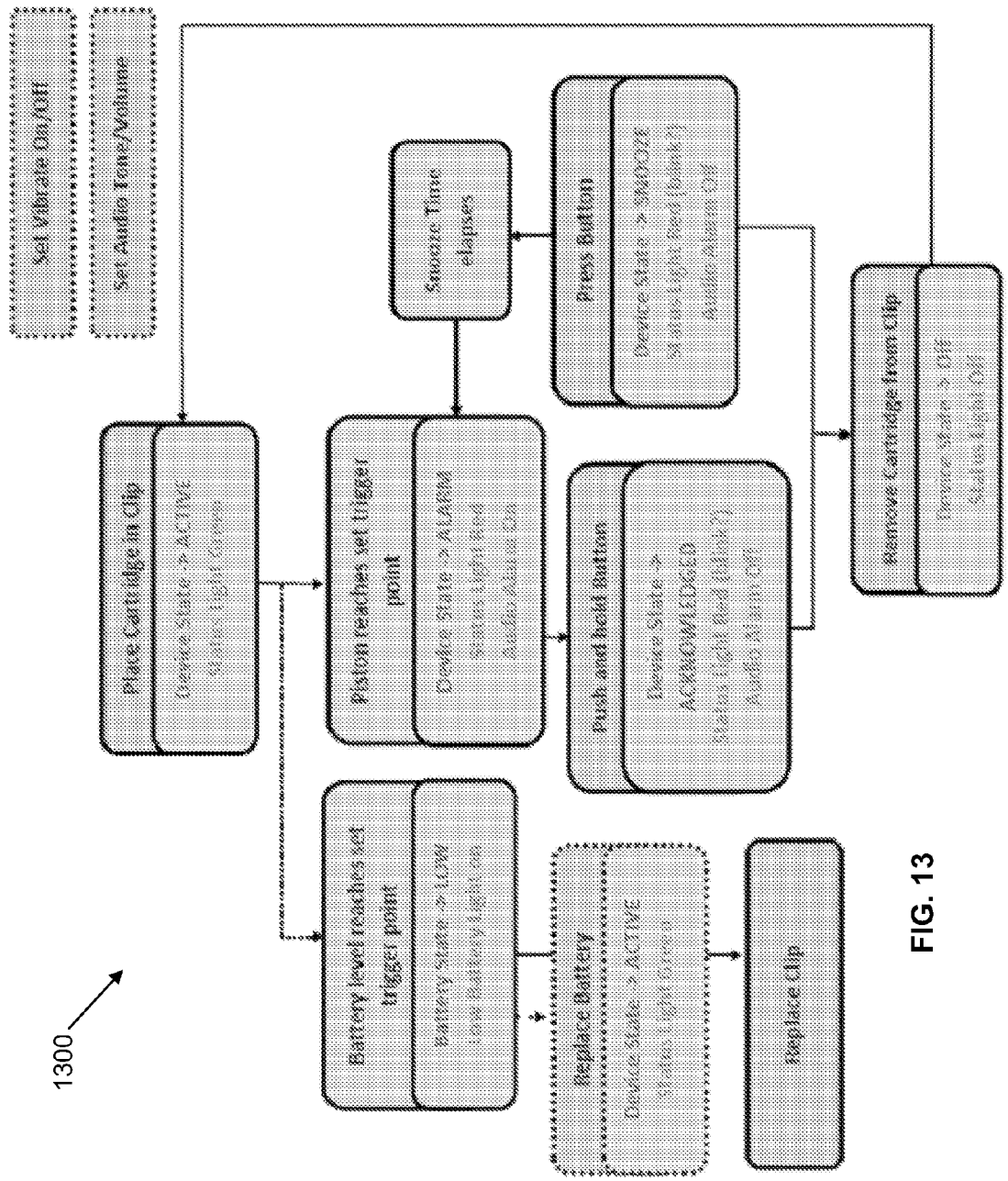
FIG. 13 is state machine diagram that depicts one variation of a state machine that may be programmed into a microcontroller of an alarm system that may be used with reduced pressure therapy devices.

Once the suction device has been detected to be in the fully depleted state, the microcontroller of an alarm system may response according to pre-programmed algorithms. For example, certain microcontroller modules may additionally comprise a programming interface that may allow scripts and instruction sets to be downloaded into the microcontroller. In some variations, the microcontroller may be programmed to implement a state machine 1300, as represented by the state machine diagram depicted in FIG. 13. The microcontroller may activate certain alarm system components (e.g., LEDs, LCD screen, amplifiers, speakers, etc.) in accordance to its current state as determined by sensor and/or user inputs. FIG. 13 merely depicts an example of a state machine that may be programmed into a microcontroller for used with an alarm system for a suction device, and it should be understood that a variety of state machines (e.g., with more or less states) may be implemented as may be suitable. In some variations, the microcontroller may be programmed to be in a "sleep" or low-power mode for the majority of its operation, and "wake" or activate every second or minute to check signals from the alarm system sensors and/or switches. In some variations, signal filters may be programmed into the microcontroller to help reduce false positive signals. If an alarm condition is detected (e.g., low battery, suction device nearing or at depletion, etc.), the microcontroller may remain in the activated state to generate the necessary alerts and indicators to trigger an action on the part of the patient and/or practitioner. The microcontroller may be programmed to drive the alert or indicator module for a certain amount of time, e.g., 1 minute, 2 minutes, 5 minutes, etc., and may be dormant or snoozed for a certain amount of time, e.g., 1 minute, 10 minutes, 30 minutes, etc., before driving the alert or indicator module again. For example, the alert module may issue a sound for 5 minutes (either continuously or in bursts), remain silent for 30 minutes, and then sound for 5 minutes if the suction device is not replaced. Optionally, a visual alert may accompany the audio alert. A snooze function may be provided where the audio alert may be silenced for a period of time (e.g., 5 minutes, 15 minutes, 25 minutes, etc.). If after the period time has elapsed and the suction device has not been replaced, the audio alert may continue to sound. Other such functions and modes may be programmed into the microcontroller as desired.

While some reduced pressure therapy systems described herein may have an alarm system, it should be understood that other variations of suction device may not have an alarm system. For example, some reduced pressure therapy systems may comprise a suction device and a clip, where the suction device and clip do not have any kind of alarm sensors or alerts. In some variations, a reduced pressure therapy system may comprise a suction device with a visual indicator (e.g., color) and a clip, without any sensor-based alarm system. In still other variations, a reduced pressure therapy system may comprise a suction device and an attachment strap, where suction device and the strap do not have any kind of alarm sensors or alerts.

Although the embodiments herein have been described in relation to certain examples, various additional embodiments and alterations to the described examples are contemplated within the scope of the invention. Thus, no part of the foregoing description should be interpreted to limit the scope of the invention as set forth in the following claims. For all of the embodiments described above, the steps of the methods need not be performed sequentially. Accordingly, it is not intended that the invention be limited, except as by the appended claims.

What is claimed:

1. A method for reduced pressure therapy, comprising:
   detaching a suction device that is attached to a wound covering, the suction device comprising a suction chamber with a slidable seal therein, wherein the slidable seal is configured to generate a reduced pressure in the suction chamber, an expandable fluid absorbent material retained within a carrier and located within the suction chamber, the material having a first and second state, wherein the material in the first state is a dry solid and the material in the second state is a semi-solid or gel and wherein the fluid absorbent material, prior to fluid absorption, has a fixed location within the suction chamber but is at least partially separable from the carrier during use upon fluid absorption and movable in the suction chamber;
   advancing the slidable seal to the distal end of the suction chamber without generating a reduced pressure;
   re-attaching the suction device to the wound covering; and
   activating the suction device to generate reduced pressure underneath the wound covering.

2. The method of claim 1, wherein the suction device is at least partially depleted prior detaching the suction device from the wound covering.

3. The method of claim 2, wherein at least a portion of the fluid absorbent material is in the second state.

4. The method of claim 3, wherein advancing the slidable seal to the distal end of the suction chamber includes blocking expulsion of the fluid absorbent material using a screen located within the suction chamber.

5. The method of claim 3, further comprising removing at least a portion of the fluid absorbent member after detaching the suction device from the wound covering.

6. The method of claim 5, further comprising removing the carrier from the suction chamber.

7. The method of claim 3, further comprising removing wound exudates collected in the suction chamber.

8. The method of claim 1, wherein the suction device further comprises a screen configured to block displacement of the expandable fluid absorbent material out of the suction device, and wherein the carrier structure is at a fixed location around an inlet opening of the suction chamber that is independent of suction device orientation.

9. The method of claim 1, wherein the fluid absorbent material is bonded to a surface of the carrier structure.

10. The method of claim 1, wherein the fluid absorbent material is releasably contained within the carrier structure.

11. The method of claim 1, wherein the carrier structure comprises a permeable pouch.

12. The method of claim 11, wherein the permeable pouch comprises two permeable layers sealed together.

13. The method of claim 8, wherein the carrier structure comprises an aperture therethrough, wherein the aperture is aligned with the inlet opening of the suction chamber.

14. The method of claim 8, wherein the screen is interposed between the inlet opening of the suction chamber and the carrier structure.

15. The method of claim 8, wherein the carrier is attached to the screen.

16. The method of claim 9, wherein the fluid absorbent material is woven into the carrier structure.

17. The method of claim 1, wherein the fluid absorbent material comprises one or more disinfecting agents.

18. The method of claim 1, wherein the fluid absorbent material comprises a deodorizer.

19. The method of claim 1, where the fluid absorbent material comprises a solidifier.

20. The method of claim 1, wherein the expandable fluid absorbent material is comprised of a pad having a first thickness before expansion and a second thickness after expansion from separation of the semi-solid or gel from the pad.

\* \* \* \* \*